(12) United States Patent
Nagy et al.

(10) Patent No.: US 12,178,835 B2
(45) Date of Patent: Dec. 31, 2024

(54) ALLOGRAFT TOLERANCE WITHOUT THE NEED FOR SYSTEMIC IMMUNE SUPPRESSION

(71) Applicant: Sinai Health System

(72) Inventors: Andras Nagy, Toronto (CA); Jeffrey Harding, Toronto (CA); Kristina Nagy, Toronto (CA)

(73) Assignee: Sinai Health System, Toronto (CA)

( * ) Notice: Subject to any disclaimer, the term of this patent is extended or adjusted under 35 U.S.C. 154(b) by 0 days.

(21) Appl. No.: 18/175,409

(22) Filed: Feb. 27, 2023

(65) Prior Publication Data

US 2023/0414677 A1 Dec. 28, 2023

Related U.S. Application Data

(63) Continuation of application No. 16/621,490, filed as application No. PCT/CA2018/050706 on Jun. 12, 2018, now abandoned.

(60) Provisional application No. 62/666,626, filed on May 3, 2018, provisional application No. 62/518,151, filed on Jun. 12, 2017.

(51) Int. Cl.

| | | |
|---|---|---|
| *C12N 5/0735* | (2010.01) | |
| *A61K 35/545* | (2015.01) | |
| *A61K 45/06* | (2006.01) | |
| *A61P 1/16* | (2006.01) | |
| *A61P 3/00* | (2006.01) | |
| *A61P 3/10* | (2006.01) | |
| *A61P 7/04* | (2006.01) | |
| *A61P 9/10* | (2006.01) | |
| *A61P 19/02* | (2006.01) | |
| *A61P 25/16* | (2006.01) | |
| *A61P 27/02* | (2006.01) | |
| *A61P 37/06* | (2006.01) | |
| *C07K 14/47* | (2006.01) | |
| *C07K 14/52* | (2006.01) | |
| *C07K 14/705* | (2006.01) | |
| *C12N 15/09* | (2006.01) | |

(52) U.S. Cl.
CPC ............ *A61K 35/545* (2013.01); *A61K 45/06* (2013.01); *A61P 1/16* (2018.01); *A61P 3/00* (2018.01); *A61P 3/10* (2018.01); *A61P 7/04* (2018.01); *A61P 9/10* (2018.01); *A61P 19/02* (2018.01); *A61P 25/16* (2018.01); *A61P 27/02* (2018.01); *A61P 37/06* (2018.01); *C07K 14/47* (2013.01); *C07K 14/521* (2013.01); *C07K 14/70503* (2013.01); *C07K 14/70532* (2013.01); *C07K 14/70575* (2013.01); *C12N 5/0606* (2013.01); *C12N 15/09* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 10,968,426 | B2 | 4/2021 | Meissner et al. |
| 2017/0058015 | A1 | 3/2017 | Seidel, III et al. |
| 2018/0044686 | A1 | 2/2018 | Nagy et al. |
| 2019/0376045 | A1 | 12/2019 | Schrepfer et al. |

FOREIGN PATENT DOCUMENTS

| | | | |
|---|---|---|---|
| CN | 104619722 | | 5/2015 |
| WO | WO 02/072798 A1 | * | 9/2002 |
| WO | WO-2006/091773 A2 | | 8/2006 |
| WO | WO-2007/047468 A2 | | 4/2007 |
| WO | WO-2009/139921 A2 | | 11/2009 |
| WO | WO-2011/100460 A2 | | 8/2011 |
| WO | WO-2014/022423 A2 | | 2/2014 |
| WO | WO-2015/009948 A1 | | 1/2015 |
| WO | WO-2015/195531 A2 | | 12/2015 |
| WO | WO-2016/081924 A1 | | 5/2016 |
| WO | WO-2016/089692 A1 | | 6/2016 |
| WO | WO-2016/141480 A1 | | 9/2016 |
| WO | WO-2016/160622 A2 | | 10/2016 |
| WO | WO-2017/066561 A2 | | 4/2017 |
| WO | WO-2021/041316 A1 | | 3/2021 |

OTHER PUBLICATIONS

Tokuriki et al., 2009, Curr. Opin. Struc. Biol. 19:596-604.*
Fenton et al. (2020, Medicinal Chemistry Research 29:1133-1146).*
Bhattacharya et al. (2017, PLoS One 12(3): e0171355, https://doi.org/10.1371/journal.pone.0171355).*
Gorczynski et al. (2014, Transplantation 98(12): 1271-1278).*
Shields et al. (2010, Science 328:749-752).*
El Haddad et al. (2011, J. Immunol. 187(5):2252-2260).*
Tan et al. (2015, Stem Cell Reports 5:741-752).*
Rong et al. (2014, Cell Stem Cell 4(1):121-130).*
Zhao et al. (2014, Stem Cell Research 13(2):342-354).*
Tena et al. (2014, Am. J. Transplantation 14(12):2713-2722).*
Harding et al. (2023, Nature Biomedical Engineering, https://doi.org/10.1038/s41551-023-01133-y, pp. 1-33).*
Chinese Office Action mailed Feb. 27, 2024 for Chinese Application No. 201880038734.5, a foreign counterpart to U.S. Appl. No. 16/621,490, 16 pages.

(Continued)

*Primary Examiner* — Elizabeth C. Kemmerer
(74) *Attorney, Agent, or Firm* — C. Rachal Winger; Chrystal Quisenberry; Lee & Hayes PC

(57) ABSTRACT

A cell genetically modified to comprise at least one mechanism for providing a local immunosuppression at a transplant site when transplanted in an allogeneic host is, and methods for making and using the same is provided. The cell comprises a set of transgenes, each transgene encoding a gene product that is cytoplasmic, membrane bound, or local acting, and whose function is one or more of: to mitigate antigen presenting cell activation and function; to mitigate graft attacking leukocyte activity or cytolytic function; to mitigate macrophage cytolytic function and phagocytosis of allograft cells; to induce apoptosis in graft attacking leukocytes; to mitigate local inflammatory proteins; and to protect against leukocyte-mediated apoptosis.

14 Claims, 21 Drawing Sheets
(3 of 21 Drawing Sheet(s) Filed in Color)

Specification includes a Sequence Listing.

(56) References Cited

OTHER PUBLICATIONS

Chinese Office Action mailed Sep. 29, 2023 for Chinese Application No. 201880038734.5, a foreign counterpart to U.S. Appl. No. 16/621,490, 9 pages.
Second Examination Report from Australian Government IP Australia, Application No. 2018285972, mailed on Apr. 6, 2023, a counterpart foreign application of U.S. Appl. No. 16/621,490, 3 pages.
First Examination Report from Australian Government IP Australia, Application Number 2018285972, mailed on Jul. 27, 2022, a coutnerpart foreign application of U.S. Appl. No. 62/518,151, 4 pgs.
Bhattacharya, et al., "Impact of Genetic Variation on Three Dimensional Structure and Function of Proteins," PLoS One, vol. 12, No. 3, 2017, 22 pgs.
Office Action for Chinese application 201880038734.5, mailed Mar. 1, 2023, "Allograft Tolerance Without the Need for Systemic Immune Suppression", 10 pages.
Fenton, et al., "Rheostat Positions: A New Classification of Protein Positions Relevant to Pharmacogenomics," Medicinal Chemistry Research, vol. 29, 2020, pp. 1133-1146.
Translated Notice of Reasons for Refusal from the Japan Patent Office for Application No. 2020-518110, mailed Aug. 2, 2022, a foreign counterpart to U.S. Appl. No. 16/621,490, 9 pgs.
Liang, et al., "Linking a Cell-Division Gene and a Suicide Gene to Define and Improve Cell Therapy Safety," Nature, vol. 563, No. 7733, 2018, 20 pgs.
McDonald, et al., "An Amyloid-Like C-Terminal Domain of Thrombospondin-1 Displays CD47 Agonist Activity Requiring Both VVM Motifs," Biochemistry, vol. 42, 2003, pp. 10001-10011.
Office Action for U.S. Appl. No. 16/621,490 mailed on Oct. 26, 2022, Andras Nagy, "Allograft Tolerance Without the Need for Systemic Immune Suppression," 17 pages.
Tokuriki & Tawfik, "Stability Effects of Mutations and Protein Evolvability," Curr. Opin. Struc. Biol., vol. 19, 2009, pp. 596-604.
Canadian Office Action mailed Jul. 13, 2023 for Canadian Patent Application No. 3,064,297, a foreign counterpart to U.S. Appl. No. 16/621,490, 4 pages.
Canadian Office Action mailed Aug. 21, 2023 for Canadian patent application No. 3123102, a counterpart foreign application of U.S. Appl. No. 17/413,314 , #6 pages.
Israeli Office Action mailed Jul. 11, 2023 for Israeli Patent Application No. 270835, a foreign counterpart to U.S. Appl. No. 16/621,490, 2 pages.
Korean Office Action mailed Aug. 30, 2023 for Korean Patent Application No. 10-2020-7000550, a foreign counterpart to U.S. Appl. No. 16/621,490, 8 pages.
Dai et al., "Targeted disruption of the alpha1,3-galactosyltransferase gene in cloned pigs," Nat Biotechnol. 20(3):251-255 (2002) (5 pages).
Chan et al., "Transgenic Monkeys Produced by Retroviral Gene Transfer into Mature Oocytes," Science. 291(5502):309-312 (2001) (5 pages).
Wang et al., "One-Step Generation of Mice Carrying Mutations in Multiple Genes by CRISPR/Cas-Mediated Genome Engineering," available in PMC Mar. 30, 2014, published in final edited form as: Cell. 153(4):910-918 (2013) (17 pages).
Yang et al., "Effective gene targeting in rabbits using RNA-guided Cas9 nucleases," J Mol Cell Biol. 6(1):97-99 (2014) (3 pages).
Lai et al., "Production of alpha-1,3-Galactosyltransferase Knockout Pigs by Nuclear Transfer Cloning," Science. 295(5557):1089-1092 (2002) (5 pages).
Abdullah et al., "Serpin-6 Expression Protects Embryonic Stem Cells From Lysis by Antigen-Specific CTL," J Immunol. 178(6):3390-9 (2007).
Gorczynski et al., "Long-Term Tolerance and Skin Allograft Survival in CD200tg Mice After Autologous Marrow Transplantation," Transplantation. 98(12):1271-1278 (2014).
Harding et al., "Induction of long-term allogenic cell acceptance and formation of immune privileged tissue in immunocompetent hosts." BIORXIV. <https://www.biorxiv.org/content/10.1101/716571v1>, dated Jul. 30, 2019.
International Search Report and Written Opinion for International Patent Application No. PCT/CA2019/051808, mailed Mar. 19, 2020 (18 pages).
Lanza et al., "Engineering Universal Cells that Evade Immune Detection," Nat Rev Immunol. 19(12):723-733 (2019).
Shields et al., "Induction of Lymphoidlike Stroma and Immune Escape by Tumors That Express the Chemokine CCL21," Science. 328(5979):749-52 (2010).
Tan et al., "MFG-E8 Is Critical for Embryonic Stem Cell-Mediated T Cell Immunomodulation," Stem Cell Reports. 5(5):741-752 (2015).
Tena et al., "Transgenic Expression of Human CD47 Markedly Increases Engraftment in a Murine Model of Pig-to-Human Hematopoietic Cell Transplantation," Am J Transplant. 14(12):2713-22 (2014).
Deuse et al., "Hypoimmunogenic derivatives of induced pluripotent stem cells evade immune rejection in fully immunocompetent allogeneic recipients," Nat Biotechnol. 37(3):252-258 (2019) (16 pages).
Han et al., "Generation of hypoimmunogenic human pluripotent stem cells," Proc Natl Acad Sci U S A. 116(21):10441-6 (2019).
Extended European Search Report for European Application No. 18818206.7, mailed Aug. 9, 2021 (14 pages).
Gorczynski, "Regulation of transplantation tolerance by antigen-presenting cells," Transplantation. 19:123-137 (2005).
Extended European Search Report for European Application No. 16760977.5, mailed Jun. 5, 2018 (9 pages).
Hara et al., "Neuron-like differentiation and selective ablation of undifferentiated embryonic stem cells containing suicide gene with Oct-4 promoter," Stem Cells Dev. 17(4):619-627 (2008) (9 Pages).
International Preliminary Report on Patentability for International Application No. PCT/CA2016/050256, issued Sep. 12, 2017 (10 pages).
International Search Report and Written Opinion for International Application No. PCT/CA2016/050256, mailed Jul. 13, 2016 (14 pages).
International Search Report and Written Opinion for International Application No. PCT/CA2018/050706, mailed Sep. 13, 2018 (16 pages).
Jung et al., "Ablation of tumor-derived stem cells transplanted to the central nervous system by genetic modification of embryonic stem cells with a suicide gene," Hum Gene Ther. 18(12):1182-92 (2007).
Kyba et al., "Enhanced hematopoietic differentiation of embryonic stem cells conditionally expressing Stat5," Proc Natl Acad Sci USA. 100(Suppl 1):11904-10 (2003).
Lee et al., "Induced pluripotent stem cells in regenerative medicine: an argument for continued research on human embryonic stem cells," Regen Med. 4(5):759-69 (2009).
Li et al., "Safeguarding clinical translation of pluripotent stem cells with suicide genes," Organogenesis. 9(1):34-9 (2013) (7 pages).
Lim et al., "Lentiviral vector mediated thymidine kinase expression in pluripotent stem cells enables removal of tumorigenic cells," PLoS One. 8(7):e70543 (2013) (16 pages).
Malecki, "'Above all, do No. harm': safeguarding pluripotent stem cell therapy against iatrogenic tumorigenesis," Stem Cell Res Ther. 5(3): 73 (2014) (10 pages).
Rong et al., "A scalable approach to prevent teratoma formation of human embryonic stem cells," J Biol Chem. 287(39):32338-45 (2012).
Rong et al., "An effective approach to prevent immune rejection of human ESC-derived allografts," Cell Stem Cell. 14(1):121-30 (2014).
Sarin et al., "Conditional telomerase induction causes proliferation of hair follicle stem cells," Nature. 436(7053):1048-52 (2005).
Wang et al., "Identification and characterization of essential genes in the human genome," available in PMC Nov. 28, 2015, published in final edited form as: Science. 350(6264):1096-1101 (2015) (13 pages).
Yolcu et al., "Induction of tolerance to cardiac allografts using donor splenocytes engineered to display on their surface an exogenous fas ligand protein," J Immunol. 181(2):931-9 (2008).

(56) References Cited

OTHER PUBLICATIONS

Zhao et al., "Heterologous expression of mutated HLA-G decreases immunogenicity of human embryonic stem cells and their epidermal derivatives," Stem Cell Res. 13(2):342-54 (2014).
Communication pursuant to Article 94(3) EPC for European Application No. 16760977.5, dated Feb. 27, 2019 (5 pages).
Liang et al., "Linking a cell-division gene and a suicide gene to define and improve cell therapy safety," Nature. 563(7733):701-4 (including supplement) (2018) (20 pages).
Di Stasi et al., "Inducible Apoptosis as a Safety Switch for Adoptive Cell Therapy," available in PMC May 3, 2012, published in final edited form as: N Engl J Med. 365(18):1673-1683 (2011) (16 pages).
Straathof et al., "An inducible caspase 9 safety switch for T-cell therapy," Blood. 105(11):4247-54 (2005) (9 pages).
Boone et al., "Human Genome. The indispensable genome," Science. 350(6264):1028-9 (2015) (3 pages).
Blomen et al., "Gene essentiality and synthetic lethality in haploid human cells," Science. 350(6264):1092-96 (2015) (6 pages).
Chen et al., "OGEE v2: an update of the online gene essentiality database with special focus on differentially essential genes in human cancer cell lines," Nucleic Acids Res. 45(D1):D940-D944 (2017).
Wang et al., "Identification and characterization of essential genes in the human genome," Science. 350(6264):1096-1101 (2015) (13 pages).
Guo et al., "Oct 4 is Critical for Survival/Antiapoptosis of Murine Embryonic Stem Cells Subjected to Stress. Effects Associated with STAT3/Survivin," available in PMC Feb. 10, 2010, published in final edited form as: Stem Cells. 26(1):30 (2008) (15 pages).
Mitsui et al., "The homeoprotein Nanog is required for maintenance of pluripotency in mouse epiblast and ES cells," Cell. 113(5):631-42 (2003).
Schwarz et al., "Nanog is Dispensable for the Generation of Induced Pluripotent Stem Cells," available in PMC Aug. 3, 2014, published in final edited form as: Curr Biol. 24(3):347-350 (2014) (9 pages).
Webb, "No role for Oct4 in regenerating adult tissues," Nat Rep Stem Cells. doi.org/10.1038/stemcells.2007.103, retrieved from <www.nature.com/articles/stemcells.2007.103> on May 2, 2019 (2007) (3 pages).
Diril et al., "Cyclin-dependent kinase 1 (Cdk1) is essential for cell division and suppression of DNA re-replication but not for liver regeneration," Proc Natl Acad Sci U S A. 109(10):3826-31 (2012).
Mansour et al., "Disruption of the proto-oncogene int-2 in mouse embryo-derived stem cells: a general strategy for targeting mutations to non-selectable genes," Nature. 336(6197):348-352 (1988).
Adhikari et al., "Inhibitory phosphorylation of Cdk1 mediates prolonged prophase I arrest in female germ cells and is essential for female reproductive lifespan," Cell Res. 26:1212-1225 (2016).
Warming et al., "Zfp423 Is Required for Normal Cerebellar Development," Mol Cell Biol. 26(18):6913-6922 (2006).
Liu et al., "A Highly Efficient Recombineering-Based Method for Generating Conditional Knockout Mutations," Genome Res. 13(3):476-484 (2003).
Liu, "PL253 Map,"<www.med.upenn.edu/robertsonlab/assets/user-content/documents/PL253_map.pdf>, retrieved on Oct. 20, 2020 (1 page).
The Japanese Office Action mailed May 9, 2023 for Japanese patent application No. 2020-518110, a foreign counterpart of U.S. Appl. No. 16/621,490, 5 pages.
Office Action Dated Sep. 29, 2023 for Chinese Application No. 201880038734.5, 9 pages.
Office Action for Korean Application No. 10-2020-7000550, Dated May 22, 2024, 5 pages.
Office Action for U.S. Appl. No. 17/413,314, Dated Jul. 19, 2024, 25 pages.

* cited by examiner

WHOLE GENOME GENE EXPRESSION LEVEL DISTRIBUTION AND THE EXPRESSION LEVELS OF THE TRANSGENES IN NT2 LINE AND NT2 DERIVED TERATOMA SUCCEEDED TO ACHIEVE ALLOGRAFT TOLERANCE

Blood vessels (arrows)

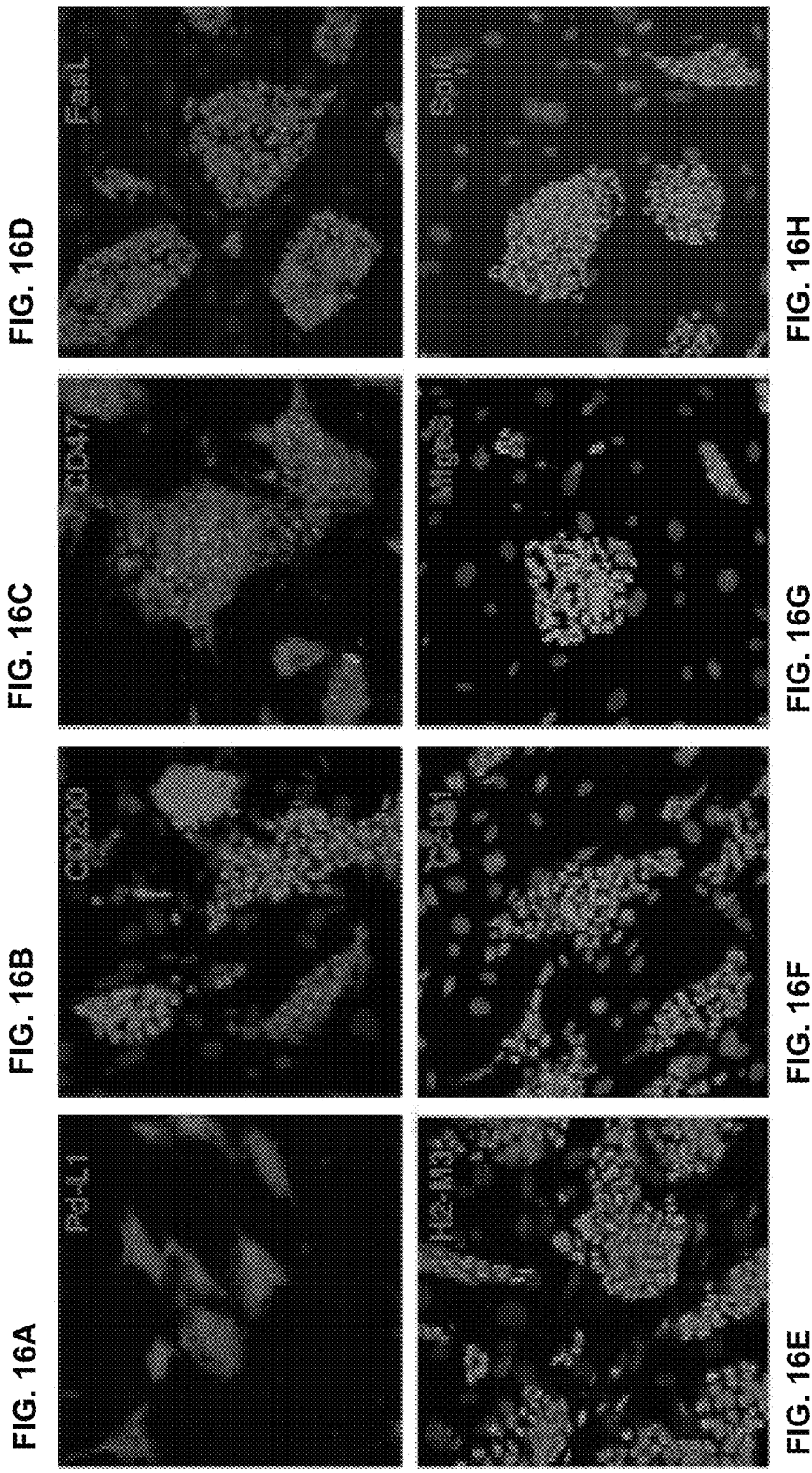

Brightfield

Alk. phos.

Oct4

SSEA1

ALLOGRAFT TOLERANCE WITHOUT THE NEED FOR SYSTEMIC IMMUNE SUPPRESSION

CROSS-REFERENCE TO RELATED APPLICATIONS

This application is a continuation of U.S. patent application Ser. No. 16/621,490, filed Dec. 11, 2019, which is a U.S. national phase application based on International Patent Application No. PCT/CA2018/050706 filed Jun. 12, 2018, which claims priority to U.S. Provisional Patent Application No. 62/666,626, filed May 3, 2018, and U.S. Provisional Patent Application No. 62/518,151, filed Jun. 12, 2017, the contents of each of which are incorporated by reference herein in their entirety as if fully set forth herein.

FIELD OF THE DISCLOSURE

The disclosure relates generally to the field of transplantation. The disclosure further relates to methods for generating local immunosuppression in the environment of transplanted cells.

BACKGROUND OF THE DISCLOSURE

The advent of human embryonic stem (ES) cells and induced pluripotent stem (iPS) cells has had a paradigm-shifting effect on regenerative and translational medicine. These cells have can self-renew indefinitely in a pluripotent state while retaining the ability to differentiate into any cell type in the human body. Such properties have allowed researchers to better understand human development and the etiology of developmental disorders. They have also given modern medicine a powerful new tool against diseases that have been intractable or impossible to treat with conventional medicine, including spinal cord injury, diabetes, blindness, multiple sclerosis, and cancer, to name a few. The efficacy and range of applicable diseases for cell therapies will only increase with our growing understanding of how to control stem cell differentiation and the biology of the differentiated cell products.

With these applications come important and critical challenges. Along with cell safety, one of the most important concerns is immune rejection of cells from a different genetic background. Immune rejection remains a critical barrier because the immune system has evolved a complex set of mechanisms to recognize and eliminate "non-self" cells that express specific protein fragments-especially those from the major histocompatibility complex (MHC in mouse, HLA in humans)—that differ between donor and recipient (Yang et al., *Nat Rev Genet.* 18:309-26 (2017)). This response is almost certainty a by-product of the evolutionary pressure to protect against opportunistic infections and malignancies, which are often defined by the presence of "foreign" proteins and epitopes. Depending on the context, rejection of transplanted cells or tissues can occur over the timescale of minutes/hours (hyperacute), days/months (acute), and months/years (chronic) (LaRosa et al., *J Immunol.* 178:7503-9 (2007)). This rejection results from the complex and coordinated effects of cell types from both innate (Murphy et al., *Immunol Rev.* 241:39-48 (2011)) and adaptive immunity (Issa et al., *Expert Rev Clin Immunol.* 6:155-69 (2010)).

One of the most important pathways to rejection is the priming of the adaptive immune system and activation of CD8+ cytotoxic T-cells. This occurs after antigen presenting cells process donor-specific peptides and then activate recipient T-cells that are specific for the same peptides in secondary lymph organs (Lechler et al., *J Exp Med.* 155:31-41 (1982); Guermonprez et al., *Annu Rev Immunol.* 20:621-67 (2002); Stockwin et al., *Immunol Cell Biol.* 78:91-102 (2000)). These T-cells then migrate to and kill transplanted cells or tissues with the release of cytolytic factors like perforin and granzyme. NK-cells can also induce apoptosis in donor cells based on foreign or no MHC expression (Kitchens et al., *Transplantation.* 81:811-7 (2006); Benichou et al., *Curr Opin Organ Transplant.* 16:47-53 (2011)), and other cell types like macrophages can support rejection with the release of pro-inflammatory cytokines at the engraftment site (Mannon, *Curr Opin Organ Transplant.* 17:20-5 (2012)). Many other cell types and subtypes also have a role in allograft rejection. Since these are the same immune pathways used to eliminate common viral and bacterial pathogens, they are—along with rejection of an allograft-highly conserved across vertebrate species.

A current solution to prevent rejection of an allograft involves the following two options: find a donor with a matched histocompatibility haplotype (mostly likely from genetically-related family), and much more commonly, use broadly-directed immunosuppressant drugs (Wiseman, *Clin J Am Soc Nephrol.* 11:332-43 (2016); Malaise et al., *Transplant Proc.* 37:2840-2 (2005)). Common drugs include those from the families of calcineurin inhibitors (Flechner et al., *Clin Transplant.* 22:1-15 (2008); Casey et al., *Curr Opin Nephrol Hypertens.* 20:610-5 (2011)), anti-proliferative agents (Hardinger et al., *World J Transplant.* 3:68-77 (2013)), mTOR inhibitors (Macdonald, *Expert Rev Clin Immunol.* 3:423-36 (2007); Neuhaus et al., *Liver Transpl.* 7:473-84 (2001)), and steroids (Steiner et al., *Semin Immunopathol.* 33:157-67 (2011))—all of which suppress T-cell proliferation or function (particularly the former three). These drugs need to be taken every day for life, and even a single missed dose can increase the risk of rejection. Yet they do not always work, and when they do, rates of chronic rejection still continually climb over time (Demetris et al., *Ann Transplant.* 2:27-44 (1997); Libby et al., *Immunity.* 14:387-97 (2001)). Most importantly, they are systemically-acting and ultimately leave patients immunocompromised with increased rates of cancer and life-threatening infections (Gallagher et al., *J Am Soc Nephrol.* 21:852-8 (2010)). Pertaining to ES cells, these drugs have shown only marginal improvements in permitting survival across an MHC barrier (Swijnenburg et al., *Proc Natl Acad Sci USA.* 105:12991-6 (2008); Toriumi et al., *Neurol Res.* 31:220-7 (2009)). While newer and more targeted immunosuppressant reagents are becoming available and tested in skin and cardiac (Larsen et al., *Nature.* 381:434-8 (1996)), as well as ES cell allograft settings (Pearl et al., *Cell Stem Cell.* 8:309-17 (2011)), they are still systemically-acting and therefore likely to leave hosts immune compromised.

One proposed benefit to the discovery of iPS cells was that they could be created from, and for, each patient. These cells should, in theory, be protected from immune rejection by the corresponding patient (Pearl et al., *Sci Transl Med.* 4:164ps25 (2012)). However, the induction of an iPS cell state involves epigenetic alterations and in-vitro-culture pressures that can create abnormalities and malignancies, so each cell line would need to be vigorously tested and/or genetically modified to achieve safety as well as function (Hussein et al., *Nature.* 471:58-62 (2011); Laurent et al., *Cell Stem Cell.* 8:106-18 (2011); Lister et al., *Nature.* 471:68-73 (2011)). Ultimately, the cost and time needed to create and test an iPS cell line for each individual patient makes this approach practically and economically unrealistic. Even if the costs were dramatically reduced, it would not help those patients who need immediate treatment for conditions like burns, heart attacks, strokes, and spinal cord injury (among many others). Furthermore, given recent findings, it remains controversial whether iPS cell-derived cell types are truly protected from immune rejection even when transplanted into the same host from where they were derived (Zhao et al., *Nature*. 474:212-5 (2011)).

One proposed solution in this regard has been to use naturally suppressive or regulatory immune cells, like Tregs or others, that are expanded and/or transferred before, during, or after transplant of therapeutic cells or tissues (Cobbold et al., *Cold Spring Harb Perspect Med.* 3 (6) (2013); Wood et al., *Nature reviews Immunology*. 12:417-30 (2012)). These strategies have been suggested based on the recognition of suppressive immune pathways, in particular the discovery of the master regulator FoxP3 that programs a subset of CD4+ cells regulatory T-cells (Hori et al., 299: 1057-61 (2003); Fontenot et al., *Nat Immunol*. 4:330-6 (2003)) and proof of their critical importance in promoting tolerance to allografts (Kendal et al., *J Exp Med*. 208:2043-53 (2011)). This thinking is in contrast to some of the first tolerance-inducing strategies which focused almost exclusively on depletion of effector T-cells with monoclonal antibodies, coupled with bone marrow transplant and the creation of donor chimerism (Cobbold et al., *Nature*. 323: 164-6 (1986); Qin et al., *J Exp Med*. 169:779-94 (1989)). The importance of suppressive T-cell phenotypes was later appreciated with strategies that did not kill the cells, but blocked critical T-cell receptors in a way that left them unresponsive to allografts (Cobbold et al., *J Immunol*. 172: 6003-10 (2004)), yet simultaneously able to suppress naïve T-cells of other specificities (Cobbold et al., *Immunol Rev*. 129:165-201 (1992); Qin et al., *Eur J Immunol*. 20:2737-45 (1990)). These cells, now recognized as Tregs, may promote tolerance by a number of mechanisms, including (but not limited to) the expression of suppressive factors like TGF beta (Nakamura et al., *The Journal of experimental medicine*. 194:629-44 (2001); Nakamura et al., *J Immunol*. 172:834-42 (2004)), CTLA4 (Tang et al., *J Immunol*. 181: 1806-13 (2008); Walker et al., *Trends Immunol*. 36:63-70 (2015)), IL10 (O'Garra et al., *J Clin Invest*. 114:1372-8 (2004); Chaudhry et al., *Immunity*. 34:566-78 (2011)), and IL35 (Collison et al., *Nature*. 450:566-9 (2007)), as well as the preferential consumption of IL-2 (Shevach et al., *Immunity*. 30:636-45 (2009); Setoguchi et al., *J Exp Med*. 201: 723-35 (2005)), manipulation or killing of antigen presenting cells (Mahnke et al., *Cell Immunol*. 250:1-13 (2007); Shevach et al., *Immunol Rev*. 212:60-73 (2006)), and depletion of local ATP (Regateiro et al., *Eur J Immunol*. 41:2955-65 (2011); Regateiro et al., *Clin Exp Immunol*. 171:1-7 (2013)) or essential amino acids (Cobbold et al., *Proc Natl Acad Sci USA*. 106:12055-60 (2009)).

Two approaches for potential therapeutic uses of Tregs involve either in-vitro expansion using donor antigens coupled with transplantation, or selective in-vivo expansion that leverages differences between regulatory and effector T-cells. While these strategies are interesting, to date no long term of acceptance of an allograft has been demonstrated solely with the use of in-vitro or in-vivo expanded Tregs. There remain many complications and unknown facets to Treg biology, including the optimal methodology for in-vitro or in-vivo expansion, as well as the therapeutically-relevant dosage and timing. It has also been shown that antigen-specific Treg suppression can be "defeated" depending on the inflammatory context (Korn et al., *Nat Med*. 13:423-31 (2007)) and that Tregs can be killed by NK-cells (Roy et al., *J Immunol*. 180:1729-36 (2008)).

In addition to Tregs, other suppressive cell types have also been explored to induce allograft tolerance, such as antigen presenting cells like dendritic cells (DCs) (Walker et al., *Trends Immunol*. 36:63-70 (2015)). DCs are the link between innate and adaptive immunity, and they can induce both effector and suppressive immune responses depending on contexts like their maturation state and the local inflammatory cues. During allograft rejection, DCs present allograft antigens inside the binding grooves of MHC (mouse) or HLA (human) molecules on their surface, along with costimulatory molecules like CD80, CD86, and CD40 (among others), which allograft-specific T-cell clones recognize to become activated (Walker et al., *Trends Immunol*. 36:63-70 (2015)). Tolerogenic DCs can be induced from the immature state by exposure to suppressive cues, which keep expression levels of MHC and costimulatory molecules low and in turn promote naïve T-cells into anergic or even Tregulatory subtypes upon DC-Tcell interactions.

Therapeutically, one application of this biology is to expand DCs in vitro exposed simultaneously to specific allograft antigens of interest and immunosuppressive factors-many of which have been tested including TGF-beta, IL10, CAMP, prostaglandin E2, histamine, neuropeptides, vitamin D2, B2 agonists, HLA-G, glucosamine, as well drugs like corticosteroids, cyclosporine, tacrolimus, rapamycin, aspirin, mecophenolate mofetil, sanglifehrin, and deoxyspergualin (Hackstein et al., *Nat Rev Immunol*. 4:24-34 (2004)). Alternatively, DCs have been genetically engineered to directly express immunomodulatory factors like TGF-beta, IL-10, VEGF, FasL, CTLA4-Ig, IDO, NFKb decoy receptors, soluble TNFR, CCR7, as well as siRNA-induced silencing of IL-12 (Morelli et al., *Immunol Rev*. 196:125-46 (2003)). These cultured or engineered DCs are then transferred into recipients concomitantly with an allograft to test whether they can prolong the survival of an allograft, with the assumption that they suppress allograft-specific T-cells, or increase the number of allograft-focused Tregulatory cells.

In one prototypical approach of this kind, bone-marrow derived DCs were transduced with SOCS1 (preventing upregulation of costimulatory molecules and MHCII), which prolonged mouse cardiac allografts (Fu et al., *Cell Mol Immunol*. 6:87-95 (2009)). In another demonstration, FasL-expressing DCs were also able to prolong mouse cardiac allografts (Min et al., *J Immunol*. 164:161-7 (2000)). In general there have been many singular and combinatorial approaches using tolerogenic DCs along these lines (Bjorck et al., *J Heart Lung Transplant*. 24:1118-20 (2005): Sun et al., *PLOS One*. 7: e52096 (2012); Li et al., *J Immunol*. 178:5480-7 (2007); Xu et al., *Transplant Proc*. 38:1561-3 (2006); Lan et al., *J Immunol*. 177:5868-77 (2006); Lutz et al., *Eur J Immunol*. 30:1813-22 (2000); Fischer et al., *Transpl Immunol*. 25:20-6 (2011)), and the outcomes are highly variable depending on the type of modification to the DCs, culture conditions, timing, and type of allograft being tested (Zhou et al., *J Immunol Res*. 2016:5730674 (2016); Xia et al., *J Evid Based Med*. 7:135-46 (2014)). Almost all of these studies have been done in mouse, although recent human testing has begun including testing for safety in healthy volunteers (Dhodapkar et al., *J Exp Med*. 193:233-8 (2001); Dhodapkar et al., *Blood*. 100:174-7 (2002)) as well as a phase I clinical trial in 10 patients with diabetes (Giannoukakis et al., *Diabetes Care*. 34:2026-32 (2011)).

There remain many unknowns to both adoptive Treg and tolerogenic DC therapies, and one of the most important is the duration of their efficacy. While in-vivo studies show that prolonged allograft survival is possible using these two approaches (with or without additional immunosuppressive drugs), it is not long-term, and in almost every case the allograft eventually dies. This is fitting with the fact that both Tregs and DCs have a finite time-span. Also, it is possible for tolerogenic phenotypes, especially among DCs, to "convert" and instead promote inflammatory pathways (Delamarre et al., *Semin Immunol.* 23:2-11 (2011); Schreibelt et al., *Cancer Immunol Immunother.* 59:1573-82 (2010); Satpathy et al., *Nat Immunol.* 14:937-48 (2013)). This is likely due to the highly adaptive nature of DCs, and their ability to sense and respond to a large breadth of inflammatory cues. It has also been shown that these cells can die very quickly after in-vivo adoptive transfer. There are also many subsets of suppressive Tregs and tolerogenic DCs that have been described, and it is still unclear which is the ideal subtype, or if it will entirely depend on the context of the allograft transplant.

Additionally, there is a huge practical and economical barrier to these kinds of approaches in that they require clinicians to manipulate and work with a complicated immune cell type in addition to the therapeutic one. Given their finite lifespan, it is still unclear if these cells would need to be continuously and/or repeatedly delivered to confer long-term tolerance to an allograft. This would compound the already expensive and timely methodology for culturing, expanding, or transducing the cells with critical immunomodulatory factors, and ultimately impede the uses for treatments that are extremely time-sensitive.

Another approach for inducing tolerance is the use of Hematopoietic Cell transplantation (HCT), in which recipients of an HLA-mismatched organ receive an HCT using hematopoietic cells from the same donor (Gozzo et al., *Surg Forum.* 21:281-4 (1970); Ildstad et al., *Nature.* 307:168-70 (1984); Sayegh et al., *Ann Intern Med.* 114:954-5 (1991); Huang et al., *J Clin Invest.* 105:173-81 (2000); Kawai et al., *N Engl J Med.* 358:353-61 (2008); Sachs et al., *Semin Immunol.* 23:165-73 (2011)). This results in a chimerism that can allow newly developing T and B-cells in the recipient to be tolerant of both the recipient and the donor antigens (Tomita et al., *J Immunol.* 153:1087-98 (1994); Tomita et al., *Transplantation.* 61:469-77 (1996); Tomita et al., *Transplantation.* 61:477-85 (1996); Khan et al., *Transplantation.* 62:380-7 (1996); Manilay et al., *Transplantation.* 66:96-102 (1998)). This is due to the role that hematopoietic cells play in positive and negative selection in the thymus, where they eliminate cells with an affinity for hematopoietic cell-containing antigens that might also be present in the allograft, ultimately leading to their rejection. (Griesemer et al., *Transplantation.* 90:465-74 (2010)). However, the inherent and dangerous risk of this approach is the potential for Graft vs. Host Disease (GVHD), in which transplanted hematopoietic cells recognize and systemically attack the recipient tissues as foreign (Sun et al., *PLOS One.* 7: e52096 (2012)). Since its inception, several variants of HCT to dampen rejection have been developed, including the use of nonmyeloablative strategies. These strategies use altered chemotherapy regimens, often involving lower dosages, so that the recipient receiving the HCT does not receive total ablation of their hematopoietic compartment. The most recent of these strategies, for instance, used a tolerance-promoting facilitating cell (FC)-based HCT to promote tolerance in HLA-mismatched kidney recipients while largely avoiding GHVD (Leventhal et al., *Sci Transl Med.* 4: 124ra28 (2012)).

Besides the risk of GHVD and risk of a secondary HCT procedure, the general limitation to these chimerism-inducing approaches is the need to have the HLA-matched donor available for the collection of marrow. While this is easily accomplished in rodent studies, it is quite demanding in humans. Donor organs should ideally be taken from the donor as soon as possible, which leaves an incredibly short window from which to collect marrow, if at all possible. It is also an expensive and logistically demanding procedure that requires a very patient and operation-specific approach. And, as with regulatory cell approaches, it is not clear how it would be practically applied to those situations where the patient could benefit from or needs therapy immediately for treatment of acute injuries or disease.

Another approach that has been tested for reducing allorejection in vivo is the removal of histocompatibility molecules (Torikai et al. *Blood.* 122:1341-9 (2013)), which are the major antigenic source of "non-self" recognition in allorejection. This fits with the empirical data that HLA-matched donors and recipients have greatly improved rates of organ survival after transplantation (Opelz et al., *Rev Immunogenet.* 1:334-42 (1999)). While there have been some positive results with this approach, removal of MHC class I renders cells extremely susceptible to NK cells (Pegram et al., *Immunol Cell Biol.* 89:216-24 (2011); Raulet et al., *Nat Rev Immunol.* 6:520-31 (2006); Huntington, *Immunol Cell Biol.* 92:208-9 (2014)). It also leaves MHC-independent killing pathways among CD8+ T-cells intact (Haspot et al., *Am J Transplant.* 14:49-58 (2014)) and does not address antigenic differences (minor antigens) outside the MHC/HLA gene family (Roopenian et al., *Immunol Rev.* 190:86-94 (2002)).

An employment of this approach involved the deletion of all classical HLA class I molecules from pluripotent stem cells, coupled with the introduction of the gene encoding HLA-E, a minimally polymorphic HLA that inhibits NK-cells (Gornalusse et al., *Nat Biotechnol.* (2017)). While this approach showed short-term resistance to NK and CD8 T-cell attack in partially immune compromised humanized mice, it was not demonstrated that these cells could survive long term in a fully immune-competent host. In another approach ES cells were engineered to express PD-L1 and CTLA4-Ig, which improved survival in allogenic hosts (Rong et al., *Cell Stem Cell.* 14:121-30 (2014)), but with the severe limitation that CTLA4-Ig can lead to systemic immune suppression. It has not yet been demonstrated that a set of modifications to ES or iPS cells allows them to escape allorejection without the potential for systemic immunosuppression and without the need for immunosuppressive drugs.

It is an object of the present disclosure to mitigate and/or obviate one or more of the above deficiencies.

SUMMARY OF THE DISCLOSURE

In an aspect, a cell genetically modified to comprise at least one mechanism for providing a local immunosuppression at a transplant site when transplanted in an allogeneic host is provided. The genetically modified cell comprises: a set of transgenes, each transgene encoding a gene product that is cytoplasmic, membrane bound, or local acting, and has one or more of the following functions: a) to mitigate antigen presenting cell activation and function; b) to mitigate graft attacking leukocyte activity or cytolytic function; c) to mitigate macrophage cytolytic function and phagocytosis of allograft cells; d) to induce apoptosis in graft attacking leukocytes; e) to mitigate local inflammatory proteins; and f) to protect against leukocyte-mediated apoptosis.

In an embodiment of the cell, the set of transgenes comprises one or more (e.g., one, two, three, four, five, six, seven, or all eight) of the following genes: PD-L1, HLA-G (or the mouse version of HLA-G, H2-M3), Cd47, Cd200, FASLG (or the mouse version of FASLG, FasL), Ccl21 (or the mouse version of Ccl21, Ccl21b), Mfge8, and Serpin B9 (or the mouse version of Serpin B9, Spi6).

In an embodiment of the cell, the set of transgenes comprises two or more of the following genes: PD-L1, HLA-G (H2-M3), Cd47, Cd200, FASLG (FasL), Ccl21 (Ccl21b), Mfge8, and Serpin B9 (Spi6).

In an embodiment of the cell, the set of transgenes genes comprises PD-L1, HLA-G (H2-M3), Cd47, Cd200, FASLG (FasL), Ccl21 (Ccl21b), Mfge8, and Serpin B9 (Spi6) or a gene encoding a biologic that acts as an agonist of PD-L1, HLA-G (H2-M3), Cd47, Cd200, FASLG (FasL), Ccl21 (Ccl21b), Mfge8, and Serpin B9 (Spi6).

In an embodiment of the cell, the cell further comprises one or more (e.g., one, two, three, four, five, six, seven, eight, nine, ten, or all eleven) of the following transgenes: TGF-β, Cd73, Cd39, Lag3, Il1r2, Ackr2, Tnfrsf22, Tnfrs23, Tnfrsf10, Dad1, and IFNγR1 d39 or a gene encoding a biologic that acts as an agonist of TGF-β, Cd73, Cd39, Lag3, Il1r2, Ackr2, Tnfrsf22, Tnfrs23, Tnfrsf10, Dad1, or IFNγR1 d39.

In an embodiment of the cell, the TGF-β or the biologic is local acting in the graft environment. In an embodiment of the cell, the TGF-β or the biologic is local acting in the graft environment with minimal systemic effect.

In various embodiments of the cell, the cell is a stem cell, a cell amenable for genome editing, and/or a source of a therapeutic cell type (e.g., a cell that can be differentiated into a therapeutic cell type, or a cell of a desired target tissue). In various embodiments, the cell is an embryonic stem cell, a pluripotent stem cell, an induced pluripotent stem cell, a hematopoietic stem cell, a mesenchymal stem cell, an endothelial stem cell, an epithelial stem cell, an adipose stem or progenitor cell, a germline stem cell, a lung stem or progenitor cells, a mammary stem cell, an olfactory adult stem cell, a hair follicle stem cell, an intestinal stem or progenitor cell, a multipotent stem cell, an amniotic stem cell, a cord blood stem cell, a neural stem or progenitor cell, an adult stem cell, a somatic stem cell, a tissue-specific stem cell, a totipotent stem cell, a fibroblast, a monocytic precursor, a B cell, an exocrine cell, a pancreatic progenitor, an endocrine progenitor, a hepatoblast, a myoblast, a preadipocyte, a hepatocyte, a chondrocyte, a smooth muscle cell, a K562 human erythroid leukemia cell line, a bone cell, a synovial cell, a tendon cell, a ligament cell, a meniscus cell, an adipose cell, a dendritic cell, a natural killer cell, a skeletal muscle cell, a cardiac muscle cell, an erythroid-megakaryocytic cell, an eosinophil, a macrophage, a T cell, an islet beta-cell, a neuron, a cardiomyocyte, a blood cell, an exocrine progenitor, a ductal cell, an acinar cell, an alpha cell, a beta cell, a delta cell, a PP cell, a cholangiocyte, a white or brown adipocyte, a hormone-secreting cell, an epidermal keratinocyte, an epithelial cell, a kidney cell, a germ cell, a skeletal joint synovium cell, a periosteum cell, a perichondrium cell, a cartilage cell, an endothelial cell, a pericardium cell, a meningeal cell, a keratinocyte precursor cell, a keratinocyte stem cell, a pericyte, a glial cell, an ependymal cell, a cell isolated from an amniotic or placental membrane, a serosal cell, a somatic cell, or a cell derived from skin, heart, brain or spinal cord, liver, lung, kidney, pancreas, bladder, bone marrow, spleen, intestine, or stomach.

In an embodiment of the cell, the cell is further genetically modified to comprise at least one (e.g., one, two, three, or more) mechanism for controlling cell proliferation (e.g., to reduce the tumorigenic potential of the modified cell or to reduce proliferation of a modified cell that has become tumorigenic). The genetically modified cell comprises: a genetic modification of one or more (e.g., one, two, three, or more) cell division locus/loci (CDL), the CDL being one or more loci whose transcription product(s) is expressed by dividing cells (e.g., all dividing cells containing one or more of the immunosuppressive transgenes), the genetic modification being one or more of: a) an ablation link (ALINK) system, the ALINK system comprising a DNA sequence encoding a negative selectable marker that is transcriptionally linked to a DNA sequence encoding the CDL; and b) an exogenous activator of regulation of a CDL (EARC) system, the EARC system comprising an inducible activator-based gene expression system that is operably linked to the CDL.

In an embodiment of the cell, the genetic modification of the CDL comprises performing targeted replacement of the CDL with one or more of: a) a DNA vector comprising the ALINK system; b) a DNA vector comprising the EARC system; and c) a DNA vector comprising the ALINK system and the EARC system; wherein the ALINK and/or EARC systems are each operably linked to the CDL.

In various embodiments of the cell, the ALINK genetic modification of the CDL is homozygous, heterozygous, hemizygous or compound heterozygous and/or the EARC genetic modification ensures that functional CDL modification can only be generated through EARC-modified alleles.

In various embodiments of the cell, the CDL is one or more (e.g., one, two, three, or more) of the loci recited in Table 5. In various embodiments, the CDL encodes a gene product that functions in one or more of: cell cycle, DNA replication, RNA transcription, protein translation, and metabolism. In various embodiments, the CDL is one or more of Cdk1/CDK1, Top2A/TOP2A, Cenpa/CENPA, Birc5/BIRC5, and Eef2/EEF2, preferably the CDL is Cdk1 or CDK1. In some embodiments, the CDL is Top2A. In some embodiments, the CDL is Eef2. In various embodiments, the CDL is two or more of Cdk1/CDK1, Top2A/TOP2A, Cenpa/CENPA, Birc5/BIRC5, and Eef2/EEF2, preferably the CDL is Cdk1 and Top2A or Cdk1 and Eef2.

In various embodiments of the cell, the ALINK system comprises a herpes simplex virus-thymidine kinase/ganciclovir system, a cytosine deaminase/5-fluorocytosine system, a carboxyl esterase/irinotecan system or an iCasp9/AP1903 system, preferably the ALINK system is a herpes simplex virus-thymidine kinase/ganciclovir system.

In various embodiments of the cell, the EARC system is a doxycycline inducible "dox-bridge" system, a cumate switch inducible system, an ecdysone inducible system, a radio wave inducible system, or a ligand-reversible dimerization system, preferably the EARC system is a dox-bridge system.

In an aspect, a method for providing a local immunosuppression at a transplant site in an allogeneic host is provided. The method comprises providing a cell; and expressing in the cell a set of transgenes, each transgene encoding a gene product that is cytoplasmic, membrane bound, or local acting, and has one or more of the following functions: a) to mitigate antigen presenting cell activation and function; b) to mitigate graft attacking leukocyte or cytolytic function; c) to mitigate macrophage cytolytic function and phagocytosis of allograft cells; d) to induce apoptosis in graft attacking leukocytes; e) to mitigate local inflammatory proteins; and f) to protect against leukocyte-mediated apoptosis.

In an embodiment of the method, the set of transgenes comprises one or more (e.g., one, two, three, four, five, six, seven, or all eight) of the following genes: PD-L1, HLA-G (H2-M3), Cd47, Cd200, FASLG (FasL), Ccl21 (Ccl21b), Mfge8, and Serpin B9 (Spi6) or a gene encoding a biologic that acts as an agonist of PD-L1, HLA-G (H2-M3), Cd47, Cd200, FASLG (FasL), Ccl21 (Ccl21b), Mfge8, or Serpin B9 (Spi6).

In an embodiment of the method, the set of transgenes comprises two or more of the following genes: PD-L1, HLA-G (H2-M3), Cd47, Cd200, FASLG (FasL), Ccl21 (Ccl21b), Mfge8, and Serpin B9 (Spi6).

In an embodiment of the method, the set of transgenes genes comprises PD-L1, HLA-G (H2-M3), Cd47, Cd200, FASLG (FasL), Ccl21 (Ccl21b), Mfge8, and Serpin B9 (Spi6) or a gene encoding a biologic that acts as an agonist of PD-L1, HLA-G (H2-M3), Cd47, Cd200, FASLG (FasL), Ccl21 (Ccl21b), Mfge8, and Serpin B9 (Spi6).

In an embodiment of the method, the method further comprises expressing one or more (e.g., one, two, three, four, five, six, seven, eight, nine, ten, or all eleven) of the following transgenes: TGF-β, Cd73, Cd39, Lag3, Il1r2, Ackr2, Tnfrsf22, Tnfrs23, Tnfrsf10, Dad1, and IFNyR1 d39 or a gene encoding a biologic that acts as an agonist of TGF-β, Cd73, Cd39, Lag3, Il1r2, Ackr2, Tnfrsf22, Tnfrs23, Tnfrsf10, Dad1, or IFNyR1 d39. In an embodiment, the TGF-β or the biologic is local acting in the graft environment. In an embodiment of the cell, the TGF-β or the biologic is local acting in the graft environment with minimal systemic effect.

In various embodiments of the method, the cell is a stem cell, a cell amenable to genome editing, and/or a source of a therapeutic cell type (e.g., a cell that can be differentiated into a therapeutic cell type, or a cell of a desired target tissue). In various embodiments, the cell is an embryonic stem cell, a pluripotent stem cell, an induced pluripotent stem cell, a hematopoietic stem cell, a mesenchymal stem cell, an endothelial stem cell, an epithelial stem cell, an adipose stem or progenitor cell, a germline stem cell, a lung stem or progenitor cells, a mammary stem cell, an olfactory adult stem cell, a hair follicle stem cell, an intestinal stem or progenitor cell, a multipotent stem cell, an amniotic stem cell, a cord blood stem cell, a neural stem or progenitor cell, an adult stem cell, a somatic stem cell, a tissue-specific stem cell, a totipotent stem cell, a fibroblast, a monocytic precursor, a B cell, an exocrine cell, a pancreatic progenitor, an endocrine progenitor, a hepatoblast, a myoblast, a preadipocyte, a hepatocyte, a chondrocyte, a smooth muscle cell, a K562 human erythroid leukemia cell line, a bone cell, a synovial cell, a tendon cell, a ligament cell, a meniscus cell, an adipose cell, a dendritic cell, a natural killer cell, a skeletal muscle cell, a cardiac muscle cell, an erythroid-megakaryocytic cell, an eosinophil, a macrophage, a T cell, an islet beta-cell, a neuron, a cardiomyocyte, a blood cell, an exocrine progenitor, a ductal cell, an acinar cell, an alpha cell, a beta cell, a delta cell, a PP cell, a cholangiocyte, a white or brown adipocyte, a hormone-secreting cell, an epidermal keratinocyte, an epithelial cell, a kidney cell, a germ cell, a skeletal joint synovium cell, a periosteum cell, a perichondrium cell, a cartilage cell, an endothelial cell, a pericardium cell, a meningeal cell, a keratinocyte precursor cell, a keratinocyte stem cell, a pericyte, a glial cell, an ependymal cell, a cell isolated from an amniotic or placental membrane, a serosal cell, a somatic cell, or a cell derived from skin, heart, brain or spinal cord, liver, lung, kidney, pancreas, bladder, bone marrow, spleen, intestine, or stomach.

In various embodiments of the method, the cell is provided (e.g., injected) to or near the transplant site. In various embodiments of the method, the cell is provided (e.g., injected or implanted) into the transplant (e.g., injected or implanted into the tissue or organ transplant before, during, or after transplantation). In some embodiments, the cell in which the transgenes are expressed is a cell of the transplant (e.g., a cell of the tissue or organ that is being transplanted is modified to express one or more (e.g., one, two, three, four, five, six, seven, or all eight) of PD-L1, HLA-G (H2-M3), Cd47, Cd200, FASLG (FasL), Ccl21 (Ccl21b), Mfge8, and Serpin B9 (Spi6)).

In an aspect, a method of controlling proliferation of a cell at a transplant site in an allogeneic host is provided (e.g., to reduce the tumorigenic potential of the cell at the transplant site or to reduce proliferation of the cell that has become tumorigenic at the transplant site). The method comprises: a) genetically modifying in the cell one or more (e.g., one, two, three, or more) cell division locus/loci (CDL), the CDL being one or more loci whose transcription product(s) is expressed by dividing cells (e.g., all dividing cells containing one or more of the immunosuppressive transgenes), the genetic modification of the CDL comprising one or more of: i) an ablation link (ALINK) system, the ALINK system comprising a DNA sequence encoding a negative selectable marker that is transcriptionally linked to a DNA sequence encoding the CDL; and i) an inducible exogenous activator of regulation of a CDL (EARC) system, the EARC system comprising an inducible activator-based gene expression system that is operably linked to the CDL; b) genetically modifying the cell to comprise at least one mechanism for providing a local immunosuppression at a transplant site; c) transplanting the cell or a population of the cells at a transplantation site in an allogeneic host; and d) permitting proliferation of the genetically modified cell comprising the ALINK system by maintaining the genetically modified cell comprising the ALINK system in the absence of an inducer of the negative selectable marker or ablating and/or inhibiting proliferation of the genetically modified cell comprising the ALINK system by exposing the cell comprising the ALINK system to the inducer of the negative selectable marker; and/or permitting proliferation of the genetically modified cell comprising the EARC system by exposing the genetically modified cell comprising the EARC system to an inducer of the inducible activator-based gene expression system or preventing or inhibiting proliferation of the genetically modified cell comprising the EARC system by maintaining the cell comprising the EARC system in the absence of the inducer of the inducible activator-based gene expression system.

In an embodiment of the method, the genetic modification of the CDL comprises performing targeted replacement of the CDL with one or more of: a) a DNA vector comprising the ALINK system; b) a DNA vector comprising the EARC system; and c) a DNA vector comprising the ALINK system and the EARC system; wherein the ALINK and/or EARC systems are each operably linked to the CDL.

In various embodiments of the method the ALINK genetic modification of the CDL is homozygous, heterozygous, hemizygous or compound heterozygous and/or the EARC genetic modification ensures that functional CDL modification can only be generated through EARC-modified alleles.

In various embodiments of the method, the CDL is one or more (e.g., one, two, three, or more) of the loci recited in Table 5. In various embodiments, the CDL encodes a gene product whose function is involved with one or more of: cell cycle, DNA replication, RNA transcription, protein translation, and metabolism. In various embodiments, the CDL is one or more of Cdk1/CDK1, Top2A/TOP2A, Cenpa/CENPA, Birc5/BIRC5, and Eef2/EEF2, preferably the CDL is Cdk1 or CDK1. In some embodiments, the CDL is Top2A. In some embodiments, the CDL is Eef2. In various embodiments, the CDL is two or more of Cdk1/CDK1, Top2A/TOP2A, Cenpa/CENPA, Birc5/BIRC5, and Eef2/EEF2, preferably the CDL is Cdk1 and Top2A or Cdk1 and Eef2.

In various embodiments of the method, the ALINK system comprises a herpes simplex virus-thymidine kinase/ganciclovir system, a cytosine deaminase/5-fluorocytosine system, a carboxyl esterase/irinotecan system or an iCasp9/AP1903 system, preferably the ALINK system is a herpes simplex virus-thymidine kinase/ganciclovir system.

In various embodiments of the method, the EARC system is a doxycycline inducible "dox-bridge" system, a cumate switch inducible system, an ecdysone inducible system, a radio wave inducible system, or a ligand-reversible dimerization system, preferably the EARC system is a dox-bridge system.

In an embodiment of the method, the genetically modified cell comprises: a set of transgenes, each transgene encoding a gene product that is cytoplasmic, membrane bound, or local acting and has one or more of the following functions: a) to mitigate antigen presenting cell activation and function; b) to mitigate graft attacking leukocyte activity or cytolytic function; c) to mitigate macrophage cytolytic function and phagocytosis of allograft cells; d) to induce apoptosis in graft attacking leukocytes; e) to mitigate local inflammatory proteins; and f) to protect against leukocyte-mediated apoptosis.

In an embodiment of the method, the set of transgenes comprises one or more (e.g., one, two, three, four, five, six, seven, or all eight) of the following genes: PD-L1, HLA-G (H2-M3), Cd47, Cd200, FASLG (FasL), Ccl21 (Ccl21b), Mfge8, and Serpin B9 (Spi6) or a gene encoding a biologic that acts as an agonist of PD-L1, HLA-G (H2-M3), Cd47, Cd200, FASLG (FasL), Ccl21 (Ccl21b), Mfge8, or Serpin B9 (Spi6).

In an embodiment of the method, the set of transgenes comprises two or more of the following genes: PD-L1, HLA-G (H2-M3), Cd47, Cd200, FASLG (FasL), Ccl21 (Ccl21b), Mfge8, and Serpin B9 (Spi6).

In an embodiment of the method, the set of transgenes genes comprises PD-L1, HLA-G (H2-M3), Cd47, Cd200, FASLG (FasL), Ccl21 (Ccl21b), Mfge8, and Serpin B9 (Spi6) or a gene encoding a biologic that acts a as an agonist of PD-L1, HLA-G (H2-M3), Cd47, Cd200, FASLG (FasL), Ccl21 (Ccl21b), Mfge8, and Serpin B9 (Spi6).

In an embodiment of the method, the cell further comprises one or more (e.g., one, two, three, four, five, six, seven, eight, nine, ten, or all eleven) of the following transgenes: TGF-β, Cd73, Cd39, Lag3, Il1r2, Ackr2, Tnfrsf22, Tnfrs23, Tnfrsf10, Dad1, and IFNyR1 d39 or a gene encoding a biologic that acts as an agonist of TGF-β, Cd73, Cd39, Lag3, Il1r2, Ackr2, Tnfrsf22, Tnfrs23, Tnfrsf10, Dad1, or IFNyR1 d39.

In an embodiment of the method, the TGF-β or the biologic is local acting in the graft environment. In an embodiment, the TGF-β or the biologic is local acting in the graft environment with minimal systemic effect In various embodiments of the method, the cell is a stem cell, a cell amenable to genome editing, and/or a source of therapeutic cell type (e.g., a cell that can be differentiated into a therapeutic cell type, or a cell of a desired target tissue). In various embodiments, the cell is an embryonic stem cell, a pluripotent stem cell, an induced pluripotent stem cell, a hematopoietic stem cell, a mesenchymal stem cell, an endothelial stem cell, an epithelial stem cell, an adipose stem or progenitor cell, a germline stem cell, a lung stem or progenitor cells, a mammary stem cell, an olfactory adult stem cell, a hair follicle stem cell, an intestinal stem or progenitor cell, a multipotent stem cell, an amniotic stem cell, a cord blood stem cell, a neural stem or progenitor cell, an adult stem cell, a somatic stem cell, a tissue-specific stem cell, a totipotent stem cell, a fibroblast, a monocytic precursor, a B cell, an exocrine cell, a pancreatic progenitor, an endocrine progenitor, a hepatoblast, a myoblast, a preadipocyte, a hepatocyte, a chondrocyte, a smooth muscle cell, a K562 human erythroid leukemia cell line, a bone cell, a synovial cell, a tendon cell, a ligament cell, a meniscus cell, an adipose cell, a dendritic cell, a natural killer cell, a skeletal muscle cell, a cardiac muscle cell, an erythroid-megakaryocytic cell, an eosinophil, a macrophage, a T cell, an islet beta-cell, a neuron, a cardiomyocyte, a blood cell, an exocrine progenitor, a ductal cell, an acinar cell, an alpha cell, a beta cell, a delta cell, a PP cell, a cholangiocyte, a white or brown adipocyte, a hormone-secreting cell, an epidermal keratinocyte, an epithelial cell, a kidney cell, a germ cell, a skeletal joint synovium cell, a periosteum cell, a perichondrium cell, a cartilage cell, an endothelial cell, a pericardium cell, a meningeal cell, a keratinocyte precursor cell, a keratinocyte stem cell, a pericyte, a glial cell, an ependymal cell, a cell isolated from an amniotic or placental membrane, a serosal cell, a somatic cell, or a cell derived from skin, heart, brain or spinal cord, liver, lung, kidney, pancreas, bladder, bone marrow, spleen, intestine, or stomach.

In various embodiments of the method, the cell is provided (e.g., injected) to or near the transplant site. In various embodiments of the method, the cell is provided (e.g., injected or implanted) into the transplant (e.g., injected or implanted into the tissue or organ transplant before, during, or after transplantation). In some embodiments, the cell in which the transgenes are expressed is a cell of the transplant (e.g., a cell of the tissue or organ that is being transplanted is modified to express one or more (e.g., one, two, three, four, five, six, seven, or all eight) of PD-L1, HLA-G (H2-M3), Cd47, Cd200, FASLG (FasL), Ccl21 (Ccl21b), Mfge8, and Serpin B9 (Spi6)).

In various embodiments of the method, the allogeneic host is a mammal. In various embodiments of the method, the allogeneic host is a mouse or a human.

In various embodiments of the method, the host has a degenerative disease or condition that can be treated with cell therapy. In various embodiments, the disease or condition is blindness, arthritis (e.g., osteoarthritis or rheumatoid arthritis), ischemia, diabetes (e.g., Type 1 or Type 2 diabetes), multiple sclerosis, spinal cord injury, stroke, cancer, a lung disease, a blood disease, a neurological disease, such as Parkinson's disease, Alzheimer's disease, Huntington's disease, and ALS, an enzyme or hormone deficiency, a metabolic disorder (e.g., a lysosomal storage disorder, Galactosemia, Maple syrup urine disease, Phenylketonuria, a glycogen storage disease, a mitochondrial disorder, Friedrich's ataxia, a peroxisomal disorder, a metal metabolism disorder, or an organic academia), an autoimmune disease (e.g., Psoriasis, Systemic Lupus Erythematosus, Grave's disease, Inflammatory Bowel Disease, Addison's Diseases, Sjogren's Syndrome, Hashimoto's Thyroiditis, Vasculitis, Autoimmune Hepatitis, Alopecia Areata, Autoimmune pancreatitis, Crohn's Disease, Ulcerative colitis, Dermatomyositis), age-related macular degeneration, retinal dystrophy, an infectious disease, hemophilia, a degenerative disease (e.g., Charcot-Marie-Tooth disease, chronic obstructive pulmonary disease, chronic traumatic encephalopathy, Creutzfeldt-Jakob disease, Cystic Fibrosis, Cytochrome C Oxidase deficiency, Ehlers-Danlos syndrome, essential tremor, Fribrodisplasia Ossificans Progressiva, infantile neuroaxonal dystrophy, keratoconus, keratoglobus, muscular dystrophy, neuronal ceroid lipofuscinosis, a prior disease, progressive supranuclear palsy, sandhoff disease, spinal muscular atrophy, retinitis pigmentosa), or an age-related disease (e.g., atherosclerosis, cardiovascular disease (e.g., angina, myocardial infarction), cataracts, osteoporosis, or hypertension).

In some embodiments of any of the foregoing aspects, one or more (e.g., one, two, three, four, five, six, seven, or all eight) of PD-L1, HLA-G (H2-M3), Cd47, Cd200, FASLG (FasL), Ccl21 (Ccl21b), Mfge8, and Serpin B9 (Spi6) is expressed at a level that is equal to or greater than the expression level of the corresponding endogenous gene in an activated leukocyte (e.g., a T cell, e.g., the expression level of the cloaking transgene is equal to the level of expression of the endogenous gene in activated leukocytes, or is 1.5, 2, 3, 4, 5, 6, 7, 8, 9, 10-fold or more higher than the level of expression of the endogenous gene in activated leukocytes). In some embodiments, all eight of PD-L1, HLA-G (H2-M3), Cd47, Cd200, FASLG (FasL), Ccl21 (Ccl21b), Mfge8, and Serpin B9 (Spi6) are expressed at a level that is equal to or greater than the expression level of the corresponding endogenous gene in an activated leukocyte.

In some embodiments of any of the foregoing aspects, one or more (e.g., one, two, three, four, five, six, seven, or all eight) of PD-L1, HLA-G (H2-M3), Cd47, Cd200, FASLG (FasL), Ccl21 (Ccl21b), Mfge8, and Serpin B9 (Spi6) is expressed at a level that is greater than the expression level of the corresponding endogenous gene in a wild-type stem cell (e.g., a wild-type ES cell from the same species, e.g., the expression level of the cloaking transgene is at least 2, 3, 4, 5, 6, 7, 8, 9, 10, 20, 30, 40, 50, 100, 500, 1,000-fold or more higher in cloaked cells compared to expression of the endogenous gene in unmodified wild-type ES cells from the same species). In some embodiments, all 8 of PD-L1, HLA-G (H2-M3), Cd47, Cd200, FASLG (FasL), Ccl21 (Ccl21b), Mfge8, and Serpin B9 (Spi6) are expressed at a level that is greater (e.g., 2, 3, 4, 5, 6, 7, 8, 9, 10, 20, 30, 40, 50, or 100-fold higher or more) than the expression level of the endogenous gene in a wild-type stem cell (e.g., an embryonic stem cell from the same species as the cloaked cell). In some embodiments, one or more (e.g., one, two, three, four, five, six, seven, or all eight) of PD-L1, HLA-G (H2-M3), Cd47, Cd200, FASLG (FasL), Ccl21 (Ccl21b), Mfge8, and Serpin B9 (Spi6) is expressed at a level that is in the top 5% of gene expression for all genes in the ES cell genome. In some embodiments, one or more (e.g., one, two, three, four, five, six, seven, or all eight) of PD-L1, HLA-G (H2-M3), Cd47, Cd200, FASLG (FasL), Ccl21 (Ccl21b), Mfge8, and Serpin B9 (Spi6) is expressed at a level that is in the top 1% of gene expression for all genes in the ES cell genome. In some embodiments, all of PD-L1, HLA-G (H2-M3), Cd47, Cd200, FASLG (FasL), Ccl21 (Ccl21b), Mfge8, and Serpin B9 (Spi6) are expressed at a level that is in the top 5% of gene expression for all genes in the ES cell genome.

In some embodiments of any of the foregoing aspects, the PD-L1 transgene encodes a protein having at least 85% identity (e.g., 85%, 90%, 95%, 96%, 97%, 98%, 99% sequence identity or more) to the amino acid sequence of SEQ ID NO: 11 or SEQ ID NO: 12.

In some embodiments of any of the foregoing aspects, the HLA-G (H2-M3) transgene encodes a protein having at least 85% identity (e.g., 85%, 90%, 95%, 96%, 97%, 98%, 99% sequence identity or more) to the amino acid sequence of SEQ ID NO: 16 or SEQ ID NO: 15.

In some embodiments of any of the foregoing aspects, the Cd47 transgene encodes a protein having at least 85% identity (e.g., 85%, 90%, 95%, 96%, 97%, 98%, 99% sequence identity or more) to the amino acid sequence of SEQ ID NO: 3 or SEQ ID NO: 4.

In some embodiments of any of the foregoing aspects, the CD200 transgene encodes a protein having at least 85% identity (e.g., 85%, 90%, 95%, 96%, 97%, 98%, 99% sequence identity or more) to the amino acid sequence of SEQ ID NO: 5 or SEQ ID NO: 6.

In some embodiments of any of the foregoing aspects, the FASLG (FasL) transgene encodes a protein having at least 85% identity (e.g., 85%, 90%, 95%, 96%, 97%, 98%, 99% sequence identity or more) to the amino acid sequence of SEQ ID NO: 10 or SEQ ID NO: 9.

In some embodiments of any of the foregoing aspects, the Ccl21 (Ccl21b) transgene encodes a protein having at least 85% identity (e.g., 85%, 90%, 95%, 96%, 97%, 98%, 99% sequence identity or more) to the amino acid sequence of SEQ ID NO: 2 or SEQ ID NO: 1.

In some embodiments of any of the foregoing aspects, the Mfge8 transgene encodes a protein having at least 85% identity (e.g., 85%, 90%, 95%, 96%, 97%, 98%, 99% sequence identity or more) to the amino acid sequence of SEQ ID NO: 13 or SEQ ID NO: 14.

In some embodiments of any of the foregoing aspects, the Serpin B9 (Spi6) transgene encodes a protein having at least 85% identity (e.g., 85%, 90%, 95%, 96%, 97%, 98%, 99% sequence identity or more) to the amino acid sequence of SEQ ID NO: 8 or SEQ ID NO: 7.

In some embodiments of any of the foregoing aspects, the IFNyR1 d39 transgene encodes a protein having at least 85% identity (e.g., 85%, 90%, 95%, 96%, 97%, 98%, 99% sequence identity or more) to the amino acid sequence of SEQ ID NO: 17.

In some embodiments of any of the foregoing aspects, the one or more transgenes is operably linked to a constitutive promoter. In some embodiments, the constitutive promoter is selected from the group consisting of the CAG promoter, the cytomegalovirus (CMV) promoter, the EF1α promoter, the PGK promoter, adenovirus late promoter, vaccinia virus 7.5K promoter, SV40 promoter, tk promoter of HSV, mouse mammary tumor virus (MMTV) promoter, LTR promoter of HIV, promoter of moloney virus, Epstein barr virus (EBV) promoter, and the Rous sarcoma virus (RSV) promoter.

In some embodiments of any of the foregoing aspects, the cell further comprises (e.g., the cell is further modified to include) a transgene encoding a therapeutic agent. In some embodiments, the therapeutic agent is a protein or antibody. In some embodiments, the antibody is an inhibitory antibody or agonist antibody. In some embodiments, the therapeutic agent is an agent listed in Table 2. In some embodiments, the therapeutic agent is the wild-type version of a gene that is mutated in the subject (e.g., the wild-type version of the mutated gene that is associated with the disease or condition in the subject, e.g., a genetic mutation that is associated with cancer, an enzyme or hormone deficiency, a metabolic disorder, or a degenerative disease). In some embodiments, the therapeutic agent is expressed using an inducible expression system selected from the group consisting of a tetracycline response element, a light inducible system, a radiogenetic system, a cumate switch inducible system, an ecdysone inducible system, a destabilization domain system, or a ligand-reversible dimerization system. In some embodiments, the therapeutic agent is expressed using a constitutive promoter selected from the group consisting of the CAG promoter, the cytomegalovirus (CMV) promoter, the EF1α promoter, the PGK promoter, adenovirus late promoter, vaccinia virus 7.5K promoter, SV40 promoter, tk promoter of HSV, mouse mammary tumor virus (MMTV) promoter, LTR promoter of HIV, promoter of moloney virus, Epstein barr virus (EBV) promoter, and the Rous sarcoma virus (RSV) promoter.

In another aspect, there is provided a population of genetically modified cells according to any of the cells described above.

In an aspect, a method for providing a local immunosuppression at a transplant site in an allogeneic host is provided. The method comprises transplanting a genetically modified cell as described above or a population of genetically modified cells as described above at a transplantation site in an allogeneic host.

In another aspect, the invention features a composition containing a cell of the invention. In some embodiments, the composition further includes a pharmaceutically acceptable excipient.

In another aspect, featured is a kit including a cell of the invention or a pharmaceutical composition of the invention.

In another aspect, featured is a method of treating a disease or condition in a subject in need thereof by administering to the subject the cell of the invention or a composition of the invention. In some embodiments, the disease or condition is blindness, arthritis (e.g., osteoarthritis or rheumatoid arthritis), ischemia, diabetes (e.g., Type 1 or Type 2 diabetes), multiple sclerosis, spinal cord injury, stroke, cancer, a lung disease, a blood disease, a neurological disease, such as Parkinson's disease, Alzheimer's disease, Huntington's disease, and ALS, an enzyme or hormone deficiency, a metabolic disorder (e.g., a lysosomal storage disorder, Galactosemia, Maple syrup urine disease, Phenylketonuria, a glycogen storage disease, a mitochondrial disorder, Friedrich's ataxia, a peroxisomal disorder, a metal metabolism disorder, or an organic academia), an autoimmune disease (e.g., Psoriasis, Systemic Lupus Erythematosus, Grave's disease, Inflammatory Bowel Disease, Addison's Diseases, Sjogren's Syndrome, Hashimoto's Thyroiditis, Vasculitis, Autoimmune Hepatitis, Alopecia Areata, Autoimmune pancreatitis, Crohn's Disease, Ulcerative colitis, Dermatomyositis), age-related macular degeneration, retinal dystrophy, an infectious disease, hemophilia, a degenerative disease (e.g., Charcot-Marie-Tooth disease, chronic obstructive pulmonary disease, chronic traumatic encephalopathy, Creutzfeldt-Jakob disease, Cystic Fibrosis, Cytochrome C Oxidase deficiency, Ehlers-Danlos syndrome, essential tremor, Fribrodisplasia Ossificans Progressiva, infantile neuroaxonal dystrophy, keratoconus, keratoglobus, muscular dystrophy, neuronal ceroid lipofuscinosis, a prior disease, progressive supranuclear palsy, sandhoff disease, spinal muscular atrophy, retinitis pigmentosa), or an age-related disease (e.g., atherosclerosis, cardiovascular disease (e.g., angina, myocardial infarction), cataracts, osteoporosis, or hypertension), or a disease or condition listed in Table 2 and/or the cell further includes a transgene encoding a corresponding therapeutic agent listed in Table 2 or the wild-type version of a gene that is mutated in the subject (e.g., the wild-type version of the mutated gene that is associated with the disease or condition in the subject, e.g., a genetic mutation associated with cancer, an enzyme or hormone deficiency, a metabolic disorder, or a degenerative disease). In some embodiments, the disease or condition is age-related macular degeneration (e.g., wet AMD) or retinal dystrophy and the therapeutic agent is a VEGF inhibitor (e.g., a soluble form of a VEGF receptors (e.g., soluble VEGFR-1 or NRP-1), platelet factor-4, prolactin, SPARC, a VEGF inhibitory antibody (e.g., bevacizumab or ranibizumab), or a soluble decoy receptor described in Holash et al., Proc Natl Acad Sci U.S.A. 99:11383-11398, 2002, e.g., VEGF-Trap$_{parental}$, VEGF-Trap$_{\Delta B1}$, VEGF-Trap$_{\Delta B2}$, VEGF-Trap$_{R1R2}$, e.g., aflibercept). In some embodiments, the disease or condition is osteoarthritis or rheumatoid arthritis and the therapeutic agent is an anti-inflammatory biologic (e.g. a TNFα inhibitor (e.g., adalimumab, etanercept, infliximab, golimumab, or certolizumab), an interleukin-6 (IL6) receptor inhibitor (e.g., tocilizumab), an IL1 receptor inhibitor (e.g., anakinra), or another agent used to treat rheumatoid arthritis (e.g., abatacept, rituximab)). In some embodiments, the disease or condition is diabetes (e.g., Type 1 diabetes or Type 2 diabetes) and the therapeutic agent is insulin. In some embodiments, the disease or condition is hemophilia and the therapeutic agent is Factor VIII. In some embodiments, the disease or condition is a metabolic deficiency and the therapeutic agent is a transgene having the nucleic acid sequence of the wild-type version of the gene that is mutated in the subject or a transgene encoding an enzyme that is deficient in the subject.

In some embodiments of any of the foregoing aspects, the cells are differentiated into a lineage restricted cell type prior to administration to the subject. In some embodiments, the disease or condition is myocardial infarction and the cells are differentiated into cardiac muscle cells. In some embodiments, the disease or condition is blindness and the cells are differentiated into photoreceptor cells. In some embodiments, the disease or condition is spinal cord injury, Parkinson's disease, Huntington's disease, or Alzheimer's disease and the cells are dissociated into neurons. In some embodiments, the disease or condition is multiple sclerosis and the cells are differentiated into glial cells.

In some embodiments of any of the foregoing aspects, the cells are administered (e.g., injected or implanted) locally to the tissue or body site in need of cells or the therapeutic agent.

In some embodiments of any of the foregoing aspects, the cells are administered intravenously, subcutaneously, intramuscularly, percutaneously, intradermally, parenterally, intraarterially, intravascularly, or by perfusion.

In some embodiments of any of the foregoing aspects, the cells are administered by subcutaneous injection to produce a cloaked subcutaneous tissue.

In some embodiments of any of the foregoing aspects, the cells are administered as a tissue. In some embodiments, the tissue is administered with a gel, biocompatible matrix, or cellular scaffold.

In some embodiments of any of the foregoing aspects, the cells are administered in an amount of 25,000 to 5,000,000,000 cells (e.g., $2.5 \times 10^4$, $5 \times 10^4$, $7.5 \times 10^4$, $1 \times 10^5$, $2 \times 10^5$, $3 \times 10^5$, $4 \times 10^5$, $6 \times 10^5$, $6 \times 10^5$, $7 \times 10^5$, $8 \times 10^5$, $9 \times 10^5$, $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, or $5 \times 10^9$ cells).

In some embodiments of any of the foregoing aspects, the cells are administered in an amount of 800,000,000 to 100,000,000,000 cells (e.g., $8 \times 10^8$, $9 \times 10^8$, $1 \times 10^9$, $2 \times 10^9$, or $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, or $1\times10^{11}$, cells).

In some embodiments of any of the foregoing methods, the method further includes administering an additional therapeutic agent. In some embodiments, the additional therapeutic agent is administered prior to administration of the cells. In some embodiments, the additional therapeutic agent is administered after administration of the cells. In some embodiments, the additional therapeutic agent is administered concurrently with administration of the cells. In some embodiments, the additional therapeutic agent is an immunosuppressive agent, a disease-modifying anti-rheumatic drug (DMARD), a biologic response modifier (a type of DMARD), a corticosteroid, or a nonsteroidal anti-inflammatory medication (NSAID), prednisone, prednisolone, methylprednisolone, methotrexate, hydroxychloroquine, sulfasalazine, leflunomide, cyclophosphamide, azathioprine, tofacitinib, adalimumab, abatacept, anakinra, kineret, certolizumab, etanercept, golimumab, infliximab, rituximab or tocilizumab, 6-mercaptopurine, 6-thioguanine, abatacept, adalimumab, alemtuzumab, an aminosalicylate, an antibiotic, an anti-histamine, Anti-TNFα, azathioprine, belimumab, beta interferon, a calcineurin inhibitor, certolizumab, a corticosteroid, cromolyn, cyclosporin A, cyclosporine, dimethyl fumarate, etanercept, fingolimod, fumaric acid esters, glatiramer acetate, golimumab, hydroxyurea, IFNγ, IL-11, leflunomide, leukotriene receptor antagonist, long-acting beta2 agonist, mitoxantrone, mycophenolate mofetil, natalizumab, ocrelizumab, pimecrolimus, a probiotic, a retinoid, salicylic acid, short-acting beta2 agonist, sulfasalazine, tacrolimus, teriflunomide, theophylline, tocilizumab, ustekinumab, or vedolizumab, bevacuzimab, ranibizumab, or aflibercept), photodynamic therapy, photocoagulation, carbidopa-levodopa, a dopamine agonist, an MAO-B inhibitor, a catechol-O-methyltransferase inhibitor, an anticholinergic, amantadine, deep brain stimulation, an anticoagulant, an anti-platelet agent, an angiotensin-converting enzyme inhibitor, an angiotensin II receptor blocker, an angiotensin receptor neprilysin inhibitor, a beta blocker, a combined alpha and beta blocker, a calcium channel blocker, a cholesterol lowering medication, a nicotinic acid, a cholesterol absorption inhibitor, a *digitalis* preparation, a diuretic, a vasodilator, a dual anti-platelet therapy, a cardiac procedure, an antiviral compound, a nucleoside-analog reverse transcriptase inhibitor (NRTI), a non-nucleoside reverse transcriptase inhibitor (NNRTI), a protease inhibitor, an antibacterial compound, an antifungal compound, an antiparasitic compound, insulin, a sulfonylurea, a biguanide, a meglitinide, a thiazolidinedione, a DPP-4 inhibitor, an SGLT2 inhibitor, an alpha-glucosidase inhibitor, a bile acid sequestrant, aspirin, a dietary regimen, a clotting factor, desmopressin, a clot-preserving medication, a fibrin sealant, physical therapy, a coenzyme, a bone marrow transplant, an organ transplant, hemodialysis, hemofiltration, exchange transfusion, peritoneal dialysis, medium-chain triacylglycerols, miglustat, enzyme supplementation therapy, a checkpoint inhibitor, a chemotherapeutic drug, a biologic drug, radiation therapy, cryotherapy, hyperthermia, surgical excision or tumor tissue, or an anti-cancer vaccine.

In some embodiments of any of the foregoing methods, the method further comprises controlling proliferation of the cell. In some embodiments, the cell comprises an ALINK system, and the method of controlling proliferation comprises: i) permitting proliferation of the cell comprising the ALINK system by maintaining the cell comprising the ALINK system in the absence of an inducer of the negative selectable marker; or ii) ablating or inhibiting proliferation of the cell comprising the ALINK system by exposing the cell comprising the ALINK system to the inducer of the negative selectable marker. In some embodiments, the cell comprises an EARC system, and the method of controlling cell proliferation comprises: i) permitting proliferation of the cell comprising the EARC system by exposing the cell comprising the EARC system to an inducer of the inducible activator-based gene expression system; or ii) preventing or inhibiting proliferation of the cell comprising the EARC system by maintaining the cell comprising the EARC system in the absence of the inducer of the inducible activator-based gene expression system.

In some embodiments of any of the foregoing methods, the cell is removed after completion of the therapy. Removal of the cell(s) can be by surgery (e.g., to remove transplanted tissue or organs, or to remove cloaked subcutaneous tissue) or by the use of the ALINK and/or EARC systems. In some embodiments, one or more (e.g., one, two, three, four, or more) ALINK and/or EARC systems are used to eliminate all of the cloaked cells.

In another aspect, the invention provides a cell of the invention or a composition of the invention for use in treating a disease or condition in a subject in need thereof. In some embodiments, disease or condition is blindness, arthritis (e.g., osteoarthritis or rheumatoid arthritis), ischemia, diabetes (e.g., Type 1 or Type 2 diabetes), multiple sclerosis, spinal cord injury, stroke, cancer, a lung disease, a blood disease, a neurological disease, such as Parkinson's disease, Alzheimer's disease, Huntington's disease, and ALS, an enzyme or hormone deficiency, a metabolic disorder (e.g., a lysosomal storage disorder, Galactosemia, Maple syrup urine disease, Phenylketonuria, a glycogen storage disease, a mitochondrial disorder, Friedrich's ataxia, a peroxisomal disorder, a metal metabolism disorder, or an organic academia), an autoimmune disease (e.g., Psoriasis, Systemic Lupus Erythematosus, Grave's disease, Inflammatory Bowel Disease, Addison's Diseases, Sjogren's Syndrome, Hashimoto's Thyroiditis, Vasculitis, Autoimmune Hepatitis, Alopecia Areata, Autoimmune pancreatitis, Crohn's Disease, Ulcerative colitis, Dermatomyositis), age-related macular degeneration, retinal dystrophy, an infectious disease, hemophilia, a degenerative disease (e.g., Charcot-Marie-Tooth disease, chronic obstructive pulmonary disease, chronic traumatic encephalopathy, Creutzfeldt-Jakob disease, Cystic Fibrosis, Cytochrome C Oxidase deficiency, Ehlers-Danlos syndrome, essential tremor, Fribrodisplasia Ossificans Progressiva, infantile neuroaxonal dystrophy, keratoconus, keratoglobus, muscular dystrophy, neuronal ceroid lipofuscinosis, a prior disease, progressive supranuclear palsy, sandhoff disease, spinal muscular atrophy, retinitis pigmentosa), or an age-related disease (e.g., atherosclerosis, cardiovascular disease (e.g., angina, myocardial infarction), cataracts, osteoporosis, or hypertension), or a disease or condition listed in Table 2.

In another aspect, the invention provides a cell of the invention or a composition of the invention for use in providing a local immunosuppression at a transplant site in an allogeneic host.

In some embodiments of any of the foregoing aspects, the cell is comprises two of the set of transgenes PD-L1, HLA-G (H2-M3), Cd47, Cd200, FASLG (FasL), Ccl21 (Ccl21b), Mfge8, and Serpin B9 (Spi6) (e.g., PD-L1 and HLA-G (H2-M3); PD-L1 and Cd47; PD-L1 and Cd200; PD-L1 and FASLG (FasL); PD-L1 and Ccl21 (Ccl21b); PD-L1 and Mfge8; PD-L1 and Serpin B9 (Spi6); HLA-G (H2-M3) and Cd47; HLA-G (H2-M3) and Cd200; HLA-G (H2-M3) and FASLG (FasL); HLA-G (H2-M3) and Ccl21 (Ccl21b); HLA-G (H2-M3) and Mfge8; HLA-G (H2-M3) and Serpin B9 (Spi6); Cd47 and Cd200; Cd47 and FASLG (FasL); Cd47 and Ccl21 (Ccl21b); Cd47 and Mfge8; Cd47 and Serpin B9 (Spi6); Cd200 and FASLG (FasL); Cd200 and Ccl21 (Ccl21b); Cd200 and Mfge8; Cd200 and Serpin B9 (Spi6); FASLG (FasL) and Ccl21 (Ccl21b); FASLG (FasL) and Mfge8; FASLG (FasL) and Serpin B9 (Spi6); Ccl21 (Ccl21b) and Mfge8; Ccl21 (Ccl21b) and Serpin B9 (Spi6); or Mfge8 and Serpin B9 (Spi6)).

In some embodiments of any of the foregoing aspects, the cell comprises three of the set of transgenes PD-L1, HLA-G (H2-M3), Cd47, Cd200, FASLG (FasL), Ccl21 (Ccl21b), Mfge8, and Serpin B9 (Spi6) (e.g., PD-L1, HLA-G (H2-M3), and Cd47; PD-L1, HLA-G (H2-M3), and Cd200; PD-L1, HLA-G (H2-M3), and FASLG (FasL); PD-L1, HLA-G (H2-M3), and Ccl21 (Ccl21b); PD-L1, HLA-G (H2-M3), and Mfge8; PD-L1, HLA-G (H2-M3), and Serpin B9 (Spi6); PD-L1, Cd47, and Cd200; PD-L1, Cd47, and FASLG (FasL); PD-L1, Cd47, and Ccl21 (Ccl21b); PD-L1, Cd47, and Mfge8; PD-L1, Cd47, and Serpin B9; PD-L1, Cd200, and FASLG (FasL); PD-L1, Cd200, and Ccl21 (Ccl21b); PD-L1, Cd200, and Mfge8; PD-L1, Cd200, and Serpin B9 (Spi6); PD-L1, FASLG (FasL), and Ccl21 (Ccl21b); PD-L1, FASLG (FasL), and Mfge8; PD-L1, FASLG (FasL), and Serpin B9 (Spi6); PD-L1, Ccl21 (Ccl21b), and Mfge8; PD-L1, Ccl21 (Ccl21b), and Serpin B9 (Spi6); PD-L1, Mfge8, and Serpin B9 (Spi6); HLA-G (H2-M3), Cd47, and Cd200; HLA-G (H2-M3), Cd47, and FASLG (FasL); HLA-G (H2-M3), Cd47, and Ccl21 (Ccl21b); HLA-G (H2-M3), Cd47, and Mfge8; HLA-G (H2-M3), Cd47, and Serpin B9; HLA-G (H2-M3), Cd200, and FASLG (FasL); HLA-G (H2-M3), Cd200, and Ccl21 (Ccl21b); HLA-G (H2-M3), Cd200, and Mfge8; HLA-G (H2-M3), Cd200, and Serpin B9; HLA-G (H2-M3), FASLG (FasL), and Ccl21 (Ccl21b); HLA-G (H2-M3), FASLG (FasL), and Mfge8; HLA-G (H2-M3), FASLG (FasL), and Serpin B9 (Spi6); HLA-G (H2-M3), Ccl21 (Ccl21b), and Mfge8; HLA-G (H2-M3), Ccl21 (Ccl21b), and Serpin B9 (Spi6); HLA-G (H2-M3), Mfge8, and Serpin B9 (Spi6); Cd47, Cd200, and FASLG (FasL); Cd47, Cd200, and Ccl21 (Ccl21b); Cd47, Cd200, and Mfge8; Cd47, Cd200, and Serpin B9 (Spi6); Cd47, FASLG (FasL), and Ccl21 (Ccl21b); Cd47, FASLG (FasL), and Mfge8; Cd47, FASLG (FasL), and Serpin B9 (Spi6); Cd47, Ccl21 (Ccl21b), and Mfge8; Cd47, Ccl21 (Ccl21b), and Serpin B9 (Spi6); Cd47, Mfge8, and Serpin B9 (Spi6); Cd200, FASLG (FasL), and Ccl21 (Ccl21b); Cd200, FASLG (FasL), and Mfge8; Cd200, FASLG (FasL), and Serpin B9 (Spi6); Cd200, Ccl21 (Ccl21b), and Mfge8; Cd200, Ccl21 (Ccl21b), and Serpin B9 (Spi6); Cd200, Mfge8, and Serpin B9 (Spi6); FASLG (FasL), Ccl21 (Ccl21b), and Mfge8; FASLG (FasL), Ccl21 (Ccl21b), and Serpin B9 (Spi6); Ccl21 (Ccl21b), Mfge8, and Serpin B9 (Spi6)).

In some embodiments of any of the foregoing aspects, the cell comprises four of the set of transgenes PD-L1, HLA-G (H2-M3), Cd47, Cd200, FASLG (FasL), Ccl21 (Ccl21b), Mfge8, and Serpin B9 (Spi6) (e.g., PD-L1, HLA-G (H2-M3), Cd47, and Cd200; PD-L1, HLA-G (H2-M3), Cd47, and FASLG (FasL); PD-L1, HLA-G (H2-M3), Cd47, and Ccl21 (Ccl21b); PD-L1, HLA-G (H2-M3), Cd47, and Mfge8; PD-L1, HLA-G (H2-M3), Cd47, and Serpin B9 (Spi6); PD-L1, HLA-G (H2-M3), Cd200, and FASLG (FasL); PD-L1, HLA-G (H2-M3), Cd200, and Ccl21 (Ccl21b); PD-L1, HLA-G (H2-M3), Cd200, and Mfge8; PD-L1, HLA-G (H2-M3), Cd200, and Serpin B9 (Spi6); PD-L1, HLA-G (H2-M3), FASLG (FasL), and Ccl21 (Ccl21b); PD-L1, HLA-G (H2-M3), FASLG (FasL), and Mfge8; PD-L1, HLA-G (H2-M3), FASLG (FasL), and Serpin B9 (Spi6); PD-L1, HLA-G (H2-M3), Ccl21 (Ccl21b), and Mfge8; PD-L1, HLA-G (H2-M3), Ccl21 (Ccl21b), and Serpin B9 (Spi6); PD-L1, HLA-G (H2-M3), Mfge8, and Serpin B9 (Spi6); PD-L1, Cd47, Cd200, and FASLG (FasL); PD-L1, Cd47, Cd200, and Ccl21 (Ccl21b); PD-L1, Cd47, Cd200, and Mfge8; PD-L1, Cd47, Cd200, and Serpin B9 (Spi6); PD-L1, Cd47, FASLG (FasL), and Ccl21 (Ccl21b); PD-L1, Cd47, FASLG (FasL), and Mfge8; PD-L1, Cd47, FASLG (FasL), and Serpin B9 (Spi6); PD-L1, Cd47, Ccl21 (Ccl21b), and Mfge8; PD-L1, Cd47, Ccl21 (Ccl21b), and Serpin B9 (Spi6); PD-L1, Cd47, Mfge8, and Serpin B9 (Spi6); PD-L1, Cd200, FASLG (FasL), and Ccl21 (Ccl21b); PD-L1, Cd200, FASLG (FasL), and Mfge8; PD-L1, Cd200, FASLG (FasL), and Serpin B9 (Spi6); PD-L1, Cd200, Ccl21 (Ccl21b), and Mfge8; PD-L1, Cd200, Ccl21 (Ccl21b), and Serpin B9 (Spi6); PD-L1, Cd200, Mfge8, and Serpin B9 (Spi6); PD-L1, FASLG (FasL), Ccl21 (Ccl21b), and Mfge8; PD-L1, FASLG (FasL), Ccl21 (Ccl21b), and Serpin B9 (Spi6); PD-L1, FASLG (FasL), Mfge8, and Serpin B9 (Spi6); PD-L1, Ccl21 (Ccl21b), Mfge8, and Serpin B9 (Spi6); HLA-G (H2-M3), Cd47, Cd200, and FASLG (FasL); HLA-G (H2-M3), Cd47, Cd200, and Ccl21 (Ccl21b); HLA-G (H2-M3), Cd47, Cd200, and Mfge8; HLA-G (H2-M3), Cd47, Cd200, and Serpin B9 (Spi6); HLA-G (H2-M3), Cd47, FASLG (FasL), and Ccl21 (Ccl21b); HLA-G (H2-M3), Cd47, FASLG (FasL), and Mfge8; HLA-G (H2-M3), Cd47, FASLG (FasL), and Serpin B9 (Spi6); HLA-G (H2-M3), Cd47, Ccl21 (Ccl21b), and Mfge8; HLA-G (H2-M3), Cd47, Ccl21 (Ccl21b), and Serpin B9 (Spi6); HLA-G (H2-M3), Cd47, Mfge8, and Serpin B9 (Spi6); HLA-G (H2-M3), Cd200, FASLG (FasL), and Ccl21 (Ccl21b); HLA-G (H2-M3), Cd200, FASLG (FasL), and Mfge8; HLA-G (H2-M3), Cd200, FASLG (FasL), and Serpin B9 (Spi6); HLA-G (H2-M3), Cd200, Ccl21 (Ccl21b), and Mfge8; HLA-G (H2-M3), Cd200, Ccl21 (Ccl21b), and Serpin B9 (Spi6); HLA-G (H2-M3), Cd200, Mfge8, and Serpin B9 (Spi6); HLA-G (H2-M3), FASLG (FasL), Ccl21 (Ccl21b), and Mfge8; HLA-G (H2-M3), FASLG (FasL), Ccl21 (Ccl21b), and Serpin B9 (Spi6); HLA-G (H2-M3), FASLG (FasL), Mfge8, and Serpin B9 (Spi6); HLA-G (H2-M3), Ccl21 (Ccl21b), Mfge8, and Serpin B9 (Spi6); Cd47, Cd200, FASLG (FasL), and Ccl21 (Ccl21b); Cd47, Cd200, FASLG (FasL), and Mfge8; Cd47, Cd200, FASLG (FasL), and Serpin B9 (Spi6); Cd47, Cd200, Ccl21 (Ccl21b), and Mfge8; Cd47, Cd200, Ccl21 (Ccl21b), and Serpin B9 (Spi6); Cd47, Cd200, Mfge8, and Serpin B9 (Spi6); Cd47, FASLG (FasL), Ccl21 (Ccl21b), and Mfge8; Cd47, FASLG (FasL), Ccl21 (Ccl21b), and Serpin B9 (Spi6); Cd47, Ccl21 (Ccl21b), Mfge8, and Serpin B9 (Spi6); Cd200, FASLG (FasL), Ccl21 (Ccl21b), and Mfge8; Cd200, FASLG (FasL), Ccl21 (Ccl21b), and Serpin B9 (Spi6); Cd200, Ccl21 (Ccl21b), Mfge8, and Serpin B9 (Spi6); or FASLG (FasL), Ccl21 (Ccl21b), Mfge8, and Serpin B9 (Spi6)).

In some embodiments of any of the foregoing aspects, the cell comprises five of the set of transgenes PD-L1, HLA-G (H2-M3), Cd47, Cd200, FASLG (FasL), Ccl21 (Ccl21b), Mfge8, and Serpin B9 (Spi6) (e.g., PD-L1, HLA-G (H2-M3), Cd47, Cd200, and FASLG (FasL); PD-L1, HLA-G (H2-M3), Cd47, Cd200, and Ccl21 (Ccl21b); PD-L1, HLA-G (H2-M3), Cd47, Cd200, and Mfge8; PD-L1, HLA-G (H2-M3), Cd47, Cd200, and Serpin B9 (Spi6); PD-L1, HLA-G (H2-M3), Cd47, FASLG (FasL), and Ccl21 (Ccl21b); PD-L1, HLA-G (H2-M3), Cd47, FASLG (FasL), and Mfge8; PD-L1, HLA-G (H2-M3), Cd47, FASLG (FasL), and Serpin B9 (Spi6); PD-L1, HLA-G (H2-M3), Cd47, Ccl21 (Ccl21b), and Mfge8; PD-L1, HLA-G (H2-M3), Cd47, Ccl21 (Ccl21b), and Serpin B9 (Spi6); PD-L1, HLA-G (H2-M3), Cd47, Mfge8, and Serpin B9 (Spi6); PD-L1, HLA-G (H2-M3), Cd200, FASLG (FasL), and Ccl21 (Ccl21b); PD-L1, HLA-G (H2-M3), Cd200, FASLG (FasL), and Mfge8, PD-L1, HLA-G (H2-M3), Cd200, FASLG (FasL), and Serpin B9 (Spi6); PD-L1, HLA-G (H2-M3), Cd200, Ccl21 (Ccl21b), and Mfge8; PD-L1, HLA-G (H2-M3), Cd200, Ccl21 (Ccl21b), and Serpin B9 (Spi6); PD-L1, HLA-G (H2-M3), Cd200, Mfge8, and Serpin B9 (Spi6); PD-L1, HLA-G (H2-M3), FASLG (FasL), Ccl21 (Ccl21b), and Mfge8; PD-L1, HLA-G (H2-M3), FASLG (FasL), Ccl21 (Ccl21b), and Serpin B9 (Spi6); PD-L1, HLA-G (H2-M3), FASLG (FasL), Mfge8, and Serpin B9 (Spi6); PD-L1, HLA-G (H2-M3), Ccl21 (Ccl21b), Mfge8, and Serpin B9 (Spi6); PD-L1, Cd47, Cd200, FASLG (FasL), and Ccl21 (Ccl21b); PD-L1, Cd47, Cd200, FASLG (FasL), and Mfge8, PD-L1, Cd47, Cd200, FASLG (FasL), and Serpin B9 (Spi6); PD-L1, Cd47, Cd200, Ccl21 (Ccl21b), and Mfge8; PD-L1, Cd47, Cd200, Ccl21 (Ccl21b), and Serpin B9 (Spi6); PD-L1, Cd47, Cd200, Mfge8, and Serpin B9 (Spi6); PD-L1, Cd47, FASLG (FasL), Ccl21 (Ccl21b), and Mfge8; PD-L1, Cd47, FASLG (FasL), Ccl21 (Ccl21b), and Serpin B9 (Spi6); PD-L1, Cd47, FASLG (FasL), Mfge8, and Serpin B9 (Spi6); PD-L1, Cd47, Ccl21 (Ccl21b), Mfge8, and Serpin B9 (Spi6); PD-L1, Cd200, FASLG (FasL), Ccl21 (Ccl21b), and Mfge8; PD-L1, Cd200, FASLG (FasL), Ccl21 (Ccl21b), and Serpin B9 (Spi6); PD-L1, Cd200, FASLG (FasL), Mfge8, and Serpin B9 (Spi6); PD-L1, Cd200, Ccl21 (Ccl21b), Mfge8, and Serpin B9 (Spi6); PD-L1, FASLG (FasL), Ccl21 (Ccl21b), Mfge8, and Serpin B9 (Spi6); HLA-G (H2-M3), Cd47, Cd200, FASLG (FasL), and Ccl21 (Ccl21b); HLA-G (H2-M3), Cd47, Cd200, FASLG (FasL), and Mfge8; HLA-G (H2-M3), Cd47, Cd200, FASLG (FasL), and Serpin B9 (Spi6); HLA-G (H2-M3), Cd47, Cd200, Ccl21 (Ccl21b), and Mfge8; HLA-G (H2-M3), Cd47, Cd200, Ccl21 (Ccl21b), and Serpin B9 (Spi6); HLA-G (H2-M3), Cd47, Cd200, Mfge8, and Serpin B9 (Spi6); HLA-G (H2-M3), Cd47, FASLG (FasL), Ccl21 (Ccl21b), and Mfge8; HLA-G (H2-M3), Cd47, FASLG (FasL), Ccl21 (Ccl21b), and Serpin B9 (Spi6); HLA-G (H2-M3), Cd47, FASLG (FasL), Mfge8, and Serpin B9 (Spi6); HLA-G (H2-M3), Cd47, Ccl21 (Ccl21b), Mfge8, and Serpin B9 (Spi6); HLA-G (H2-M3), Cd200, FASLG (FasL), Ccl21 (Ccl21b), and Mfge8; HLA-G (H2-M3), Cd200, FASLG (FasL), Mfge8, and Serpin B9 (Spi6); HLA-G (H2-M3), Cd200, Ccl21 (Ccl21b), Mfge8, and Serpin B9 (Spi6); Cd47, Cd200, FASLG (FasL), Ccl21 (Ccl21b), and Mfge8; Cd47, Cd200, FASLG (FasL), Ccl21 (Ccl21b), and Serpin B9 (Spi6); Cd47, Cd200, FASLG (FasL), Mfge8, and Serpin B9 (Spi6); Cd47, Cd200, FASLG (FasL), Ccl21 (Ccl21b), Mfge8, and Serpin B9 (Spi6); Cd47, FASLG (FasL), Ccl21 (Ccl21b), Mfge8, and Serpin B9 (Spi6); or Cd200, FASLG (FasL), Ccl21 (Ccl21b), Mfge8, and Serpin B9 (Spi6)). In some embodiments of any of the foregoing aspects, the cell comprises six of the set of transgenes PD-L1, HLA-G (H2-M3), Cd47, Cd200, FASLG (FasL), Ccl21 (Ccl21b), Mfge8, and Serpin B9 (Spi6) (e.g., PD-L1, HLA-G (H2-M3), Cd47, Cd200, FASLG (FasL), and Ccl21 (Ccl21b); PD-L1, HLA-G (H2-M3), Cd47, Cd200, FASLG (FasL), and Mfge8; PD-L1, HLA-G (H2-M3), Cd47, Cd200, FASLG (FasL), and Serpin B9 (Spi6); PD-L1, HLA-G (H2-M3), Cd47, Cd200, Ccl21 (Ccl21b), and Mfge8; PD-L1, HLA-G (H2-M3), Cd47, Cd200, Ccl21 (Ccl21b), and Serpin B9 (Spi6); PD-L1, HLA-G (H2-M3), Cd47, Cd200, Mfge8, and Serpin B9 (Spi6); PD-L1, HLA-G (H2-M3), Cd47, FASLG (FasL), Ccl21 (Ccl21b), and Mfge8; PD-L1, HLA-G (H2-M3), Cd47, FASLG (FasL), Ccl21 (Ccl21b), and Serpin B9 (Spi6); PD-L1, HLA-G (H2-M3), Cd47, FASLG (FasL), Mfge8, and Serpin B9 (Spi6); PD-L1, HLA-G (H2-M3), Cd200, FASLG (FasL), Ccl21 (Ccl21b), and Mfge8; PD-L1, HLA-G (H2-M3), Cd200, FASLG (FasL), Ccl21 (Ccl21b), and Serpin B9 (Spi6); PD-L1, HLA-G (H2-M3), Cd200, FASLG (FasL), Mfge8, and Serpin B9 (Spi6); PD-L1, HLA-G (H2-M3), Cd200, Ccl21 (Ccl21b), Mfge8, and Serpin B9 (Spi6); PD-L1, Cd47, Cd200, FASLG (FasL), Ccl21 (Ccl21b), and Mfge8; PD-L1, Cd47, Cd200, FASLG (FasL), Ccl21 (Ccl21b), and Serpin B9 (Spi6); PD-L1, Cd47, Cd200, FASLG (FasL), Mfge8, and Serpin B9 (Spi6); PD-L1, Cd47, Cd200, Ccl21 (Ccl21b), Mfge8, and Serpin B9 (Spi6); PD-L1, Cd47, FASLG (FasL), Ccl21 (Ccl21b), Mfge8, and Serpin B9 (Spi6); PD-L1, Cd200, FASLG (FasL), Ccl21 (Ccl21b), Mfge8, and Serpin B9 (Spi6); HLA-G (H2-M3), Cd47, Cd200, FASLG (FasL), Ccl21 (Ccl21b), and Mfge8; HLA-G (H2-M3), Cd47, Cd200, FASLG (FasL), Ccl21 (Ccl21b), and Serpin B9 (Spi6); HLA-G (H2-M3), Cd47, Cd200, FASLG (FasL), Mfge8, and Serpin B9 (Spi6); HLA-G (H2-M3), Cd47, Cd200, Ccl21 (Ccl21b), Mfge8, and Serpin B9 (Spi6); HLA-G (H2-M3), Cd47, FASLG (FasL), Ccl21 (Ccl21b), Mfge8, and Serpin B9 (Spi6); HLA-G (H2-M3), Cd200, FASLG (FasL), Ccl21 (Ccl21b), Mfge8, and Serpin B9 (Spi6); or Cd47, Cd200, FASLG (FasL), Ccl21 (Ccl21b), Mfge8, and Serpin B9 (Spi6)).

In some embodiments of any of the foregoing aspects, the cell comprises seven of the set of transgenes PD-L1, HLA-G (H2-M3), Cd47, Cd200, FASLG (FasL), Ccl21 (Ccl21b), Mfge8, and Serpin B9 (Spi6) (e.g., PD-L1, HLA-G (H2-M3), Cd47, Cd200, FASLG (FasL), Ccl21 (Ccl21b), and Mfge8; PD-L1, HLA-G (H2-M3), Cd47, Cd200, FASLG (FasL), Ccl21 (Ccl21b), and Serpin B9 (Spi6); PD-L1, HLA-G (H2-M3), Cd47, Cd200, FASLG (FasL), Mfge8, and Serpin B9 (Spi6); PD-L1, HLA-G (H2-M3), Cd47, Cd200, Ccl21 (Ccl21b), Mfge8, and Serpin B9 (Spi6); PD-L1, HLA-G (H2-M3), Cd47, FASLG (FasL), Ccl21 (Ccl21b), Mfge8, and Serpin B9 (Spi6); PD-L1, HLA-G (H2-M3), Cd200, FASLG (FasL), Ccl21 (Ccl21b), Mfge8, and Serpin B9 (Spi6); PD-L1, Cd47, Cd200, FASLG (FasL), Ccl21 (Ccl21b), Mfge8, and Serpin B9 (Spi6); or HLA-G (H2-M3), Cd47, Cd200, FASLG (FasL), Ccl21 (Ccl21b), Mfge8, and Serpin B9 (Spi6)).

In some embodiments of any of the foregoing aspects, the cell comprises all eight of the set of transgenes PD-L1, HLA-G (H2-M3), Cd47, Cd200, FASLG (FasL), Ccl21 (Ccl21b), Mfge8, and Serpin B9 (Spi6).

In some embodiments of any of the foregoing aspects, the cell comprises one or more (e.g., one, two, three, four, five, six, or all seven) of the set of transgenes HLA-G (H2-M3), Cd47, Cd200, FASLG (FasL), Ccl21 (Ccl21b), Mfge8, and Serpin B9 (Spi6).

In some embodiments of any of the foregoing aspects, the cell comprises one or more (e.g., one, two, three, four, five, six, or all seven) of the set of transgenes PD-L1, HLA-G (H2-M3), Cd47, Cd200, Ccl21 (Ccl21b), Mfge8, and Serpin B9 (Spi6).

In some embodiments of any of the foregoing aspects, the cell comprises one or more (e.g., one, two, three, four, five, or all six) of the set of transgenes HLA-G (H2-M3), Cd47, Cd200, Ccl21 (Ccl21b), Mfge8, and Serpin B9 (Spi6).

In some embodiments of any of the foregoing aspects, the cell is not modified to express PD-L1.

In some embodiments of any of the foregoing aspects, the cell is not modified to express FasL.

In some embodiments of any of the foregoing aspects, the cell is not modified to express TGF-β. In some embodiments of any of the foregoing aspects, the cell is not modified to express CTLA4 or CLTA4-Ig. In some embodiments of any of the foregoing aspects, the cell is not modified to express IDO. In some embodiments of any of the foregoing aspects, the cell is not modified to express IL-35. In some embodiments of any of the foregoing aspects, the cell is not modified to express IL-10. In some embodiments of any of the foregoing aspects, the cell is not modified to express VEGF. In some embodiments of any of the foregoing aspects, the cell is not modified to express an NFκb decoy receptor. In some embodiments of any of the foregoing aspects, the cell is not modified to express soluble TNFR. In some embodiments of any of the foregoing aspects, the cell is not modified to express CCR7. In some embodiments of any of the foregoing aspects, the cell is not modified to express SOCS1. In some embodiments of any of the foregoing aspects, the cell is not modified to express HLA-E. In some embodiments of any of the foregoing aspects, the cell is not modified to express siRNA directed to IL-12.

Definitions

Unless defined otherwise, all technical and scientific terms used herein have the same meaning as commonly understood by one of ordinary skill in the art to which this disclosure belongs.

As used herein, the term "about" refers to a value that is no more than 10% above or below the value being described. For example, the term "about 5 nM" indicates a range of from 4.5 nM to 5.5 nM.

As used herein, the term "activated leukocyte" refers to the state of a leukocyte (e.g., a granulocyte, such as a neutrophil, eosinophil, or basophil; a monocyte, or a lymphocyte, such as a B or T cell) caused by response to a perceived insult. When leukocytes become activated, they can proliferate, secrete cytokines, differentiate, present antigens, become more polarized, become more phagocytic, and/or become more cytotoxic. Factors that stimulate immune cell activation include pro-inflammatory cytokines, pathogens, and non-self antigen presentation. Activated leukocytes can be isolated from lymphoid organs. Leukocytes, such as T cells, can also be activated in vitro using anti-CD3/CD28 beads or other methods employed by those of skill in the art (see, e.g., Frauwith and Thompson, *J. Clin Invest* 109:295-299 (2002); and Trickett and Kwan, *J Immunol Methods* 275:251-255 (2003)).

As used herein, "allogeneic" means cells, tissue, DNA, or factors taken or derived from a different subject of the same species.

As used herein, the term "stem cell" refers to a cell that can differentiate into one or more specialized cells and has the capacity for self-renewal. Stem cells include pluripotent stem cells (PSCs), such as embryonic stem cells (ESCs) and induced pluripotent stem cells (iPSCs), and multipotent stem cells, such as cord blood stem cells, mesenchymal stromal cells and adult stem cells, which are found in various tissues. The term "stem cell" also includes cells amenable for genome editing, cells that can serve as a source of a therapeutic cell type (e.g., cells that can be directed to differentiate into a lineage restricted or terminally differentiated cell that is used for cell therapy, or cells of a desired target tissue), and cells with "artificial" cell acquired stem cell properties (e.g., pluripotency or multipotency or self-renewal).

As used herein, the terms "embryonic stem cell" and "ES cell" refer to an embryo-derived totipotent or pluripotent stem cell, derived from the inner cell mass of a blastocyst that can be maintained in an in vitro culture under suitable conditions. ES cells are capable of differentiating into cells of any of the three vertebrate germ layers, e.g., the endoderm, the ectoderm, or the mesoderm. ES cells are also characterized by their ability propagate indefinitely under suitable in vitro culture conditions. See, for example, Thomson et al., *Science* 282:1145 (1998).

As used herein, the terms "induced pluripotent stem cell," "iPS cell," and "iPSC" refer to a pluripotent stem cell that can be derived directly from a differentiated somatic cell. Human iPS cells can be generated by introducing specific sets of reprogramming factors into a non-pluripotent cell that can include, for example, Oct3/4, Sox family transcription factors (e.g., Sox1, Sox2, Sox3, Sox15), Myc family transcription factors (e.g., c-Myc, l-Myc, n-Myc), Kruppel-like family (KLF) transcription factors (e.g., KLF1, KLF2, KLF4, KLF5), and/or related transcription factors, such as NANOG, LIN28, and/or Glis1. Human iPS cells can also be generated, for example, by the use of miRNAs, small molecules that mimic the actions of transcription factors, or lineage specifiers. Human iPS cells are characterized by their ability to differentiate into any cell of the three vertebrate germ layers, e.g., the endoderm, the ectoderm, or the mesoderm. Human iPS cells are also characterized by their ability propagate indefinitely under suitable in vitro culture conditions. See, for example, Takahashi and Yamanaka, Cell 126:663 (2006).

As used herein, the term "mitigate antigen presenting cell activation and function" refers to a transgene that encodes a gene product whose function is to inhibit antigen presenting cell activation or the ability of an antigen presenting cell to promote the activation of graft attacking leukocytes (Fiorentino et al., *J Immunol.* 146:3444-51 (1991); Salio et al., *Eur J Immunol.* 29:3245-53 (1999)). In an embodiment, mitigation of antigen presenting cell activation and function refers to a decrease in APC activation and function of at least about 10%, 20%, 30%, 40%, 50%, 60%, 70%, 80%, 90%, 95% or 100%, relative to a control (e.g., as determined using an assay for antigen presenting cell activation, such as reduced proliferation, reduced secretion of pro-inflammatory cytokines (e.g., interleukin-1 (IL-1, e.g., IL-1B), IL-5, IL-6, IL-8, IL-10, IL-12, IL-13, IL-18, tumor necrosis factor (TNF, e.g., TNFα), interferon gamma (IFNγ), and granulocyte macrophage colony stimulating factor (GMCSF), which can be measured using an ELISA or Western Blot analysis of culture media or a patient sample, such as a blood sample), or reduced levels of cell surface markers (e.g., CD11c, CD11b, HLA molecules (e.g., MHC-II), CD40, B7, IL-2, CD80 or CD86, which can be assessed using flow cytometry, immunohistochemistry, in situ hybridization, and other assays that allow for measurement of cell surface markers)). Antigen presenting cells include dendritic cells, B cells, and macrophages. Mast cells and neutrophils can also be induced to present antigens. Methods for determining mitigation of antigen presenting cell activation and function are known in the art. Examples of gene products that mitigate antigen presenting cell activation and function include, but are not limited to: Ccl21 (Ccl21b) and PD-L1. Such transgenes may be referred herein to "cloaking" or "cloaked" genes.

As used herein, the term "mitigate graft attacking leukocyte activity or cytolytic function" refers to a transgene that encodes a gene product whose function is to inhibit or prevent graft attacking leukocyte activity or cytolytic function near allograft cells (MacDonald et al., *J Immunol.* 126:1671-5 (1981); Bongrand et al., *Eur J Immunol.* 13:424-9 (1983); MacDonald et al., *Eur J Immunol.* 9:466-70 (1979)). In an embodiment, mitigation of graft attacking leukocyte activity or cytolytic function refers to a decrease in leukocyte activity or cytolytic function of at least about 10%, 20%, 30%, 40%, 50%, 60%, 70%, 80%, 90%, 95% or 100%, relative to a control (e.g., as determined using an assay for leukocyte activation, such as reduced proliferation, reduced secretion of pro-inflammatory cytokines (e.g., interleukin-1 (IL-1, e.g., IL-1β), IL-5, IL-6, IL-8, IL-10, IL-12, IL-13, IL-18, tumor necrosis factor (TNF, e.g., TNFα), interferon gamma (IFNγ), and granulocyte macrophage colony stimulating factor (GMCSF), which can be measured using an ELISA or Western Blot analysis of culture media or a patient sample, such as a blood sample), or reduced polarization (e.g., a reduction in the level of IL-12, TNF, IL-1β, IL-6, IL-23, MARCO, MHC-II, CD86, INOS, CXCL9, and CXCL10 in a macrophage or monocyte, or a reduction in the level of a Th1-specific marker (e.g., T-bet, IL-12R, STAT4), a chemokine receptor (e.g., CCR5, CXCR6, or CXCR3); or a Th2-specific marker: (e.g., CCR3, CXCR4, STAT6, GATA3, or IL-4Ra) in a T cell, which can be assessed using flow cytometry, immunohistochemistry, situ hybridization, qPCR, or western blot analysis for cell surface markers or intracellular proteins, and ELISA or western blot analysis for secreted proteins); or as determined using an assay for cytolytic function (e.g., by incubating leukocytes with a target cell line that has been pre-coated with antibodies to a surface antigen expressed by the target cell line and measuring the number of surviving target cells with a fluorescent viability stain, or by measuring the secretion of cytolytic granules (e.g., perforin, granzymes, or other cytolytic proteins released from immune cells) from the leukocytes). Methods for determining mitigation of graft attacking leukocyte activity or cytolytic function are known in the art. Examples of gene products that mitigate graft attacking leukocyte activity or cytolytic function include, but are not limited to: PD-L1, HLA-G (H2-M3), Cd39, Cd73, and Lag3. Such transgenes may be referred herein to "cloaking" or "cloaked" genes.

As used herein, the term "mitigate macrophage cytolytic function and phagocytosis of allograft cells" refers to a transgene that encodes a gene product whose function is to inhibit or prevent macrophage cytolytic function and/or phagocytosis of allograft cells (Fish et al., *Toxicology.* 19:127-38. (1981); Sung et al., *J Biol Chem.* 260:546-54 (1985); Amash et al., *J Immunol.* 196:3331-40 (2016)). In an embodiment, mitigation of macrophage cytolytic function and phagocytosis of allograft cells refers to a decrease in macrophage cytolytic function and/or phagocytosis of allograft cells of at least about 10%, 20%, 30%, 40%, 50%, 60%, 70%, 80%, 90%, 95% or 100%, relative to a control (e.g., as determined using an assay for macrophage cytolytic function (e.g., by incubating macrophages with a target cell line that has been pre-coated with antibodies to a surface antigen expressed by the target cell line and measuring the number of surviving target cells with a fluorescent viability stain, or by measuring the secretion of cytolytic granules (e.g., perforin, granzymes, or other cytolytic proteins released from immune cells) released from the macrophages; or as determined using an assay for macrophage phagocytosis (e.g., culturing macrophages with fluorescent beads or a target cell line that has been pre-coated with antibodies to a surface antigen expressed by the target cell line and measuring fluorescence inside the immune cell or quantifying the number of beads or cells engulfed)). Methods for determining mitigation of macrophage cytolytic function and phagocytosis of allograft cells are known in the art. Examples of gene products that mitigate macrophage cytolytic function include, but are not limited to: Cd47, Cd200, Mfge8, and Il1r2. Such transgenes may be referred herein to "cloaking" or "cloaked" genes.

As used herein, the term "induce apoptosis in graft attacking leukocytes" refers to a transgene that encodes a gene product whose function is to kill graft attacking leukocytes near allograft cells (Huang et al., *Proc Natl Acad Sci USA.* 96:14871-6 (1999); Suzuki et al., *Proc Natl Acad Sci USA.* 97:1707-12 (2000); Simon et al., *Proc Natl Acad Sci USA.* 98:5158-63 (2001)). In an embodiment, induction of apoptosis in graft attacking leukocytes refers to an increase in apoptosis in graft attacking leukocytes of at least about 10%, 20%, 30%, 40%, 50%, 60%, 70%, 80%, 90%, 95% or 100%, relative to a control (e.g., as determined using an assay for apoptosis, such as TUNEL staining, caspase staining, or Annexin-V staining, or use of fluorescent viability stains). Methods for determining induction of apoptosis in graft attacking leukocytes are known in the art. Examples of gene products that can induce apoptosis in graft attacking leukocytes include, but are not limited to: FASLG (FasL) and Tnfsf10. Such transgenes may be referred herein to "cloaking" or "cloaked" genes.

As used herein, the term "mitigate local inflammatory proteins" refers to a transgene that encodes a gene product whose function is to inhibit the activity of local proteins, where the function of said proteins is to promote graft attacking leukocyte accumulation, and/or their cytolytic function (Felix et al., *Nat Rev Immunol.* 17:112-29 (2017)). In an embodiment, mitigation of local inflammatory proteins refers to a reduction in local inflammatory proteins of at least about 10%, 20%, 30%, 40%, 50%, 60%, 70%, 80%, 90%, 95% or 100%, relative to a control (e.g., as determined using an assay for inflammatory proteins that promote leukocyte activation or migration to a site of inflammation (e.g., a chemokine, such as CCL2, CCL3, CCL5, CXCL1, CXCL2, and CXCL8, or a pro-inflammatory cytokine, such as IL-1β, IL-5, IL-6, IL-8, IL-10, IL-12, IL-13, IL-18, TNFα, IFNγ, or GMCSF, which can be measured using an ELISA, Western blot analysis, or other techniques known in the art for measuring secreted proteins)). Methods for determining mitigation of local inflammatory proteins are known in the art. Examples of gene products that mitigate local inflammatory proteins include, but are not limited to: PD-L1, Il1r2, and Ackr2. Such transgenes may be referred herein to "cloaking" or "cloaked" genes.

As used herein, the term "protect against leukocyte-mediated apoptosis" refers to a transgene that encodes a gene product whose function is to inhibit any cell component that may induce apoptosis or cytolysis of an allograft cell (Abdullah et al., *J Immunol.* 178:3390-9 (2007)). In an embodiment, protection against leukocyte-mediated apoptosis refers to a decrease in leukocyte-mediated apoptosis of at least about 10%, 20%, 30%, 40%, 50%, 60%, 70%, 80%, 90%, 95% or 100%, relative to a control (e.g., as determined using an assay for leukocyte-mediated apoptosis (e.g., by incubating leukocytes with a target cell line that has been pre-coated with antibodies to a surface antigen expressed by the target cell line and measuring the number of surviving target cells with a fluorescent viability stain, or by measuring the secretion of cytolytic granules (e.g., perforin, granzymes, or other cytolytic proteins released from immune cells) released from the leukocyte). Methods for determining protection against leukocyte-mediated apoptosis are known in the art. Examples of gene products that protect against leukocyte-mediated apoptosis include, but are not limited to: Serpin B9 (Spi6) and Dad1. Such transgenes may be referred herein to "cloaking" or "cloaked" genes.

As used herein, the term "biologic" refers to a designed polypeptide and corresponding encoding DNA, which can be expressed as a transgene. The polypeptide may agonize or inhibit the function of an endogenous gene or inhibit or activate a biological process. Methods for determining whether a polypeptide has agonist or antagonist activity or function are generally known in the art. In an embodiment, the agonist function is at least about 10%, 20%, 30%, 40%, 50%, 60%, 70%, 80%, 90, 95% or 100% of the function, relative to the function of a control. In an embodiment, the antagonist function is at least about 10%, 20%, 30%, 40%, 50%, 60%, 70%, 80%, 90, 95% or 100% of the function, relative to the function of a control.

As used herein, the term "operably linked" refers to a first molecule joined to a second molecule, wherein the molecules are so arranged that the first molecule affects the function or expression of the second molecule. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. Additionally, two portions of a transcription regulatory element are operably linked to one another if they are joined such that the transcription-activating functionality of one portion is not adversely affected by the presence of the other portion. Two transcription regulatory elements may be operably linked to one another by way of a linker nucleic acid (e.g., an intervening non-coding nucleic acid) or may be operably linked to one another with no intervening nucleotides present.

As used herein, the term "promoter" refers to a recognition site on DNA that is bound by an RNA polymerase. The polymerase drives transcription of the transgene.

"Percent (%) sequence identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps, if necessary, to achieve the maximum percent sequence identity. Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full length of the sequences being compared. For example, percent sequence identity values may be generated using the sequence comparison computer program BLAST. As an illustration, the percent sequence identity of a given nucleic acid or amino acid sequence, A, to, with, or against a given nucleic acid or amino acid sequence, B, (which can alternatively be phrased as a given nucleic acid or amino acid sequence, A that has a certain percent sequence identity to, with, or against a given nucleic acid or amino acid sequence, B) is calculated as follows:

100 multiplied by (the fraction $X/Y$)

where X is the number of nucleotides or amino acids scored as identical matches by a sequence alignment program (e.g., BLAST) in that program's alignment of A and B, and where Y is the total number of nucleic acids in B. It will be appreciated that where the length of nucleic acid or amino acid sequence A is not equal to the length of nucleic acid or amino acid sequence B, the percent sequence identity of A to B will not equal the percent sequence identity of B to A.

As used herein, the term "pharmaceutical composition" refers to a mixture containing a therapeutic agent, optionally in combination with one or more pharmaceutically acceptable excipients, diluents, and/or carriers, to be administered to a subject, such as a mammal, e.g., a human, in order to prevent, treat or control a particular disease or condition affecting or that may affect the subject.

As used herein, the term "pharmaceutically acceptable" refers to those compounds, materials, compositions and/or dosage forms, which are suitable for contact with the tissues of a subject, such as a mammal (e.g., a human) without excessive toxicity, irritation, allergic response and/or other problem complications commensurate with a reasonable benefit/risk ratio.

As used herein, the term "wild-type" refers to a genotype with the highest frequency for a particular gene in a given organism.

The terms "cell division locus", "cell division loci", and "CDL" as used herein, refer to a genomic locus (or loci) whose transcription product(s) is expressed by dividing cells. When a CDL comprises a single locus, absence of CDL expression in a cell (or its derivatives) means that tumour initiation and/or formation is prohibited either because the cell(s) will be ablated in the absence of CDL expression or because proliferation of the cell(s) will be blocked or compromised in the absence of CDL expression. When a CDL comprises multiple loci, absence of expression by all or subsets of the loci in a cell (or its derivatives) means that tumour initiation and/or formation is prohibited either because the cell(s) will be ablated in the absence of CDL expression or because proliferation of the cell(s) will be blocked or compromised in the absence of CDL expression. A CDL may or may not be expressed in non-dividing and/or non-proliferating cells. A CDL may be endogenous to a host cell or it may be a transgene. If a CDL is a transgene, it may be from the same or different species as a host cell or it may be of synthetic origin. In an embodiment, a CDL is a single locus that is transcribed during cell division. For example, in an embodiment, a single locus CDL is CDK1. In an embodiment, a CDL comprises two or more loci that are transcribed during cell division. For example, in an embodiment, a multi-locus CDL comprises two MYC genes (c-Myc and N-myc) (Scognamiglio et al., 2016). In an embodiment, a multi-locus CDL comprises AURORA B and C kinases, which may have overlapping functions (Fernandez-Miranda et al., 2011). Cell division and cell proliferation are terms that may be used interchangeably herein.

The terms "normal rate of cell division", "normal cell division rate", "normal rate of cell proliferation", and "normal cell proliferation rate" as used herein, refer to a rate of cell division and/or proliferation that is typical of a non-cancerous healthy cell. A normal rate of cell division and/or proliferation may be specific to cell type. For example, it is widely accepted that the number of cells in the epidermis, intestine, lung, blood, bone marrow, thymus, testis, uterus and mammary gland is maintained by a high rate of cell division and a high rate of cell death. In contrast, the number of cells in the pancreas, kidney, cornea, prostate, bone, heart and brain is maintained by a low rate of cell division and a low rate of cell death (Pellettieri and Sánchez Alvarado, 2007).

The terms "inducible negative effector of proliferation" and "iNEP" as used herein, refer to a genetic modification that facilitates use of CDL expression to control cell division and/or proliferation by: i) inducibly stopping or blocking CDL expression, thereby prohibiting cell division and proliferation; ii) inducibly ablating at least a portion of CDL-expressing cells (i.e., killing at least a portion of proliferating cells); or iii) inducibly slowing the rate of cell division relative to a cell's normal cell division rate, such that the rate of cell division would not be fast enough to contribute to tumor formation.

The terms "ablation link" and "ALINK" as used herein, refer to an example of an iNEP, which comprises a transcriptional link between a CDL and a sequence encoding a negative selectable marker. The ALINK modification allows a user to inducibly kill proliferating host cells comprising the ALINK or inhibit the host cell's proliferation by killing at least a portion of proliferating cells by exposing the ALINK-modified cells to an inducer of the negative selectable marker. For example, a cell modified to comprise an ALINK at a CDL may be treated with an inducer (e.g., a prodrug) of the negative selectable marker in order to ablate proliferating cells or to inhibit cell proliferation by killing at least a portion of proliferating cells.

The terms "exogenous activator of regulation of CDL" and "EARC" as used herein, refer to an example of an iNEP, which comprises a mechanism or system that facilitates exogenous alteration of non-coding or coding DNA transcription or corresponding translation via an activator. An EARC modification allows a user to inducibly stop or inhibit division of cells comprising the EARC by removing from the EARC-modified cells an inducer that permits transcription and/or translation of the EARC-modified CDL. For example, an inducible activator-based gene expression system may be operably linked to a CDL and used to exogenously control expression of a CDL or CDL translation, such that the presence of a drug inducible activator and corresponding inducer drug are required for CDL transcription and/or translation. In the absence of the inducer drug, cell division and/or proliferation would be stopped or inhibited (e.g., slowed to a normal cell division rate). For example, the CDL Cdk1/CDK1 may be modified to comprise a dox-bridge, such that expression of Cdk1/CDK1 and cell division and proliferation are only possible in the presence of an inducer (e.g., doxycycline).

The term "proliferation antagonist system" as used herein, refers to a natural or engineered compound(s) whose presence inhibits (completely or partially) proliferation of a cell.

The term "dox-bridge" as used herein, refers to a mechanism for separating activity of a promoter from a target transcribed region by expressing rtTA (Gossen et al., 1995) by the endogenous or exogenous promoter and rendering the transcription of target region under the control of TRE. As used herein, "rtTA" refers to the reverse tetracycline transactivator elements of the tetracycline inducible system (Gossen et al., 1995) and "TRE" refers to a promoter consisting of TetO operator sequences upstream of a minimal promoter. Upon binding of rtTA to the TRE promoter in the presence of doxycycline, transcription of loci downstream of the TRE promoter increases. The rtTA sequence may be inserted in the same transcriptional unit as the CDL or in a different location of the genome, so long as the transcriptional expression's permissive or non-permissive status of the target region is controlled by doxycycline. A dox-bridge is an example of an EARC.

As used herein, the term "fail-safe cell" refers to a cell that contains one or more homozygous, heterozygous, hemizygous or compound heterozygous ALINKs or EARCs in one or more CDLs (e.g., at least two, three, four, or five CDLs). Fail-safe cells may contain either ALINKs or EARCs or both ALINK and EARC modifications (e.g., ALINK and EARC modifications in different CDLs or in a single CDL).

As used herein, the term "fail-safe" refers to a property of a cell that is unlikely to exhibit uncontrolled (e.g., tumorigenic) proliferation. A cell can be considered "fail safe" when cell proliferation is under the control of a negative regulator or inducer, and the possibility of the cell losing the activity of the system that controls proliferation due to genetic mutation is low. The fail-safe volume will depend on the number of ALINKs and the number of ALINK-targeted CDLs (e.g., a cell with homozygous modifications of two different CDLs has a higher fail safe volume (e.g., it is less likely to lose all systems that control proliferation through genetic mutation) than a cell with a heterozygous modification of a single CDL). The fail-safe property is further described in Table 3.

DESCRIPTION OF THE DRAWINGS

The patent or application file contains at least one drawing in color. Copies of this patent or patent application publication with color drawing(s) will be provided by the Office upon request and payment of the necessary fee.

These and other features of the disclosure will become more apparent in the following detailed description in which reference is made to the appended drawings wherein:

FIG. 5A shows teratomas in C3H mice, FIG. 5B shows teratomas in FVB/N mice, and FIG. 5C shows teratomas in CD1 mice.

FIG. 8A shows FasL expression, FIG. 8B shows Ccl21b expression, FIG. 8C shows Cd200 expression, FIG. 8D shows Cd47 expression, FIG. 8E shows Mfge8 expression, FIG. 8F shows Spi6 expression, FIG. 8G H2-M3 expression, and FIG. 8H shows PD-L1 expression.

FIG. 11B is an enlarged image of the teratoma indicated by the arrow in FIG. 11A.

(FIG. 13C) is a photomicrograph showing allogenic host blood vessels.

FIG. 14A, FIG. 14B, and FIG. 14C show the three germ layers (ec=ectoderm, shown in FIG. 14A; en=endoderm, shown in FIG. 14C; me=mesoderm, shown in FIG. 14B). FIG. 14D shows a blood vessel, indicated by the red arrow, confirming that the tissues are well vascularized.

FIGS. 16A-16H are fluorescent photomicrographs showing the expression of proteins encoded by the cloaking transgenes in ES cells. FIG. 16A shows the expression of PD-L1, FIG. 16B shows the expression of CD200, FIG. 16C shows the expression of CD47, FIG. 16D shows the expression of FasL, FIG. 16E shows the expression of H2-M3, FIG. 16F shows the expression of Ccl21, FIG. 16G shows the expression of Mfge8, and FIG. 16H shows the expression of Spi6.

DETAILED DESCRIPTION OF THE DISCLOSURE

Description of Cells and Methods

Figure 1A:
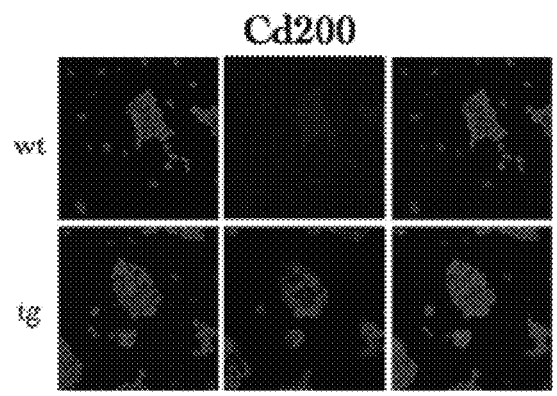
FIGS. 1A-1D depict representative images showing the expression of cloaking proteins (Cd200 (FIG. 1A), FasL (FIG. 1B), H2-M3 (FIG. 1C) and Cd47 (FIG. 1D)) in C57BL/6 mouse embryonic stem cell line C2 using immunohistochemistry.
Figure 1B:
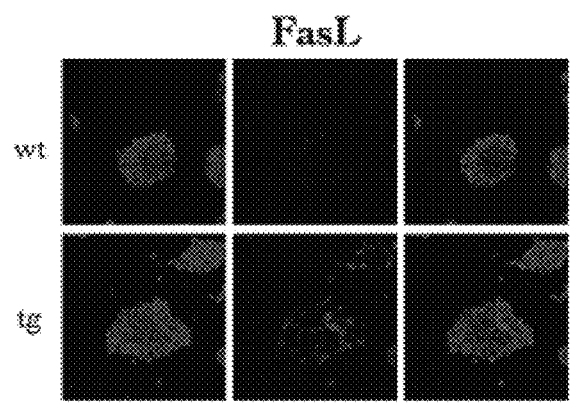
Figure 1C:
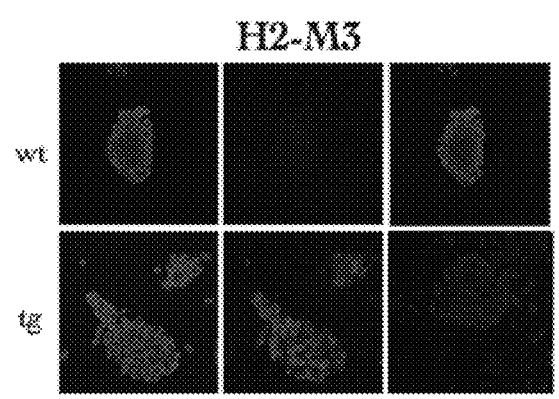
Figure 1D:
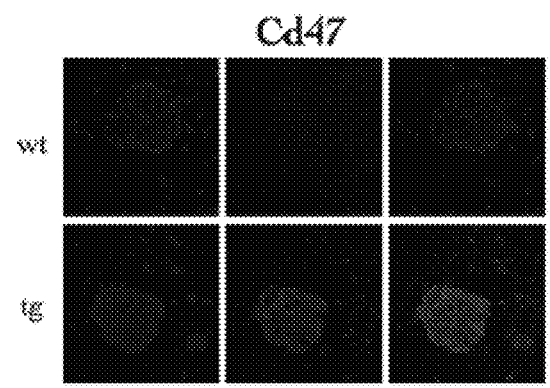

Featured are tools, such as genetically modified cells, and methods for providing a local immune suppression at a transplant site using the cells, e.g., when the cells are transplanted in an allogeneic host. The genetically modified cell comprises: one or a set of transgenes, each transgene encoding a gene product that is cytoplasmic, membrane bound, or local acting and whose function is to mitigate function of the host immune system (e.g., graft attacking leukocyte and NK cell activation) or act as a defense mechanism against attacking leukocytes.

Various cytoplasmic, membrane-bound, or local acting immune factors have been found to regulate the local immune compartment and local immune populations. Immune factors like PD-L1 (Brown et al., *J Immunol.* 170:1257-66 (2003: Curiel et al., *Nat Med.* 9:562-7 (2003); Dong et al., *Nat Med.* 8:793-800 (2002)), CD47 ((Willingham et al., *Proc Natl Acad Sci USA.* 109:6662-7 (2012); Liu et al., *PLOS One.* 10: e0137345 (2015); Demeure et al., *J Immunol.* 164:2193-9 (2000)), CD200 (Jenmalm et al., *J Immunol.* 176:191-9 (2006); Cherwinski et al., *J Immunol.* 174:1348-56 (2005); Kretz-Rommel et al., *J Immunol.* 178: 5595-605 (2007)), FasL (O'Connell et al., *J Exp Med.* 184:1075-82 (1996); Ju et al., *Nature.* 373:444-8 (1995); Mazar et al., *J Biol Chem.* 284:22022-8 (2009)), and Spi6 (Medema *Proceedings of the National Academy of Sciences of the United States of America.* 98:11515-20 (2001); Zhang et al., *Immunity.* 24:451-61 (2006); Soriano et al., *Lung Cancer.* 77:38-45 (2012)) are among the very many that have been described, including their role in immune modulation. We discovered that expression of one or more of these immune regulatory factors in an allogenic cell can be used to provide local immune suppression and/or reduce allorejection in a host to which the cells are administered.

We modified allogenic cells through the use of specific immunomodulatory factors introduced into a cell or population of cells. The modified cells evade immune rejection through the simultaneous modulation of many different local immune pathways. Such genetically engineered cells can be transplanted "off the shelf" into many recipients regardless of genetic background and without rejection by the recipient's immune system. This immunomodulatory approach overcomes the requirement for systemic immunosuppression of the transplant recipient, which can be dangerous to the recipient. Thus, although an immunosuppressive agent(s) can be administered to a patient that receives the modified cells described herein, the therapy need not include the administration of an immunosuppressive agent(s). This immunomodulatory approach also overcomes the costly and impractical methodology of deriving patient-specific iPS cells, manipulating regulatory cells, or inducing chimerism through hematopoietic cell transplantation (HCT).

Cells can be genetically modified to express a set of transgenes encoding gene products that are cytoplasmic, membrane bound, or local acting, and whose function is to mitigate immune function (e.g., graft attacking leukocyte and NK cell activation) or to act as a defense mechanism against the immune response (e.g., attacking leukocytes). The set of transgenes may be selected from the genes having a role in the immune modulatory pathways described above. Such genes include, but are not limited to those provided in Table 1.

TABLE 1

Genes that can be expressed by allogenic cells for local immunosuppression

| Gene | Function |
| --- | --- |
| PD-L1 | Induces cell death in PD-L1 expressing T cells and macrophages |
| HLA-G (mouse gene: H2-M3) | Inhibits NK cells from attacking cells lacking MHC molecules |
| Cd47 | Negative regulator of macrophages and killer T cells |
| Cd200 | Inhibits macrophage activation |
| FASLG (mouse gene: FasL) | Induces apoptosis in Fas expressing CD8+ T cells |
| Clc21 (mouse gene: Ccl21b) | Chemo-attractant for antigen presenting cells (APCs) |
| Mfge8 | Inhibition of macrophage phagocytosis |
| Serpin B9 (mouse gene: Spi6) | Inhibition of granzyme/perforin attack |
| Dad1 | Negative regulator of programmed cell death |
| Tnfrsf10 | Induces apoptosis in leukocytes expressing the TRAIL receptor |
| Cd39 | Converts ATP to AMP, inhibits T-cells |
| Cd73 | Converts AMP to adenosine, inhibits T-cells, suppresses dendritic cells |
| Lag3 | Inhibits T-cell activation, proliferation, function |
| ll1r2 | Blocks IL-1B activity, blocks inflammation and innate cell activation |
| Ackr2 | Decoy receptor for chemokines, prevents leukocyte accumulation |
| Tnfrsf22 | Decoy receptor, blocks TRAIL-induced apoptosis from T-cells |
| Tnfrsf23 | Decoy receptor, blocks TRAIL-induced apoptosis from T-cells |
| IFNγR1 d39 | Dominant negative interferon gamma receptor 1, prevents IFNγ-mediated upregulation of MHCs in ES cells |

C-C motif chemokine ligand 21 (Ccl21) is expressed by local lymph nodes where it acts to attract activated antigen presenting cells (APCs). This key function offers an opportunity to "reverse" the migration of APCs by overexpressing this gene on grafted cells. Indeed, some melanomas express Ccl21 and recruit CCR7+ cells that, in turn, can reorganize portions of their tumor stroma as "self". This leads to a stromal reconstruction that directs the recruitment and maintenance of Cd4+ Tregs (Zindl et al., *Science.* 328:697-8 (2010)). In fact, the expression of Ccl21 on tumors can protect co-implanted Ccl21 deficient tumor cells from rejection in a syngeneic allograft setting (Shields et al., *Science.* 328:749-52 (2010)). Ccl21b is the mouse ortholog of human Ccl21.

The amino acid sequences of mouse and human Ccl21 are:

```
Mouse Ccl21
                                      (SEQ ID NO: 1)
MAQMMTLSLLSLVLALCIPWTQGSDGGGQDCCLKYSQKKI

PYSIVRGYRKQEPSLGCPIPAILFLPRKHSKPELCANPEE
```

```
GWVQNLMRRLDQPPAPGKQSPGCRKNRGTSKSGKKGKGSK

GCKRTEQTQPSRG

Human Ccl21
                                      (SEQ ID NO: 2)
MAQSLALSLLILVLAFGIPRTQGSDGGAQDCCLKYSQRKI

PAKVVRSYRKQEPSLGCSIPAILFLPRKRSQAELCADPKE

LWVQQLMQHLDKTPSPQKPAQGCRKDRGASKTGKKGKGSK

GCKRTERSQTPKGP
```

Expression of Cd47 in umbilical cord blood can promote the development of hyporesponsive T-cells (Avice et al., *J Immunol.* 167:2459-68 (2001)). Erythrocytes also up-regulate Cd47 to avoid dendritic cell activation due to their lack of "self" presentation (van den Berg et al., *Immunity.* 43:622-4 (2015)). More recently, it was shown that expression of human Cd47 increases engraftment in a mouse model of pig-to-human hematopoietic cell transplantation (Tena et al., *Am J Transplant.* 14:2713-22 (2014)).

The amino acid sequences of mouse and human Cd47 are:

```
Mouse Cd47
                                      (SEQ ID NO: 3)
MWPLAAALLLGSCCCGSAQLLFSNVNSIEFTSCNETVVIP

CIVRNVEAQSTEEMFVKWKLNKSYIFIYDGNKNSTTTDQN

FTSAKISVSDLINGIASLKMDKRDAMVGNYTCEVTELSRE

GKTVIELKNRTVSWFSPNEKILIVIFPILAILLFWGKFGI

LTLKYKSSHTNKRIILLLVAGLVLTVIVVVGAILLIPGEK

PVKNASGLGLIVISTGILILLQYNVFMTAFGMTSFTIAIL

ITQVLGYVLALVGLCLCIMACEPVHGPLLISGLGIIALAE

LLGLVYMKFVASNQRTIQPPRNR
```

```
Human Cd47
                                        (SEQ ID NO: 4)
MWPLVAALLLGSACCGSAQLLFNKTKSVEFTFCNDTVVIP

CFVTNMEAQNTTEVYVKWKFKGRDIYTFDGALNKSTVPTD

FSSAKIEVSQLLKGDASLKMDKSDAVSHTGNYTCEVTELT

REGETIIELKYRVVSWFSPNENILIVIFPIFAILLFWGQF

GIKTLKYRSGGMDEKTIALLVAGLVITVIVIVGAILFVPG

EYSLKNATGLGLIVTSTGILILLHYYVFSTAIGLTSFVIA

ILVIQVIAYILAVVGLSLCIAACIPMHGPLLISGLSILAL

AQLLGLVYMKFVASNQKTIQPPRKAVEEPLNAFKESKGMM

NDE
```

Cd200 is also as an important immunoregulatory molecule; increased expression can reduce the severity of allograft rejection, autoimmunity, and allergic disease (Gorczynski et al., *J Immunol.* 172:7744-9 (2004)). It has been shown that, in vitro, APC expression of Cd200 suppresses production of interferon gamma (IFN-γ) and cytolytic granules by activated Cd8+ T-cells (Misstear et al., *J Virol.* 86:6246-57 (2012)). Most interestingly, overexpression of Cd200 increases the survival of skin and cardiac allografts in mice by promoting of Foxp3+ Treg cells (Gorczynski et al., *Transplantation.* 98:1271-8 (2014)).

The amino acid sequences of mouse and human Cd200 are:

```
Mouse Cd200
                                        (SEQ ID NO: 5)
MGSLVFRRPFCHLSTYSLIWGMAAVALSTAQVEVVTQDER

KALHTTASLRCSLKTSQEPLIVTWQKKKAVSPENMVTYSK

THGVVIQPAYKDRINVTELGLWNSSITFWNTTLEDEGCYM

CLFNTFGSQKVSGTACLTLYVQPIVHLHYNYFEDHLNITC

SATARPAPAISWKGTGTGIENSTESHFHSNGTTSVTSILR

VKDPKTQVGKEVICQVLYLGNVIDYKQSLDKGFWFSVPLL

LSIVSLVILLVLISILLYWKRHRNQERGESSQGMQRMK

Human Cd200
                                        (SEQ ID NO: 6)
MERLVIRMPFSHLSTYSLVWVMAAVVLCTAQVQVVTQDER

EQLYTPASLKCSLQNAQEALIVTWQKKKAVSPENMVTFSE

NHGVVIQPAYKDKINITQLGLQNSTITFWNITLEDEGCYM

CLFNTFGFGKISGTACLTVYVQPIVSLHYKFSEDHLNITC

SATARPAPMVFWKVPRSGIENSTVTLSHPNGTTSVTSILH

IKDPKNQVGKEVICQVLHLGTVTDFKQTVNKGYWFSVPLL

LSIVSLVILLVLISILLYWKRHRNQDRGELSQGVQKMT
```

Spi6 is an endogenous inhibitor of the cytotoxic effector molecule granzyme B released by activated Cd8+ T-cells (Sun et al., *J Biol Chem.* 272:15434-41 (1997)). Some data shows that Mesenchymal Stem Cells (MSCs) escape immune rejection by upregulating this molecule (El Haddad et al., *Blood.* 117:1176-83 (2011)). It has also recently been demonstrated that the ability of dendritic cells to present antigen to cytotoxic T cells without themselves being killed through contact mediated cytotoxicity is mediated by Spi6 (Lovo et al., *J Immunol.* 188:1057-63 (2012)). Spi6 is also known as Serpin B9.

The amino acid sequences of mouse Spi6 and the human counterpart, Serpin B9, are:

```
Mouse Spi6
                                        (SEQ ID NO: 7)
MNTLSEGNGTFAIHLLKMLCQSNPSKNVCYSPASISSALA

MVLLGAKGQTAVQISQALGLNKEEGIHQGFQLLLRKLNKP

DRKYSLRVANRLFADKTCEVLQTFKESSLHFYDSEMEQLS

FAEEAEVSRQHINTWVSKQTEGKIPELLSGGSVDSETRLV

LINALYFKGKWHQPFNKEYTMDMPFKINKDEKRPVQMMCR

EDTYNLAYVKEVQAQVLVMPYEGMELSLVVLLPDEGVDLS

KVENNLTFEKLTAWMEADFMKSTDVEVFLPKFKLQEDYDM

ESLFQRLGVVDVFQEDKADLSGMSPERNLCVSKFVHQSVV

EINEEGTEAAAASAIIEFCCASSVPTFCADHPFLFFIRHN

KANSILFCGRFSSP

Human Serpin B9
                                        (SEQ ID NO: 8)
METLSNASGTFAIRLLKILCQDNPSHNVFCSPVSISSALA

MVLLGAKGNTATQMAQALSLNTEEDIHRAFQSLLTEVNKA

GTQYLLRTANRLFGEKTCQFLSTFKESCLQFYHAELKELS

FIRAAEESRKHINTWVSKKTEGKIEELLPGSSIDAETRLV

LVNAIYFKGKWNEPFDETYTREMPFKINQEEQRPVQMMYQ

EATFKLAHVGEVRAQLLELPYARKELSLLVLLPDDGVELS

TVEKSLTFEKLTAWTKPDCMKSTEVEVLLPKFKLQEDYDM

ESVLRHLGIVDAFQQGKADLSAMSAERDLCLSKFVHKSFV

EVNEEGTEAAAASSCFVVAECCMESGPRFCADHPFLFFIR

HNRANSILFCGRFSSP
```

Activated, cytotoxic, Cd8+ can kill target cells by expression of FasL, which binds to the FAS receptor and activates a caspase-mediated apoptosis in targeted cells. However, many tumors have developed a "counterattack" by upregulating FasL on their surface (Chen et al., *J Immunol.* 171:1183-91 (2003)). Selective expression of FasL in the vasculature of human and mouse solid tumors has been associated with scarce Cd8+ T-cell infiltration and a predominance of FoxP3+ Treg cells (Motz et al. *Nat Med.* 20:607-15 (2014)). Most recently, it was shown that B-lymphocytes also use the expression of FasL to kill T helper cells at the effector stage of immune responses (Lundy et al., *Front Immunol.* 6:122 (2015)). FasL is the mouse ortholog of human FASLG.

The amino acid sequences of mouse FasL and the human counterpart, FASLG, are:

```
Mouse FasL
                                        (SEQ ID NO: 9)
MQQPMNYPCPQIFWVDSSATSSWTPPGSVFPCPSSGPRGP

DQRRPPPPPPPVSPLPPPSQPLPLPPLTPLKKKDHNTNLW

LPVVFFMVLVALVGMGLGMYQLFHLQKELAELREFTNQSL
```

```
KVSSFEKQIANPSTPSEKKELRSVAHLTGNPHSRSIPLEW

EDTYGTALISGVKYKKGSLVINEAGLYFVYSKVYFRGQSC

NNQPLNHKVYMRNSKYPGDLVLMEEKRLNYCTTGQIWAHS

SYLGAVFNLTSADHLYVNISQLSLINFEESKTFFGLYKL

Human FASLG
                                (SEQ ID NO: 10)
MQQPFNYPYPQIYWVDSSASSPWAPPGTVLPCPTSVPRRP

GQRRPPPPPPPPLPPPPPPPPLPPLPLPPLKKRGNHSTG

LCLLVMFFMVLVALVGLGLGMFQLFHLQKELAELRESTSQ

MHTASSLEKQIGHPSPPPEKKELRKVAHLTGKSNSRSMPL

EWEDTYGIVLLSGVKYKKGGLVINETGLYFVYSKVYFRGQ

SCNNLPLSHKVYMRNSKYPQDLVMMEGKMMSYCTTGQMWA

RSSYLGAVFNLTSADHLYVNVSELSLVNFEESQTFFGLYK

L
```

PD-L1 is a critical immune modulatory molecule that binds to Programmed Cell Death 1 (PD-1). PD-1 is expressed on T-cells, and binding to PD-L1 results in T-cell anergy (MacDonald et al., *J Immunol.* 126:1671-5 (1981)).

The amino acid sequences of mouse and human PD-L1 are:

```
Mouse PD-L1
                                (SEQ ID NO: 11)
MRIFAGIIFTACCHLLRAFTITAPKDLYVVEYGSNVTMEC

RFPVERELDLLALVVYWEKEDEQVIQFVAGEEDLKPQHSN

FRGRASLPKDQLLKGNAALQITDVKLQDAGVYCCIISYGG

ADYKRITLKVNAPYRKINQRISVDPATSEHELICQAEGYP

EAEVIWTNSDHQPVSGKRSVTTSRTEGMLLNVTSSLRVNA

TANDVFYCTFWRSQPGQNHTAELIIPELPATHPPQNRTHW

VLLGSILLFLIVVSTVLLFLRKQVRMLDVEKCGVEDTSSK

NRNDTQFEET

Human PDL1 (CD274)
                                (SEQ ID NO: 12)
MRIFAVFIFMTYWHLLNAFTVTVPKDLYVVEYGSNMTIEC

KFPVEKQLDLAALIVYWEMEDKNIIQFVHGEEDLKVQHSS

YRQRARLLKDQLSLGNAALQITDVKLQDAGVYRCMISYGG

ADYKRITVKVNAPYNKINQRILVVDPVTSEHELTCQAEGY

PKAEVIWTSSDHQVLSGKTTTTNSKREEKLFNVTSTLRIN

TTTNEIFYCTFRRLDPEENHTAELVIPELPLAHPPNERTH

LVILGAILLCLGVALTFIFRLRKGRMMDVKKCGIQDTNSK

KQSDTHLEET
```

Inflammatory environments, like those induced by allograft transplants, attracts macrophages and inflammatory monocytes, among many other innate immune cells. The milk fat globule epidermal growth factor-8 (Mfge-8) is expressed by many murine tumours (Neutzner et al., *Cancer Res.* 67:6777-85 (2007)) and has been shown to contribute to local immune suppression by polarizing incoming monocytes to suppressive, M2-like macrophages (Soki et al., *J Biol Chem.* 289:24560-72 (2014)).

The amino acid sequences of mouse and human MFGE-8 are:

```
Mouse MFGE8
                                (SEQ ID NO: 13)
MQVSRVLAALCGMLLCASGLFAASGDFCDSSLCLNGGTCL

TGQDNDIYCLCPEGFTGLVCNETERGPCSPNPCYNDAKCL

VTLDTQRGDIFTEYICQCPVGYSGIHCETETNYYNLDGEY

MFTTAVPNTAVPTPAPTPDLSNNLASRCSTQLGMEGGAIA

DSQISASSVYMGFMGLQRWGPELARLYRTGIVNAWTASNY

DSKPWIQVNLLRKMRVSGVMTQGASRAGRAEYLKTFKVAY

SLDGRKFEFIQDESGGDKEFLGNLDNNSLKVNMFNPTLEA

QYIKLYPVSCHRGCTLRFELLGCELHGCSEPLGLKNNTIP

DSQMSASSSYKTWNLRAFGWYPHLGRLDNQGKINAWTAQS

NSAKEWLQVDLGTQRQVTGIITQGARDFGHIQYVASYKVA

HSDDGVQWTVYEQGSSKVFQGNLDNNSHKKNIFEKPFMAR

YVRVLPVSWHNRITLRLELLGC

Human MFGE8
                                (SEQ ID NO: 14)
MPRPRLLAALCGALLCAPSLLVALDICSKNPCHNGGLCEE

ISQEVRGDVFPSYTCTCLKGYAGNHCETKCVEPLGMENGN

IANSQIAASSVRVTFLGLQHWVPELARLNRAGMVNAWTPS

SNDDNPWIQVNLLRRMWVTGVVTQGASRLASHEYLKAFKV

AYSLNGHEFDFIHDVNKKHKEFVGNWNKNAVHVNLFETPV

EAQYVRLYPTSCHTACTLRFELLGCELNGCANPLGLKNNS

IPDKQITASSSYKTWGLHLFSWNPSYARLDKQGNFNAWVA

GSYGNDQWLQVDLGSSKEVTGIITQGARNFGSVQFVASYK

VAYSNDSANWTEYQDPRTGSSKIFPGNWDNHSHKKNLFET

PILARYVRILPVAWHNRIALRLELLGC
```

The potent killing potential of NK cells is also absolutely critical in graft rejection. NK cells can kill targets cells that lack MHC class I molecules, as well as other cells within an inflammatory setting. H2-M3, the murine homologue of human HLA-G has recently been shown to have a regulatory effect on NK cells, licensing them to ignore cells that lack "self molecules" (Andrews et al., *Nat Immunol.* 13:1171-7 (2012)). This is thought to be achieved by binding of HLA-G, immunosuppressive receptors on both NK and T-cells (Carosella et al., *Adv Immunol.* 127:33-144 (2015)). H2-M3 is the mouse ortholog of human HLA-G.

The amino acid sequences of mouse H2-M3 and the human counterpart, HLA-G, are:

```
Mouse H2-M3
                                (SEQ ID NO: 15)
SIEEIPRMEPRAPWMEKERPEYWKELKLKVKNIAQSARAN

LRTLLRYYNQSEGGSHILQWMVSCEVGPDMRLLGAHYQAA

YDGSDYITLNEDLSSWTAVDMVSQITKSRLESAGTAEYFR
```

-continued
AYVEGECLELLHRFLRNGKEILQRADPPKAHVAHHPRPKG

DVTLRCWALGFYPADITLTWQKDEEDLTQDMELVETRPSG

DGTFQKWAAVVVPSGEEQRYTCYVHHEGLTEPLALKWGRS

SQSSVVIMV

Human HLA-G (SEQ ID NO: 16)
MVVMAPRTLFLLLSGALTLTETWAGSHSMRYFSAAVSRPG

RGEPRFIAMGYVDDTQFVRFDSDSACPRMEPRAPWVEQEG

PEYWEEETRNTKAHAQTDRMNLQTLRGYYNQSEASSHTLQ

WMIGCDLGSDGRLLRGYEQYAYDGKDYLALNEDLRSWTAA

DTAAQISKRKCEAANVAEQRRAYLEGTCVEWLHRYLENGK

EMLQRADPPKTHVTHHPVFDYEATLRCWALGFYPAEIILT

WQRDGEDQTQDVELVETRPAGDGTFQKWAAVVVPSGEEQR

YTCHVQHEGLPEPLMLRWKQSSLPTIPIMGIVAGLVVLAA

VVTGAAVAAVLWRKKSSD

A set of transgenes that includes one or more (e.g., one, two, three, four, five, six, seven, or all eight) of PD-L1, H2-M3, Cd47, Cd200, FasL, Ccl21b, Mfge8, and Spi6A can be expressed in cells. The cells may be, for example, stem cells or a cell that is amenable to genome editing, such as a cell that can be used for therapy and/or differentiated into a therapeutic cell type. The stem cells may be, for example, embryonic stem (ES) cells or induced pluripotent stem (iPS) cells. The set of transgenes may comprise 1, 2, 3, 4, 5, 6, 7, or all 8 of these genes or may comprise at least 1, at least 2, at least 3, at least 4, at least 5, at least 6, at least 7 of these genes. The cell may be further genetically modified to express one or more of TGF-β, Cd73, Cd39, Lag3, Il1r2, Ackr2, Tnfrsf22, Tnfrs23, Tnfrsf10, Dad1, and/or IFNγR1 d39. The TGF-β transgene may be modified to express the gene product in a membrane-bound form (i.e., such that the gene product is expressed on the cell surface of the allograft), using methods known to those skilled in the art. For example, a method for localizing TGF-β to the membrane is to co-express TGF-β with an additional transgene encoding the LRRC32 protein or any other polypeptide that results in localization of TGF-β to the cell membrane. This protein anchors TGF-β to the membrane. (Tran DQ et al., Proc Natl Acad Sci U.S.A 106:13445-50 (2009)).

The amino acid sequence of IFNγR1 d39 is:

(SEQ ID NO: 17)
MGPQAAAGRMILLVVLMLSAKVGSGALTSTEDPEPPSVPV

PTNVLIKSYNLNPVVCWEYQNMSQTPIFTVQVKVYSGSWT

DSCTNISDHCCNIYGQIMYPDVSAWARVKAKVGQKESDYA

RSKEFLMCLKGKVGPPGLEIRRKKEEQLSVLVFHPEVVVN

GESQGTMFGDGSTCYTFDYTVYVEHNRSGEILHTKHTVEK

EECNETLCELNISVSTLDSRYCISVDGISSFWQVRTEKSK

DVCIPPFHDDRKDSIWILVVAPLTVFTVVILVFAYWYTKK

NSFKRKSIMLPKSLLSVVKSATLETKPESKYSLVTPHQPA

VLESETVICEEPLSTVTAPDSPEAAEQEELSKETKALEAG

GSTSAMTPDSPPTPTQRRSFSLLSSNQSGPCSLTAYHSRN

GSDSGLVGSGSSSDLESLPNNNSETKMAEHDPPPVRKA

The genes may be human genes or murine genes. In an embodiment, the gene is of the same species as the recipient of the allograft recipient in which the cell is to be transplanted. In an embodiment, the gene is of any species in which the function of the gene is conserved or in which a designed biologic has the agonist function of the endogenous counterpart. Methods for introducing and expressing these transgenes in cells are described herein and are also known to those skilled in the art. Cells expressing these transgenes may be referred to as "cloaked" due to their ability to evade allorejection without systemic immunosuppression and without the need for immunosuppressive drugs.

It is contemplated herein that populations of cells derived from the above-described cloaked cells can also be used to produce a local immunosuppression when transplanted at a transplant site of an allogeneic recipient.

Before or after generating the cloaked cells of the disclosure, the cells can first be modified to be fail-safe cells. Fail-safe cells use cell division loci (CDLs) to control cell proliferation in animal cells. CDLs, as provided herein, are loci whose transcription product(s) are expressed during cell division. CDLs may be genetically modified, as described herein, to comprise a negative selectable marker and/or an inducible activator-based gene expression system, which allows a user to permit, ablate, and/or inhibit proliferation of the genetically modified cell(s) by adding or removing an appropriate inducer. Methods for making and using fail-safe cells are described, for example, in WO 2016/141480, the entire teachings of which are incorporated herein by reference. A cell may be made fail-safe first and then cloaked afterwards. Alternatively, a cell may be cloaked first and then made fail-safe afterwards.

The cell may be a vertebrate cell, for example, a mammalian cell, such as a human cell or a mouse cell. The cell may also be a vertebrate stem cell, for example, a mammalian stem cell, such as a human stem cell or a mouse stem cell. Preferably, the cell or stem cell is amenable to genetic modification. Preferably, the cell or stem cell is deemed by a user to have therapeutic value, meaning that the cell or stem cell may be used to treat a disease, disorder, defect or injury in a subject in need of treatment for same.

In some embodiments, the cell is a stem cell or progenitor cell (e.g., iPSC, embryonic stem cell, hematopoietic stem cell, mesenchymal stem cell, endothelial stem cell, epithelial stem cell, adipose stem or progenitor cells, germline stem cells, lung stem or progenitor cells, mammary stem cells, olfactory adult stem cells, hair follicle stem cells, multipotent stem cells, amniotic stem cells, cord blood stem cells, or neural stem or progenitor cells). In some embodiments, the stem cells are adult stem cells (e.g., somatic stem cells or tissue specific stem cells). In some embodiments, the stem or progenitor cell is capable of being differentiated (e.g., the stem cell is totipotent, pluripotent, or multipotent). In some embodiments, the cell is isolated from embryonic or neonatal tissue. In some embodiments, the cell is a fibroblast, monocytic precursor, B cell, exocrine cell, pancreatic progenitor, endocrine progenitor, hepatoblast, myoblast, preadipocyte, progenitor cell, hepatocyte, chondrocyte, smooth muscle cell, K562 human erythroid leukemia cell line, bone cell, synovial cell, tendon cell, ligament cell, meniscus cell, adipose cell, dendritic cells, or natural killer cell. In some embodiments, the cell is manipulated (e.g., converted or differentiated) into a muscle cell, erythroid-megakaryocytic cell, eosinophil, iPS cell, macrophage, T cell, islet beta-cell, neuron, cardiomyocyte, blood cell, endocrine progenitor, exocrine progenitor, ductal cell, acinar cell, alpha cell, beta cell, delta cell, PP cell, hepatocyte, cholangiocyte, or brown adipocyte. In some embodiments, the cell is a muscle cell (e.g., skeletal, smooth, or cardiac muscle cell), erythroid-megakaryocytic cell, eosinophil, iPS cell, macrophage, T cell, islet beta-cell, neuron, cardiomyocyte, blood cell (e.g., red blood cell, white blood cell, or platelet), endocrine progenitor, exocrine progenitor, ductal cell, acinar cell, alpha cell, beta cell, delta cell, PP cell, hepatocyte, cholangiocyte, or white or brown adipocyte. In some embodiments, the cell is a hormone-secreting cell (e.g., a cell that secretes insulin, oxytocin, endorphin, vasopressin, serotonin, somatostatin, gastrin, secretin, glucagon, thyroid hormone, bombesin, cholecystokinin, testosterone, estrogen, or progesterone, renin, ghrelin, amylin, or pancreatic polypeptide), an epidermal keratinocyte, an epithelial cell (e.g., an exocrine secretory epithelial cell, a thyroid epithelial cell, a keratinizing epithelial cell, a gall bladder epithelial cell, or a surface epithelial cell of the cornea, tongue, oral cavity, esophagus, anal canal, distal urethra, or vagina), a kidney cell, a germ cell, a skeletal joint synovium cell, a periosteum cell, a bone cell (e.g., osteoclast or osteoblast), a perichondrium cell (e.g., a chondroblast or chondrocyte), a cartilage cell (e.g., chondrocyte), a fibroblast, an endothelial cell, a pericardium cell, a meningeal cell, a keratinocyte precursor cell, a keratinocyte stem cell, a pericyte, a glial cell, an ependymal cell, a cell isolated from an amniotic or placental membrane, or a serosal cell (e.g., a serosal cell lining body cavities). In some embodiments, the cell is a somatic cell. In some embodiments, the cells are derived from skin or other organs, e.g., heart, brain or spinal cord, liver, lung, kidney, pancreas, bladder, bone marrow, spleen, intestine, or stomach. The cells can be from humans or other mammals (e.g., rodent, non-human primate, bovine, or porcine cells) it is contemplated herein that cloaked cells may be of use in cell-based therapies wherein it may be desirable to evade allorejection at a localized transplant site.

In some embodiments, the cloaked cells described herein survive in a host without stimulating the host immune response for one week or more (e.g., one week, two weeks, one month, two months, three months, 6 months, one year, two years, three years, four years, five years or more, e.g., for the life of the cell and/or its progeny). The cells maintain expression of the cloaking transgenes for as long as they survive in the host (e.g., if cloaking transgenes are no longer expressed, the cloaked cells may be removed by the host's immune system). In some embodiments, the cloaked cells further express a transgene encoding a protein that allows the cloaked cells to be detected in vivo (e.g., a fluorescent protein, such as GFP or other detectable marker).

It is contemplated herein that the combination of cloaked and fail-safe cells may be of use in cell-based therapies wherein it may be desirable to evade allorejection at a localized transplant site, while also being able to eliminate cells exhibiting undesirable growth rates, irrespective of whether such cells are generated before or after grafting the cells into a host. The combined cloaking and fail-safe technologies allows for localized immunoprotection while addressing the risk that the recipient will develop a malignancy because the cells are providing local immunosuppression.

Methods of Producing Cloaked Cells

The compositions and methods described herein can be used to reduce rejection of allogenic cells through expression of cloaking transgenes. A wide array of methods has been established for the delivery of proteins to mammalian cells and for the stable expression of genes encoding proteins in mammalian cells, which can be used to produce the cloaked cells described herein.

Polynucleotides Encoding Cloaking Proteins or Therapeutic Agents

One platform that can be used to achieve therapeutically effective expression of cloaking proteins or therapeutic agents in mammalian cells is via the stable expression of a gene encoding a cloaking protein or therapeutic agent (e.g., by integration into the nuclear or mitochondrial genome of a mammalian cell, or by episomal concatemer formation in the nucleus of a mammalian cell). The gene is a polynucleotide that encodes the primary amino acid sequence of the corresponding protein. In order to introduce exogenous genes into a mammalian cell, genes can be incorporated into a vector. Vectors can be introduced into a cell by a variety of methods, including transformation, transfection, transduction, direct uptake, projectile bombardment, and by encapsulation of the vector in a liposomes. Examples of suitable methods of transfecting or transforming cells include calcium phosphate precipitation, electroporation, microinjection, infection, lipofection and direct uptake. Such methods are described in more detail, for example, in Green, et al., Molecular Cloning: A Laboratory Manual, Fourth Edition (Cold Spring Harbor University Press, New York 2014); and Ausubel, et al., Current Protocols in Molecular Biology (John Wiley & Sons, New York 2015), the disclosures of each of which are incorporated herein by reference.

Cloaking proteins or therapeutic agents can also be introduced into a mammalian cell by targeting vectors containing portions of a gene encoding a cloaking protein or therapeutic agent to cell membrane phospholipids. For example, vectors can be targeted to the phospholipids on the extracellular surface of the cell membrane by linking the vector molecule to a VSV-G protein, a viral protein with affinity for all cell membrane phospholipids. Such a construct can be produced using methods well known to those of skill in the field.

Recognition and binding of the polynucleotide encoding a cloaking protein or therapeutic agent by mammalian RNA polymerase is important for gene expression. As such, one may include sequence elements within the polynucleotide that exhibit a high affinity for transcription factors that recruit RNA polymerase and promote the assembly of the transcription complex at the transcription initiation site. Such sequence elements include, e.g., a mammalian promoter, the sequence of which can be recognized and bound by specific transcription initiation factors and ultimately RNA polymerase.

Polynucleotides suitable for use in the compositions and methods described herein also include those that encode a cloaking protein or therapeutic agent downstream of a mammalian promoter. Promoters that are useful for the expression of a cloaking protein or therapeutic agent in mammalian cells include constitutive promoters. Constitutive promoters include the CAG promoter, the cytomegalovirus (CMV) promoter, the EF1α promoter, and the PGK promoter. Alternatively, promoters derived from viral genomes can also be used for the stable expression of these agents in mammalian cells. Examples of functional viral promoters that can be used to promote mammalian expression of these agents include adenovirus late promoter, vaccinia virus 7.5K promoter, SV40 promoter, tk promoter of HSV, mouse mammary tumor virus (MMTV) promoter, LTR promoter of HIV, promoter of moloney virus, Epstein barr virus (EBV) promoter, and the Rous sarcoma virus (RSV) promoter.

Once a polynucleotide encoding a cloaking protein or a therapeutic agent described herein below has been incorporated into the nuclear DNA of a mammalian cell, the transcription of this polynucleotide can be induced by methods known in the art. For example expression can be induced by exposing the mammalian cell to an external chemical reagent, such as an agent that modulates the binding of a transcription factor and/or RNA polymerase to the mammalian promoter and thus regulates gene expression. The chemical reagent can serve to facilitate the binding of RNA polymerase and/or transcription factors to the mammalian promoter, e.g., by removing a repressor protein that has bound the promoter. Alternatively, the chemical reagent can serve to enhance the affinity of the mammalian promoter for RNA polymerase and/or transcription factors such that the rate of transcription of the gene located downstream of the promoter is increased in the presence of the chemical reagent. Examples of chemical reagents that potentiate polynucleotide transcription by the above mechanisms include tetracycline and doxycycline. These reagents are commercially available (Life Technologies, Carlsbad, CA) and can be administered to a mammalian cell in order to promote gene expression according to established protocols.

Other DNA sequence elements that may be included in the nucleic acid vectors for use in the compositions and methods described herein include enhancer sequences. Enhancers represent another class of regulatory elements that induce a conformational change in the polynucleotide containing the gene of interest such that the DNA adopts a three-dimensional orientation that is favorable for binding of transcription factors and RNA polymerase at the transcription initiation site. Thus, polynucleotides for use in the compositions and methods described herein include those that encode a cloaking protein or therapeutic agent and additionally include a mammalian enhancer sequence. Many enhancer sequences are now known from mammalian genes, and examples include enhancers from the genes that encode mammalian globin, elastase, albumin, a-fetoprotein, and insulin. Enhancers for use in the compositions and methods described herein also include those that are derived from the genetic material of a virus capable of infecting a eukaryotic cell. Examples include the SV40 enhancer on the late side of the replication origin (bp 100-270), the cytomegalovirus early promoter enhancer, the polyoma enhancer on the late side of the replication origin, and adenovirus enhancers. Additional enhancer sequences that induce activation of eukaryotic gene transcription are disclosed in Yaniv, et al., Nature 297:17 (1982). An enhancer may be spliced into a vector containing a polynucleotide encoding a cloaking protein or therapeutic agent, for example, at a position 5' or 3' to this gene. In a preferred orientation, the enhancer is positioned at the 5' side of the promoter, which in turn is located 5' relative to the polynucleotide encoding a cloaking protein or therapeutic agent.

The nucleic acid vectors described herein may include a Woodchuck Posttranscriptional Regulatory Element (WPRE). The WPRE acts at the transcriptional level, by promoting nuclear export of transcripts and/or by increasing the efficiency of polyadenylation of the nascent transcript, thus increasing the total amount of mRNA in the cell. The addition of the WPRE to a vector can result in a substantial improvement in the level of transgene expression from several different promoters, both in vitro and in vivo.

In some embodiments, the nucleic acid vectors for use in the compositions and methods described herein include a reporter sequence, which can be useful in verifying gene expression, for example, in specific cells and tissues. Reporter sequences that may be provided in a transgene include DNA sequences encoding B-lactamase, β-galactosidase (LacZ), alkaline phosphatase, thymidine kinase, green fluorescent protein (GFP), chloramphenicol acetyltransferase (CAT), luciferase, and others well known in the art. When associated with regulatory elements which drive their expression, the reporter sequences provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA), and immunohistochemistry. For example, where the marker sequence is the LacZ gene, the presence of the vector carrying the signal is detected by assays for B-galactosidase activity. Where the transgene is green fluorescent protein or luciferase, the vector carrying the signal may be measured visually by color or light production in a luminometer.

Techniques for Introducing Transgenes into Cells

Transfection

Techniques that can be used to introduce a transgene, such as a cloaking transgene or a therapeutic transgene described herein, into a target cell (e.g., a mammalian cell) are well known in the art. For instance, electroporation can be used to permeabilize mammalian cells (e.g., human target cells) by the application of an electrostatic potential to the cell of interest. Mammalian cells, such as human cells, subjected to an external electric field in this manner are subsequently predisposed to the uptake of exogenous nucleic acids. Electroporation of mammalian cells is described in detail, e.g., in Chu et al., Nucleic Acids Research 15:1311 (1987), the disclosure of which is incorporated herein by reference. A similar technique, Nucleofection™, utilizes an applied electric field in order to stimulate the uptake of exogenous polynucleotides into the nucleus of a eukaryotic cell. Nucleofection™ and protocols useful for performing this technique are described in detail, e.g., in Distler et al., Experimental Dermatology 14:315 (2005), as well as in US 2010/0317114, the disclosures of each of which are incorporated herein by reference.

Additional techniques useful for the transfection of target cells include the squeeze-poration methodology. This technique induces the rapid mechanical deformation of cells in order to stimulate the uptake of exogenous DNA through membranous pores that form in response to the applied stress. This technology is advantageous in that a vector is not required for delivery of nucleic acids into a cell, such as a human target cell. Squeeze-poration is described in detail, e.g., in Sharei et al., Journal of Visualized Experiments 81: e50980 (2013), the disclosure of which is incorporated herein by reference.

Lipofection represents another technique useful for transfection of target cells. This method involves the loading of nucleic acids into a liposome, which often presents cationic functional groups, such as quaternary or protonated amines, towards the liposome exterior. This promotes electrostatic interactions between the liposome and a cell due to the anionic nature of the cell membrane, which ultimately leads to uptake of the exogenous nucleic acids, for instance, by direct fusion of the liposome with the cell membrane or by endocytosis of the complex. Lipofection is described in detail, for instance, in U.S. Pat. No. 7,442,386, the disclosure of which is incorporated herein by reference. Similar techniques that exploit ionic interactions with the cell membrane to provoke the uptake of foreign nucleic acids include contacting a cell with a cationic polymer-nucleic acid complex. Exemplary cationic molecules that associate with polynucleotides so as to impart a positive charge favorable for interaction with the cell membrane include activated dendrimers (described, e.g., in Dennig, Topics in Current Chemistry 228:227 (2003), the disclosure of which is incorporated herein by reference) polyethylenimine, and diethylaminoethyl (DEAE)-dextran, the use of which as a transfection agent is described in detail, for instance, in Gulick et al., Current Protocols in Molecular Biology 40:1:9.2:9.2.1 (1997), the disclosure of which is incorporated herein by reference. Magnetic beads are another tool that can be used to transfect target cells in a mild and efficient manner, as this methodology utilizes an applied magnetic field in order to direct the uptake of nucleic acids. This technology is described in detail, for instance, in US 2010/0227406, the disclosure of which is incorporated herein by reference.

Another useful tool for inducing the uptake of exogenous nucleic acids by target cells is laserfection, also called optical transfection, a technique that involves exposing a cell to electromagnetic radiation of a particular wavelength in order to gently permeabilize the cells and allow polynucleotides to penetrate the cell membrane. The bioactivity of this technique is similar to, and in some cases found superior to, electroporation.

Impalefection is another technique that can be used to deliver genetic material to target cells. It relies on the use of nanomaterials, such as carbon nanofibers, carbon nanotubes, and nanowires. Needle-like nanostructures are synthesized perpendicular to the surface of a substrate. DNA containing the gene, intended for intracellular delivery, is attached to the nanostructure surface. A chip with arrays of these needles is then pressed against cells or tissue. Cells that are impaled by nanostructures can express the delivered gene(s). An example of this technique is described in Shalek et al., PNAS 107:1870 (2010), the disclosure of which is incorporated herein by reference.

Magnetofection can also be used to deliver nucleic acids to target cells. The magnetofection principle is to associate nucleic acids with cationic magnetic nanoparticles. The magnetic nanoparticles are made of iron oxide, which is fully biodegradable, and coated with specific cationic proprietary molecules varying upon the applications. Their association with the gene vectors (DNA, siRNA, viral vector, etc.) is achieved by salt-induced colloidal aggregation and electrostatic interaction. The magnetic particles are then concentrated on the target cells by the influence of an external magnetic field generated by magnets. This technique is described in detail in Scherer et al., Gene Therapy 9:102 (2002), the disclosure of which is incorporated herein by reference.

Another useful tool for inducing the uptake of exogenous nucleic acids by target cells is sonoporation, a technique that involves the use of sound (typically ultrasonic frequencies) for modifying the permeability of the cell plasma membrane permeabilize the cells and allow polynucleotides to penetrate the cell membrane. This technique is described in detail, e.g., in Rhodes et al., Methods in Cell Biology 82:309 (2007), the disclosure of which is incorporated herein by reference.

Microvesicles represent another potential vehicle that can be used to modify the genome of a target cell according to the methods described herein. For instance, microvesicles that have been induced by the co-overexpression of the glycoprotein VSV-G with, e.g., a genome-modifying protein, such as a nuclease, can be used to efficiently deliver proteins into a cell that subsequently catalyzes the site-specific cleavage of an endogenous polynucleotide sequence so as to prepare the genome of the cell for the covalent incorporation of a polynucleotide of interest, such as a gene or regulatory sequence. The use of such vesicles, also referred to as Gesicles, for the genetic modification of eukaryotic cells is described in detail, e.g., in Quinn et al., Genetic Modification of Target Cells by Direct Delivery of Active Protein [abstract]. In: Methylation changes in early embryonic genes in cancer [abstract], in: Proceedings of the 18th Annual Meeting of the American Society of Gene and Cell Therapy; 2015 May 13, Abstract No. 122.

Viral Infection

In addition to achieving high rates of transcription and translation, stable expression of an exogenous gene in a mammalian cell can be achieved by integration of the polynucleotide containing the gene into the nuclear genome of the mammalian cell. A variety of vectors for the delivery and integration of polynucleotides encoding exogenous proteins into the nuclear DNA of a mammalian cell have been developed. Examples of expression vectors are disclosed in, e.g., WO 1994/011026 and are incorporated herein by reference. Expression vectors for use in the compositions and methods described herein contain a cloaking transgene or therapeutic transgene, as well as, e.g., additional sequence elements used for the expression of these agents and/or the integration of these polynucleotide sequences into the genome of a mammalian cell. Certain vectors that can be used for the expression of cloaking transgenes or therapeutic transgenes include plasmids that contain regulatory sequences, such as promoter and enhancer regions, which direct gene transcription. Other useful vectors for expression of cloaking transgenes or therapeutic transgenes contain polynucleotide sequences that enhance the rate of translation of these genes or improve the stability or nuclear export of the mRNA that results from gene transcription. These sequence elements include, e.g., 5' and 3' untranslated regions and a polyadenylation signal site in order to direct efficient transcription of the gene carried on the expression vector. The expression vectors suitable for use with the compositions and methods described herein may also contain a polynucleotide encoding a marker for selection of cells that contain such a vector. Examples of a suitable marker include genes that encode resistance to antibiotics, such as ampicillin, chloramphenicol, kanamycin, or nourseothricin.

Viral Vectors for Nucleic Acid Delivery

Viral genomes provide a rich source of vectors that can be used for the efficient delivery of a gene of interest into the genome of a target cell (e.g., a mammalian cell, such as a human cell). Viral genomes are particularly useful vectors for gene delivery because the polynucleotides contained within such genomes are typically incorporated into the nuclear genome of a mammalian cell by generalized or specialized transduction. These processes occur as part of the natural viral replication cycle, and do not require added proteins or reagents in order to induce gene integration. Examples of viral vectors include a retrovirus (e.g., Retroviridae family viral vector), adenovirus (e.g., Ad5, Ad26, Ad34, Ad35, and Ad48), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses, such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, modified vaccinia Ankara (MVA), fowlpox and canarypox). Other viruses include Norwalk virus, togavirus, flavivirus, reoviruses, papovavirus, hepadnavirus, human papilloma virus, human foamy virus, and hepatitis virus, for example. Examples of retroviruses include: avian leukosis-sarcoma, avian C-type viruses, mammalian C-type, B-type viruses, D-type viruses, oncoretroviruses, HTLV-BLV group, lentivirus, alpharetrovirus, gammaretrovirus, spumavirus (Coffin, J. M., Retroviridae: The viruses and their replication, Virology, Third Edition (Lippincott-Raven, Philadelphia, 1996)). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, U.S. Pat. No. 5,801,030, the disclosure of which is incorporated herein by reference as it pertains to viral vectors for use in gene therapy.

AAV Vectors for Nucleic Acid Delivery

In some embodiments, cloaking transgenes or therapeutic transgenes described herein are incorporated into rAAV vectors and/or virions in order to facilitate their introduction into a cell. rAAV vectors useful in the compositions and methods described herein are recombinant nucleic acid constructs that include (1) a promoter, (2) a heterologous sequence to be expressed (e.g., a cloaking transgene or therapeutic transgene described herein), and (3) viral sequences that facilitate integration and expression of the heterologous genes. The viral sequences may include those sequences of AAV that are required in cis for replication and packaging (e.g., functional ITRs) of the DNA into a virion. Such rAAV vectors may also contain marker or reporter genes. Useful rAAV vectors have one or more of the AAV WT genes deleted in whole or in part, but retain functional flanking ITR sequences. The AAV ITRs may be of any serotype suitable for a particular application. Methods for using rAAV vectors are described, for example, in Tal et al., J. Biomed. Sci. 7:279 (2000), and Monahan and Samulski, Gene Delivery 7:24 (2000), the disclosures of each of which are incorporated herein by reference as they pertain to AAV vectors for gene delivery.

The transgenes and vectors described herein (e.g., a promoter operably linked to a cloaking transgene or therapeutic transgene) can be incorporated into a rAAV virion in order to facilitate introduction of the polynucleotide or vector into a cell. The capsid proteins of AAV compose the exterior, non-nucleic acid portion of the virion and are encoded by the AAV cap gene. The cap gene encodes three viral coat proteins, VP1, VP2 and VP3, which are required for virion assembly. The construction of rAAV virions has been described, for instance, in U.S. Pat. Nos. 5,173,414; 5,139,941; 5,863,541; 5,869,305; 6,057,152; and 6,376,237; as well as in Rabinowitz et al., *J. Virol.* 76:791 (2002) and Bowles et al., *J. Virol.* 77:423 (2003), the disclosures of each of which are incorporated herein by reference as they pertain to AAV vectors for gene delivery.

rAAV virions useful in conjunction with the compositions and methods described herein include those derived from a variety of AAV serotypes including AAV 1, 2, 3, 4, 5, 6, 7, 8, 9, 10, rh10, rh39, rh43, and rh74. Construction and use of AAV vectors and AAV proteins of different serotypes are described, for instance, in Chao et al., Mol. Ther. 2:619 (2000); Davidson et al., Proc. Natl. Acad. Sci. USA 97:3428 (2000); Xiao et al., J. Virol. 72:2224 (1998); Halbert et al., J. Virol. 74:1524 (2000); Halbert et al., J. Virol. 75:6615 (2001); and Auricchio et al., Hum. Molec. Genet. 10:3075 (2001), the disclosures of each of which are incorporated herein by reference as they pertain to AAV vectors for gene delivery.

Also useful in conjunction with the compositions and methods described herein are pseudotyped rAAV vectors. Pseudotyped vectors include AAV vectors of a given serotype (e.g., AAV9) pseudotyped with a capsid gene derived from a serotype other than the given serotype (e.g., AAV1, AAV2, AAV3, AAV4, AAV5, AAV6, AAV7, AAV8, etc.). Techniques involving the construction and use of pseudotyped rAAV virions are known in the art and are described, for instance, in Duan et al., J. Virol. 75:7662 (2001); Halbert et al., J. Virol. 74:1524 (2000); Zolotukhin et al., Methods, 28:158 (2002); and Auricchio et al., Hum. Molec. Genet. 10:3075 (2001).

AAV virions that have mutations within the virion capsid may be used to infect particular cell types more effectively than non-mutated capsid virions. For example, suitable AAV mutants may have ligand insertion mutations for the facilitation of targeting AAV to specific cell types. The construction and characterization of AAV capsid mutants including insertion mutants, alanine screening mutants, and epitope tag mutants is described in Wu et al., J. Virol. 74:8635 (2000). Other rAAV virions that can be used in methods described herein include those capsid hybrids that are generated by molecular breeding of viruses as well as by exon shuffling. See, e.g., Soong et al., Nat. Genet., 25:436 (2000) and Kolman and Stemmer, Nat. Biotechnol. 19:423 (2001).

Genome Editing

In addition to the above, a variety of tools have been developed that can be used for the incorporation of a gene of interest into a target cell, such as a mammalian cell. One such method that can be used for incorporating polynucleotides encoding target genes into target cells involves the use of transposons. Transposons are polynucleotides that encode transposase enzymes and contain a polynucleotide sequence or gene of interest flanked by 5' and 3' excision sites. Once a transposon has been delivered into a cell, expression of the transposase gene commences and results in active enzymes that cleave the gene of interest from the transposon. This activity is mediated by the site-specific recognition of transposon excision sites by the transposase. In some instances, these excision sites may be terminal repeats or inverted terminal repeats. Once excised from the transposon, the gene of interest can be integrated into the genome of a mammalian cell by transposase-catalyzed cleavage of similar excision sites that exist within the nuclear genome of the cell. This allows the gene of interest to be inserted into the cleaved nuclear DNA at the complementary excision sites, and subsequent covalent ligation of the phosphodiester bonds that join the gene of interest to the DNA of the mammalian cell genome completes the incorporation process. In certain cases, the transposon may be a retrotransposon, such that the gene encoding the target gene is first transcribed to an RNA product and then reverse-transcribed to DNA before incorporation in the mammalian cell genome. Exemplary transposon systems are the piggybac transposon (described in detail in, e.g., WO 2010/085699) and the sleeping beauty transposon (described in detail in, e.g., US 2005/0112764), the disclosures of each of which are incorporated herein by reference as they pertain to transposons for use in gene delivery to a cell of interest.

Another tool for the integration of target genes into the genome of a target cell is the clustered regularly interspaced short palindromic repeats (CRISPR)/Cas system, a system that originally evolved as an adaptive defense mechanism in bacteria and archaea against viral infection. The CRISPR/Cas system includes palindromic repeat sequences within plasmid DNA and an associated Cas9 nuclease. This ensemble of DNA and protein directs site specific DNA cleavage of a target sequence by first incorporating foreign DNA into CRISPR loci. Polynucleotides containing these foreign sequences and the repeat-spacer elements of the CRISPR locus are in turn transcribed in a host cell to create a guide RNA, which can subsequently anneal to a target sequence and localize the Cas9 nuclease to this site. In this manner, highly site-specific cas9-mediated DNA cleavage can be engendered in a foreign polynucleotide because the interaction that brings cas9 within close proximity of the target DNA molecule is governed by RNA: DNA hybridization. As a result, one can design a CRISPR/Cas system to cleave any target DNA molecule of interest. This technique has been exploited in order to edit eukaryotic genomes (Hwang et al., Nature Biotechnology 31:227 (2013)) and can be used as an efficient means of site-specifically editing target cell genomes in order to cleave DNA prior to the incorporation of a gene encoding a target gene. The use of CRISPR/Cas to modulate gene expression has been described in, for example, U.S. Pat. No. 8,697,359, the disclosure of which is incorporated herein by reference as it pertains to the use of the CRISPR/Cas system for genome editing. Alternative methods for site-specifically cleaving genomic DNA prior to the incorporation of a gene of interest in a target cell include the use of zinc finger nucleases (ZFNs) and transcription activator-like effector nucleases (TALENs). Unlike the CRISPR/Cas system, these enzymes do not contain a guiding polynucleotide to localize to a specific target sequence. Target specificity is instead controlled by DNA binding domains within these enzymes. The use of ZFNs and TALENs in genome editing applications is described, e.g., in Urnov et al., Nature Reviews Genetics 11:636 (2010); and in Joung et al., Nature Reviews Molecular Cell Biology 14:49 (2013), the disclosure of each of which are incorporated herein by reference as they pertain to compositions and methods for genome editing.

Additional genome editing techniques that can be used to incorporate polynucleotides encoding target genes into the genome of a target cell include the use of ARCUS™ meganucleases that can be rationally designed so as to site-specifically cleave genomic DNA. The use of these enzymes for the incorporation of genes encoding target genes into the genome of a mammalian cell is advantageous in view of the defined structure-activity relationships that have been established for such enzymes. Single chain meganucleases can be modified at certain amino acid positions in order to create nucleases that selectively cleave DNA at desired locations, enabling the site-specific incorporation of a target gene into the nuclear DNA of a target cell. These single-chain nucleases have been described extensively in, for example, U.S. Pat. Nos. 8,021,867 and 8,445,251, the disclosures of each of which are incorporated herein by reference as they pertain to compositions and methods for genome editing.

Expression of Cloaking Transgenes

The cloaking transgenes described herein (e.g., one of, or any combination of, PD-L1, HLA-G (H2-M3), Cd47, Cd200, FASLG (FasL), Ccl21 (Ccl21b), Mfge8, and Serpin B9 (Spi6)) are expressed in an amount sufficient to produce a cloaking effect (e.g., in an amount sufficient to prevent rejection when injected into a subject, e.g., a mammalian subject, such as a mouse, rat, or human). Transgene expression can be considered to produce a cloaking effect if subcutaneous injection of cloaked cells generates a teratoma that is not removed by the subject's immune system. The cloaking transgenes are also expressed at a level that is sufficient to promote production of the proteins encoded by said transgenes. Protein production can be detected using routine methods known to those of skill in the art (e.g., immunohistochemistry, Western Blot analysis, or other methods that allow for visualization or proteins). Preferably, the expression of the cloaking transgenes is such that all 8 proteins encoded by the cloaking transgenes (PD-L1, H2-M3, Cd47, Cd200, FasL, Ccl21b, Mfge8, and Spi6) can be detected in cloaked cells (e.g., detected by immunohistochemistry using antibodies directed against the proteins encoded by the cloaking transgenes).

In some embodiments, cloaking transgenes are expressed at similar levels in cloaked cells to levels of endogenous gene expression in activated leukocytes, such as T cells (e.g., activated leukocytes from the same species, such as an activated leukocyte isolated from a lymph organ, for example expression in a cloaked mouse cell is similar to expression in an activated leukocyte isolated from a murine lymphoid organ). The expression of one or more cloaking transgenes (e.g., 1, 2, 3, 4, 5, 6, 7, or 8 of PD-L1, HLA-G (H2-M3), Cd47, Cd200, FASLG (FasL), Ccl21 (Ccl21b), Mfge8, and Serpin B9 (Spi6)) is greater than or equal to expression of the endogenous gene in activated leukocytes (e.g., T cells) from the same species (e.g., expression level of the cloaking transgene is equal to the level of expression of the endogenous gene in activated leukocytes, or is 1.5, 2, 3, 4, 5, 6, 7, 8, 9, 10-fold or more higher than the level of expression of the endogenous gene in activated leukocytes). In some embodiments, all 8 cloaking transgenes are expressed at a level that is greater than or equal to the expression level of the endogenous gene in an activated leukocyte from the same species. Activated leukocytes can be isolated from lymphoid organs, or leukocytes, such as T cells, can activated in vitro using anti-CD3/CD28 beads or other methods employed by those of skill in the art (see, e.g., Frauwith and Thompson, J. Clin Invest 109:295-299 (2002); and Trickett and Kwan, J Immunol Methods 275:251-255 (2003)). Transgene expression in cloaked cells can also be compared to gene expression levels reported in profiling studies of activated T cells (see, e.g., Palacios et al., PLOSone 2: e1222 (2007)). In some embodiments, cloaking transgene expression is compared to expression of the endogenous gene in a wild-type version of the cell (e.g., a stem cell, e.g., an embryonic stem cell from the same species as the cloaked cell). The expression of one or more cloaking transgenes (e.g., 1, 2, 3, 4, 5, 6, 7, or 8 of PD-L1, HLA-G (H2-M3), Cd47, Cd200, FASLG (FasL), Ccl21 (Ccl21b), Mfge8, and Serpin B9 (Spi6)) is at least 2, 3, 4, 5, 6, 7, 8, 9, 10, 20, 30, 40, 50, 100, 500, 1,000-fold or more higher in cloaked cells compared to expression of the endogenous gene in unmodified wild-type cells of the same cell type as the cloaked cell (e.g., stem cells, such as embryonic stem cells from the same species). In some embodiments, all 8 cloaking transgenes are expressed at a level that is greater (e.g., 2, 3, 4, 5, 6, 7, 8, 9, 10, 20, 30, 40, 50, or 100-fold higher or more) than the expression level of the endogenous gene in a wild-type version of the cell (e.g., a stem cell, e.g., an embryonic stem cell from the same species as the cloaked cell). Gene expression can be evaluated through direct comparison to isolated ES cells, or compared to stem cell expression (e.g., ES cell expression) in the Project Grandiose dataset (www.stemformatics.org/project_grandiose). Gene expression can be measured using techniques known in the art (e.g., quantitative polymerase chain reaction (qPCR)).

Methods of Providing a Local Immunosuppression at a Transplant Site

Also featured is a method of providing local immunosuppression at a transplant site.

The method comprises providing a cell; and expressing in the cell a set of transgenes, each transgene encoding a gene product that is cytoplasmic, membrane bound, or local acting and whose function is to mitigate function of graft attacking leukocyte and NK cell activation or act as a defense mechanism against attacking leukocytes.

The set of transgenes comprises one or more (e.g., two, three, four, five, six, seven, or all eight) of the following genes: PD-L1, HLA-G (H2-M3), Cd47, Cd200, FASLG (FasL), Ccl21 (Ccl21b), Mfge8, and Serpin B9 (Spi6). In an embodiment, the set of transgenes genes comprises Pd-L1, H2-M3, Cd47, Cd200, FasL, Ccl21b, Mfge8, and Spi6.

Optionally, the method further comprises expressing one or more of the following transgenes in the cell: TGF-β, Cd73, Cd39, Lag3, Il1r2, Ackr2, Tnfrsf22, Tnfrs23, Tnfrsf10, Dad1, and IFNγR1 d39. In an embodiment, the TGF-β or the biologic is local acting.

Techniques for introducing into animal cells various genetic modifications, such as transgenes are described herein and are generally known in the art.

In an embodiment of the method, the cell is a stem cell, a cell amenable to genome editing, and/or a source of therapeutic cell type (e.g., a cell that can be differentiated into a lineage restricted cell for cell therapy, or a cell of a desired target tissue). In an embodiment, the cell is an embryonic stem cell, an induced pluripotent stem cell, an adult stem cell, a tissue-specific stem cell, a hematopoietic stem cell, a mesenchymal stem cell, an endothelial stem cell, an epithelial stem cell, an adipose stem or progenitor cells, germline stem cell, a lung stem or progenitor cell, a mammary stem cell, an olfactory adult stem cell, a hair follicle stem cell, a multipotent stem cell, an amniotic stem cell, a cord blood stem cell, or a neural stem or progenitor cell. In some embodiments, the cell is derived from a target tissue, e.g., skin, heart, brain or spinal cord, liver, lung, kidney, pancreas, bladder, bone marrow, spleen, intestine, or stomach. In some embodiments, the cell is a fibroblast, an epithelial cell, or an endothelial cell. The cell may be a vertebrate cell, for example, a mammalian cell, such as a human or mouse cell. In some embodiments, the cell that is modified to express one or more (e.g., two, three, four, five, six, seven, or all eight) of PD-L1, HLA-G (H2-M3), Cd47, Cd200, FASLG (FasL), Ccl21 (Ccl21b), Mfge8, and Serpin B9 (Spi6) is a cell in the tissue or organ to be transplanted. In some embodiments, the cloaked cells (e.g., cloaked stem cells) are differentiated in vitro using methods known by those of skill in the art into a tissue or organ for transplantation.

In some embodiments, one million to one hundred billion cloaked cells (e.g., $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, or $1\times10^{11}$ cloaked cells) are administered to or near a transplant site in a subject, or into an organ or tissue to be transplanted.

Techniques for transplanting the genetically modified cells into a transplant site of an allogeneic host are described herein and are generally known in the art.

Expression of Therapeutic Agents by Cloaked Cells

The cloaked cells described herein can be further modified to express a therapeutic agent. In some embodiments, the therapeutic agent is a protein. The therapeutic protein can be a wild type form of a protein that is deficient in a subject, such as a protein that is mutated or produced in insufficient quantity (e.g., produced at low levels or not produced) by the subject's cells. In some embodiments, the therapeutic protein is an inhibitory antibody (e.g., an antibody that blocks or neutralizes protein function). The cloaked cells may be modified to produce an inhibitory antibody to treat a subject having or at risk of developing a disease or condition related to overproduction or aberrant production of a protein (e.g., production by cells that do not normally produce the protein, production of a protein at a time or in a location at which the protein is not normally produced, or production of an excessive amount of a protein). In some embodiments, the therapeutic antibody is an agonist antibody (e.g., an activating antibody). The agonist antibody can act by binding to and activating an endogenous receptor (e.g., inducing or increasing signaling downstream of receptor activation or changing the conformation of the endogenous receptor to an open or active state). The cloaked cells may be modified to produce an agonist antibody to treat a subject having or at risk of developing a disease or condition related to under activation of a receptor or signaling pathway. The cloaked cells can be modified to produce the therapeutic protein or antibody using the methods described herein or using other methods known by those of skill in the art. Cloaked cells that produce a secreted protein or antibody can be delivered as circulating cells, injected into the tissue, organ, or body site in need of the therapeutic protein or antibody, or injected subcutaneously to produce a cloaked subcutaneous tissue. Cloaked cells that produce a transmembrane or membrane-bound protein, can be injected at or near the site of the endogenous cells that respond to the therapeutic protein.

In some embodiments, the cloaked cells described herein provide a wild-type copy of a gene that is mutated in the subject (e.g., the cloaked cell is a "wild-type cell" that does not have the genetic cause of the disease and that expresses one, two, three, four, five, six, seven or all eight of PD-L1, HLA-G (H2-M3), Cd47, Cd200, FASLG (FasL), Ccl21 (Ccl21b), Mfge8, and Serpin B9 (Spi6)). Such cells can be used to treat subjects having a disease or condition caused by a mutation in an endogenous gene (e.g., subjects having a metabolic disorder associated with one or more mutations described herein below).

A list of exemplary therapeutic agents that can be administered with or produced by cloaked cells and the associated diseases or conditions that can be treated using these therapeutic agents are provided in Table 2 below.

TABLE 2

Exemplary therapeutic agents that can be administered with or expressed by cloaked cells to treat disease

| Disease or Condition | Therapeutic Agent |
|---|---|
| Diabetes, altered glycemic states | Insulin, insulotropin, glucagon |
| Skeletal growth retardation | Human growth hormone |
| Anemia | Erythropoietin (EPO), hemoglobins |
| Obesity | Ob gene translation product (leptin) |
| Immunodeficiency (e.g., AIDS) | Adenosine deaminase, purine nucleoside phosphorylase, CD-4 |
| Hemophilia A | Factor VIII |
| Hemophilia B | Factor IX |
| Emphysema | $\alpha_1$-antitrypsin |
| Hypercholesterolemia | LDL receptor protein |
| Pernicious anemia | Intrinsic factor |
| Hypoalbuminemia | Albumin |
| Gaucher's disease | B-glucosidase (glucocerebrosidase) |
| Cystic fibrosis | CF transmembrane conductance regulator |
| Cardiovascular disease | Tissue Plasminogen Activator (tPA), urokinase, streptokinase, antithrombin III, Apolipoproteins (e.g., APO B48, A1), Low Density lipoprotein receptor, vascular endothelial growth factor (VEGF) |
| Calcium mineral diseases | Calcitonin, parathyroid hormone (PTH), PTH-like hormone |
| Severe Combined Immunodeficiency (SCID) | Adenosine deaminase |
| Phenylketonuria | Phenylalanine hydroxylase |
| von Willebrand's disease | von Willebrand Factor |
| Cancers, cancer suppression | Tumor Necrosis Factors (TNFs), cytokines, anti-neoplastic agents (e.g., vincristine, doxorubicin, tamoxifen, methotrexate), interleukins (ILs), interferons (INFs), p53 and related, anti-BRCAs, anti-VEGF (bevacizumab), anti-Epidermal Growth Factor (EGF), oncogene anti-sense RNAs, antibodies (e.g., Rituximab; Daclizumab; Basiliximab; Palivizumab; Infliximab; Trastuzumab; Gemtuzumab ozogamicin; Alemtuzumab; Ibritumomab tiuxetan; Adalimumab; Omalizumab; Tositumomab-I-131; Efalizumab; Cetuximab; Bevacizumab; Natalizumab; Tocilizumab; Panitumumab; Ranibizumab; Eculizumab; Certolizumab pegol; Golimumab; Canakinumab; Ustekinumab; Ofatumumab; Denosumab; Motavizumab; Raxibacumab; Belimumab; Ipilimumab; Brentuximab Vedotin; Pertuzumab; Ado-trastuzumab emtansine; or Obinutuzumab), or checkpoint inhibitors (e.g., nivolumab, pidilizumab/CT-011, pembrolizumab, ipilimumab, or tremelimumab) |
| Peripheral vascular disease | VEGF, endothelins |
| Neurodegenerative states, and post neural trauma conditions | Ciliary Neurotrophic Factor (CNTF), Brain Derived Neurite Factor (BDNF), Nerve Growth Factor (NGF), tyrosine hydroxylase |
| Retarded fracture healing | Bone morphogenic proteins (BMP) |
| Lactose insufficiency | Lactase |
| Wound healing | Epidermal Growth Factors, Transforming Growth Factors, Granulocyte-Colony Stimulating Factors, Fibroblast Growth Factors, Interferons, Interleukins, Insulin-like growth Factors |
| Thrombosis, hypercoagulability | Antithrombins, urokinases, tPAs, hirudins, streptokinase |
| Diabetes insipidus | Antidiuretic hormone (ADH) |
| Psychiatric Disorders | Selective Serotonin Reuptake Inhibitors, anti-psychotic bio-substances |
| Pain Control | Endorphins |
| Endocrineopathies | Estrogens, Androgens, mineralocorticoids, glucocorticoids, anabolic steroids, etc. |
| Hypothyroidism | Thyroid hormones, thyroglobulins |
| Muscular dystrophy | Dystrophin |
| Infections (bacterial, fungal, viral) | Anti-microbial polypeptides |
| Shock, Sepsis | Lipid Binding Protein (LBP) |
| Leukemia | L-asparaginase |
| Disorders of digestive, pancreatic states | Pepsin, trypsin, chymotrypsin, cholecystokinin, sucrase, carboxypeptidase |
| Oxidative Stress, Neurodegenerative Disorders | Catalase |

TABLE 2-continued

Exemplary therapeutic agents that can be administered with or expressed by cloaked cells to treat disease

| Disease or Condition | Therapeutic Agent |
| --- | --- |
| Hypouricasemia, Gout | Uricase |
| Ehlers Danlos | Elastase |
| Thrombocytopenia | Thrombopoietin (TPO) |
| SCID/ADA deficiency | Adenosine deamidase |
| Porphyria | Porphobilinogen deaminase |
| Inborn errors of carboxylic and amino acid metabolism, (e.g., glutaric acidemia) | Specific enzymes catalyzing transformations at genetic block points, (e.g., glutaryl CoA dehydrogenase) |
| Homocystinuria | Cystathionine B-synthase |
| Wilson's Disease, Menke's Disease | Specific copper transporting ATPase's |
| Thalassemia | ß-globin |
| Sickle Cell Anemia | α-globin |
| Baldness | Sonic hedgehog gene products |
| Hashimoto's Thyroiditis, | Thyroid hormone |
| Wet Age-Related Macular Degeneration or Retinal Dystrophy | VEGF trap (e.g., a soluble decoy receptor described in Holash et al., Proc Natl Acad Sci U.S.A. 99:11383-11398, 2002, e.g., VEGF-Trap$_{parental}$, VEGF-Trap$_{AB1}$, VEGF-Trap$_{AB2}$, VEGF-Trap$_{R1R2}$, e.g., aflibercept), soluble forms of VEGF receptors (e.g., soluble VEGFR-1 or NRP-1), platelet factor-4, prolactin, SPARC, VEGF inhibitory antibodies (e.g., bevacizumab or ranibizumab). |
| Osteoarthritis or Rheumatoid Arthritis | TNFα inhibitors (adalimumab, etanercept, infliximab, golimumab, certolizumab), interleukin-6 (IL6) receptor inhibitors (e.g., tocilizumab), IL1 receptor inhibitors (e.g., anakinra), or other agents used to treat RA (e.g., abatacept, rituximab) |
| Inflammatory Bowel Disease, Crohn's disease, Ulcerative Colitis | TNFα inhibitors (adalimumab, etanercept, infliximab, golimumab, certolizumab), mesalazine, prednisone, azathioprine, methotrexate |
| Addison's Disease | Aldosterone, cortisol, glucocorticoids, mineralocorticoids, androgens |
| Hurler syndrome | Alpha-L iduronidase |
| Niemann-Pick disease | Sphingomyelin phosphodiesterase1 (SMPD1), NPC1 protein, or NPC2 protein |
| Tay-Sachs disease | beta-hexosaminidase A |
| Fabry disease | alpha galactosidase |
| Krabbe disease | Galactosylceramidase |
| Galactosemia | Galactokinase or galactose-1-phosphate uridyltransferase |
| Maple syrup urine disease | Enzymes of the branched-chain alpha-keto acid dehydrogenase complex |
| Phenylketonuria | Phenylalanine hydroxylase |
| Glycogen storage diseases (GSDs) | GSD0: Glycogen synthase (GYS2); GSD1/von Gierke's disease: Glucose-6-phosphatase (G6PC); GSD 2/Pompe's disease: Acid alpha-glucosidase (GAA); GSD 3/Cori's disease or Forbes' disease: Glycogen debranching enzyme (AGL); GSD 4/Andersen disease: Glycogen branching enzyme (GBE1); GSD 5/McArdle disease: Muscle glycogen phosphorylase (myophosphorylase) (PYGM); GSD 6/Hers' disease: Liver glycogen phosphorylase (PYGL) or muscle phosphoglycerate mutase (PGAM2); GSD 7/Tarui's disease: Muscle phosphofructokinase (PKFM); GSD 9: Glycogen phosphorylase kinase B (PHKA2, PHKB, PHKG2, or PHKA1), GSD 10: Enolase 3 (ENO3); GSD 11: Muscle lactate dehydrogenase (LDHA); Fanconi-Bickel syndrome: Glucose transporter 2 (GLUT2); GSD 12: Aldolase A (ALDOA); GSD 13: ß-enolase (ENO3); GSD 15: Glycogenin-1 (GYG1) |
| Mitochondrial disorders | Leber's hereditary optic neuropathy (LHON): NADH dehydrogenase; Leigh syndrome: thiamine-diphosphate kinase, thiamine triphosphate, or pyruvate |

TABLE 2-continued

Exemplary therapeutic agents that can be administered with or expressed by cloaked cells to treat disease

| Disease or Condition | Therapeutic Agent |
|---|---|
| | dehydrogenase; Neuropathy, ataxia, retinitis pigmentosa, and ptosis (NARP: ATP synthase; Myoneurogenic gastrointestinal encephalopathy (MNGIE): thymidine phosphorylase (TYMP); Mitochondria myopathy, encephalomyopathy, lactic acidosis, stroke-like symptoms (MELAS): NADH dehydrogenase |
| Friedrich's ataxia | Frataxin (FXN) |
| Peroxisomal disorders | Zellweger syndrome: Proteins encoded by PEX1, PEX2, PEX3, PEX5, PEX6, PEX10, PEX12, PEX13, PEX14, PEX16, PEX19, or PEX26; Adrenoleukodystrophy: protein encoded by ABCD1 |
| Metal metabolism disorders | Wilson disease: Wilson disease protein (ATP7B); Hemochromatosis: Human hemochromatosis protein (HFE) |
| Organic acidemias | Methylmalonic acidemia: methylmalonyl CoA mutase, methylmalonyl CoA epimerase, adenosylcobalamin Propionic academia: propionyl-CoA carboxylase |
| Urea cycle disorders | Ornithine transcarbamylase (OTC), deficiency: Ornithine transcarbamylase; Arginase (ARG1) deficiency: Arginase; Argininosuccinate lyase (ASL) deficiency: Argininosuccinate lyase; Argininosuccinate synthase 1 (ASS1) deficiency: Argininosuccinate synthase 1; Citrin deficiency: Citrin; Carbamoyl phosphate synthase 1 (CPSI) deficiency: Carbamoyl phosphate synthase 1; N-acetylglutamate synthase (NAGS) deficiency: N-acetylglutamate synthase; Ornithine translocase (ORNT1) deficiency: Ornithine translocase |

Inducible Systems for Expression of Therapeutic Agents

If continuous administration of a therapeutic agent expressed by cloaked cells is needed to treat a disease or condition, the therapeutic agent can be expressed using a constitutive promoter described herein or known by those of skill in the art (e.g., CAG, CMV, or another constitutive promoter). If the therapeutic agent is needed intermittently (e.g., needed during a period of relapse or flare up that occurs during a disease or condition, but not needed when a subject is asymptomatic), it can be expressed by an inducible promoter, which provides the capability of expressing the therapeutic agent only when it is needed. One exemplary class of therapeutic agents that could be delivered using an inducible promoter is TNFα inhibitors. TNFα inhibitors are currently used to treat rheumatoid arthritis, but are only administered intermittently during flare-ups of joint inflammation as constitutive administration of TNFα can lead to systemic immunosuppression. If cloaked cells are modified to express TNFα inhibitors under the control of an inducible promoter, cloaked cells can be used to deliver TNFα intermittently, thus, obviating the need for repeated injections. Other therapeutic agents that have potentially adverse effects if administered continuously can also be expressed intermittently using inducible promoters as described herein. Exemplary inducible expression systems are described below.

Tetracycline Response Element

One widely used inducible expression system is based on tetracycline-controlled transcriptional activation. In this system, the antibiotic tetracycline, or one of its derivatives (e.g., doxycycline), is used to reversibly activate or inhibit gene expression. To use this system, a tetracycline response element (TRE) is placed upstream of a gene of interest (e.g., a therapeutic transgene to be expressed by cloaked cells), typically along with a minimal promoter that has very low basal expression. A protein called rtTA, which also needs to be expressed by the cloaked cells, binds to the TRE and activates transcription in the presence of tetracycline or doxycycline. When tetracycline or doxycycline is removed, rtTA no longer binds to the TRE and the gene of interest is no longer expressed. Advanced versions of this system, Tet-On Advanced transactivator (rtTA2$^s$-M2) and Tet-On 3G, may be particularly useful for human therapy as they are human codon optimized and respond to low concentrations of doxycycline, Light Inducible Systems Another method for inducible activation of gene expression involves the use of optogenetics, which uses light sensitive proteins to manipulate gene expression. A recent development in optogenetics that can be used to inducibly express therapeutic agents in cloaked cells involves a class of proteins that undergo a conformational change and dimerize in response to blue light. These proteins have been fused to DNA-binding and transcriptional components that have been shown to bind to specific promoter sequences and activate transcription when brought together by exposure to blue light (Wang et al., Nat Methods, 9:266-269, 2012). This method of inducibly activating gene expression could be used to control the production of therapeutic agents in cloaked cells that are administered subcutaneously, as blue light can be shone onto the skin near the cloaked subcutaneous tissue to induce production of a therapeutic agent by the cloaked cells.

Radiogenetics

A third method of inducibly activating gene expression (e.g., expression of a therapeutic agent by cloaked cells) involves the use of radio waves. In one version of a radio wave-inducible expression system, the TRPV1 receptor is fused to a GFP binding domain and co-expressed with a form of ferritin that is linked to GFP (Stanley et al., Nat Med 21:92-98, 2015). The GFP-ferritin binds to the GFP binding domain of the TRPV1 receptor. When a radio wave of a specific frequency is applied to the cell, ferritin interacts with TRPV1 and allows for an influx of calcium, which activates the transcription factor NFAT. Therapeutic agents can be inducibly expressed using this system if they are operably linked to an NFAT-sensitive promoter element, such as SRE-CRE-NFATRE, and co-expressed with TRPV1-GFP and GFP-ferritin. Radio wave-induced expression provides the advantage of being able to induce expression in cells that are further from the outside of the body, as radio waves can pass through tissue. For example, radiogenetics could be used to regulate gene expression in the retina. This method could, therefore, be used to inducibly express therapeutic transgenes in cloaked cells with non-invasive and non-harmful radio waves.

Destabilization Domain System

Gene expression can also be regulated using destabilization domain systems. A transgene encoding a protein of interest (e.g., a therapeutic agent described herein) can also include destabilizing domains, such that the resulting protein product includes the protein of interest fused to a destabilizing domain. Exemplary destabilizing domains include mutants of the human FK506- and rapamycin-binding protein (FKBP12), which confer instability to the proteins to which they are fused. FKBP12 mutants include N-terminal mutants F15S, V24A, H25R, E60G, and L106P, and C-terminal mutants M66T, R71G, D100G, D100N, E102G, and K105I, as characterized in Banaszynski et al., Cell 126:995 (2006), the disclosure of which is incorporated herein by reference as it pertains to FKBP12 destabilizing domains. Destabilizing domains promote protein degradation. A small molecule synthetic ligand can be used to stabilize the destabilizing domain-containing proteins when expression of the protein of interest (e.g., a therapeutic agent) is desired. The small molecule ligand Shield-1 (Shld1) can be used to stabilize FKBP12 mutant-containing proteins by protecting them from degradation. Other destabilizing domains that can be used to regulate expression proteins of interest include mutants of the *E. coli* dihydrofolate reductase (ecDHFR) and mutants of the human estrogen receptor ligand binding domain (ERLBD), which confer instability resulting in degradation when fused to a protein of interest and can be stabilized by small molecule ligand trimethoprim (TMP), or by CMP8 or 4-hydroxytamoxifen (4OHT), respectively, as described in Iwamoto et al., Chem Biol. 17:981 (2010) and Miyazaki et al., J Am Chem Soc., 134:3942 (2012), the disclosures of each of which are incorporated herein by reference as they pertain to destabilization domain systems.

Cumate Switch Inducible System

Another method for inducible activation of gene expression involves the use of the cumate gene-switch system. In the repressor configuration of this system, regulation is mediated by the binding of the repressor (CymR) to the operator site (CuO), placed downstream of a strong constitutive promoter. Addition of cumate, a small molecule, relieves the repression, allowing for expression of the transgene. Alternatively, a reverse-cumate-Trans-Activator (rcTA) may be inserted upstream of a minimal CMV promoter that is operably linked to a transgene encoding a therapeutic agent. A 6-times repeat of a Cumate Operator (6×CuO) may be inserted just before the translational start (ATG) of the therapeutic transgene. In the absence of cumate, rcTA cannot bind to the 6×CuO, so the transgene encoding the therapeutic agent will not be transcribed because the 6×CuO is not active. When cumate is added, it will form a complex with rcTA, which allows for binding to 6×CuO and transcription of the transgene encoding the therapeutic agent (Mullick et al., 2006).

Ecdysone Inducible System

Another example of an inducible gene expression system is the ecdysone inducible system, in which a retinoid X receptor (RXR) and an N-terminal truncation of ecdysone receptor (EcR) fused to the activation domain of Vp16 (VpEcR) are inserted in the 5' untranslated region of a gene expressed by the cloaked cell such that they are co-expressed by an endogenous promoter. An ecdysone responsive element (EcRE), with a downstream minimal promoter, can be inserted just upstream of the start codon of the transgene encoding the therapeutic agent. Co-expressed RXR and VpEcR can heterodimerize with each other. In the absence of ecdysone or synthetic drug analog muristerone A, dimerized RXR/VpEcR cannot bind to EcRE, so the transgene encoding the therapeutic agent is not transcribed. In the presence of ecdysone or muristerone A, dimerized RXR/VpEcR can bind to EcRE, such that the transgene encoding the therapeutic agent is transcribed (No et al., 1996). As ecdysone administration has no apparent effect on mammals, its use for regulating genes should be excellent for transient inducible expression of any gene.

Ligand-Reversible Dimerization System

In another example, the transgene encoding a therapeutic agent can be modified so that it is functionally divided in to parts/domains, such as a 5' portion and a 3' portion, and an FKBP peptide sequence can be inserted into each domain. An IRES (internal ribosomal entry site) sequence may be placed between the two domains, which allows for simultaneous transcription of the two different domains to generate two separate proteins. In the absence of a dimerization agent, the two separate domains of the therapeutic agent will be functionally inactive. Upon introduction of a dimerization agent, such as rapamycin or AP20187, the FKBP peptides will dimerize, bringing together the 5' and 3' domains of the therapeutic agent and reconstituting an active protein (Rollins et al., 2000).

Cell-Based Delivery of a Therapeutic Agent

Treatment of Age-Related Macular Degeneration or Retinal Dystrophy

In one example, cloaked cells can be modified to produce a VEGF inhibitor, such as VEGF trap (e.g., a soluble decoy receptor described in Holash et al., Proc Natl Acad Sci U.S.A. 99:11383-11398, 2002, incorporated herein by reference, such as aflibercept) to treat age-related macular degeneration (AMD) or retinal dystrophy. VEGF trap is a biologic that binds to and inhibits VEGF, an angiogenic protein that can promote the formation of aberrant blood vessels. VEGF trap is used to treat wet AMD, which features aberrant growth of blood vessels beneath the retina that can lead to retinal detachment and progressive vision loss. To treat AMD, VEGF trap is typically delivered by regular injection into the eye. Cloaked cells can be modified to produce VEGF trap or another VEGF inhibitor by expression of a transgene encoding VEGF trap or another VEGF inhibitor operably linked to a constitutive or inducible promoter. Cloaked cells (e.g., stem cells) that express a VEGF inhibitor (e.g., VEGF trap) can be differentiated into retinal pigmented epithelium (RPE) cells before administration to the eye using methods known by those of skill in the art, or isolated RPE cells can be modified to express cloaking transgenes and a VEGF inhibitor. Twenty five thousand to one hundred thousand cloaked RPE cells (e.g., 25,000, 50,000, 75,000 or 100,000 cloaked RPE cells) expressing a VEGF inhibitor (e.g., VEGF trap) can be injected into the subretinal space of each eye to treat wet AMD or retinal dystrophy. Other VEGF inhibitors suitable for use in the compositions and methods described herein include soluble forms of VEGF receptors (e.g., soluble VEGFR-1 or NRP-1), platelet factor-4, prolactin, SPARC, and VEGF inhibitory antibodies (e.g., bevacizumab and ranibizumab).

Treatment of Parkinson's Disease

In another example, cloaked cells, such as dopaminergic neurons or cells (e.g., stem cells) that can be differentiated in vitro to produce dopaminergic neurons using methods known by those of skill in the art, can be administered to subjects suffering from Parkinson's disease, which is characterized by loss of dopaminergic neurons. Twenty five thousand to one hundred thousand cloaked dopaminergic neurons (e.g., 25,000, 50,000, 75,000 or 100,000 cloaked dopaminergic neurons) can be administered to the brain of a subject suffering from Parkinson's disease (e.g., stereotactically injected into the substantia nigra).

Treatment of Cardiac Infarction

The cloaked cells described herein can also be used to treat cardiac infarction (e.g., myocardial infarction, commonly known as a heart attack). Cardiac infarction occurs when blood flow decreases or stops to a part of the heart, causing damage to the heart muscle. To treat subjects who have suffered a cardiac infarction, cloaked cells (e.g., stem cells) can be differentiated into cardiac muscle cells using methods known by those of skill in the art, or isolated cardiac muscle cells can be modified to express cloaking transgenes. Five hundred million to five billion cloaked cardiac muscle cells (e.g., $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, or $5 \times 10^9$ cloaked cardiac muscle cells) can be administered to a subject by injection into the cardiac muscle to treat a subject who has suffered a cardiac infarction (e.g., to replace dead or damaged cardiac muscle cells).

Treatment of Osteoarthritis and Rheumatoid Arthritis

In another example, the cloaked cells described herein can be used to treat osteoarthritis or rheumatoid arthritis. Osteoarthritis and rheumatoid arthritis (RA) are characterized by joint inflammation, and are commonly treated with anti-inflammatory therapeutics. To treat subjects suffering from osteoarthritis or RA, cloaked cells can be modified to express anti-inflammatory biologics, such as inhibitors of TNFα (e.g., TNFα inhibitory antibodies), which are already in clinical use for the treatment of RA. Cloaked cells can be modified to produce an anti-inflammatory biologic, such as a TNFα inhibitor, by expression of a transgene encoding an anti-inflammatory biologic operably linked to a constitutive or inducible promoter. Cloaked cells (e.g., stem cells) that express an anti-inflammatory biologic (e.g., a TNFα inhibitor) can be differentiated into articular fibroblasts before administration to a joint using methods known by those of skill in the art, or isolated articular fibroblasts can be modified to express cloaking transgenes and an anti-inflammatory biologic. One million to one hundred million cloaked articular fibroblasts (e.g., $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, or $1 \times 10^8$ cloaked articular fibroblasts) expressing an anti-inflammatory biologic can be injected into an arthritic or inflamed joint (depending on joint size) to treat osteoarthritis or RA. Anti-inflammatory biologics that can be expressed by cloaked cells to treat osteoarthritis or RA include TNFα inhibitors (adalimumab, etanercept, infliximab, golimumab, certolizumab), interleukin-6 (IL6) receptor inhibitors (e.g., tocilizumab), IL1 receptor inhibitors (e.g., anakinra), or other agents used to treat RA (e.g., abatacept, rituximab).

Treatment of Diabetes

The cloaked cells can be used to treat diabetes (e.g., Type 1 or Type 2 diabetes). Type 1 diabetes results from a failure of the pancreas to produce enough insulin. Type 2 diabetes begins with insulin resistance, but a lack of insulin may develop as the disease progresses. To treat subjects suffering from diabetes, cloaked cells can be modified to express insulin, or insulin-expressing cells from a healthy subject (e.g., pancreatic beta cells from a subject without diabetes) can be modified to express one or more (e.g., one, two, three, four, five, six, seven or all eight) of cloaking transgenes PD-L1, HLA-G (H2-M3), Cd47, Cd200, FASLG (FasL), Ccl21 (Ccl21b), Mfge8, and Serpin B9 (Spi6) and administered to a subject with diabetes. Cloaked cells can be modified to produce insulin by expression of a transgene encoding insulin operably linked to a constitutive or inducible promoter. Cloaked cells (e.g., stem cells) that express insulin can be differentiated into insulin producing cells (e.g., pancreatic beta cells) prior to administration using methods known by those of skill in the art or can be administered without differentiation, or isolated pancreatic beta cells can be modified to express cloaking transgenes and, optionally, to express a transgene encoding insulin. Eight hundred million to three billion cloaked pancreatic beta cells (e.g., $8 \times 10^8$, $9 \times 10^8$, $1 \times 10^9$, $2 \times 10^9$, or $3 \times 10^9$ cloaked pancreatic beta cells) expressing insulin (e.g., expressing insulin endogenously or expressing insulin due to expression of a transgene encoding insulin) to can be injected subcutaneously in a subject to create a cloaked subcutaneous tissue that produces insulin for treating diabetes.

Treatment of Hemophilia

In another example, the cloaked cells described herein can be used to treat hemophilia. Patients with hemophilia do not produce a functional Factor VIII protein, which is a critical blood component needed for blood clotting. These patients can have severe bleeding, and the standard of care involved multiple injections per week of a purified Factor VIII protein. To treat subjects suffering from hemophilia, cloaked cells can be modified to express an additional transgene that encodes Factor VIII. Factor VIII would be expressed constitutively in cloaked cells by being operably linked to a constitutive promoter, such as CMV or CAG. Cloaked cells (e.g., stem cells) that express Factor VIII can be differentiated into cells that produce blood coagulation factors (e.g., liver sinusoidal cells or endothelial cells) prior to administration using methods known by those of skill in the art or can be administered without differentiation, or isolated Factor VIII-expressing liver sinusoidal cells or endothelial cells from a healthy subject (e.g., a subject without hemophilia) can be modified to express one or more (e.g., one, two, three, four, five, six, seven or all eight) of cloaking transgenes PD-L1, HLA-G (H2-M3), Cd47, Cd200, FASLG (FasL), Ccl21 (Ccl21b), Mfge8, and Serpin B9 (Spi6) and administered to a subject with hemophilia. Isolated Factor VIII-expressing liver sinusoidal cells or endothelial cells from a healthy subject that are modified to express one or more cloaking transgenes, can be further modified to express a transgene encoding Factor VIII, if desired to ensure that Factor VIII is expressed at high levels. Eight hundred million to three billion cloaked cells (e.g., $8\times10^8$, $9\times10^8$, $1\times10^9$, $2\times10^9$, or $3\times10^9$ cloaked cells) expressing Factor VIII (e.g., expressing Factor VIII endogenously or expressing Factor VIII due to expression of a transgene encoding Factor VIII) can be injected subcutaneously in a subject to create a cloaked subcutaneous tissue that produces Factor VIII for treating hemophilia.

Treatment of Metabolic Disorders

The cloaked cells of the invention can also be used to treat inherited metabolic disorders. In most inherited metabolic disorders, a single enzyme is not produced by the body or it is produced in a form that is defective. Inherited metabolic disorders include lysosomal storage disorders, such as Hurler syndrome (deficiency in alpha-L iduronidase), Niemann-Pick disease (mutations in SMPD1, NPC1, or NPC2), Tay-Sachs disease (mutation in HEXA), Gaucher's disease (mutation in GBA gene), Fabry disease (deficiency in alpha galactosidase due to mutation in GLA), and Krabbe disease (deficiency in galactosylceramidase due to mutations in GALC); Galactosemia (deficiency in Galactokinase or galactose-1-phosphate uridyltransferase); Maple syrup urine disease (deficiency in enzyme BCKD); Phenylketonuria (deficiency in enzyme PAH); glycogen storage diseases (GSDs), such as GSD0 (deficiency in glycogen synthase (GYS2)), GSD1/von Gierke's disease (deficiency in glucose-6-phosphatase (G6PC)), GSD 2/Pompe's disease (deficiency in acid alpha-glucosidase (GAA)), GSD 3/Cori's disease or Forbes' disease (deficiency in glycogen debranching enzyme AGL), GSD 4/Andersen disease (deficiency in glycogen branching enzyme (GBE1)), GSD 5/McArdle disease (deficiency in muscle glycogen phosphorylase (PYGM)), GSD 6/Hers' disease (deficiency in liver glycogen phosphorylase (PYGL) or muscle phosphoglycerate mutase (PGAM2)), GSD 7/Tarui's disease (deficiency in muscle phosphofructokinase (PKFM)), GSD 9 (deficiency in phosphorylase kinase (PHKA2, PHKB, PHKG2, or PHKA1)), GSD 10 (deficiency in enolase 3 (ENO3)), GSD 11 (deficiency in muscle lactate dehydrogenase (LDHA)), Fanconi-Bickel syndrome (deficiency in glucose transporter 2 (GLUT2)), GSD 12 (deficiency in aldolase A (ALDOA)), GSD 13 (deficiency in β-enolase (ENO3)), or GSD 15 (deficiency in glycogenin-1 (GYG1)); mitochondrial disorders, such as mitochondrial myopathy (Kearns-Sayre syndrome (KSS, caused by a deletion in mitochondrial DNA) and Chronic progressive external opthalmoplegia (CPEO, caused by a deletion or duplication in mitochondrial DNA or a mutation in ANT1, POLG, POLG2, or PEO1), diabetes mellitus and deafness (DAD, caused by a mutation in mitochondrial DNA at position 3243, which encodes tRNALeu (UUR)), Leber's hereditary optic neuropathy (LHON, caused by mutations in MT-ND1, MT-ND4, MT-ND4L, and MT-ND6), Leigh syndrome (associated with mutations in SURF1, MT-ATP6, MT-ND2, MT-ND3, MT-ND5, MT-ND6, BCS1L, NDUFA10, SDHA, NDUFS4, NDUFAF2, NDUFA2, NDUFAF6, COX15, NDUFS3, NDUFS8, FOXRED1, NDUFA9, NDUFA12, NDUFS7), Neuropathy, ataxia, retinitis pigmentosa, and ptosis (NARP, caused by mutations in MT-ATP6), myoneurogenic gastrointestinal encephalopathy (MNGIE, caused by mutations in TYMP), myoclonic epilepsy with ragged red fibers (MERRF, caused by mutation sin MT-TK, MT-TL1, MT-TH, MT-TS1, MT-TS2, or MT-TF), or mitochondria myopathy, encephalomyopathy, lactic acidosis, stroke-like symptoms (MELAS, caused by mutations in MT-ND1, MT-ND5, MT-TH, MT-TL1, or MT-TV); Friedrich's ataxia (mutation in FXN); peroxisomal disorders, such as Zellweger syndrome (mutations in PEX1, PEX2, PEX3, PEX5, PEX6, PEX10, PEX12, PEX13, PEX14, PEX16, PEX19, or PEX26) and adrenoleukodystrophy (mutations in ABCD1); metal metabolism disorders, such as Wilson disease (mutation in Wilson disease protein ATP7B) and hemochromatosis (mutation in human hemochromatosis protein HFE); organic acidemias, such as methylmalonic acidemia (mutations in MUT, MMAA, MMAB, MMADHC, or MCEE) and propionic academia (mutations in PCCA or PCCB); urea cycle disorders, such as ornithine transcarbamylase (OTC), deficiency, arginase (ARG1) deficiency, argininosuccinate lyase (ASL) deficiency, argininosuccinate synthase 1 (ASS1) deficiency, citrin deficiency, carbamoyl phosphate synthase 1 (CPSI) deficiency, N-acetylglutamate synthase (NAGS) deficiency, and ornithine translocase (ORNT1) deficiency.

To treat subjects suffering from a metabolic disorder, cloaked cells can be modified to express the wild-type form of the gene that is mutated in the subject or a transgene encoding the enzyme that is missing or deficient in the subject (see Table 2), or cells from a healthy subject (e.g., a subject that does not have a metabolic disorder) that express the wild-type form of the gene that is mutated in the subject or the enzyme that is deficient in the subject can be modified to express one or more (e.g., one, two, three, four, five, six, seven or all eight) of cloaking transgenes PD-L1, HLA-G (H2-M3), Cd47, Cd200, FASLG (FasL), Ccl21 (Ccl21b), Mfge8, and Serpin B9 (Spi6) and administered to a subject with a metabolic disorder. The wild-type form of the gene that is mutated in the subject or a transgene encoding the enzyme that is missing or deficient in the subject can be expressed constitutively in cloaked cells by being operably linked to a constitutive promoter, such as CMV or CAG, or can be inducibly expressed using one of the inducible expression systems described herein. Cloaked cells (e.g., stem cells) that are modified to express the wild-type form of the gene that is mutated in the subject or the enzyme that is missing or deficient in the subject can be differentiated into cells that normally express the gene or enzyme prior to administration using methods known by those of skill in the art or can be administered without differentiation, or isolated cells from a healthy subject that express the wild-type form of the gene or enzyme that is mutated or deficient in the subject can be modified to express one or more (e.g., one, two, three, four, five, six, seven or all eight) of cloaking transgenes PD-L1, HLA-G (H2-M3), Cd47, Cd200, FASLG (FasL), Ccl21 (Ccl21b), Mfge8, and Serpin B9 (Spi6) and administered to a subject with a metabolic disorder. If the subject has not already been diagnosed as having a particular mutation prior to treatment, the subject can be evaluated using standard methods to identify the mutated gene related to the metabolic disorder, to ensure that the cloaked cells express the corresponding wild-type gene. Eight hundred million to three billion cloaked cells (e.g., $8\times10^8$, $9\times10^8$, $1\times10^9$, $2\times10^9$, or $3\times10^9$ cloaked cells) expressing the wild-type form of the gene that is mutated in the subject can be injected subcutaneously to create a cloaked subcutaneous tissue that produces the corresponding wild-type protein.

Methods of Controlling Division of a Cloaked Cell

In an aspect, a method of controlling proliferation of cell at a transplant site in an allogeneic host is provided (e.g., to reduce the tumorigenic potential of a cell at the transplant site or to reduce proliferation of a cell that has become tumorigenic at a transplant site).

The method comprises: providing a cell genetically modified to comprise at least one mechanism for providing a local immunosuppression at a transplant site when transplanted in an allogeneic host the cell or a population of such cells; genetically modifying in the cell a cell division locus/loci (CDL), the CDL being one or more loci whose transcription product(s) is expressed by dividing cells (e.g., all dividing cells containing one or more of the immunosuppressive transgenes), the genetic modification of the CDL comprising one or more of: a) an ablation link (ALINK) system, the ALINK system comprising a DNA sequence encoding a negative selectable marker that is transcriptionally linked to a DNA sequence encoding the CDL; and b) an inducible exogenous activator of regulation of a CDL (EARC) system, the EARC system comprising an inducible activator-based gene expression system that is operably linked to the CDL; permitting proliferation of the genetically modified cell comprising the ALINK system by maintaining the genetically modified cell comprising the ALINK system in the absence of an inducer of the negative selectable marker or ablating and/or inhibiting proliferation of the genetically modified cell comprising the ALINK system by exposing the cell comprising the ALINK system to the inducer of the negative selectable marker; and/or permitting proliferation of the genetically modified cell comprising the EARC system by exposing the genetically modified cell comprising the EARC system to an inducer of the inducible activator-based gene expression system or preventing or inhibiting proliferation of the genetically modified cell comprising the EARC system by maintaining the cell comprising the EARC system in the absence of the inducer of the inducible activator-based gene expression system; and transplanting the cell or a population of the cells at a transplantation site in an allogeneic host. Cells that have been modified to control cell division using one or more ALINK and/or EARC systems in one or more CDLs (e.g., 2, 3, 4, or more CDLs) may be referred to as "fail-safe cells". The number of cells that can be grown from a single fail-safe cell (clone volume) before the cell loses activity of all of the systems (e.g., ALINKs or EARCs) that control cell division through genetic mutation (e.g., the number of cell divisions it would take for a cell to "escape" from control and exhibit uncontrollable cell proliferation based on mathematical modeling) determines the fail-safe volume. The fail-safe volume will depend on the number of ALINKs and the number of ALINK-targeted CDLs. The fail-safe property is further described in Table 3.

In an embodiment, a CDL has a CRISPR score (CS) of less than about-1.0 (Table 5, column 5).

In various embodiments, a CDL is a locus/loci that encodes a gene product that is relevant to cell division and/or replication (Table 5, column 6). For example, in various embodiments, a CDL is a locus/loci that encodes a gene product that is relevant to one or more of: i) cell cycle; ii) DNA replication; iii) RNA transcription and/or protein translation; and iv) metabolism (Table 5, column 7).

In an embodiment, a CDL is one or more cyclin-dependent kinases that are involved with regulating progression of the cell cycle (e.g., control of G1/S G2/M and metaphase-to-anaphase transition), such as CDK1, CDK2, CDK3, CDK4, CDK5, CDK6, CDK7, CDK8, CDK9 and/or CDK11 (Morgan, 2007). In an embodiment, a CDL is one or more cyclins that are involved with controlling progression of the cell cycle by activating one or more CDK, such as, for example, cyclinB, cyclinE, cyclinA, cyclinC, cyclinD, cyclinH, cyclinC, cyclinT, cyclinL and/or cyclinF (FUNG and POON, 2005). In an embodiment, a CDL is one or more loci involved in the anaphase-promoting complex that controls the progression of metaphase to anaphase transition in the M phase of the cell cycle (Peters, 2002). In an embodiment, a CDL is one or more loci involved with kinetochore components that control the progression of metaphase to anaphase transition in the M phase of the cell cycle (Fukagawa, 2007). In an embodiment, a CDL is one or more loci involved with microtubule components that control microtubule dynamics required for the cell cycle (Cassimeris, 1999).

In various embodiments, a CDL is a locus/loci involved with housekeeping. As used herein, the term "housekeeping gene" or "housekeeping locus" refers to one or more genes that are required for the maintenance of basic cellular function. Housekeeping genes are expressed in all cells of an organism under normal and patho-physiological conditions.

In various embodiments, a CDL is a locus/loci that encodes a gene product that is relevant to cell division and/or proliferation and has a CRISPR score of less than about-1.0. For example, in an embodiment, a CDL is a locus/loci that encodes a gene product that is relevant to one or more of: i) cell cycle; ii) DNA replication; iii) RNA transcription and/or protein translation; and iv) metabolism, and has a CRISPR

TABLE 3

Fail-safe cell volumes and their relationship to a human body were calculated using mathematical modeling. The model did not take into account an event in which CDL expression was co-lost with the loss of negative selectable marker activity, compromising cell proliferation. Therefore the values are underestimates and were calculated assuming $10^6$ forward mutation rate for the negative selectable marker. The estimated number of cells in a human body as $3.72 \times 10^{13}$ was taken from (Bianconi et al., 2013).

| CDL # | ALINK # | Genotype in CDLs | Fail-safe volume (#cells) | Relative (x) to a human body = $3.72 \times 10^{13}$ cells | Estimated weight of clones |
|---|---|---|---|---|---|
| 1 | 1 | het | 512 | 0.0000000000137 | 1 µg |
| 1 | 2 | hom | 16777216 | 0.000000451 | 31 mg |
| 2 | 3 | het, hom | 1.374E+11 | 0.004 | 0.26 kg |
| 2 | 4 | hom, hom | 1.13E+15 | 30 | 2100 kg |

In various embodiments, a CDL is a locus identified as an "essential gene" as set forth in Wang et al., 2015, which is incorporated herein by reference as if set forth in its entirety. Essential genes in Wang et al., 2015, were identified by computing a score (i.e., a CRISPR score) for each gene that reflects the fitness cost imposed by inactivation of the gene.

score of less than about-1.0. In an embodiment, the CDL may also be a housekeeping gene.

In some embodiments, the CDL is Cdk1/CDK1, Top2A/TOP2A, Cenpa/CEPNA, Birc5/BIRC5, or Eef2/EEF2. In some embodiments, the CDL is Cdk1/CDK1. In some embodiments, the CDL is Top2A/TOP2A. In some embodiments, the CDL is Eef2/EEF2. In some embodiments, the CDLs are Cdk1/CDK1 and Top2A/TOP2A or Cdk1/CDK1 and Eef2/EEF2.

A cell can be modified to be a "fail-safe" cell by linking the expression of a CDL with that of a DNA sequence encoding a negative selectable marker, thereby allowing drug-induced ablation of mitotically active cells expressing both the CDL and the negative selectable marker. Ablation of proliferating cells may be desirable, for example, when cell proliferation is uncontrolled and/or accelerated relative to a cell's normal division rate (e.g., uncontrolled cell division exhibited by cancerous cells), or when therapeutic need for the cells has passed. Ablation of proliferating cells may be achieved via a genetic modification to the cell, referred to herein as an "ablation link" (ALINK), which links the expression of a DNA sequence encoding a negative selectable marker to that of a CDL, thereby allowing elimination or sufficient inhibition of ALINK-modified proliferating cells consequently expressing the CDL locus (sufficient inhibition being inhibition of cell expansion rate to a rate that is too low to contribute to tumour formation). In the presence of a pro-drug or other inducer of the negatively selectable system, cells expressing the negative selectable marker will stop proliferating or die, depending on the mechanism of action of the selectable marker. Cells may be modified to comprise homozygous, heterozygous, hemizygous or compound heterozygous ALINKS. In one embodiment, to improve fidelity of ablation, a negative selectable marker may be introduced into all alleles functional of a CDL. In one preferred embodiment, a negative selectable marker may be introduced into all functional alleles of a CDL. The fail-safe system can be used to eliminate all of the cloaked cells, if desired.

An ALINK may be inserted in any position of CDL, which allows co-expression of the CDL and the negative selectable marker.

In some embodiments, the ALINK system comprises a herpes simplex virus-thymidine kinase/ganciclovir system, a cytosine deaminase/5-fluorocytosine system, a carboxyl esterase/irinotecan system or an iCasp9/AP1903 system.

DNA encoding a negatively selectable marker (e.g., HSV-TK), may be inserted into a CDL (e.g., CDK1) in a host cell, such that expression of the negative selectable marker causes host cells expressing the negative selectable marker and, necessarily, the CDL, to be killed in the presence of an inducer (e.g., prodrug) of the negative selectable marker (e.g., ganciclovir (GCV)). In this example, host cells modified with the ALINK will produce thymidine kinase (TK) and the TK protein will convert GCV into GCV monophosphate, which is then converted into GCV triphosphate by cellular kinases. GCV triphosphate incorporates into the replicating DNA during S phase, which leads to the termination of DNA elongation and cell apoptosis (Halloran and Fenton, 1998).

A modified HSV-TK gene (Preuβ et al., 2010) is disclosed herein as one example of DNA encoding a negative selectable marker that may be used in an ALINK genetic modification to selectively ablate cells comprising undesirable cell division rate.

It is contemplated herein that alternative and/or additional negative selectable systems could be used in the tools and/or methods provided herein. Various negative selectable marker systems are known in the art (e.g., dCK.DM (Neschadim et al., 2012)).

For example, various negative selectable system having clinical relevance have been under active development in the field of "gene-direct enzyme/prodrug therapy" (GEPT), which aims to improve therapeutic efficacy of conventional cancer therapy with no or minimal side-effects (Hedley et al., 2007; Nawa et al., 2008). Frequently, GEPT involves the use of viral vectors to deliver a gene into cancer cells or into the vicinity of cancer cells in an area of the cancer cells that is not found in mammalian cells and that produces enzymes, which can convert a relatively non-toxic prodrug into a toxic agent.

HSV-TK/GCV, cytosine deaminase/5-fluorocytosine (CD/5-FC), and carboxyl esterase/irinotecan (CE/CPT-11) are examples of negative selectable marker systems being evaluated in GEPT pre- and clinical trials (Danks et al., 2007; Shah, 2012).

To overcome the potential immunogenicity of a Herpes Simplex Virus type 1 thymidine kinase/ganciclovir (TK/GCV) system, a "humanized" suicide system has been developed by engineering the human deoxycytidine kinase enzyme to become thymidine-active and to work as a negative selectable (suicide) system with non-toxic prodrugs: bromovinyl-deoxyuridine (BVdU), L-deoxythymidine (LdT) or L-deoxyuridine (LdU) (Neschadim et al., 2012).

The CD/5-FC negative selectable marker system is a widely used "suicide gene" system. Cytosine deaminase (CD) is a non-mammalian enzyme that may be obtained from bacteria or yeast (e.g., from *Escherichia coli* or *Saccharomyces cerevisiae*, respectively) (Ramnaraine et al., 2003). CD catalyzes conversion of cytosine into uracil and is an important member of the pyrimidine salvage pathway in prokaryotes and fungi, but it does not exist in mammalian cells. 5-fluorocytosine (5-FC) is an antifungal prodrug that causes a low level of cytotoxicity in humans (Denny, 2003). CD catalyzes conversion of 5-FC into the genotoxic agent 5-FU, which has a high level of toxicity in humans (Ireton et al., 2002).

The CE/CPT-11 system is based on the carboxyl esterase enzyme, which is a serine esterase found in a different tissues of mammalian species (Humerickhouse et al., 2000). The anti-cancer agent CPT-11 is a prodrug that is activated by CE to generate an active referred to as 7-ethyl-10-hydroxycamptothecin (SN-38), which is a strong mammalian topoisomerase I inhibitor (Wierdl et al., 2001). SN-38 induces accumulation of double-strand DNA breaks in dividing cells (Kojima et al., 1998).

Another example of a negative selectable marker system is the iCasp9/AP1903 suicide system, which is based on a modified human caspase 9 fused to a human FK506 binding protein (FKBP) to allow chemical dimerization using a small molecule AP1903, which has tested safely in humans. Administration of the dimerizing drug induces apoptosis of cells expressing the engineered caspase 9 components. This system has several advantages, such as, for example, including low potential immunogenicity, since it consists of human gene products, the dimerizer drug only effects the cells expressing the engineered caspase 9 components (Straathof et al., 2005). The iCasp/AP1903 suicide system is being tested in clinical settings (Di Stasi et al., 2011).

It is contemplated herein that the negative selectable marker system of the ALINK system could be replaced with a proliferation antagonist system. The term "proliferation antagonist" as used herein, refers to a natural or engineered compound(s) whose presence inhibits (completely or partially) division of a cell. For example, Omomyc$^{ER}$ is the fusion protein of MYC dominant negative Omomyc with mutant murine estrogen receptor (ER) domain. When induced with tamoxifen (TAM), the fusion protein Omomyc$^{ER}$ localizes to the nucleus, where the dominant negative Omomyc dimerizes with C-Myc, L-Myc and N-Myc, sequestering them in complexes that are unable to bind the Myc DNA binding consensus sequences (Soucek et al., 2002). As a consequence of the lack of Myc activity, cells are unable to divide (Oricchio et al., 2014). Another example of a proliferation antagonist is A-Fos, a dominant negative to activation protein-1 (AP1) (a heterodimer of the oncogenes Fos and Jun) that inhibits DNA binding in an equimolar competition (Olive et al., 1997). A-Fos can also be fused to ER domain, rendering its nuclear localization to be induced by TAM. Omomyc$^{ER}$/tamoxifen or A-Fos$^{ER}$/tamoxifen could be a replacement for TK/GCV to be an ALINK.

A cell can also be modified to be "fail-safe" by operably linking the CDL with an EARC, such as an inducible activator-based gene expression system. Under these conditions, the CDL will only be expressed (and the cell can only divide) in the presence of the inducer of the inducible activator-based gene expression system. Under these conditions, EARC-modified cells stop dividing, significantly slow down, or die in the absence of the inducer, depending on the mechanism of action of the inducible activator-based gene expression system and CDL function. Cells may be modified to comprise homozygous or compound heterozygous EARCs or may be altered such that only EARC-modified alleles can produce functional CDLs. In an embodiment, an EARC modification may be introduced into all alleles of a CDL, for example, to provide a mechanism for cell division control.

An EARC may be inserted in any position of CDL that permits co-expression of the CDL and the activator component of the inducible system in the presence of the inducer.

In an embodiment, an "activator" based gene expression system is preferable to a "repressor" based gene expression system. For example, if a repressor is used to suppress a CDL a loss of function mutation of the repressor could release CDL expression, thereby allowing cell proliferation. In a case of an activation-based suppression of cell division, the loss of activator function (mutation) would shut down CDL expression, thereby disallowing cell proliferation.

In some embodiments, the EARC system is a dox-bridge system, a cumate switch inducible system, an ecdysone inducible system, a radio wave inducible system, or a ligand-reversible dimerization system.

A dox-bridge may be inserted into a CDL (e.g., CDK1) in a host cell, such that in the presence of an inducer (e.g., doxycycline or "DOX") the dox-bridge permits CDL expression, thereby allowing cell division and proliferation. Host cells modified with a dox-bridge EARC may comprise a reverse tetracycline Trans-Activator (rtTA) gene (Urlinger et al., 2000) under the transcriptional control of a promoter, which is active in dividing cells (e.g., in the CDL). This targeted insertion makes the CDL promoter no longer available for CDL transcription. To regain CDL transcription, a tetracycline responder element promoter (for example TRE (Agha-Mohammadi et al., 2004)) is inserted in front of the CDL transcript, which will express the CDL gene only in a situation when rtTA is expressed and doxycycline is present. When the only source of CDL expression is dox-bridged alleles, there is no CDL gene expression in the absence of doxycycline. The lack of CDL expression causes the EARC-modified cells to be compromised in their proliferation, either by death, stopping cell division, or by rendering the cell mitotic rate so slow that the EARC-modified cell could not contribute to tumor formation.

The term "dox-bridge" as used herein, refers to a mechanism for separating activity of a promoter from a target transcribed region by expressing rtTA (Gossen et al., 1995) by the endogenous or exogenous promoter and rendering the transcription of target region under the control of TRE. As used herein, "rtTA" refers to the reverse tetracycline trans-activator elements of the tetracycline inducible system (Gossen et al., 1995) and "TRE" refers to a promoter consisting of TetO operator sequences upstream of a minimal promoter. Upon binding of rtTA to the TRE promoter in the presence of doxycycline, transcription of loci downstream of the TRE promoter increases. The rtTA sequence may be inserted in the same transcriptional unit as the CDL or in a different location of the genome, so long as the transcriptional expression's permissive or non-permissive status of the target region is controlled by doxycycline. A dox-bridge is an example of an EARC.

Introduction of an EARC system into the 5' regulatory region of a CDL is also contemplated herein.

It is contemplated herein that alternative and/or additional inducible activator-based gene expression systems could be used in the tools and or methods provided herein to produce EARC modifications. Various inducible activator-based gene expression systems are known in the art.

For example, destabilizing protein domains (Banaszynski et al., 2006) fused with an acting protein product of a coding CDL could be used in conjunction with a small molecule synthetic ligand to stabilize a CDL fusion protein when cell division and/or proliferation is desirable. In the absence of a stabilizer, destabilized-CDL-protein will be degraded by the cell, which in turn would stop proliferation. When the stabilizer compound is added, it would bind to the destabilized-CDL-protein, which would not be degraded, thereby allowing the cell to proliferate.

For example, transcription activator-like effector (TALE) technology (Maeder et al., 2013) could be combined with dimerizer-regulated expression induction (Pollock and Clackson, 2002). The TALE technology could be used to generate a DNA binding domain designed to be specific to a sequence, placed together with a minimal promoter replacing the promoter of a CDL. The TALE DNA binding domain also extended with a drug dimerizing domain. The latter can bind to another engineered protein having corresponding dimerizing domain and a transcriptional activation domain.

For example, a reverse-cumate-Trans-Activator (rcTA) may be inserted in the 5' untranslated region of the CDL, such that it will be expressed by the endogenous CDL promoter. A 6-times repeat of a Cumate Operator (6×CuO) may be inserted just before the translational start (ATG) of CDL. In the absence of cumate in the system, rcTA cannot bind to the 6×CuO, so the CDL will not be transcribed because the 6×CuO is not active. When cumate is added, it will form a complex with rcTA, enabling binding to 6×CuO and enabling CDL transcription (Mullick et al., 2006).

For example, a retinoid X receptor (RXR) and an N-terminal truncation of ecdysone receptor (EcR) fused to the activation domain of Vp16 (VpEcR) may be inserted in the 5' untranslated region of a CDL such that they are co-expressed by an endogenous CDL promoter. Ecdysone responsive element (EcRE), with a downstream minimal promoter, may also be inserted in the CDL, just upstream of the starting codon. Co-expressed RXR and VpEcR can heterodimerize with each other. In the absence of ecdysone or a synthetic drug analog muristerone A, dimerized RXR/VpEcR cannot bind to EcRE, so the CDL is not transcribed. In the presence of ecdysone or muristerone A, dimerized RXR/VpEcR can bind to EcRE, such that the CDL is transcribed (No et al., 1996).

For example, a transient receptor potential vanilloid-1 (TRPV1), together with ferritin, may be inserted in the 5' untranslated region of a CDL and co-expressed by an endogenous CDL promoter. A promoter inducible by NFAT (NFATre) may also be inserted in the CDL, just upstream of the starting codon. In a normal environment, the NFAT promoter is not active. However, upon exposure to low-frequency radio waves, TRPV1 and ferritin create a wave of $Ca^{++}$ entering the cell, which in turn converts cytoplasmatic-NFAT (NFATc) to nuclear-NFAT (NFATn), that ultimately will activate the NFATre and transcribe the CDL (Stanley et al., 2015).

For example, a CDL may be functionally divided in to parts/domains: 5'-CDL and 3'CDL, and a FKBP peptide sequence may be inserted into each domain. An IRES (internal ribosomal entry site) sequence may be placed between the two domains, which will be transcribed simultaneously by a CDL promoter but will generate two separate proteins. Without the presence of an inducer, the two separate CDL domains will be functionally inactive. Upon introduction of a dimerization agent, such as rapamycin or AP20187, the FKBP peptides will dimerize, bringing together the 5' and 3' CDL parts and reconstituting an active protein (Rollins et al., 2000).

In an embodiment of the method, the genetically modified cell comprises: a set of transgenes, each transgene encoding a gene product that is cytoplasmic, membrane bound, or local acting and whose function is to mitigate function of graft attacking leukocyte and NK cell activation or act as a defense mechanism against attacking leukocytes.

Methods for genetically modifying cell to comprise at least one mechanism for providing a local immunosuppression at a transplant site when transplanted in an allogeneic host the cell or a population of such cells are described, for example, in WO 2016/141480, the entire teachings of which are incorporated herein by reference.

The set of transgenes comprises one or more of the following genes: PD-L1, HLA-G (H2-M3), Cd47, Cd200, FASLG (FasL), Ccl21 (Ccl21b), Mfge8, and Serpin B9 (Spi6). In an embodiment, the set of transgenes genes comprises PD-L1, HLA-G (H2-M3), Cd47, Cd200, FASLG (FasL), Ccl21 (Ccl21b), Mfge8, and Serpin B9 (Spi6).

Optionally, the method further comprises expressing one or more of the following transgenes in the cell: TGF-β, Cd73, Cd39, Lag3, Il1r2, Ackr2, Tnfrsf22, Tnfrs23, Tnfrsf10, Dad1, and IFNγR1 d39. In an embodiment, the TGF-β or the biologic is local acting in the graft environment.

Techniques for introducing into animal cells various genetic modifications, such as transgenes are described herein and are generally known in the art.

In an embodiment of the method, the cell is a stem cell, a cell amenable to genome editing, or a cell that can serve as a source of a therapeutic cell type (e.g., a cell that can be directed to differentiate into a lineage restricted or terminally differentiated cell that can be used for cell therapy, or a cell of a desired target tissue). In an embodiment, the cell is an embryonic stem cell, an induced pluripotent stem cell, an adult stem cell, a tissue-specific stem cell, a hematopoietic stem cell, a mesenchymal stem cell, an endothelial stem cell, an epithelial stem cell, an adipose stem or progenitor cells, germline stem cell, a lung stem or progenitor cell, a mammary stem cell, an olfactory adult stem cell, a hair follicle stem cell, a multipotent stem cell, an amniotic stem cell, a cord blood stem cell, or a neural stem or progenitor cell. In some embodiments, the cell is derived from a target tissue, e.g., skin, heart, brain or spinal cord, liver, lung, kidney, pancreas, bladder, bone marrow, spleen, intestine, or stomach. In some embodiments, the cell is a fibroblast, an epithelial cell, or an endothelial cell. The cell may be a vertebrate cell, for example a mammalian cell, such as a human or mouse cell.

Techniques for transplanting the genetically modified cells into a transplant site of an allogeneic host are described herein and are generally known in the art.

In various embodiments of any of the methods of the disclosure, the host has a degenerative disease or a condition that can be treated with cell therapy. Examples of such diseases or conditions include, but are not limited to: blindness, arthritis (e.g., osteoarthritis or rheumatoid arthritis), ischemia, diabetes (e.g., Type 1 or Type 2 diabetes), multiple sclerosis, spinal cord injury, stroke, cancer, a lung disease, a blood disease, a neurological disease, such as Parkinson's disease, Alzheimer's disease, Huntington's disease, and ALS, an enzyme or hormone deficiency, a metabolic disorder (e.g., a lysosomal storage disorder, Galactosemia, Maple syrup urine disease, Phenylketonuria, a glycogen storage disease, a mitochondrial disorder, Friedrich's ataxia, a peroxisomal disorder, a metal metabolism disorder, or an organic academia), an autoimmune disease (e.g., Psoriasis, Systemic Lupus Erythematosus, Grave's disease, Inflammatory Bowel Disease, Addison's Diseases, Sjogren's Syndrome, Hashimoto's Thyroiditis, Vasculitis, Autoimmune Hepatitis, Alopecia Areata, Autoimmune pancreatitis, Crohn's Disease, Ulcerative colitis, Dermatomyositis), age-related macular degeneration, retinal dystrophy, an infectious disease, hemophilia, a degenerative disease (e.g., Charcot-Marie-Tooth disease, chronic obstructive pulmonary disease, chronic traumatic encephalopathy, Creutzfeldt-Jakob disease, Cystic Fibrosis, Cytochrome C Oxidase deficiency, Ehlers-Danlos syndrome, essential tremor, Fribrodisplasia Ossificans Progressiva, infantile neuroaxonal dystrophy, keratoconus, keratoglobus, muscular dystrophy, neuronal ceroid lipofuscinosis, a prior disease, progressive supranuclear palsy, sandhoff disease, spinal muscular atrophy, retinitis pigmentosa), or an age-related disease (e.g., atherosclerosis, cardiovascular disease (e.g., angina, myocardial infarction), cataracts, osteoporosis, or hypertension).

Pharmaceutical Compositions

The cloaked cells described herein may be incorporated into a vehicle for administration into a patient, such as a human patient receiving a transplant or suffering from a disease or condition described herein. Pharmaceutical compositions containing cloaked cells can be prepared using methods known in the art. For example, such compositions can be prepared using, e.g., physiologically acceptable carriers, excipients or stabilizers (Remington: The Science and Practice of Pharmacology 22nd edition, Allen, L. Ed. (2013); incorporated herein by reference), and in a desired form, e.g., in the form of aqueous solutions.

The cloaked cells described herein can be administered in any physiologically compatible carrier, such as a buffered saline solution. Pharmaceutically acceptable carriers and diluents include saline, aqueous buffer solutions, solvents and/or dispersion media. The use of such carriers and diluents is well known in the art. Other examples include liquid media, for example, Dulbeccos modified eagle's medium (DMEM), sterile saline, sterile phosphate buffered saline, Leibovitz's medium (L15, Invitrogen, Carlsbad, Calif.), dextrose in sterile water, and any other physiologically acceptable liquid. Dispersions may also be prepared in glycerol, liquid polyethylene glycols, and mixtures thereof and in oils. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. In many cases, it will be preferable to include isotonic agents, for example, sugars or sodium chloride. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosol, and the like. Solutions of the invention can be prepared by using a pharmaceutically acceptable carrier or diluent and, as required, other ingredients enumerated above, followed by filtered sterilization, and then incorporating the cloaked cells as described herein.

For example, a solution containing a pharmaceutical composition described herein may be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. The person responsible for administration will, in any event, determine the appropriate dose for the individual subject. Moreover, for human administration, preparations may meet sterility, pyrogenicity, general safety, and purity standards as required by FDA Office of Biologics standards.

Pharmaceutical compositions comprising cloaked cells in a semi-solid or solid carrier are typically formulated for surgical implantation at the site of transplantation or at the affected site of a disease or condition in the subject. It will be appreciated that liquid compositions also may be administered by surgical procedures. In particular embodiments, semi-solid or solid pharmaceutical compositions may comprise semi-permeable gels, matrices, cellular scaffolds and the like, which may be non-biodegradable or biodegradable. For example, in certain embodiments, it may be desirable or appropriate to sequester the cloaked cells from their surroundings, yet enable the cells to secrete and deliver biological molecules (e.g., a therapeutic agent listed in Table 2) to surrounding cells.

In other embodiments, different varieties of degradable gels and networks are utilized for the pharmaceutical compositions of the invention. For example, degradable materials include biocompatible polymers, such as poly(lactic acid), poly(lactic acid-co-glycolic acid), methylcellulose, hyaluronic acid, collagen, and the like.

In another embodiment, one or more hydrogels are used for the pharmaceutical compositions. The one or more hydrogels may include collagen, atelocollagen, fibrin constructs, hydrophilic vinyl and acrylic polymers, polysaccharides such as calcium alginate, and poly(ethylene oxide). Further, the hydrogel may be formed of poly(2-hydroxyethyl methacrylate), poly(acrylic acid), self-assembling peptides (e.g., RAD16), poly(methacrylic acid), poly(N-vinyl-2-pyrrolidinone), poly(vinyl alcohol) and their copolymers with each other and with hydrophobic monomers such as methyl methacrylate, vinyl acetate, and the like. Also preferred are hydrophilic polyurethanes containing large poly(ethylene oxide) blocks. Other preferred materials include hydrogels comprising interpenetrating networks of polymers, which may be formed by addition or by condensation polymerization, the components of which may comprise hydrophilic and hydrophobic monomers such as those just enumerated. In situ-forming degradable networks are also suitable for use in the invention (see, e.g., Anseth, K S et al. *J. Controlled Release,* 2002; 78:199-209; Wang, D. et al., *Biomaterials,* 2003; 24:3969-3980; U.S. Patent Publication 2002/0022676). These in situ forming materials are formulated as fluids suitable for injection; then may be induced to form a hydrogel by a variety of means such as change in temperature, pH, and exposure to light in situ or in vivo. In one embodiment, the construct contains fibrin glue containing gels. In another embodiment, the construct contains atelocollagen containing gels.

A polymer used to form a matrix may be in the form of a hydrogel. In general, hydrogels are cross-linked polymeric materials that can absorb more than 20% of their weight in water while maintaining a distinct three-dimensional structure. This definition includes dry cross-linked polymers that will swell in aqueous environments, as well as water-swollen materials. A host of hydrophilic polymers can be cross-linked to produce hydrogels, whether the polymer is of biological origin, semi-synthetic or wholly synthetic. The hydrogel may be produced from a synthetic polymeric material. Such synthetic polymers can be tailored to a range of properties and predictable lot-to-lot uniformity, and represent a reliable source of material that generally is free from concerns of immunogenicity. The matrices may include hydrogels formed from self assembling peptides, such as those discussed in U.S. Pat. Nos. 5,670,483 and 5,955,343, U.S. Patent Application No. 2002/0160471, and PCT Application No. WO 02/062969.

Properties that make hydrogels valuable in drug delivery applications include the equilibrium swelling degree, sorption kinetics, solute permeability, and their in vivo performance characteristics. Permeability to compounds depends, in part, upon the swelling degree or water content and the rate of biodegradation. Since the mechanical strength of a gel may decline in proportion to the swelling degree, it is also well within the contemplation of the present invention that the hydrogel can be attached to a substrate so that the composite system enhances mechanical strength. In some embodiments, the hydrogel can be impregnated within a porous substrate, so as to gain the mechanical strength of the substrate, along with the useful delivery properties of the hydrogel.

In other embodiments, the pharmaceutical composition comprises a biocompatible matrix made of natural, modified natural or synthetic biodegradable polymers, including homopolymers, copolymers and block polymers, as well as combinations thereof.

Examples of suitable biodegradable polymers or polymer classes include any biodegradable polymers discussed within this disclosure, including but not limited to, fibrin, collagen types I, II, III, IV and V, elastin, gelatin, vitronectin, fibronectin, laminin, thrombin, poly(aminoacid), oxidized cellulose, tropoelastin, silk, ribonucleic acids, deoxyribonucleic acids; proteins, polynucleotides, gum arabic, reconstituted basement membrane matrices, starches, dextrans, alginates, hyaluron, chitin, chitosan, agarose, polysaccharides, hyaluronic acid, poly(lactic acid), poly(glycolic acid), polyethylene glycol, decellularized tissue, self-assembling peptides, polypeptides, glycosaminoglycans, their derivatives and mixtures thereof. Suitable polymers also include poly(lactide) (PLA) which can be formed of L(+) and D(−) polymers, polyhydroxybutyrate, polyurethanes, polyphoshazenes, poly(ethylene glycol)-poly(lactide-co-glycolide) co-polymer, degradable polycyanoacrylates and degradable polyurethanes. For both glycolic acid and lactic acid, an intermediate cyclic dimer is may be prepared and purified prior to polymerization. These intermediate dimers are called glycolide and lactide, respectively.

Other useful biodegradable polymers or polymer classes include, without limitation, aliphatic polyesters, poly(alkylene oxalates), tyrosine derived polycarbonates, polyiminocarbonates, polyorthoesters, polyoxaesters, polyamidoesters, polyoxaesters containing amine groups, poly(propylene fumarate), polyfumarates, polydioxanones, polycarbonates, polyoxalates, poly(alpha-hydroxyacids), poly(esters), polyurethane, poly(ester urethane), poly(ether urethane), polyanhydrides, polyacetates, polycaprolactones, poly(orthoesters), polyamino acids, polyamides and blends and copolymers thereof. Additional useful biodegradable polymers include, without limitation stereopolymers of L- and D-lactic acid, copolymers of bis(para-carboxyphenoxy) propane and sebacic acid, sebacic acid copolymers, copolymers of caprolactone, poly(lactic acid)/poly(glycolic acid)/polyethyleneglycol copolymers, copolymers of polyurethane and poly(lactic acid), copolymers of alpha-amino acids, copolymers of alpha-amino acids and caproic acid, copolymers of alpha-benzyl glutamate and polyethylene glycol, copolymers of succinate and poly(glycols), polyphosphazene, poly(hydroxyalkanoates) and mixtures thereof. Binary and ternary systems also are contemplated.

In general, the material used to form a matrix is desirably configured so that it: (1) has mechanical properties that are suitable for the intended application; (2) remains sufficiently intact until tissue has in-grown and healed; (3) does not invoke an inflammatory or toxic response; (4) is metabolized in the body after fulfilling its purpose; (5) is easily processed into the desired final product to be formed; (6) demonstrates acceptable shelf-life; and (7) is easily sterilized.

In another embodiment, the population of cloaked cells can be administered by use of a scaffold. The composition, shape, and porosity of the scaffold may be any described above. Typically, these three-dimensional biomaterials contain the living cells attached to the scaffold, dispersed within the scaffold or incorporated in an extracellular matrix entrapped in the scaffold. Once implanted into the target region of the body, these implants become integrated with the host tissue, wherein the transplanted cells gradually become established.

Non-limiting examples of scaffolds that may be used include textile structures, such as weaves, knits, braids, meshes, non-wovens, and warped knits; porous foams, semi-porous foams, perforated films or sheets, microparticles, beads, and spheres and composite structures being a combination of the above structures. Nonwoven mats may, for example, be formed using fibers comprised of a synthetic absorbable copolymer of glycolic and lactic acids (PGA/PLA), sold under the tradename VICRYL sutures (Ethicon, Inc., Somerville, N.J.). Foams, composed of, for example, poly(epsilon-caprolactone)/poly(glycolic acid) (PCL/PGA) copolymer, formed by processes such as freeze-drying, or lyophilized, as discussed in U.S. Pat. No. 6,355,699, also may be utilized.

In another embodiment, the framework is a felt, which can be composed of a multifilament yarn made from a bioabsorbable material. The yarn can be made into a felt using standard textile processing techniques consisting of crimping, cutting, carding and needling. In another embodiment, cells are seeded onto foam scaffolds that may be used as composite structures.

The framework may be molded into a useful shape, such as to fill a tissue void. The framework can therefore be shaped to not only provide a channel for neural growth, but also provide a scaffold for the supporting and surrounding tissues, such as vascular tissue, muscle tissue, and the like. Furthermore, it will be appreciated that the population of cells may be cultured on pre-formed, non-degradable surgical or implantable devices.

Pharmaceutical compositions may include preparations made from cloaked cells that are formulated with a pharmaceutically acceptable carrier or medium. Suitable pharmaceutically acceptable carriers include any discussed within this disclosure, including but not limited to, water, salt solution (such as Ringer's solution), alcohols, oils, gelatins, polyvinyl pyrrolidine, carbohydrates such as lactose, amylose, or starch, fatty acid esters, and hydroxymethylcellulose. Such preparations can be sterilized, and if desired, mixed with auxiliary agents such as lubricants, preservatives, stabilizers, wetting agents, emulsifiers, salts for influencing osmotic pressure, buffers, and coloring agents. Pharmaceutical carriers suitable for use in the present invention are known in the art and are described, for example, in Pharmaceutical Sciences (17$^{th}$ Ed., Mack Pub. Co., Easton, Pa.) and WO 96/05309.

Methods of Treatment

The cloaked cells and compositions described herein may be administered to a subject in need thereof (e.g., a subject who is receiving or has received a transplant, or a subject having a disease or condition described herein) by a variety of routes, such as local administration to or near the site of a transplant, local administration to the site affected by the disease or condition (e.g., injection to a joint for treating RA, injection into the subretinal space for treating wet AMD, direct administration to the central nervous system (CNS) (e.g., intracerebral, intraventricular, intrathecal, intracisternal, or stereotactic administration) for treating a neurological disease, such as Parkinson's disease, direct injection into the cardiac muscle for treating cardiac infarction), intravenous, parenteral, intradermal, transdermal, intramuscular, intranasal, subcutaneous, percutaneous, intratracheal, intraperitoneal, intraarterial, intravascular, inhalation, perfusion, lavage, and oral administration. The most suitable route for administration in any given case will depend on the particular cells or composition administered, the patient, pharmaceutical formulation methods, administration methods (e.g., administration time and administration route), the patient's age, body weight, sex, severity of the disease being treated, the patient's diet, and the patient's excretion rate. Compositions may be administered once, or more than once (e.g., once annually, twice annually, three times annually, bimonthly, or monthly). For local administration, the cloaked cells may be administered by any means that places the population of cells in a desired location, including catheter, syringe, shunt, stent, microcatheter, pump, implantation with a device, or implantation with a scaffold.

As described herein, before administration, the population of cells can be incubated in the presence of one or more factors, or under conditions, that stimulate stem cell differentiation into a desired cell type (e.g., a neuron, a cardiac muscle cell, an RPE cell, an insulin producing cell, a blood coagulation factor producing cell, an articular fibroblast, or other cell types described herein). Such factors are known in the art and the skilled artisan will appreciate that determination of suitable conditions for differentiation can be accomplished with routine experimentation. Such factors include growth or trophic factors, chemokines, cytokines, cellular products, demethylating agents, and other stimuli which are known to stimulate differentiation, for example, of stem cells along angiogenic, hemangiogenic, vasculogenic, skeletal muscle, vascular smooth muscle, pericyte, neuronal, or vascular endothelial pathways or lineages. Alternatively, the composition administered to the patient includes a population of cloaked cells with one or more factors that stimulate cell differentiation into a desired cell type, where the cell differentiation occurs in vivo at the tissue site. In some embodiments, the cloaked cells can be differentiated into an organ or tissue in vitro using methods known by those of skill in the art and administered to a subject in need of an organ or tissue transplant.

In some embodiments, cells of a specific cell type are collected from the patient or from a donor (e.g., from an HLA-matched or mis-matched donor that is, e.g., free of the disease or condition), modified to express one or more (e.g., one, two, three, four, five, six, seven, or eight) cloaking transgenes, and subsequently administered to a subject. Such an approach is useful for treating subjects carrying a mutation in a particular gene, as the cloaked donor cells can endogenously express the wild-type version of the gene, or for subjects deficient in a particular secreted protein or enzyme (e.g., using cloaked donor cells that endogenously express the protein or enzyme that is deficient in the subject). This approach can also be used for treatment of subjects receiving an organ or tissue transplant, as cells in the organ or tissue transplant can be modified to express one or more (e.g., one, two, three, four, five, six, seven, or eight) of the cloaking transgenes before the transplant is performed.

Subjects that may be treated as described herein are subjects that have received a transplant, or subjects having a disease or condition described herein (e.g., wet AMD or retinal dystrophy, a neurodegenerative disease, such as Parkinson's disease, cardiac infarction, osteoarthritis or RA, diabetes, hemophilia, a metabolic disorder, or a disease or condition listed in Table 2). The cells, compositions, and methods described herein can be used to treat a disease or condition caused by or associated with loss of cells, a mutation or deficiency in a protein, or aberrant production of a protein, which could be treated using cell replacement protein or cellular therapy, production of a therapeutic protein, production of an agonist antibody, or production of an inhibitory antibody. The methods described herein may include a step of screening a subject for mutations in genes associated with deficient protein production prior to treatment with or administration of the compositions described herein. A subject can be screened for a genetic mutation using standard methods known to those of skill in the art (e.g., genetic testing). The methods described herein may also include a step of evaluating the symptoms of the disease or condition in a subject prior to treatment with or administration of the cloaked cells or compositions described herein. The subject can then be evaluated using the same diagnostic tests after administration of the cloaked cells or compositions to determine whether the subject's condition has improved. The compositions and methods described herein may be administered as a preventative treatment to patients who have received a tissue or organ transplant before the patient shows any signs of tissue or organ rejection.

The cloaked cells, compositions, and methods described herein can be used to replace dead or dying cells in a subject (e.g., to replace neurons in a subject suffering from a neurodegenerative disease, or to replace cardiac muscle cells in a subject who has had a myocardial infarction). The cloaked cells, compositions, and methods described herein can also be used to provide immunosuppression in the region of a tissue or organ transplant, or to reduce the risk of rejection of the tissue or organ transplant. Cloaked cells that express a therapeutic agent, such as a protein or agonist antibody, compositions including such cells, or methods of administering such cells, may be used to replace or supply wild type versions of proteins that are mutated or deficient in a subject (e.g., proteins that are produced but do not function correctly due to a genetic mutation, such as truncated proteins or proteins with altered charge, polarity, or binding properties; or proteins that are not produced or that are produced in insufficient quantities, e.g., deficient protein production that is associated with a disease or condition in Table 2). Cloaked cells that express a therapeutic agent, such as an inhibitory or neutralizing antibody, compositions including such cells, or methods of administering such cells, may be used to block or neutralize proteins that are overexpressed in a subject or proteins that are aberrantly produced (e.g., proteins that are produced in at a time or in a location that differs from production of that protein in healthy subjects, e.g., aberrant protein production that is associated with a disease or condition listed in Table 2).

Treatment may include administration of cloaked cells or a composition containing cloaked cells in various unit doses. Each unit dose will ordinarily contain a predetermined-quantity of the cloaked cells described herein. The quantity to be administered, and the particular route of administration and formulation, are within the skill of those in the clinical arts. A unit dose need not be administered as a single injection but may comprise continuous infusion over a set period of time. Dosing may be performed using a catheter, syringe, shunt, stent, microcatheter, pump, implantation with a device, or implantation with a scaffold. The number of cells administered may vary depending on whether the cells are administered to a tissue, organ, or body site associated with a disease or injury, or are administered subcutaneously to produce a cloaked subcutaneous tissue. For administration to a tissue, organ, or body site, the cloaked cells may be administered to the patient at a dose of, for example $1\times10^4$ cells to $1\times10^{10}$ cells (e.g., $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$ cells). The number of cells administered will depend on the size of the recipient tissue, organ, or body site. For example, $2.5\times10^4$ to $1\times10^5$ cells (e.g., $2.5\times10^4$, $3\times10^4$, $4\times10^4$, $5\times10^4$, $6\times10^4$, $7\times10^4$, $8\times10^4$, $9\times10^4$, or $1\times10^5$ cells) can be administered (e.g., injected) to the subretinal space of the eye or to a specific brain region; $1\times10^6$ to $1\times10^8$ cells (e.g., $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, or $1\times10^8$ cells) can be administered (e.g., injected) to a joint, with the quantity of cells depending on the size of the joint; and $5\times10^8$ to $5\times10^9$ cells (e.g., $5\times10^8$, $6\times10^8$, $7\times10^8$, $8\times10^8$, $9\times10^8$, $1\times10^9$, $2\times10^9$, $3\times10^9$, $4\times10^9$, or $5\times10^9$ cells) can be administered to the cardiac muscle. For creating cloaked subcutaneous tissue, $8\times10^8$ cells to $3\times10^9$ cells (e.g., $8\times10^8$, $9\times10^8$, $1\times10^9$, $2\times10^9$, $3\times10^9$ cells) can be administered (e.g., injected) subcutaneously. Cloaked cells can be administered in two or more doses (e.g., two, three, four, five, or more different doses, e.g., to joints of different sizes in a patient with RA) or at the same dose two or more times (e.g., two, three, four, five, six, or more times over the course of an hour, day, week, month, or year). In some embodiments, the cloaked cells described herein are administered as a tissue (e.g., a tissue that has been grown and/or differentiated in vitro from cloaked cells). In some embodiments, the cloaked tissue is administered (e.g., implanted) with a gel, biocompatible matrix, or scaffold.

The compositions described herein are administered in an amount sufficient to prevent or reduce transplant rejection or to improve symptoms of a disease or condition listed in Table 2 (e.g., to reduce symptoms of osteoarthritis or RA (e.g., reduce inflammation, joint pain, stiffness, or immobility); reduce symptoms of retinal dystrophy or wet AMD (e.g., improve vision, slow or reduce vascularization of the eye); reduce symptoms of Parkinson's disease (e.g., reduce tremors, rigidity, bradykinesia, or improve posture or gait); reduce symptoms of diabetes (e.g., improve insulin levels, reduce the need for regular insulin injections); reduce symptoms of cardiac infarction (e.g., improve heart function, reduce infarct size); reduce symptoms of hemophilia (e.g., increase level of blood coagulation factors, such as Factor VIII, reduce excessive bleeding, reduce bruising, reduce nosebleeds, reduce joint pain or swelling); or reduce symptoms of metabolic disorders (e.g., increase appetite, growth, or weight gain, or reduce lethargy, weight loss, jaundice, seizures, abdominal pain, or vomiting)). Transplant rejection may be evaluated using standard methods known by those of skill in the art and may be reduced by 5% or more (e.g., 5%, 10%, 15%, 20%, 30%, 40%, 50%, 60%, 70%, 80%, 90%, 100% or more) compared to rates of transplant rejection typically observed without treatment. In some embodiments, administration of the cloaked cells or compositions described herein results in an equivalent outcome in transplant rejection as that observed in subjects administered immunosuppressive agent(s). Symptoms of diseases and conditions described herein can be evaluated using standard methods known to those of skill in the art and may be reduced (e.g., the subject's condition may be improved) by 5% or more (e.g., 5%, 10%, 15%, 20%, 30%, 40%, 50%, 60%, 70%, 80%, 90%, 100% or more) compared to symptoms prior to administration of the cloaked cells or compositions described herein. These effects may occur, for example, within 1 week, 2 weeks, 3 weeks, 4 weeks, 5 weeks, 6 weeks, 7 weeks, 8 weeks, 9 weeks, 10 weeks, 15 weeks, 20 weeks, 25 weeks, or more, following administration of the compositions described herein. The patient may be evaluated 1 month, 2 months, 3 months, 4 months, 5 months, 6 months or more following administration of the cloaked cell or composition depending on the dose and route of administration used for treatment. Depending on the outcome of the evaluation, the patient may receive additional treatments.

Combination Therapy

In some embodiments, the cloaked cells described herein are administered in combination with one or more additional therapeutic agents. The additional therapeutic agent(s) can be administered prior to administration of the cloaked cells, after administration of the cloaked cells, or concurrently with administration of the cloaked cells. The cloaked cells and additional therapeutic agents can also be administered simultaneously via co-formulation. The cloaked cells and therapeutic agent(s) can also be administered sequentially, such that the action of the cloaked cells and therapeutic agent(s) overlaps and their combined effect is such that the reduction in a symptom, or other parameter related to the disorder is greater than what would be observed with the cloaked cells or therapeutic agent delivered alone or in the absence of the other. The effect of the cloaked cells and therapeutic agent(s) can be partially additive, wholly additive, or greater than additive (e.g., synergistic). Sequential or substantially simultaneous administration of cloaked cells and therapeutic agent(s) can be effected by any appropriate route including, but not limited to oral routes, intravenous routes, intramuscular routes, local routes, or subcutaneous routes. The cloaked cells and therapeutic agent(s) can be administered by the same route or by different routes. For example, cloaked cells may be administered by subcutaneous injection while the additional therapeutic agent is administered orally. The cloaked cells may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the additional therapeutic agent.

In one example, the additional therapeutic agent is an immunosuppressive agent(s) commonly given for organ or tissue transplant. The immunosuppressive agent(s) may be an agent that is given immediately after transplantation to prevent acute rejection (e.g., methylprednisolone, atgam, thymoglobulin, OKT3, basiliximab, or daclizumab) or an immunosuppressive agent(s) used for maintenance (e.g., prednisone, a calcineurin inhibitor (e.g., cyclosporine, tacrolimus), Mycophenolate Mofetil, Azathioprine or Rapamycin). Other immunosuppressive agents given after organ transplantation include corticosteroids (e.g., methylprednisolone, dexamethasone, prednisolone), cytotoxic immunosuppressants (e.g., azathioprine, chlorambucil, cyclophosphamide, mercaptopurine, methotrexate), immunosuppressant antibodies (e.g., antithymocyte globulins, basiliximab, infliximab), sirolimus derivatives (e.g., everolimus, sirolimus), and anti-proliferative agents (e.g., mycophenolate mofetil, mycophenolate sodium, and azathioprine). In this case, the cloaked cell(s) is administered to or near the transplant site, or the tissue to be transplanted is modified to express one or more (e.g., one, two, three, four, five, six, seven, or eight) cloaking transgenes, and the immunosuppressive agent(s) is administered as an additional source of immunosuppression, if needed.

For use in treating inflammatory and autoimmune related diseases or conditions, the additional agent may be a disease-modifying anti-rheumatic drug (DMARD), a biologic response modifier (a type of DMARD), a corticosteroid, or a nonsteroidal anti-inflammatory medication (NSAID). In some embodiments, the additional agent is prednisone, prednisolone, methylprednisolone, methotrexate, hydroxychloroquine, sulfasalazine, leflunomide, cyclophosphamide, azathioprine, or a biologic such as tofacitinib, adalimumab, abatacept, anakinra, kineret, certolizumab, etanercept, golimumab, infliximab, rituximab or tocilizumab. In some embodiments, the additional agent is 6-mercaptopurine, 6-thioguanine, abatacept, adalimumab, alemtuzumab (Lemtrada), an aminosalicylate (5-aminoalicylic acid, sulfasalazine, mesalamine, balsalazide, olsalazine), an antibiotic, an anti-histamine, Anti-TNFα (infliximab, adalimumab, certolizumab pegol, natalizumab), azathioprine, belimumab, beta interferon, a calcineurin inhibitor, certolizumab, a corticosteroids, cromolyn, cyclosporin A, cyclosporine, dimethyl fumarate (tecfidera), etanercept, fingolimod (Gilenya), fumaric acid esters, glatiramer acetate (Copaxone), golimumab, hydroxyurea, IFNγ, IL-11, infliximab, leflunomide, leukotriene receptor antagonist, long-acting beta2 agonist, mitoxantrone, mycophenolate mofetil, natalizumab (tysabri), ocrelizumab, pimecrolimus, a probiotic (VSL #3), a retinoid, rituximab, salicylic acid, short-acting beta2 agonist, sulfasalazine, tacrolimus, teriflunomide (Aubagio), theophylline, tocilizumab, ustekinumab (anti-IL-12/IL-23), or vedolizumab (Anti alpha3 beta7 integrin). In this case, the cloaked cell(s) could be administered to replace a tissue or organ damaged by the inflammatory or autoimmune-related disease or condition. In another example, the cloaked cell(s) administered could be modified to express a biologic therapeutic agent (e.g., an antibody) directed to treatment of a particular inflammatory or autoimmune-related disease or condition, and the additional agent could be a compound or general anti-inflammatory agent (e.g., an NSAID or corticosteroid).

For example, if the disease is rheumatoid arthritis, the additional agent may be one or more of: prednisone, prednisolone and methylprednisolone, methotrexate, hydroxychloroquine, sulfasalazine, leflunomide, cyclophosphamide and azathioprine, tofacitinib, adalimumab, abatacept, anakinra, kineret, certolizumab, etanercept, golimumab, infliximab, rituximab or tocilizumab. The cloaked cell(s) administered could be cartilage or bone producing cells of the joints. In some embodiments, the cloaked cell(s) can be modified to produce an anti-TNFα antibody and can be administered in combination with an anti-inflammatory agent (e.g., a corticosteroid).

In another example, for use in treating AMD or retinal dystrophy, the additional therapeutic agent may be an additional biologic agent (e.g., bevacuzimab, ranibizumab, or aflibercept), photodynamic therapy, or photocoagulation. The cloaked cell(s) administered could be retinal cells (e.g., RPE cells). In some embodiments, the cloaked cell(s) can be modified to produce a VEGF inhibitor and can be administered in combination with photodynamic therapy or photocoagulation.

For use in treating Parkinson's disease, the cloaked cells described herein can be administered with carbidopa-levodopa, a dopamine agonist (e.g., pramipexole, ropinirole, rotigotine, or apomorphine), an MAO-B inhibitor (e.g., selegiline or rasagiline), a catechol-O-methyltransferase inhibitor (e.g., entacapone or tolcapone), anticholinergic (e.g., benztropine or trihexyphenidyl), amantadine, or deep brain stimulation. The cloaked cell(s) administered could be dopaminergic neurons.

Additional agents for treating cardiac infarction include anticoagulants (e.g., rivaroxaban, dabigatran, apixaban, heparin, warfarin), anti-platelet agents (e.g., aspirin, clopidogrel, dipyramidole, prasugrel, ticagrelor), angiotensin-converting enzyme inhibitors (e.g., benazepril, captopril, enalapril, fosinopril, Lisinopril, moexipril, perindopril, quinapril, Ramipril, trandolapril), angiotensin II receptor blockers (e.g., candesartan, eprosartan, irbesartan, losartan, telmisartan, valsartan), angiotensin receptor neprilysin inhibitors (e.g., sacubitril/valsartan), beta blockers (e.g., acebutelol, atenolol, betaxolol, bisoprolol, metoprolol, nadolol, propranolol, sotalol), combined alpha and beta blockers (e.g., carvedilol, labetalol hydrochloride), calcium channel blockers (e.g., amlodipine, diltiazem, felodipine, nifedipine, nimodipine, nisoldipine, verapamil), cholesterol lowering medication (e.g., statins (e.g., atorvastatin, rosuvastatin), nicotinic acids (e.g., lovastatin), cholesterol absorption inhibitors (e.g., ezetimibe/simvastatin)), *digitalis* preparation (e.g., lanoxin), diuretics (e.g., amiloride, bumentanide, chlorothiazide, chlorthalidone, furosemide, hydro-chlorothiazide, indipamide, spironolactone), vasodilators (e.g., isosorbide dinitrate, nesiritide, hydralazine, nitrates, minoxidil), dual anti-platelet therapy (e.g., aspirin and a P2Y12 inhibitor), or a cardiac procedure (e.g., an angioplasty, artificial heart valve surgery, atherectomy, bypass surgery, cardiomyoplasty, heart transplant, minimally invasive heart surgery, radiofrequency ablation, stent procedure, or trans-myocardial revascularization). The cloaked cell(s) administered could be cardiac muscle cells.

For use in treating infectious disease, the additional agent may be an antiviral compound (e.g., vidarabine, acyclovir, gancyclovir, valgancyclovir, nucleoside-analog reverse transcriptase inhibitor (NRTI) (e.g., AZT (Zidovudine), ddI (Didanosine), ddC (Zalcitabine), d4T (Stavudine), or 3TC (Lamivudine)), non-nucleoside reverse transcriptase inhibitor (NNRTI) (e.g., (nevirapine or delavirdine), protease inhibitor (saquinavir, ritonavir, indinavir, or nelfinavir), ribavirin, or interferon); an antibacterial compound; an antifungal compound; an antiparasitic compound. The cloaked cell(s) administered could be immune cells (e.g., cell that could assist in fighting the infectious disease, e.g., a cloaked T cell or B cell).

For use in treating diabetes, the additional agent may be insulin, a sulfonylurea (e.g., chlorpropamide, glipizide, glyburide, glimepiride), a biguanide (e.g., metformin), a meglitinide (e.g., repaglinide, nateglinide), a thiazolidinedione (e.g., rosiglitazone, pioglitazone), a DPP-4 inhibitor (sitagliptin, saxagliptin, linagliptin, alogliptin), an SGLT2 inhibitor (e.g., canagliflozin, dapagliflozin), an alpha-glucosidase inhibitor (e.g., acarbose, miglitol), a bile acid sequestrant (e.g., colesevelam), aspirin, or a dietary regimen. The cloaked cell(s) administered could be pancreatic beta cells, which can optionally be modified to express a transgene encoding insulin.

For use in treating hemophilia, the additional therapeutic agent may be a clotting factor, desmopressin, a clot-preserving medication (e.g., an anti-fibrinolytic, e.g., aprotinin, aminocaproic acid, fibrigongen, or tranexamic acid), a fibrin sealant, or physical therapy. The cloaked cell(s) administered could be liver sinusoidal cells or endothelial cells, which can optionally be modified to express a transgene encoding Factor VIII.

For treatment of a metabolic deficiency or disorder, the additional therapeutic agent may be a coenzyme (e.g., biotin, hydroxycobalamine, riboflavin, pyridoxine, folate, thiamin, ubichinone, tetrahydrobiopterine), a bone marrow transplant, an organ transplant (e.g., a liver, kidney, or heart transplant), hemodialysis, hemofiltration, exchange transfusion, peritoneal dialysis, medium-chain triacylglycerols, miglustat, enzyme supplementation therapy, or dietary restriction (e.g., low protein or phenylalanine-restricted diet for subjects with phenylketonuria), The cloaked cell(s) can be cells that carry a wild-type copy of the gene that is mutated in a subject with a metabolic disorder or cells that endogenously produce the enzyme that is deficient in subject with a metabolic disorder (e.g., a liver cell, kidney cell, heart cell, or any other cell that carries a wild-type copy of a gene that is mutated in a subject with a metabolic disorder or produces an enzyme that is deficient in a subject with a metabolic disorder).

For use in treating cancer, the additional agent may be a checkpoint inhibitor, a chemotherapeutic drug, a biologic drug, a non-drug therapy (e.g., radiation therapy, cryotherapy, hyperthermia, or surgical excision or tumor tissue), or an anti-cancer vaccine. The cloaked cell(s) could be an immune cell that could help fight the cancer (e.g., a macrophage, natural killer cell, dendritic cell, or T cell).

Checkpoint inhibitors can be broken down into at least 4 major categories: i) agents such as antibodies that block an inhibitory pathway directly on T cells or natural killer (NK) cells (e.g., PD-1 targeting antibodies such as nivolumab, pidilizumab/CT-011, and pembrolizumab, antibodies targeting TIM-3, and antibodies targeting LAG-3, 2B4, CD160, A2aR, BTLA, CGEN-15049, or KIR), ii) agents such as antibodies that activate stimulatory pathways directly on T cells or NK cells (e.g., antibodies targeting OX40, GITR, or 4-1BB), iii) agents such as antibodies that block a suppressive pathway on immune cells or rely on antibody-dependent cellular cytotoxicity to deplete suppressive populations of immune cells (e.g., CTLA-4 targeting antibodies such as ipilimumab or tremelimumab, antibodies targeting VISTA, and antibodies targeting PD-L2 (e.g., a PDL2/Ig fusion protein such as AMP 224), Gr1, or Ly6G), and iv) agents such as antibodies or small molecules that block a suppressive pathway directly on cancer cells or that rely on antibody-dependent cellular cytotoxicity to enhance cytotoxicity to cancer cells (e.g., rituximab, antibodies or small molecules targeting PD-L1 (e.g., MPDL3280A/RG7446; MEDI4736; MSB0010718C; BMS 936559), and antibodies or small molecule inhibitors targeting B7-H3 (e.g., MGA271), B7-H4, Gal-9, or MUC1). In one embodiment, the inhibitor of checkpoint is an inhibitor (e.g., an inhibitory antibody or small molecule inhibitor) of HVEM, CD160, CHK 1, CHK2, B-7 family ligands, or a combination thereof. Such agents described herein can be designed and produced, e.g., by conventional methods known in the art (e.g., Templeton, Gene and Cell Therapy, 2015; Green and Sambrook, Molecular Cloning, 2012). In one embodiment, the inhibitor of checkpoint is an inhibitory antibody (e.g., a monospecific antibody such as a monoclonal antibody). The antibody may be, e.g., humanized or fully human. In other embodiments, the inhibitor of checkpoint is a fusion protein, e.g., an Fc-receptor fusion protein. In some embodiments, the inhibitor of checkpoint is an agent, such as an antibody, that interacts with a checkpoint protein. In other embodiments, the inhibitor of checkpoint is an agent, such as an antibody, that interacts with the ligand of a checkpoint protein.

Chemotherapeutic agents include alkylating agents, antimetabolites, folic acid analogs, pyrimidine analogs, purine analogs and related inhibitors, vinca alkaloids, epipodopyllotoxins, antibiotics, L-asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII; dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel; chloranbucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the cloaked cells described herein. Suitable dosing regimens of combination chemotherapies are known in the art.

Anti-cancer biologics include cytokines (e.g., interferon or an interleukin (e.g., IL-2)) used in cancer treatment. In other embodiments the biologic is an anti-angiogenic agent, such as an anti-VEGF agent, e.g., bevacizumab. In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include Rituximab; Daclizumab; Basiliximab; Palivizumab; Infliximab; Trastuzumab; Gemtuzumab ozogamicin; Alemtuzumab; Ibritumomab tiuxetan; Adalimumab; Omalizumab; Tositumomab-I-131; Efalizumab; Cetuximab; Bevacizumab; Natalizumab; Tocilizumab; Panitumumab; Ranibizumab; Eculizumab; Certolizumab pegol; Golimumab; Canakinumab; Ustekinumab; Ofatumumab; Denosumab; Motavizumab; Raxibacumab; Belimumab; Ipilimumab; Brentuximab Vedotin; Pertuzumab; Ado-trastuzumab emtansine; and Obinutuzumab. Also included are antibody-drug conjugates.

Kits

The invention also features a kit containing the cloaked cells described herein (e.g., cloaked cells expressing a set of the cloaking transgenes described herein (e.g., 1, 2, 3, 4, 5, 6, 7, or 8 of PD-L1, H2-M3, Cd47, Cd200, FasL, Ccl21b, Mfge8, and Spi6), optionally further expressing one or more of the following transgenes: TGF-β, Cd73, Cd39, Lag3, Il1r2, Ackr2, Tnfrsf22, Tnfrs23, Tnfrsf10, Dad1, and IFNγR1 d39). In some embodiments, the cloaked cells are further modified to contain one or more systems for regulating cell division (e.g., an ALINK or EARC system), and/or a therapeutic agent (e.g., a transgene encoding a protein or antibody). The cloaked cells may be provided in a pharmaceutical composition. The kit may further include a syringe for administration of the cloaked cells or pharmaceutical composition and instructions for administering the cloaked cells or pharmaceutical composition for treating a disease or condition described herein.

EXAMPLES

The following examples are provided to further illustrate some embodiments of the present invention, but are not intended to limit the scope of the invention; it will be understood by their exemplary nature that other procedures, methodologies, or techniques known to those skilled in the art may alternatively be used.

Example 1: Materials and Methods

Construction of Vectors that Express Target Genes Essential for Allo-Tolerance

Plasmids containing the cDNA sequences of genes involved in allo-tolerance were obtained as follows:
PD-L1: Mount Sinai Hospital, clone #V102001
FasL: Mount Sinai Hospital, #75719
Cd47: Mount Sinai Hospital, #V75535
Cd200: GE Dharmacon, ID #17470
H2-M3: Mount Sinai Hospital, clone #8188
Ccl21: Mount Sinai Hospital, clone #V77120
Mfge8: Mount Sinai Hospital, clone #V72614
Spi6: Mount Sinai Hospital, clone #V8907

Figure 15:
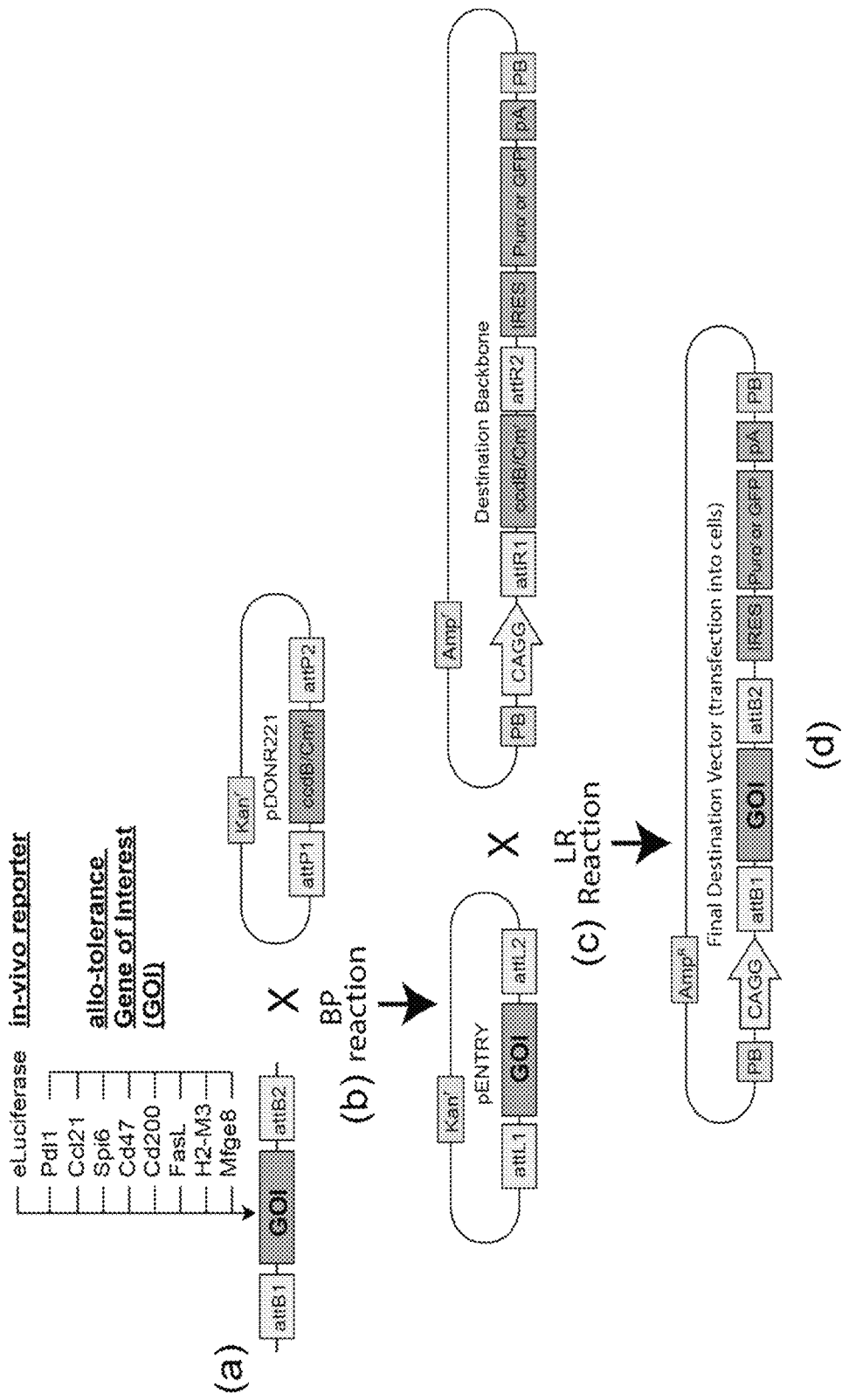
FIG. 15 is a schematic showing the construction of vectors that express target genes essential for allo-tolerance.

Expression vectors that contain these Genes of Interest (GOI), or the luciferase enzyme, were generated using the Gateway cloning system (Thermo Fisher). Cd47, Ccl21, Mfge8 and Spi6 cDNAs were acquired in a form that contained cDNA-flanking attB sites. For H2-M3, Cd200, FasL, and PD-L1, primers were designed to amplify the cDNA sequence, and add attB sites (FIG. 15(a)). Following PCR amplification, attB-containing cDNA was recombined into pDONR221 vectors (Thermo Fisher, #1256017) by the BP (recombination between attB and attP sites) reaction to create entry (pENTRY) clones (FIG. 15(b)). The BP reaction entails mixing the attB-flanked transgene cDNA with the pDONR221 plasmid in a 1 ml tube, along with buffers and the BP enzyme provided by Invitrogen, where the BP enzyme recombines the GOI into the docking site of the pDONR221 plasmid. Insertion of the transgene into the pDONR221 plasmid was verified by DNA sequencing (TCAG Sequencing Facility at the Centre for Applied Genomics, Toronto). pENTRY clones that contained the GOI were then recombined into destination vectors via the gateway LR (recombination between attL and attR sites) reaction (FIG. 15(c)). The LR reaction entails mixing the GOI-containing pDONR221 plasmid and the destination vector in a 1 mL tube, along with buffers and the LR enzyme provided by Invitrogen, where the LR enzyme recombines the GOI cassette from the pDONR221 plasmid into the docking site of the destination plasmid. Destination vectors, which were used for all transgene constructions, contain a CAGG promoter followed by a Gateway entry site, internal ribosomal entry site (IRES) and either a Puromycin resistance selectable marker or a green fluorescent protein (GFP) reporter. The entire cassette is flanked by transposable PB sites. Following LR recombination, the final destination vectors containing the GOI (FIG. 15(d)) were verified by restriction enzyme digestion.

ES Cell Culture, Transfection, Selection and Cloning

Mouse ES cells derived from the inbred C57BL/6N mouse strain (Gertsenstein 2010) were cultured in DMEM high glucose supplemented with 15% fetal bovine serum (FBS, tested for compatibility with ES cell cultures) and standard amounts of Sodium Pyruvate, non-essential amino acid (NEAA), Glutamax, Penicillin/Streptomycin, Beta-mercapto-ethanol and leukemia inhibitory factor (LIF) (Behringer et al 2014). Cells were cultured on a feeder layer of MitomycinC-inactivated Murine Embryonic Fibroblasts (MEFs). Cultures were kept in a standard cell culture incubator at 37° C. and 5% CO2.

Transfection was performed using JetPRIME reagent (Polyplus, catalog #14-07) per manufacturer protocol, and was done in three steps: 1) transfection with PD-L1-IRES-GFP destination vector only, 2) transfection with all the other transgenes carrying a Puromycin selectable marker, and 3) transfection with an eLuciferase-IRES-GFP transgene.

Step 1: Following transfection with PD-L1-IRES-GFP, cells were plated at low density so that after multiple rounds of proliferation 5-6 days later, individual cell clones-existing as cell aggregates (colonies)—were selected based on the intensity of GFP expression and then expanded as a clonal cell culture. The clone with the highest and most consistent GFP expression was chosen for the next step.

Step 2: 24 hours after transfection with transgenes containing a Puromycin selection marker, Puromycin was added to the culture media. On the third day, cells were plated at clonal density and Puromycin selection was continued until individual colonies were picked and expanded as clones. A large number of these clones were screened in vivo and the one capable of forming a teratoma in an allogeneic setting was designated "NT2".

Step 3: NT2 was transfected with PB-CAG-eLuciferase-IRES-GFP as described above and plated at clonal density. GFP+ clones were picked and expanded. 10 clones with high levels of GFP expression were chosen for further studies.

Evaluation of Transgene Expression Levels

RNA was isolated from cultures grown on 30 mm culture plates, as well as from tumours grown in vivo. Cells were dissociated with Trypsin, centrifuged, and the supernatant removed. The cell pellet was immediately frozen on dry ice and stored at −80° C. Tumour tissues were dissected, immediately frozen on dry ice and stored at −80° C. RNA was isolated per standard protocols using Sigma GeneElute Total RNA Miniprep kit #RTN350. cDNA was obtained by reverse transcriptase reaction using the Qiagen Quantifast Reverse Transcriptase kit #205313. Quantitative PCR was performed using Sensifast mastermix from Bioline, #Bio-98020, gene specific primers and RNA at a 1:50 dilution. Samples were plated in 384 well plates using the Eppendorf epMotion 5070 robot and the quantitative PCR was performed on BioRad CFX384 Real-Time System C1000 Thermal cycler according to standard protocols. qPCR data was captured by BioRad CFX Manager 3.1 software and expression levels calculated with Microsoft Excel.

Teratoma Assay

Matrigel Matrix High Concentration (Corning cat #354248) was diluted 1:1 with cold DMEM media on ice. $5 \times 10^7$ cells were suspended into 500 µL of DMEM and equal volume of Matrigel. 100 ul 5×10 cells of the suspension was injected subcutaneously into each dorsal flank of B6N (isogenic) or FVB/N (allogeneic) mice. The resulting teratomas formed 2-4 weeks after injection. Teratoma size was measured using calipers, and the volume was calculated with the formula $V=(L \times W \times H)/2$. The tumours were allowed to grow to approximately 500 $mm^2$, a size that is well-tolerated and also well-suited for downstream experiments. All of the transgenes were delivered into cells that contain "Fail-safe system" (as described, for example, in WO 2016/141480, the entire contents of which are incorporated herein by reference. This genetic system allows for the complete inhibition of cell division with the administration of Ganciclovir (GCV). Once teratomas from the previously described experiments reached 500 $mm^2$, mice were injected into the peritoneal cavity with 50 mg/kg GCV every 2-3 days for 2-3 weeks. This treatment regimen resulted in an initial brief shrinkage of the tumours, followed by stabilization of tumour size at 400-500 $mm^2$ after 2-3 weeks of treatment. At the endpoint of the experiment, mice were sacrificed and tumours were dissected. A small portion of tissue was snap-frozen for RNA extraction while the rest was fixed in 4% paraformaldehyde.

Bioluminescence Imaging

Mice that developed teratomas derived from cells transfected with the eLuciferase transgene were injected with 30 mg/mL VivoGlo Luciferin at 100 uL/25 g body mass (Promega #P104C) 10 min before imaging. Animals were anaesthetized with Isoflurane and placed in an IVIS Lumina II imager (Caliper Life Sciences) driven by Living Image software. Exposure times were set between 5 seconds and 5 minutes depending on signal intensity.

Histology

Fixed tumours were embedded in paraffin, sectioned and stained with Hematoxylin/Eosin for histological analysis at the CMHD Pathology Core. Histology images were processed with NDPview2 software.

Example 2: Generation of Cloaked Cells

Transgenes encoding the genes in Table 1 were cloned into expression vectors and sequence verified both by polymerase chain reaction (PCR), restriction enzyme digestion and sequencing, all using standard methods know in the art.

A set of constructs containing transgenes Cd47, Cd200, FasL and H2-M3 (Set 1) were transfected into mouse embryonic stem cells derived from the inventors' C57BL/6 mouse ES line (C2). The presence of the transgenes was verified by PCR and expression of the expressed proteins was documented by immunohistochemistry (FIGS. 1A-D). A second set of constructs containing transgenes Ccl21, Mfge8, TGF-β and Spi6 (Set 2) were transfected into ES cells derived from FVB/N (ES line C2).

Similar methods were used to generate cloaked B16F10 melanoma cells, except that the media used DMEM containing 10% fetal bovine serum (FBS).

Example 3: Screening Process for Inhibition of T-cell Activation

A modified in vitro Mixed Lymphocyte Reaction (MLR) assay was used to screen for the transgene combination resulting in the most efficient inhibition of T-cell activation. Cell lines transfected with Set 1 and Set 2 cloaking transgenes from Example 1 were used. Donor OT-I splenocytes were labeled with carboxyfluorescein succinimidyl ester CFSE and 60,000 cells were added to each well of the 96-well plate. ES or melanoma cells were mixed 10:1 with ova expressing cells. 10,000 of these were added to each well of splenocytes. IL-2 was added as a general activator and T-cell proliferation was measured by flow cytometry 3 days later (FIGS. 2A-2E). Cells were initially gated to include CD8+ cells only and all conditions were set up in 4 replicates.

Figure 2A:
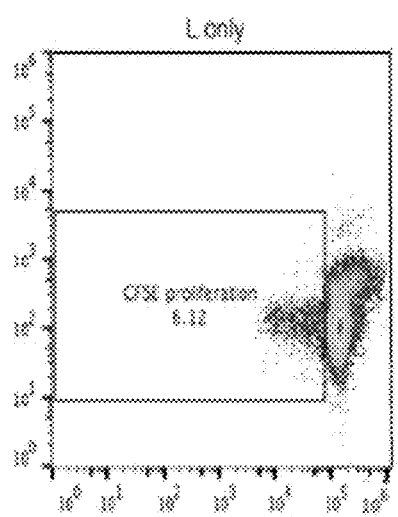
FIGS. 2A-2E are flow cytometry plots showing T-cell activation using splenocytes (FIG. 2A), wt B16 melanoma cells (FIG. 2B), cloaked B16 melanoma cells (FIG. 2C), wt ES cells (FIG. 2D), and cloaked ES cells (FIG. 2E) in a mixed lymphocyte reaction.
Figure 2B:
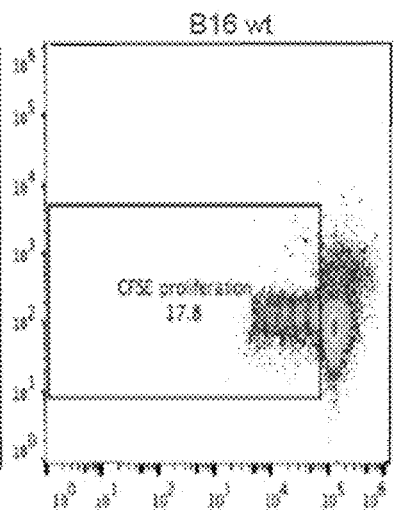
Figure 2C:
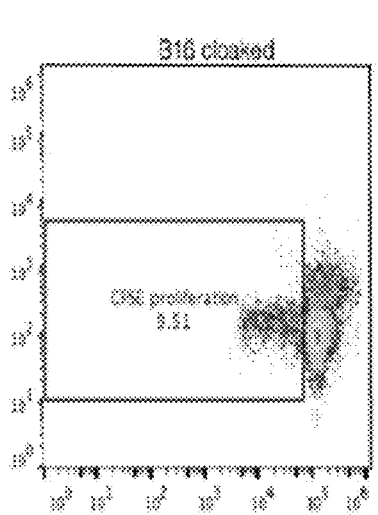
Figure 2D:
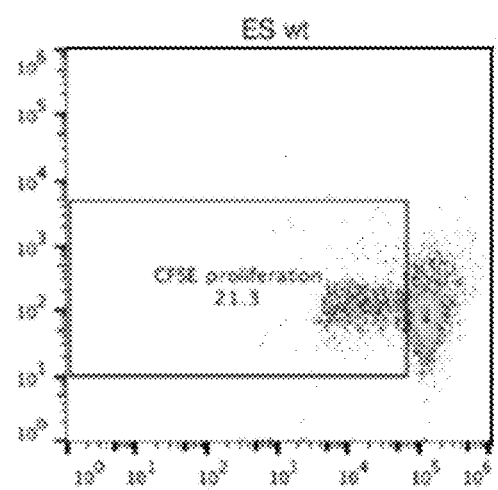
Figure 2E:
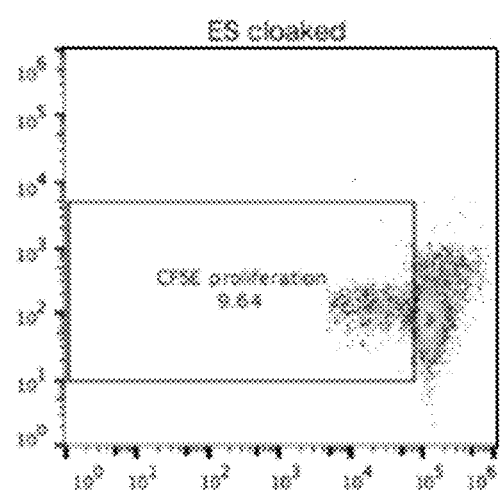

The negative control (splenocytes only) resulted in a baseline 6.12% proliferation rate (FIG. 2A). Wildtype B16 melanoma (+10% ova expressing) cells resulted in distinct acceleration of proliferation to 17.1% (FIG. 2B), while cloaked cells reduced this proliferation to 9.51% (FIG. 2C). Similar results were obtained for wildtype (FIG. 2D) versus cloaked ES cells (FIG. 2E).

Example 4: Studies with WT and Cloaked Cancer Cells in Iso- and Allografted B16F10 Melanoma Cells Since some of the candidate cloaking transgenes are intended to inhibit or modulate the initiation phase of the immune recognition cascade, the effect of these transgenes could be evaluated by the MLR alone as these events act on the maturation and physical migration of host APCs to local lymph nodes where they subsequently activate naïve T and B cells.

This called for an alternative assay that can screen a large number of transgene combinations in an in vivo allogeneic setting. Intraperitoneal and intravenous injection ES cells harboring a variety of transgene combinations was tried as an option. However, teratoma formation is dependent on the aggregation of a minimum number of ES cells ($1 \times 10^5$-$5 \times 10^6$ depending on site of injection), rendering this option not compatible with such a screen. However, the murine melanoma cancer cell line B16F10 derived from C57BL/6 mice is not limited in such a way. Intravenous injection of less than $5 \times 10^3$ results in the efficient induction of a multitude of small cancer nodules in the lung. By limiting number of cells injected, one can anticipate that the cancer cells are trapped in the lung alveoli will form nodules derived from single or just a very small number of cells. By isolating and genotyping these nodules, the transgene can be identified.

Figure 3A:
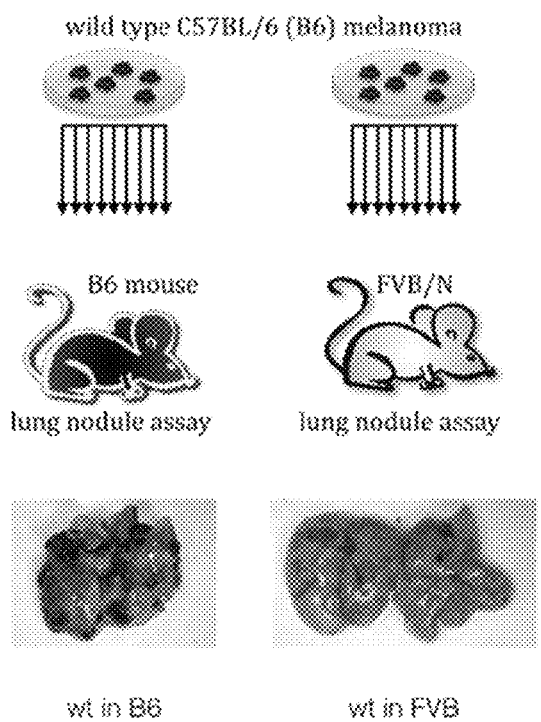
FIGS. 3A-3B are schematics and images showing that cloaked (FIG. 3B) B16F10 cancer cells in an allogenic model are protected from rejection compared to their WT counterparts (FIG. 3A). Representative images of uncloaked cells in C57BL/6 (n=5) and uncloaked cells in FVB/N (n=4) (FIG. 3A); cloaked cells in C57BL/6 (n=5) and cloaked cells in FVB/N (n=6) (FIG. 3B).

Injection B16F10 melanoma cells into the blood-stream of C57BL/6 mice (isogenic graft control) resulted in the formation of cancer nodules in the lung (FIG. 3A, left panel). However, small melanoma nodules formed also in the lungs of the negative controls-wild type B16F10 melanoma grafted into allogeneic control FVB mice when observed at day 14 post injection. However, when the melanoma was allowed to grow for 24 days, the nodules regressed almost completely (FIG. 3A, right panel).

Figure 3B:
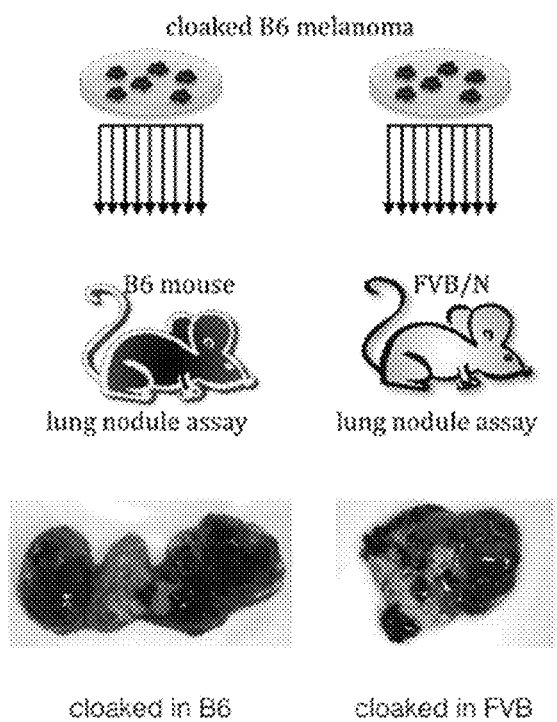

The above experiment was repeated, by injecting a mixture of cancer cells that expressed random combinations of the candidate cloaking genes, generated using the PiggyBac transposon system. Lung nodules developed in the allogeneic settings contained the successful combination(s) needed to protect the allograft from recognition and rejection (FIG. 3B, right panel). The same immune cloaked cells also gave rise to an accelerated development in the isogenic host (FIG. 3B, left panel).

Example 5: Non-Cloaked Embryonic Stem Cells do not Form Teratoma in Allogenic Settings As shown in Table 4, it was verified that wild-type ESCs derived from C57BL/6 mice are not capable of forming teratomas in FVB/N mice. Likewise, we have also shown that wild-type ESCs derived from the FVB/N background are not capable of forming teratomas in C57BL/6 hosts. ES cell colonies were dissociated with Trypsin, washed once with DMEM without additives and resuspended in Matrigel HC at a concentration of about 50 million cells per milliliter. Recipient mice were anaesthetized and one hundred microliter injected subcutaneously in each flank area. Developing teratomas were followed for 12 weeks and verified by palpation and measurement of volume with caliper.

TABLE 4

Teratomas formed in FVB/N mice and C57BL/6 hosts injected with wild-type ESCs derived from C57BL/6 mice or wild-type ESCs derived from the FVB/N background

| Donor ESCs | Recipient mouse | # injection sites | # teratomas |
|---|---|---|---|
| C57BL/6 | C57BL/6 | 18 | 14 |
| C57BL/6 | FVB | 22 | 0 |
| FVB | FVB | 8 | 8 |
| FVB | C57BL/6 | 8 | 0 |

Example 6: Cloaked ES Cells can Proliferate in Isogenic Hosts and Allogenic Hosts To verify the cloaking ability of the candidate transgenes, ESCs were transfected with the same transgenes while also adding a Luciferase transgene that can be detected by imaging. Briefly, ES cells were prepared as described above. The presence of viable cells were repeatedly measured by imaging. The images in FIG. 4 were taken on day 17 post injection.

Figure 4:
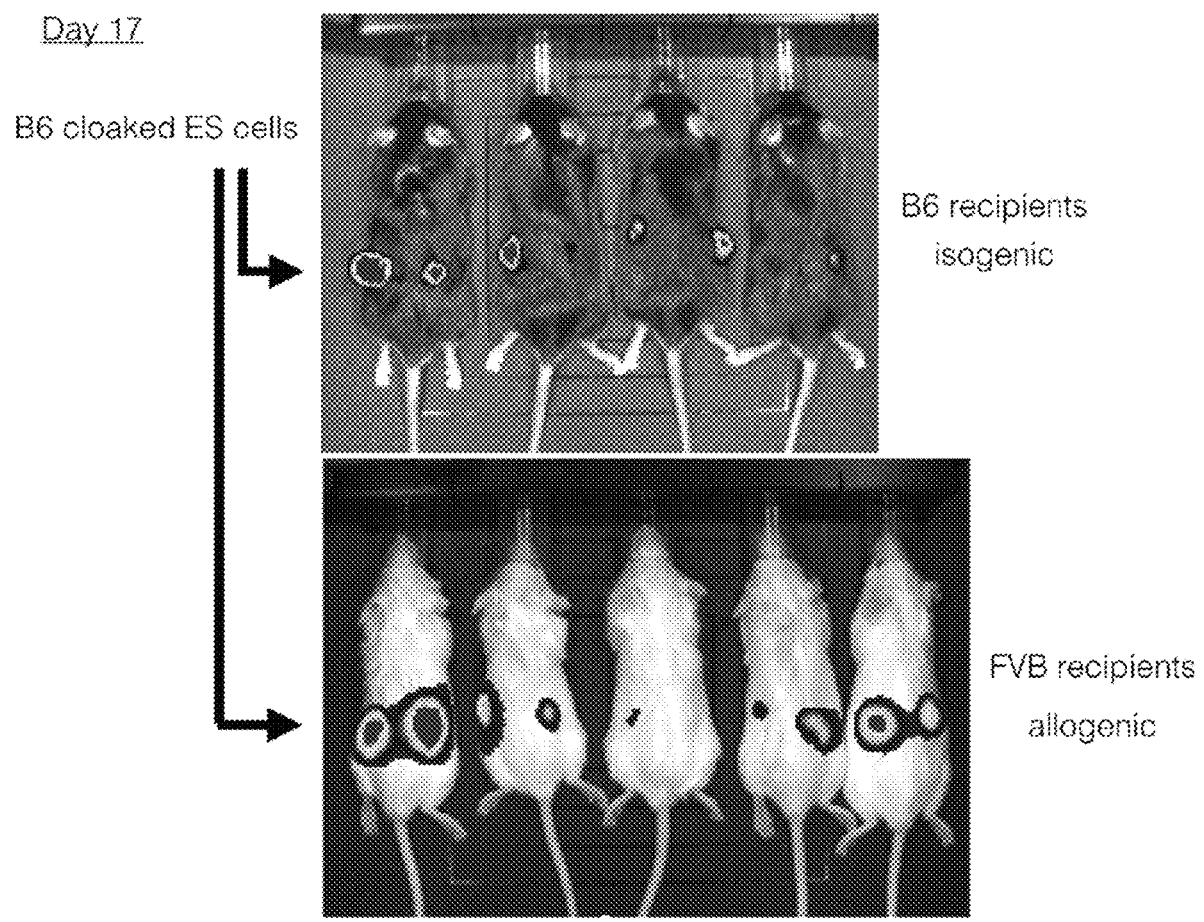
FIG. 4 is a schematic showing that cloaked embryonic stem cells form tumors in isogenic B6 mouse recipients (upper panel) and in FVB allogenic recipients (lower panel).

In FIG. 4, the top panel shows the proliferation of immune cloaked cells in isogenic hosts, while the lower panel shows the proliferation of immune cloaked cells in allogeneic hosts.

Figure 5A:
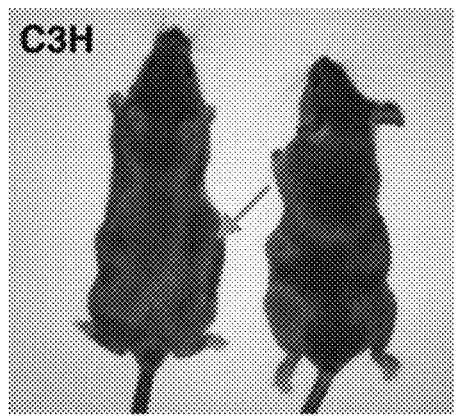
FIGS. 5A-5C are a series of photographs depicting allogenic mice bearing teratomas formed from subcutaneous injection of cloaked C57BL/6 ES cells. Red arrows indicate teratomas.
Figure 5B:
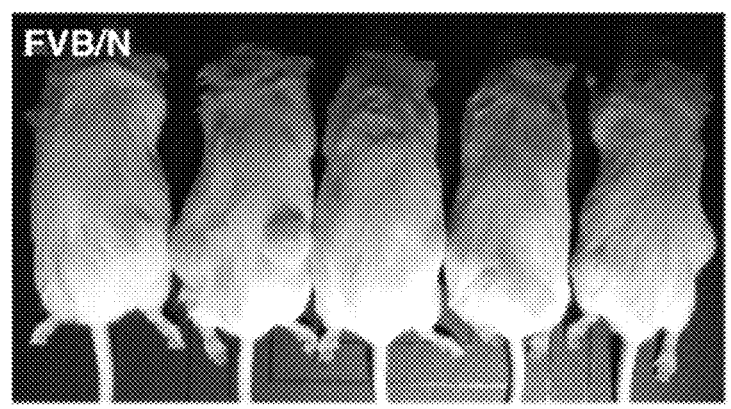
Figure 5C:
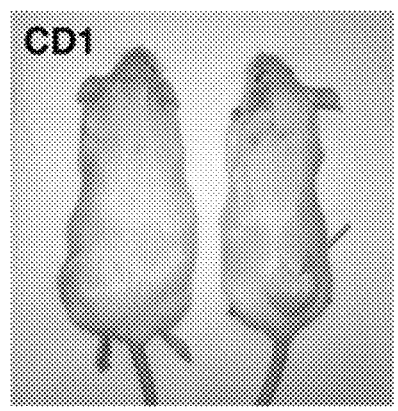

In another experiment, cloaked ES cells from C57BL/6 mice that had high expression of the 8 immunomodulatory transgenes (clone NT2) were injected subcutaneously into different allogenic mouse strains (C3H, FVB/N, and CD1) with mismatched MHC alleles. Red arrows indicate the teratoma that formed (FIGS. 5A-5C).

Example 7: Mice with Cloaked Tissues are not Immune Compromised

Figure 6:
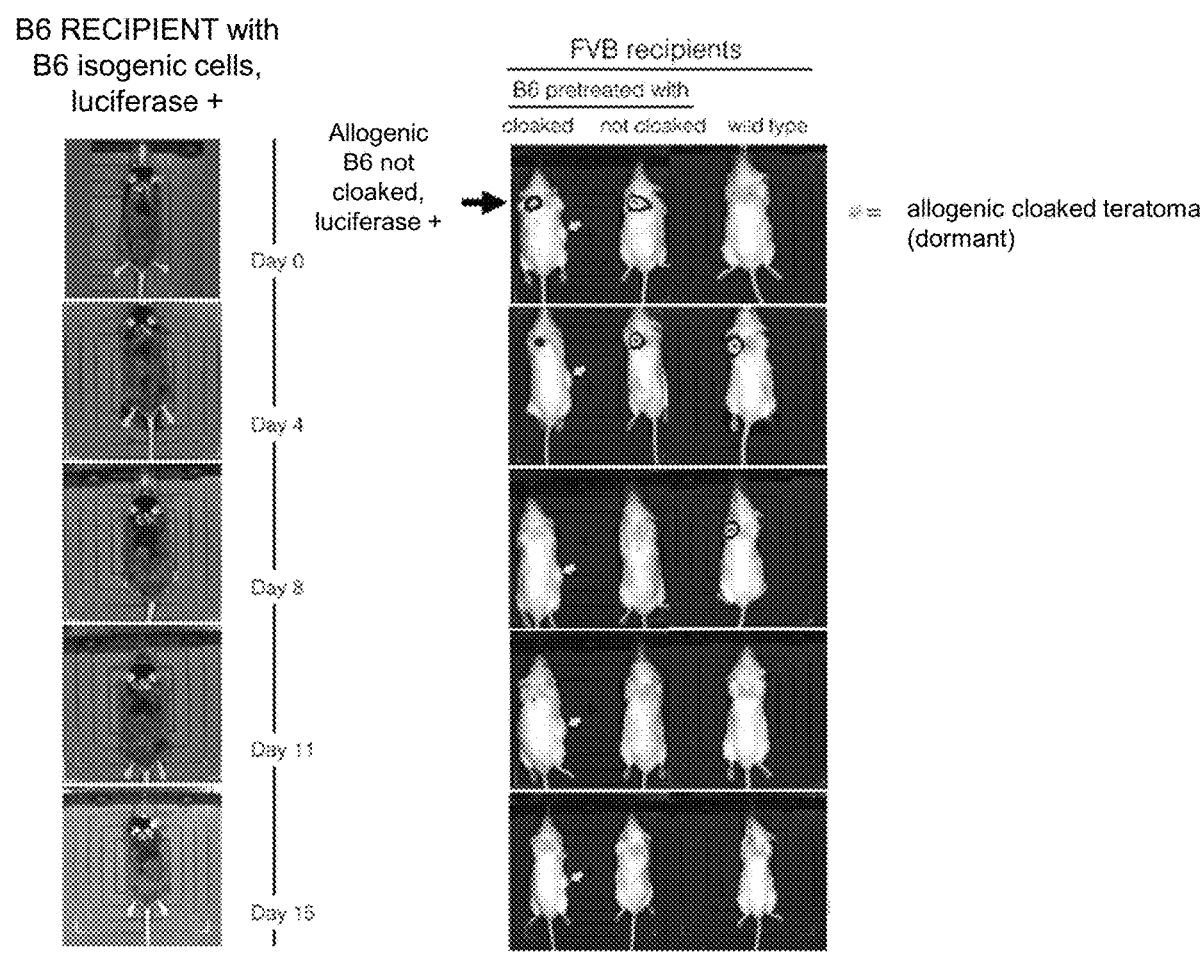
FIG. 6 is a schematic and series of images showing that animals with cloaked tissue are not immune compromised.

Non-immune cloaked (wild type) ESCs were transplanted into mice carrying an existing immune cloaked tissue and the mouse was evaluated to determine if it could effectively reject a non-immune cloaked graft (FIG. 6). The same mice were imaged several times over a period of 15 days. As shown in the left panel of FIG. 6, in isogenic mouse controls, the graft was not rejected over time. With allogenic FVB mice, the left mouse in the right panel of FIG. 6 had a pre-existing immune cloaked graft (arrows). The middle mouse in the right panel of FIG. 6 had previously been grafted with C57BL/6 allogeneic ESCs but rejected the graft (while not being bound to a theory, the rejection may have been due to pre-formed antibodies against C57BL/6 cells). The mouse on the right in the right panel of FIG. 6 had never been grafted before. All three mice successfully rejected the non-immune cloaked graft. The mouse on the right rejected the graft slower, which may have been because it did not have any preformed antibodies against C57BL/6 cells.

Figure 7:
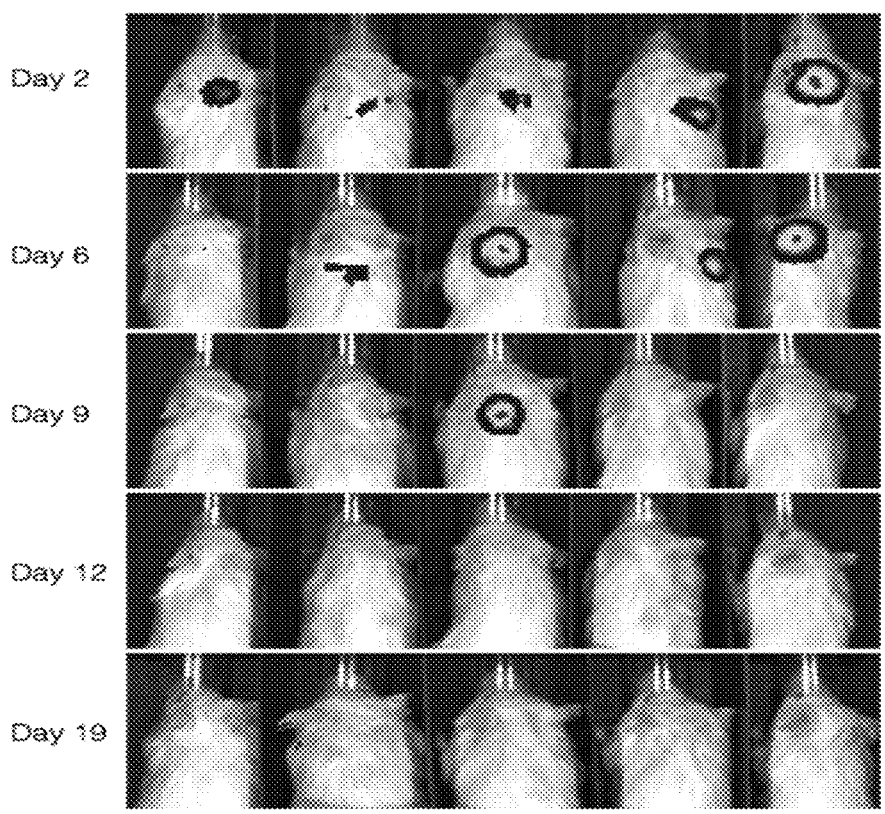
FIG. 7 is a series of images of FVB/N mice showing additional results showing that animals with cloaked tissues are not immune compromised.
Figure 8A:
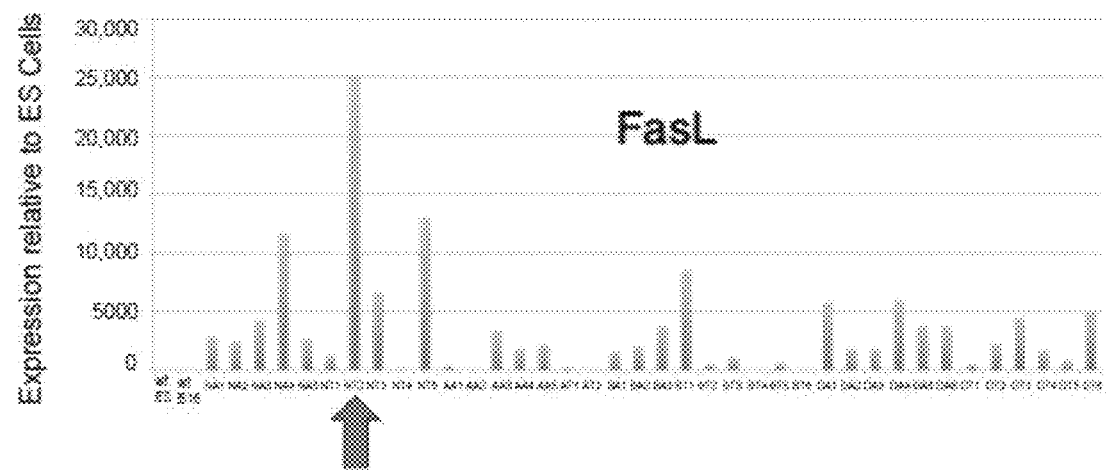
FIGS. 8A-8H show transgene expression in clonal Fail-Safe containing embryonic stem cells derived from C57BL/6 mice.
Figure 8B:
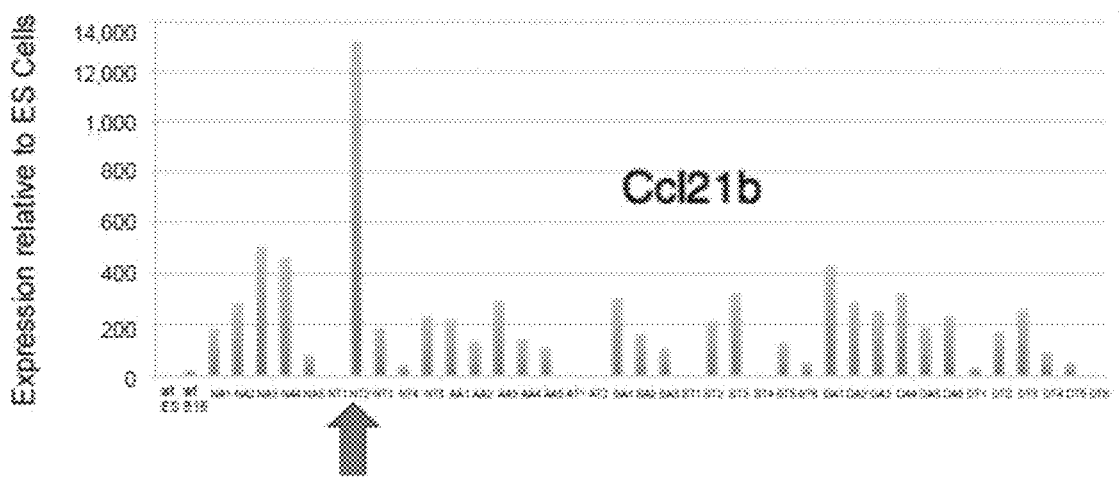
Figure 8C:
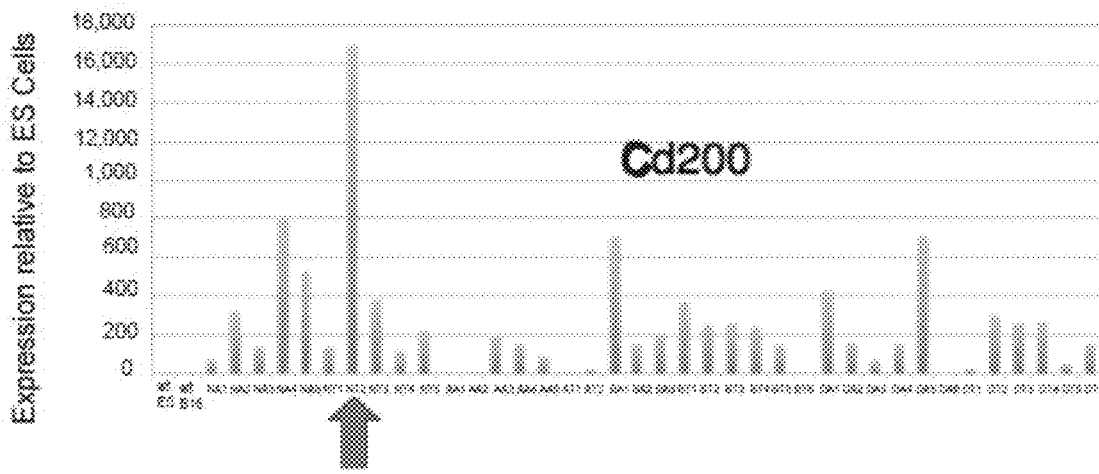
Figure 8D:
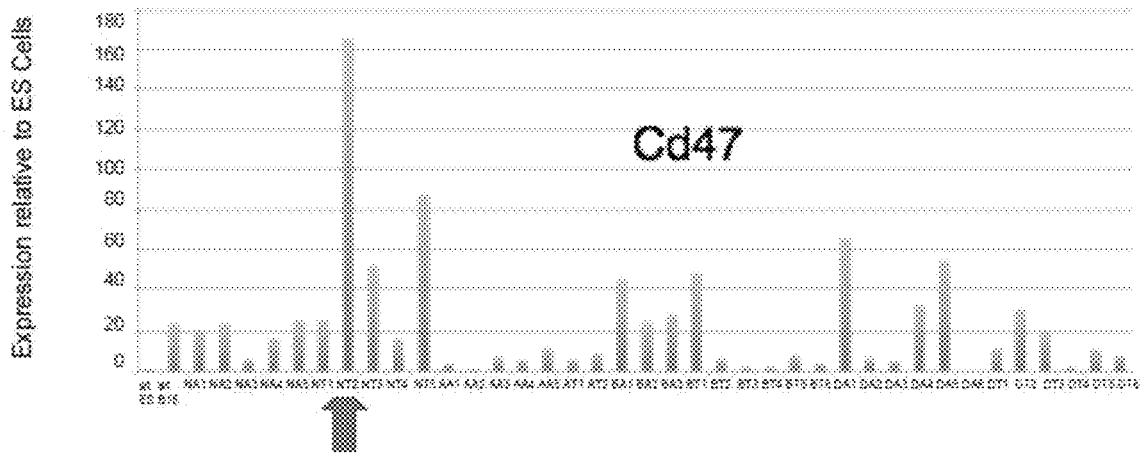
Figure 8E:
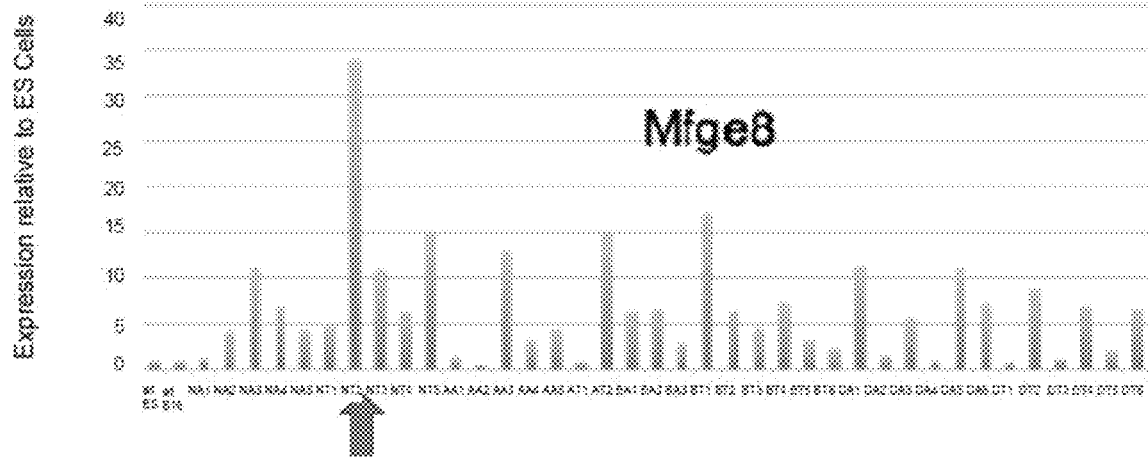
Figure 8F:
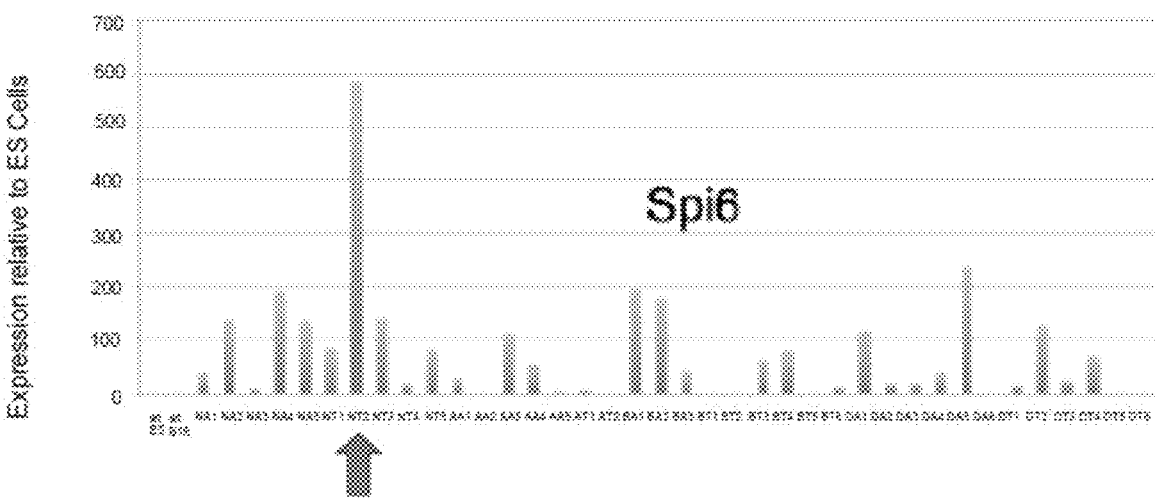
Figure 8G:
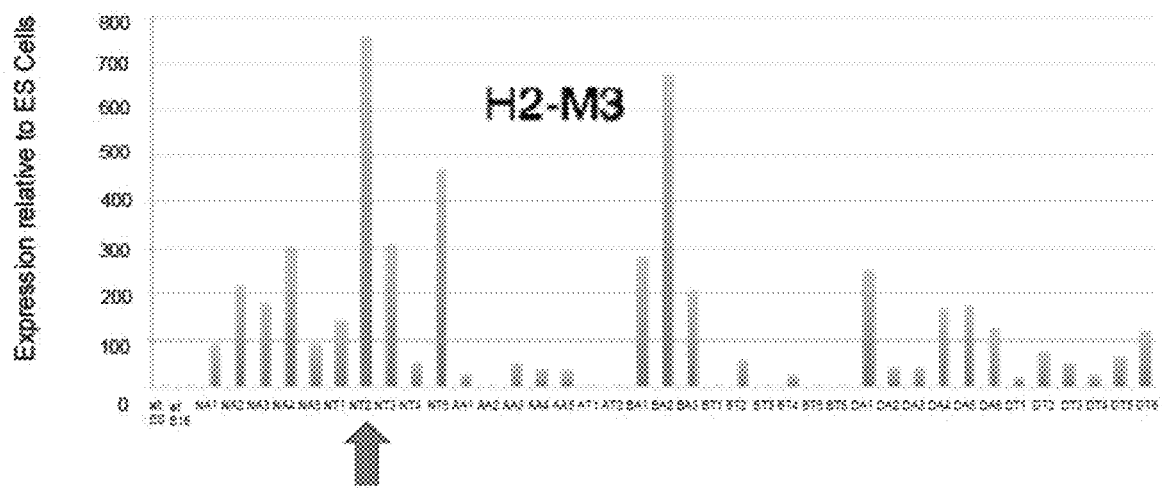
Figure 8H:
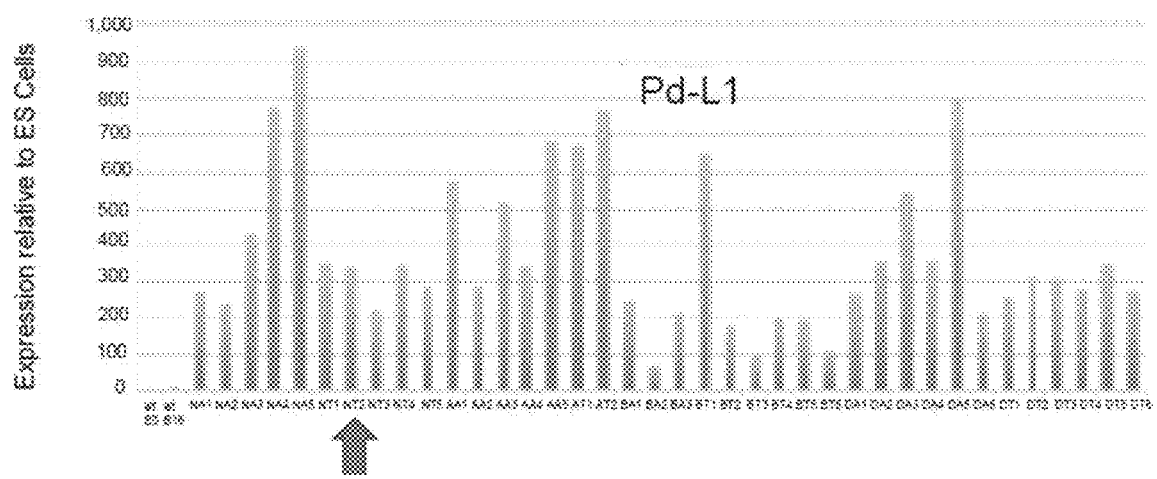

A similar experiment was conducted where wild type embryonic stem cells were detected up to 9 days post injection into FVB/N mice with cloaked teratomas (FIG. 7). However, at day 12, no evidence of cells remaining could be detected. Control animals were C57BL/6 mice also carrying the cloaked tumors. The signal in these mice increased over the time-course of the experiment.

Example 8: Cloaked and Fail-Safe Embryonic Stem Cell Line

When a Fail-Safe C57BL/6 ES cell line (as described, for example, in WO/2016/141480) was co-transfected with 5 candidate cloaking transgenes (PD-L1, FasL, Cd47, Cd200 and H2-M3), none of these transgene lines resulted in teratomas in allograft settings. When the set of co-transfected genes was expanded by three additional candidate cloaking genes: Spi6, Ccl21b and Mfge8, 38 clonal lines were generated. One of these lines, NT2, created teratomas in an allogeneic recipient (FVB). The expression levels of the cloaking genes in the 38 clonal lines, including the NT2 line (see arrows in FIGS. 8A-H), were measured using quantitative PCR (FIGS. 8A-H). Of the 38 clones, NT2 was the highest overexpression of Ccl21b (16,000×), FasL (25,000×), Cd200 (1700×), Cd47 (16×), Mfge8 (34×), Spi6 (600×) and H2-M3 (750×) compared to WT ES cells. PD-L1, although not the highest level expresser among the clones, the 350× expression over ES cells was also a significant increase. The expression of these genes was also checked in the Project Grandiose dataset (www.stemformatics.org/project_grandiose) and found that Ccl21b, FasL, Cd200, PD-L1 and Spi6 expression is under the detection threshold, therefore, their relative-to-ES cells expression is very high. Based on this data these eight, highly activated genes could have a primary role in inducing immune tolerance of an allograft.

Figures 11A, 11B:
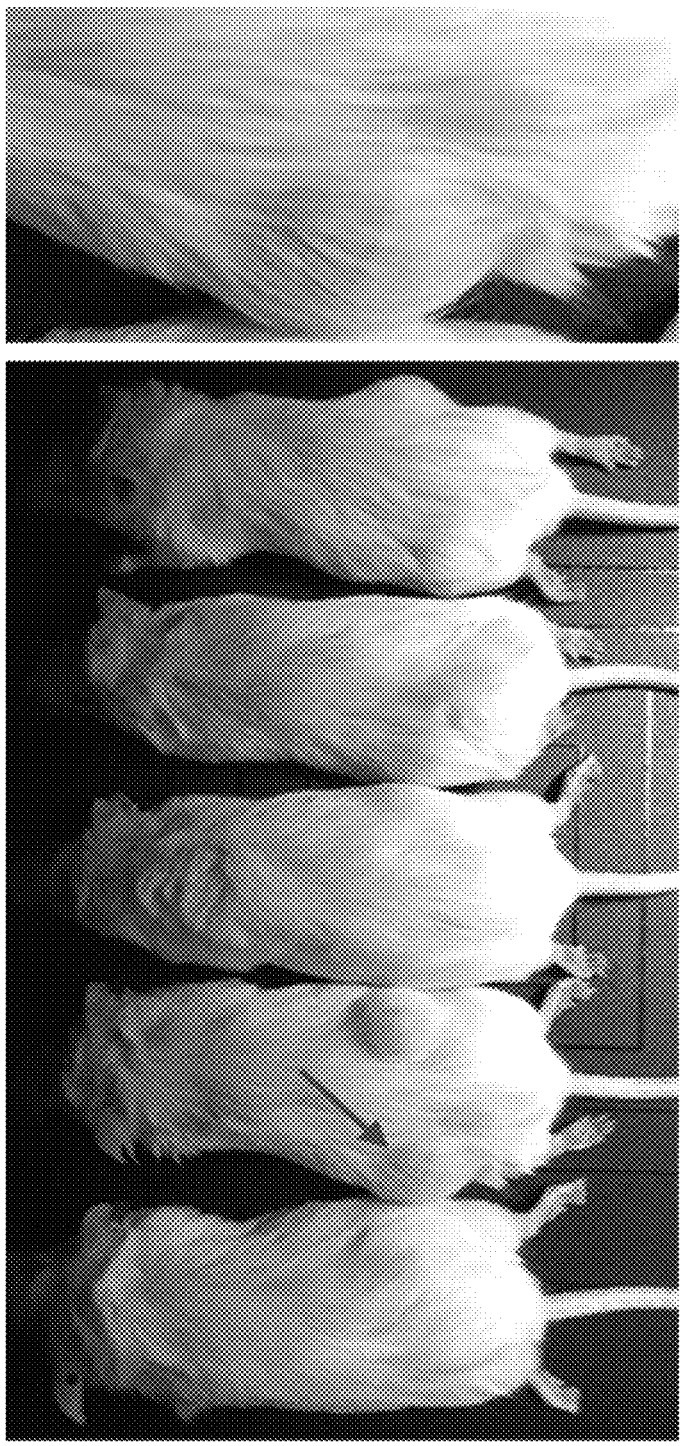
FIGS. 11A-11B are photographs showing C57BL/6 derived teratomas in FVB/N mice. The transgenic line, NT2, resulted in 9 teratomas out of 10 injection sites. Images were taken 3 months post injection.
Figure 12A:
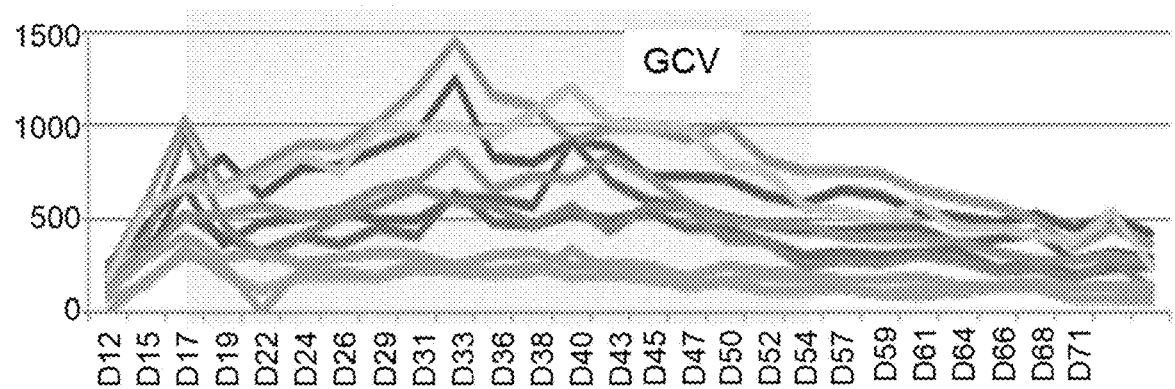
FIGS. 12A-12B are graphs showing the teratoma tumor size in isogenic (FIG. 12A) and allogenic (FIG. 12B) mice treated with ganciclovir.
Figure 12B:
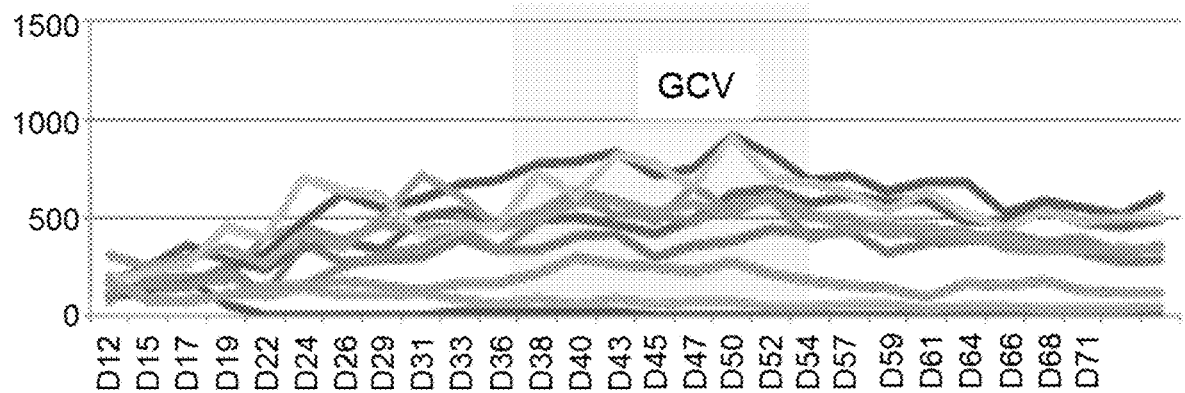

NT2 cells were injected into both C57BL/6 to create teratomas in an FVB allogenic setting (FIGS. 11A-11B) and an FVB iso C57Bl/6 isogenic setting. Allogenic teratomas (n=6) were steadily growing from day 12 to day 38. At the size of 500 mm², ganciclovir (GCV) treatment was started to remove the proliferative component of the tumors (FIGS. 12A-12B, upper panel (FIG. 12A) isogenic teratomas; bottom panel (FIG. 12B) allogenic teratomas)). Twenty days of treatment stopped the allograft growth. This experiment shows that: 1) Fail-safe and cloaked (NT2) cell-derived teratomas respond similarly to GCV treatment; they enter to dormancy after brief GCV exposure; 2) After GCV the teratomas remain stable. There is no sign of rejection of the dormant tissue; and 3). The dynamics of teratoma growth in FVB animals is different than in C57BL/6.

Figure 19:
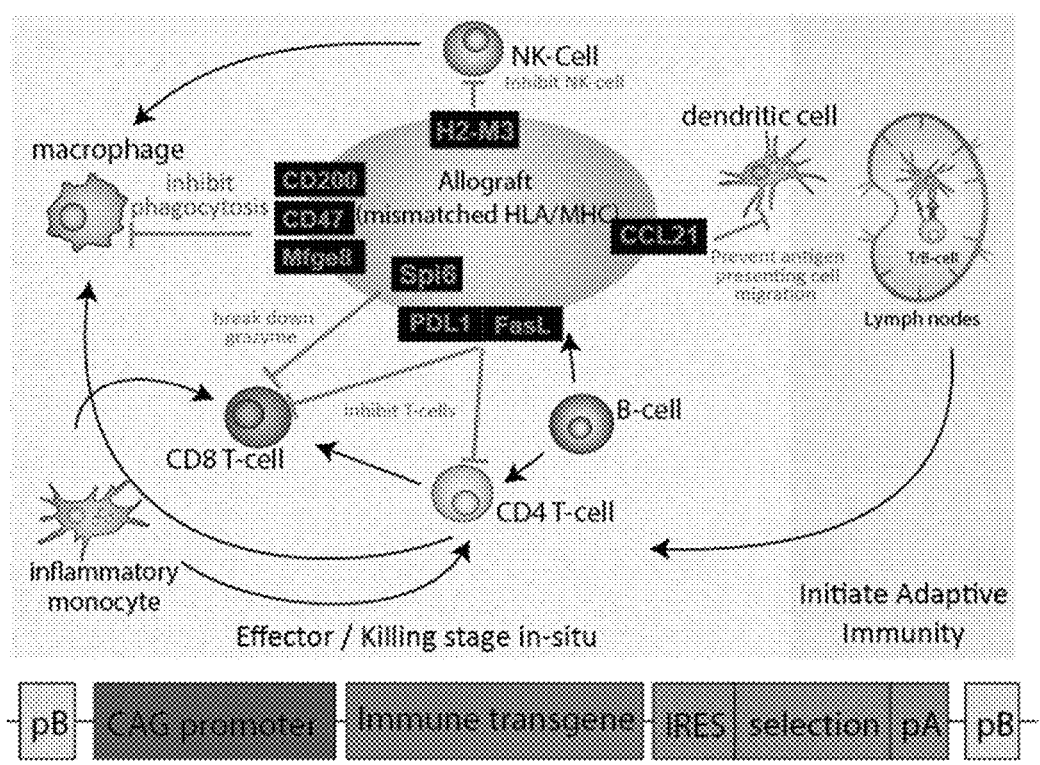
FIG. 19 is a schematic depicting the immune processes that are inhibited by the cloaking transgenes (top) and the expression cassette (bottom) used to express the cloaking transgenes in ES cells.

Cloaking transgenes expressed at a high level survive to form teratomas in an allogenic mouse. In our system, the cloaking transgenes are expressed under a very strong synthetic promoter, CAG (depicted in the schematic in FIG. 19). The CAG promoter is a combination of the cytomegalovirus early enhancer element, the splicer acceptor of the rabbit beta-globin gene, and also the promoter, first exon and first intron of the chicken beta-actin gene. We have performed extensive qPCR analysis on the level of transgene transcripts in many different ES cell clones, each of which has a different expression level of the transgenes. Only those ES clones that have the highest expression of cloaking transgenes survive in allogenic hosts.

Figure 9:
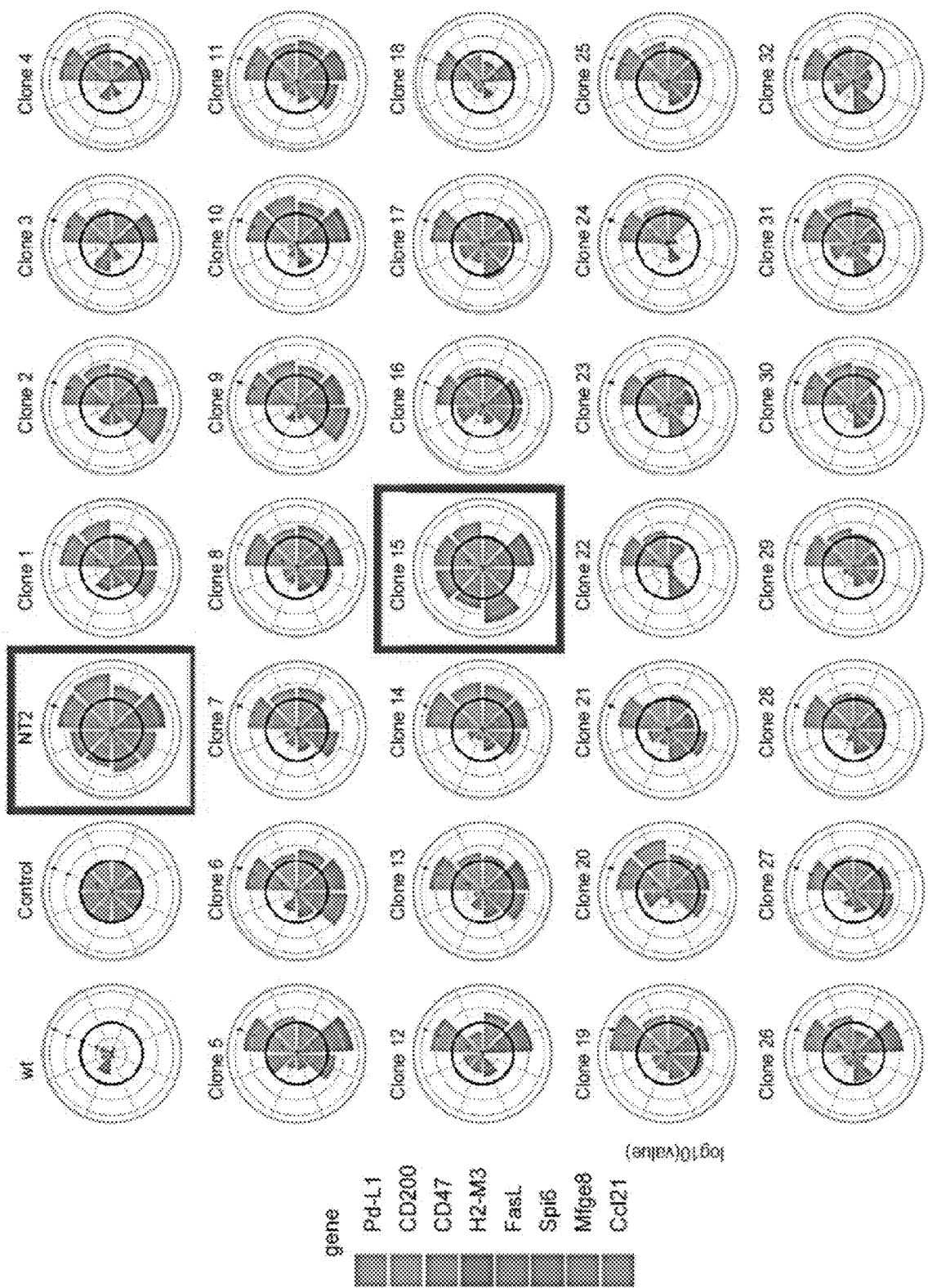
FIG. 9 is a series of graphs depicting cloaking transgene expression in ES cell clones. Each cloaking transgene is depicted in a different color. Concentric circles represent expression level on a log 10 scale. The thick black circle represents 1× expression normalized to positive controls (activated leukocytes isolated from murine lymph organs), with the next outer ring representing 10× and 100× expression compared to positive controls, respectively. The innermost ring is 0.1× expression compared to positive controls. Clones NT2 and 15 (indicated with red squares) had the highest expression of the cloaking genes. These clones survived in allogenic hosts.

As shown in FIG. 9, transcript expression level of the immunomodulatory genes relevant to the cloaking technology varied between ES cell clones. Concentric circles are depicted on a log 10 scale. The thick black line is 1×, the next outer ring is 10×, and then 100×. The innermost ring is 0.1×. All values are normalized to positive controls, which were activated leukocytes isolated from murine lymph organs that naturally express the immunomodulatory transgenes. The upper left panel shows wild-type ES cells with no transgenic modifications for reference-they express little or none of the relevant immunomodulatory transgenes. By contrast, clone NT2 and clone 15 (indicated by red squares), both with high expression of the genes, survived in allogenic hosts. All other clones shown in FIG. 9 did not survive in allogenic hosts.

Figure 10:
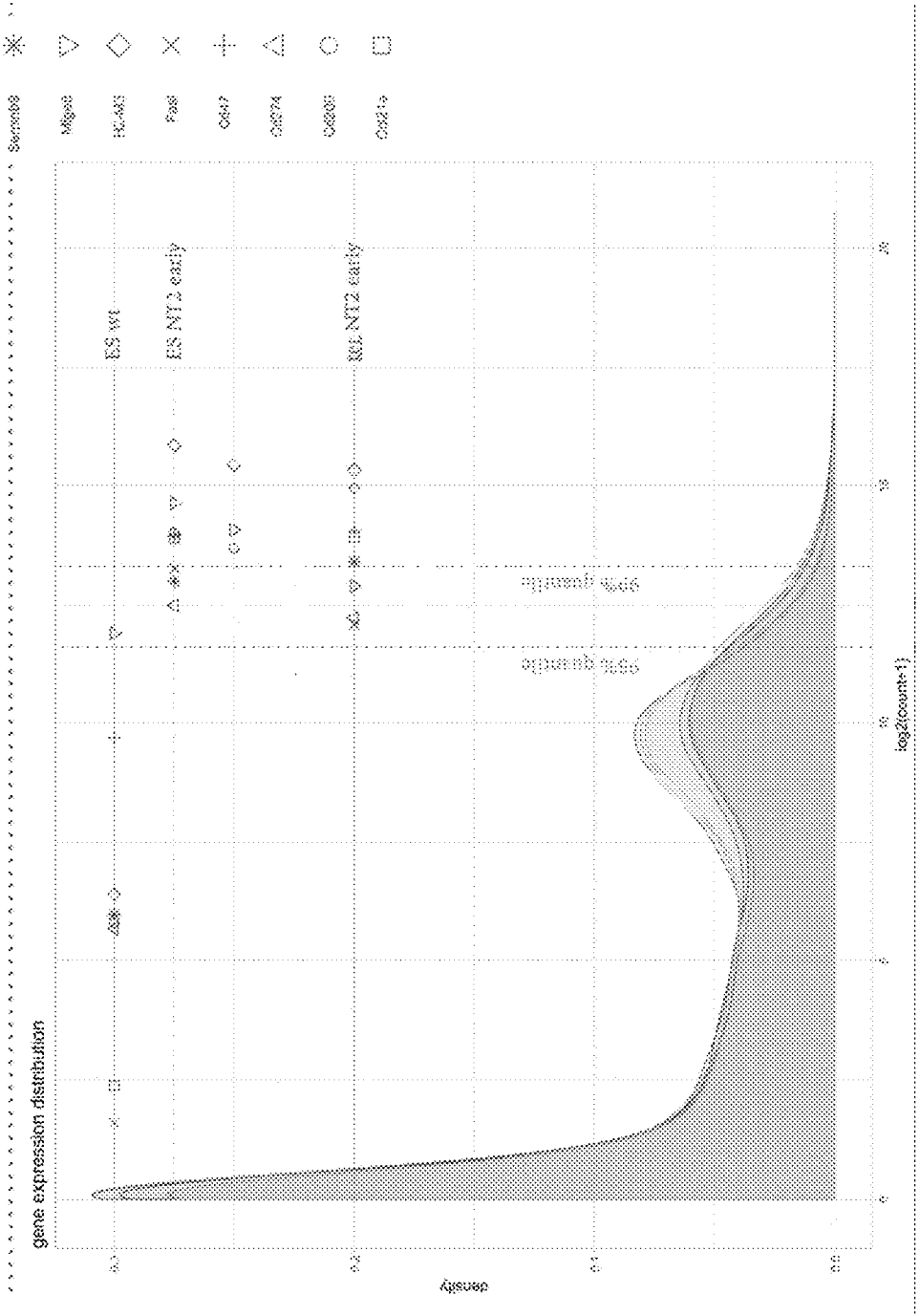
FIG. 10 is a graph depicting the expression of the cloaking transgenes among the whole genome gene expression level distribution for the whole genome of ES cells. All 8 cloaking transgenes in the NT2 cell line and NT2-derived teratoma had an expression level that was among the top 5% of all genes in the ES cell genome, with 5 of the cloaking transgenes having an expression level in the top 1% of all genes in the ES cell genome. The expression levels of the transgenes in the NT2 line and NT2-derived teratoma succeeded to achieve allograft tolerance.

The high expression of the cloaking transgenes is also depicted in FIG. 10. As shown in FIG. 10, all 8 cloaking transgenes in the NT2 cell line and NT2-derived teratoma had an expression level that was among the top 5% of all genes in the ES cell genome, with 5 of the cloaking transgenes having an expression level in the top 1% of all genes in the ES cell genome. The expression of these genes is much lower in WT ES cells, as only one of the genes has an expression level among the top 5% of all genes in the genome.

Figure 13A:
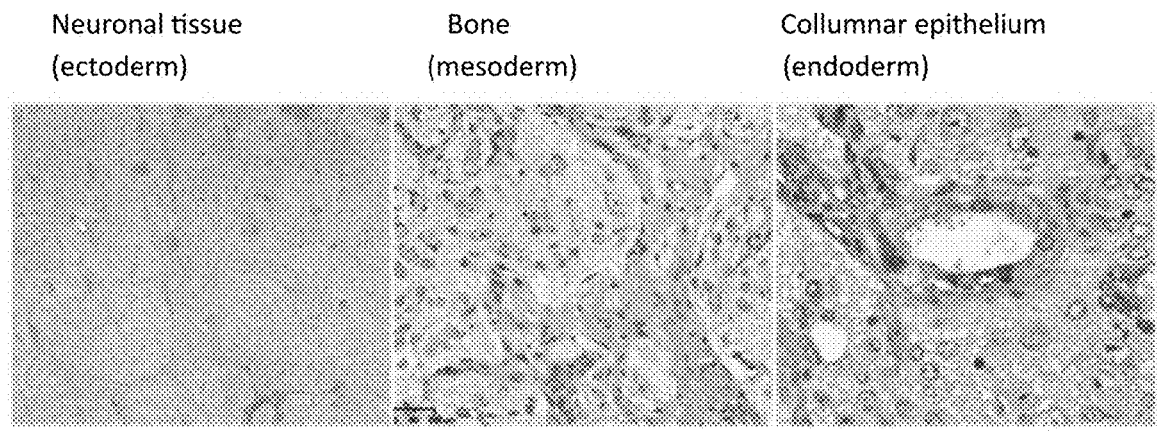
FIGS. 13A-13C are a series of photomicrographs showing that cloaked embryonic stem cells, injected into both isogenic (FIG. 13A) and allogenic (FIG. 13B) hosts, can differentiate into all three cell lineages.
Figure 13B:
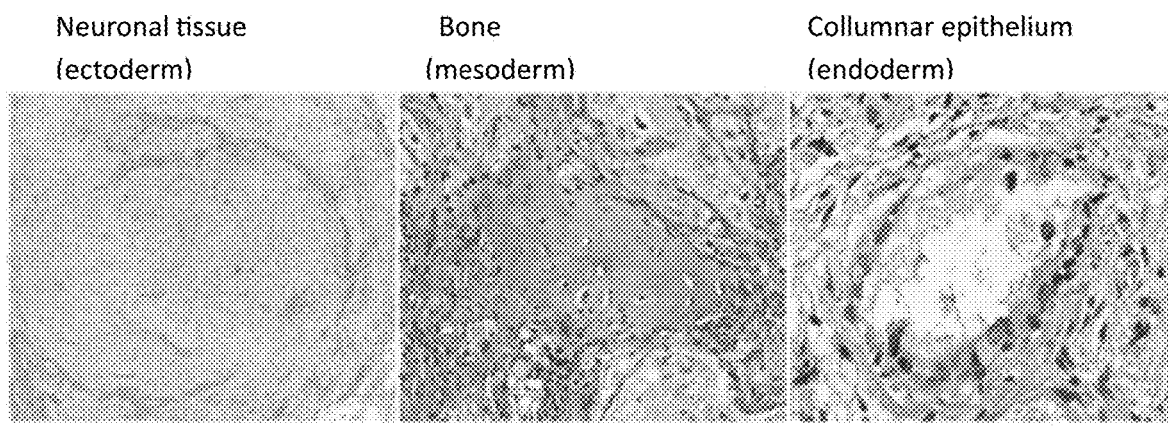
Figure 13C:
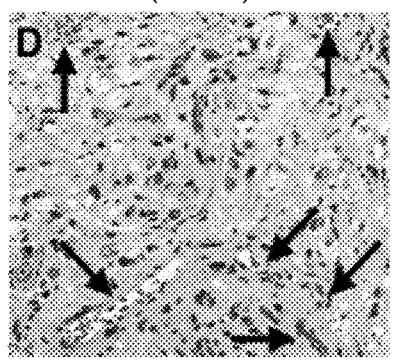

Example 9: Cloaked ESCs Contribute to all Three Germ Layers in Allogenic Teratomas It was next asked if immune cloaking would allow the full pluripotent developmental potential of ESCs to unfold in teratomas. Teratomas resulting from the injection of cloaked and uncloaked ESCs derived from C57BL/6 mice into isogenic and allogeneic hosts were analyzed by histopathology (hematoxylin and eosin staining). FIGS. 13A-13B (isogenic host neuronal, bone and columnar epithelium in upper panels (FIG. 13A); and allogenic host neuronal, bone, columnar epithelium and blood vessels in lower panels (FIG. 13B)) shows representative images obtained from both backgrounds, proving that the expression of the cloaking transgenes do not interfere with the normal developmental potential of these ES cells and the tumors are well vascularized. Both isogenic and allogenic tissues did not show any immune cell infiltration.

In another experiment, we tested if the cloaked ES cell were truly pluripotent by testing whether they could form cells from all three germ layers-endoderm, ectoderm, and mesoderm (FIGS. 14A-14D). This was assayed by injecting between 106 and 107 cloaked ES cells subcutaneously into a mouse and allowing them to proliferate and differentiate into a tissue mass named a teratoma. The teratoma was then removed 3-4 weeks after ES cell injection, and tissue sections cut and stained with H&E. These sections were analyzed under the microscope for cell morphology to determine if all three germ layers were present.

Figure 14A:
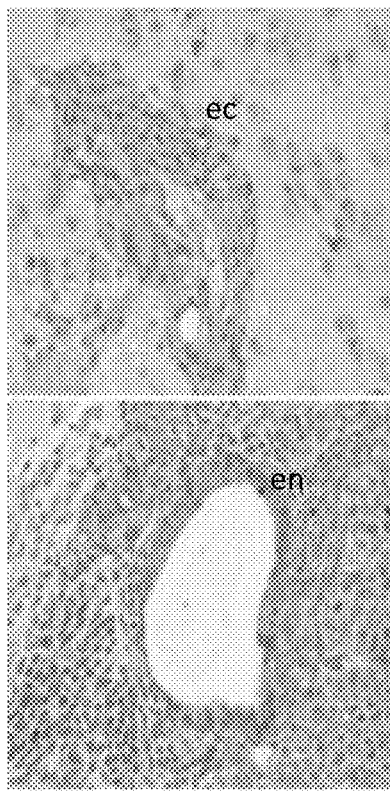
FIGS. 14A-14D are photomicrographs showing the formation of all three germ layers in a teratoma formed from subcutaneous injection of cloaked ES cells into a mouse.
Figure 14B:
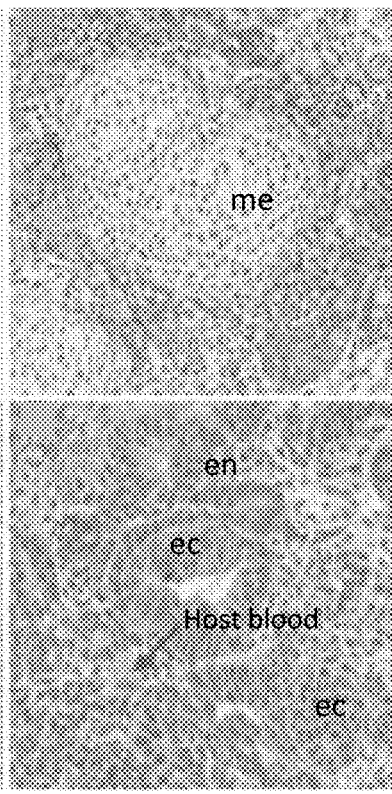
Figure 14C:
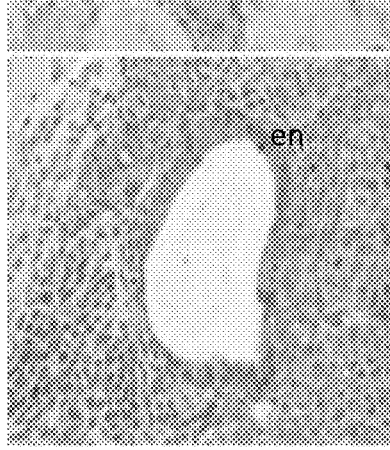
Figure 14D:
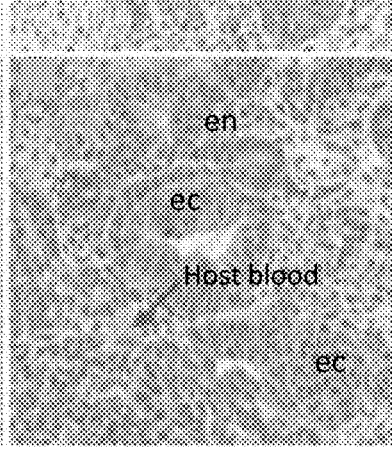

We asked whether the 8 cloaking transgenes inserted into ES cells and expressed at high levels would disrupt their ability to form all three germ layers. They did not. FIGS. 14A-14C show the three germ layers (ec=ectoderm, shown in FIG. 14A; en=endoderm, shown in FIG. 14C; me=mesoderm, shown in FIG. 14B). FIG. 14D shows a blood vessel, which verifies that these tissues are well-vascularized.

Example 10: ES Cells that Express Cloaking Transgenes Produce the Proteins Encoded by the Transgenes We confirmed the presence of the proteins encoded by the cloaking transgenes in NT2 ES cells (one of the clones with the highest expression) directly using fluorescent antibody-based microscopy (FIGS. 16A-16H). These data confirm that the proteins encoded by the transgenes are expressed in ES cells at easily detectable levels, which is expected based on the high levels of mRNA expression.

Figure 17A:
FIGS. 17A-17B are photomicrographs showing that cloaked ES cells have typical ES cell morphology (FIG. 17A) and express the ES cell marker alkaline phosphatase (FIG. 17B).
Figure 17B:
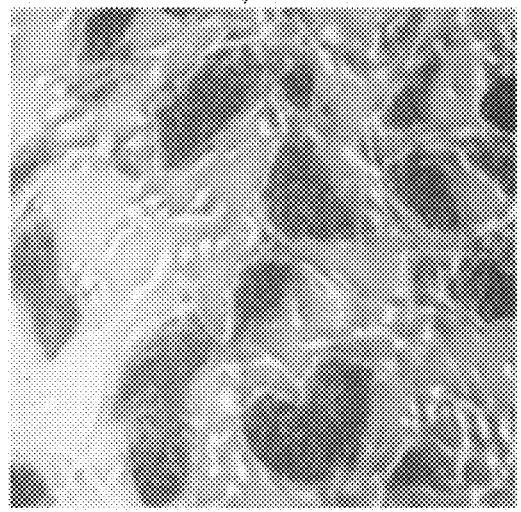
Figure 18A:
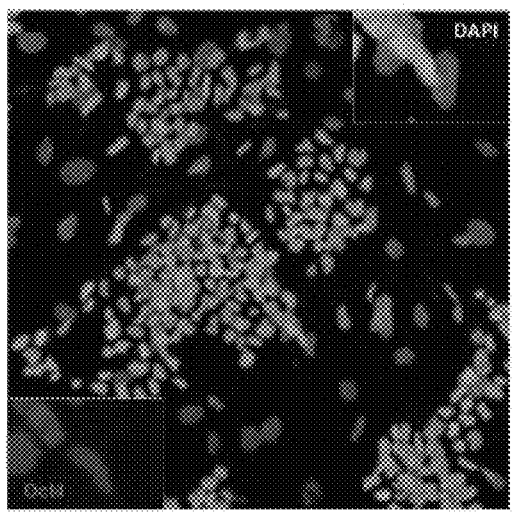
FIGS. 18A-18B are fluorescent photomicrographs showing the expression of markers of pluripotent ES cells (Oct4 (FIG. 18A) and SSEA1 (FIG. 18B)) in cloaked ES cells. The insets in FIGS. 18A-18B show single channel images of the fluorescent micrographs for the ES cell markers (Oct4 and SSEA) and DAPI, which labels the nucleus, to demonstrate that staining for the ES cell markers colocalizes with the cloaked cells.
Figure 18B:
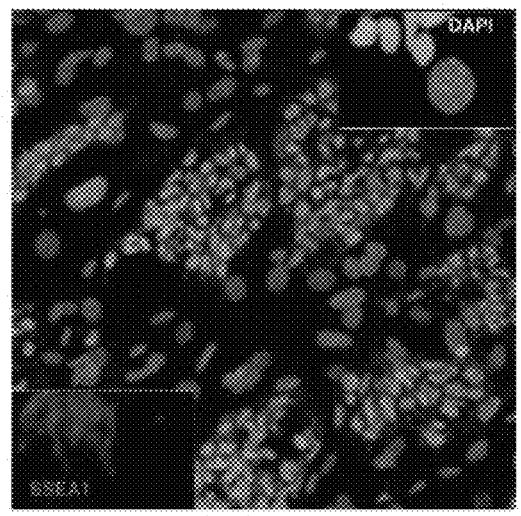

Example 11: ES Cells that Express High Levels of Cloaking Transgenes have Typical Morphology and Express Common ES Cell Markers We analyzed cloaked ES cells to determine whether they expressed markers of ES cells and retained a normal ES cell morphology. Cloaked ES cells have the typical morphology observed with healthy and pluripotent ES cells (FIG. 17A) and also stain positively for alkaline phosphatase (FIG. 17B), which is characteristic of healthy and pluripotent ES cells. Furthermore, our cloaked ES cells stained positively for the transcription factor Oct4 (FIG. 18A) as well as SSEA (FIG. 18B) using fluorescent antibodies, both common markers of normal pluripotent ES cells. These data show that ES cells that express high levels of the 8 immunomodulatory cloaking transgenes appear as normal ES cells with respect to their morphology and expression of common ES cell markers. The insets show that staining for Oct4 and SSEA1 (lower left inset) colocalizes with ES cells (visualized using DAPI in upper right insets).

Example 12: IFNγR1 d39 Prevents Upregulation of MHCs in ES Cells

Activated T-cells secrete IFNγ, which binds to the IFNγR1/R2 complex expressed on many cell types, including tissues and cells derived from ES cells. IFNγ binding to the IFNγ receptor induces upregulation of HLA (MHC in mice) and HLA-related molecules on the cell surface, which increases the allogenicity of the allograft and the likelihood of immune rejection. Differences in HLA proteins (also called major antigens) between the donor and recipient are the primary cause of rejection in all allogenic transplants.

To evaluate whether disrupting IFNγ signaling prevents or reduces HLA upregulation, we transfected C57BL/6 ES cells with piggyback-integratable vectors containing a wild-type IFNγR1 or dominant negative IFNγR1 (IFNγR1 d39, which lacks 39 amino acids in the cytoplasmic tail) transgene. These transgenes were expressed under the control of a constitutive CAG promoter upstream of the transgene contained on the same piggyback-integrated cassette.

Figure 20:
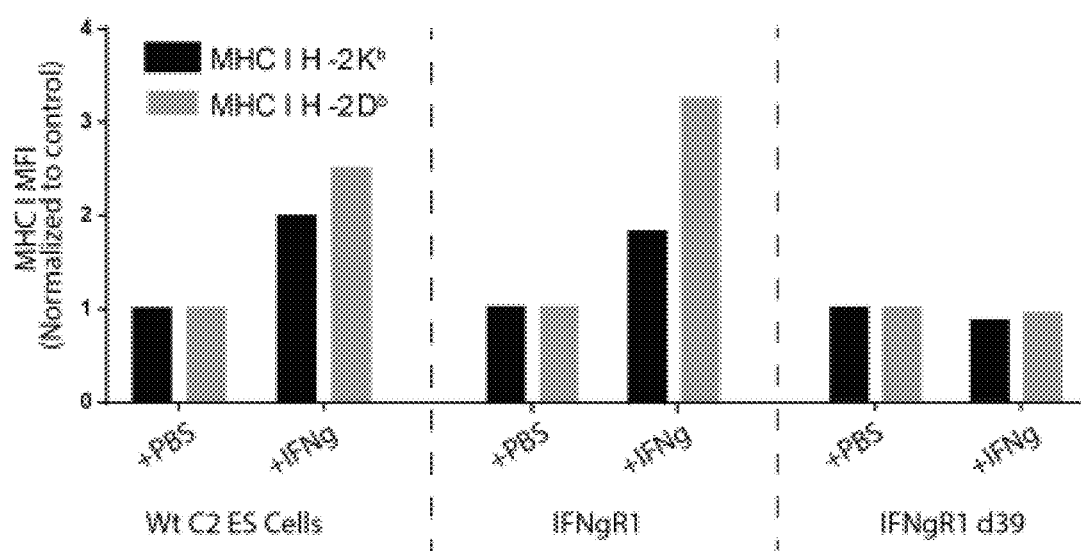
FIG. 20 is a series of graphs depicting the effect of interferon gamma (IFNγ) on MHC levels in ES cells. IFNγ increased MHC levels in wild-type ES cells and ES cells overexpressing the wild-type IFNγ receptor IFNyR1, but did not increase MHC levels in ES cells overexpressing a dominant negative form of the IFNγ receptor (IFNyR1 d39), indicating that IFNyR1 d39 completely inhibited the IFNγ-mediated upregulation of MHCs in ES cells.

Wild type and transfected ES cells were then grown in culture and exposed to 100 ng/ml of IFNγ ligand for 24 hours. In wild-type ES and IFNγR1-transfected cells (left and middle panels of FIG. 20, respectively), IFNγ exposure resulted in increased expression of the H-2 kb and H-2 Db major histocompatibility surface molecules (MHC class I), but not in IFNγR1 d39 cells (right panel of FIG. 20). Exposure to PBS alone had no effect. MHC class I levels were detected by fluorescent antibody staining, and the expression level quantified by measuring the mean fluorescent intensity (MFI) by flow cytometry. These data show that overexpression of IFNγR1 d39 completely inhibits IFNγ-mediated upregulation of MHCs in ES cells, indicating that expression of IFNγR1 d39 in ES cells can be used to prevent activation of the immune system and reduce the likelihood of immune rejection. Therefore, IFNγR1 d39 is a useful immunosuppressive transgene that can be expressed by the cloaked cells described herein to reduce immune activation and transplant rejection.

Example 13: Administration of Cloaked Cells Expressing a VEGF Inhibitor to a Subject with Wet AMD According to the methods disclosed herein, a physician of skill in the art can treat a patient, such as a human patient, with wet AMD to reduce vascularization of the eye or prevent or reduce disease progression. To this end, a physician of skill in the art can administer to the human patient cloaked cells (e.g., cloaked RPE cells or cloaked stem cells that have been differentiated into RPE cells) that express one or more (e.g., one, two, three, four, five, six, seven, or all eight) of PD-L1, HLA-G (H2-M3), Cd47, Cd200, FASLG (FasL), Ccl21 (Ccl21b), Mfge8, and Serpin B9 (Spi6) under the control of a constitutive promoter (e.g., CMV or CAG) and a VEGF inhibitor (e.g., VEGF-Trap, e.g., aflibercept) under the control of a constitutive promoter (e.g., CMV or CAG). The cloaked cells may be administered to the patient, for example, by local administration to the eye (e.g., injection into the subretinal space), to treat wet AMD. Twenty five thousand to one hundred thousand cloaked cells (e.g., 25,000, 50,000, 75,000, or 100,000 cloaked cells) can be administered to each affected eye.

Following administration of the cloaked cells to a patient, a practitioner of skill in the art can monitor the expression of the VEGF inhibitor, and the patient's improvement in response to the therapy, by a variety of methods. For example, a physician can monitor the patient's vision and the vascularization of the eye using standard approaches. A finding that the patient's vision improves or does not worsen, or that vascularization of the eye decreases or does not worsen compared to measurements taken prior to administration of the cloaked cells indicates that the patient is responding favorably to the treatment. Subsequent doses can be determined and administered as needed.

Example 14: Administration of Cloaked Dopaminergic Neurons to a Subject with Parkinson's Disease (PD)

According to the methods disclosed herein, a physician of skill in the art can treat a patient, such as a human patient, with PD to reduce motor symptoms of PD (e.g., bradykinesia, tremors, or rigidity) or prevent or reduce disease progression. To this end, a physician of skill in the art can administer to the human patient cloaked cells (e.g., dopaminergic neurons that have been modified to express cloaking transgenes or cloaked stem cells that have been differentiated into dopaminergic neurons) that express one or more (e.g., one, two, three, four, five, six, seven, or all eight) of PD-L1, HLA-G (H2-M3), Cd47, Cd200, FASLG (FasL), Ccl21 (Ccl21b), Mfge8, and Serpin B9 (Spi6) under the control of a constitutive promoter (e.g., CMV or CAG). The cloaked cells may be administered to the patient, for example, by local administration to the central nervous system (e.g., stereotactic injection into the substantia nigra), to treat PD. Twenty five thousand to one hundred thousand cloaked cells (e.g., 25,000, 50,000, 75,000, or 100,000 cloaked cells) can be administered. The patient can optionally be administered an additional therapy for PD, such as a dopamine agonist.

Following administration of the cloaked cells to a patient, a practitioner of skill in the art can monitor the patient's improvement in response to the therapy by a variety of methods. For example, a physician can monitor the patient's movement using standard neurological tests. A finding that the patient's motor symptoms improve or do not worsen compared to measurements taken prior to administration of the cloaked cells indicates that the patient is responding favorably to the treatment. Subsequent doses can be determined and administered as needed.

Example 15: Administration of Cloaked Cardiac Muscle Cells to a Subject that has Suffered a Myocardial Infarction According to the methods disclosed herein, a physician of skill in the art can treat a patient, such as a human patient, who has recently suffered a myocardial infarction to improve cardiac function (e.g., to replace or dead or damaged cardiac muscle cells). To this end, a physician of skill in the art can administer to the human patient cloaked cells (e.g., cloaked cardiac muscle cells or cloaked stem cells that have been differentiated into cardiac muscle cells) that express one or more (e.g., one, two, three, four, five, six, seven, or all eight) of PD-L1, HLA-G (H2-M3), Cd47, Cd200, FASLG (FasL), Ccl21 (Ccl21b), Mfge8, and Serpin B9 (Spi6) under the control of a constitutive promoter (e.g., CMV or CAG). The cloaked cells may be administered to the patient, for example, by local administration to the heart (e.g., injection into the cardiac muscle), to promote recovery after the myocardial infarction. The cells can be injected into the cardiac muscle as a monotherapy, or the cells can be delivered during the performance of a bypass surgery or another open heart surgical procedure. One million to five billion cloaked cardiac muscle cells (e.g., $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, or $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, or $5\times10^9$ cloaked cells) can be administered.

Following administration of the cloaked cells to a patient, a practitioner of skill in the art can monitor the patient's improvement in response to the therapy by a variety of methods. For example, a physician can monitor the patient's cardiac function using standard approaches (e.g., EKG, echocardiogram, angiogram, stress test, or nuclear imaging). A finding that the patient's cardiac function improves or stabilizes compared to measurements taken prior to administration of the cloaked cells indicates that the patient is responding favorably to the treatment. Subsequent doses can be determined and administered as needed.

Example 16: Administration of Cloaked Cells Expressing a TNFα Inhibitor to a Subject with RA According to the methods disclosed herein, a physician of skill in the art can treat a patient, such as a human patient, with rheumatoid arthritis to reduce join stiffness, swelling, or pain. To this end, a physician of skill in the art can administer to the human patient cloaked cells (e.g., cloaked articular fibroblasts or cloaked stem cells that have been differentiated into articular fibroblasts) that express one or more (e.g., one, two, three, four, five, six, seven, or all eight) of PD-L1, HLA-G (H2-M3), Cd47, Cd200, FASLG (FasL), Ccl21 (Ccl21b), Mfge8, and Serpin B9 (Spi6) under the control of a constitutive promoter (e.g., CMV or CAG) and a TNFα inhibitor (e.g., a TNFα inhibitory antibody, such as adalimumab) under the control of an inducible promoter (e.g., a tetracycline response element). The cloaked cells may be administered to the patient, for example, by local administration to a joint (e.g., injection into an arthritic joint, such as joint in the hand), to treat RA. One million to one hundred million cloaked articular fibroblasts expressing an anti-inflammatory biologic (e.g., $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, or $1\times10^8$ cloaked articular fibroblasts) can be administered to each affected joint. When the patient experiences a flare up of RA symptoms, the patient can be treated with tetracycline or doxycycline to drive expression of the TNFα inhibitor. Tetracycline or doxycycline can be withdrawn when the patient's flare up has resolved.

Following administration of the cloaked cells and tetracycline or doxycycline to a patient, a practitioner of skill in the art can monitor the expression of the TNFα inhibitor, and the patient's improvement in response to the therapy, by a variety of methods. For example, a physician can monitor the patient's joint pain, swelling, and stiffness using standard approaches. A finding that the patient's joint pain, swelling, or stiffness is reduced compared to measurements taken prior to administration of the cloaked cells indicates that the patient is responding favorably to the treatment. Subsequent doses can be determined and administered as needed.

Example 17: Administration of Cloaked Cells Expressing Insulin to a Subject with Type 1 Diabetes According to the methods disclosed herein, a physician of skill in the art can treat a patient, such as a human patient, with Type 1 diabetes to increase insulin levels. To this end, a physician of skill in the art can administer to the human patient cloaked cells (e.g., cloaked stem cells, cloaked pancreatic beta cells, or cloaked stem cells that have been differentiated into pancreatic beta cells) that express one or more (e.g., one, two, three, four, five, six, seven, or all eight) of PD-L1, HLA-G (H2-M3), Cd47, Cd200, FASLG (FasL), Ccl21 (Ccl21b), Mfge8, and Serpin B9 (Spi6) under the control of a constitutive promoter (e.g., CMV or CAG) and insulin under the control of a constitutive promoter (e.g., CMV or CAG). The cloaked cells may be administered to the patient, for example, by subcutaneous injection (e.g., to create a cloaked subcutaneous tissue), to treat Type 1 diabetes. One million to three billion cloaked cells expressing insulin (e.g., $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, or $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, or $3\times10^9$ cloaked cells) can be administered subcutaneously.

Following administration of the cloaked cells to a patient, a practitioner of skill in the art can monitor the expression of the patient's improvement in response to the therapy by a variety of methods. For example, a physician can monitor insulin levels or symptoms of Type 1 diabetes (e.g., unintended weight loss, fatigue, or blurred vision) using standard approaches. A finding that the patient's insulin levels are increased or the symptoms of Type 1 diabetes are reduced compared to measurements taken prior to administration of the cloaked cells indicates that the patient is responding favorably to the treatment. Subsequent doses can be determined and administered as needed.

Example 18: Administration of Cloaked Cells Expressing Factor VIII to a Subject with Hemophilia According to the methods disclosed herein, a physician of skill in the art can treat a patient, such as a human patient, with hemophilia to increase the levels of a blood clotting factor or reduce excessive bleeding or bruising. To this end, a physician of skill in the art can administer to the human patient cloaked cells (e.g., cloaked stem cells, cloaked endothelial cells, or cloaked stem cells that have been differentiated into endothelial cells) that express one or more (e.g., one, two, three, four, five, six, seven, or all eight) of PD-L1, HLA-G (H2-M3), Cd47, Cd200, FASLG (FasL), Ccl21 (Ccl21b), Mfge8, and Serpin B9 (Spi6) under the control of a constitutive promoter (e.g., CMV or CAG) and Factor VIII under the control of a constitutive promoter (e.g., CMV or CAG). The cloaked cells may be administered to the patient, for example, by subcutaneous injection (e.g., to create a cloaked subcutaneous tissue), to treat hemophilia. One million to three billion cloaked cells expressing Factor VIII (e.g., $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, or $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, or $3\times10^9$ cloaked cells) can be administered subcutaneously.

Following administration of the cloaked cells to a patient, a practitioner of skill in the art can monitor the expression of the patient's improvement in response to the therapy by a variety of methods. For example, a physician can monitor Factor VIII levels or symptoms of hemophilia (e.g., excessive bleeding or frequent bruising) using standard approaches. A finding that the patient's Factor VIII levels are increased or the symptoms of hemophilia are reduced compared to measurements taken prior to administration of the cloaked cells indicates that the patient is responding favorably to the treatment. Subsequent doses can be determined and administered as needed.

Example 19: Administration of Cloaked Cells Expressing Glucocerebrosidase to a Subject with Gaucher's Disease According to the methods disclosed herein, a physician of skill in the art can treat a patient, such as a human patient, with Gaucher's disease to reduce the accumulation of glucocerebroside or to reduce symptoms of Gaucher's disease (e.g., fatigue, anemia, low blood platelet count, enlarged liver or spleen). To this end, a physician of skill in the art can administer to the human patient cloaked cells (e.g., cloaked stem cells) that express one or more (e.g., one, two, three, four, five, six, seven, or all eight) of PD-L1, HLA-G (H2-M3), Cd47, Cd200, FASLG (FasL), Ccl21 (Ccl21b), Mfge8, and Serpin B9 (Spi6) under the control of a constitutive promoter (e.g., CMV or CAG) and glucocerebrosidase under the control of a constitutive promoter (e.g., CMV or CAG). The cloaked cells may be administered to the patient, for example, by subcutaneous injection (e.g., to create a cloaked subcutaneous tissue), to treat Gaucher's disease. One million to three billion cloaked cells expressing glucocerebrosidase (e.g., $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, or $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, or $3\times10^9$ cloaked cells) can be administered subcutaneously.

Following administration of the cloaked cells to a patient, a practitioner of skill in the art can monitor the expression of the patient's improvement in response to the therapy by a variety of methods. For example, a physician can monitor accumulation of glucocerebroside or symptoms of Gaucher's disease (e.g., fatigue, anemia, low blood platelet count, enlarged liver or spleen) using standard approaches. A finding of a reduction in the patient's accumulation of glucocerebroside or symptoms of Gaucher's disease compared to measurements taken prior to administration of the cloaked cells indicates that the patient is responding favorably to the treatment. Subsequent doses can be determined and administered as needed.

Example 20: Administration of Cloaked Cells to a Subject Receiving a Liver Transplant According to the methods disclosed herein, a physician of skill in the art can treat a patient, such as a human patient, who is receiving a liver transplant to reduce the risk of transplant rejection. To this end, a physician of skill in the art can administer to the human patient cloaked cells (e.g., cloaked stem cells, cloaked liver cells, or cloaked stem cells that have been differentiated into liver cells) that express one or more (e.g., one, two, three, four, five, six, seven, or all eight) of PD-L1, HLA-G (H2-M3), Cd47, Cd200, FASLG (FasL), Ccl21 (Ccl21b), Mfge8, and Serpin B9 (Spi6) under the control of a constitutive promoter (e.g., CMV or CAG). The cloaked cells may be administered to the patient, for example, by injection into the liver or near the site of the transplanted liver, to reduce the risk of transplant rejection. One million to one hundred billion cloaked cells (e.g., $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, or $1\times10^{11}$ cloaked cells) can be administered to or near the liver.

Following administration of the cloaked cells to a patient, a practitioner of skill in the art can monitor the expression of the patient's improvement in response to the therapy by a variety of methods. For example, a physician can monitor the patient for symptoms that predict transplant rejection using standard approaches. A finding of an equivalent outcome in transplant rejection as that observed in subjects administered immunosuppressive agent(s) indicates that the patient is responding favorably to the treatment. Subsequent doses can be determined and administered as needed.

Example 21: Administration of Cloaked and Fail Safe Cells Expressing Insulin to a Subject with Type 1 Diabetes According to the methods disclosed herein, a physician of skill in the art can treat a patient, such as a human patient, with Type 1 diabetes to increase insulin levels. To this end, a physician of skill in the art can administer to the human patient cloaked cells (e.g., cloaked stem cells, cloaked pancreatic beta cells, or cloaked stem cells that have been differentiated into pancreatic beta cells) that express one or more (e.g., one, two, three, four, five, six, seven, or all eight) of PD-L1, HLA-G (H2-M3), Cd47, Cd200, FASLG (FasL), Ccl21 (Ccl21b), Mfge8, and Serpin B9 (Spi6) under the control of a constitutive promoter (e.g., CMV or CAG) and insulin under the control of a constitutive promoter (e.g., CMV or CAG). The cloaked cells can also be modified to allow for control of their proliferation by linking the expression of a CDL with that of a DNA sequence encoding a negative selectable marker. For example, the cloaked cells can be modified to contain homozygous ALINKS (e.g., HSV-TK systems) in two CDL loci (e.g., Cdk1 and Top2A). The cloaked cells may be administered to the patient, for example, by subcutaneous injection (e.g., to create a cloaked subcutaneous tissue), to treat Type 1 diabetes. One million to three billion cloaked cells expressing insulin (e.g., $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, or $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, or $3\times10^9$ cloaked cells) can be administered subcutaneously.

Following administration of the cloaked cells to a patient, a practitioner of skill in the art can monitor the expression of the patient's improvement in response to the therapy by a variety of methods. For example, a physician can monitor insulin levels or symptoms of Type 1 diabetes (e.g., unintended weight loss, fatigue, or blurred vision) using standard approaches. A finding that the patient's insulin levels are increased or the symptoms of Type 1 diabetes are reduced compared to measurements taken prior to administration of the cloaked cells indicates that the patient is responding favorably to the treatment. Subsequent doses can be determined and administered as needed.

A practitioner of skill in the art can also monitor the size of the cloaked subcutaneous tissue. If it appears that the cloaked subcutaneous tissue is becoming tumorigenic, the practitioner can administer ganciclovir to the subject to ablate the proliferating cloaked cells. Non-proliferating cloaked cells will not express the CDLs, and, therefore, will not be ablated by ganciclovir treatment.

Example 22: Administration of Cloaked and Fail Safe Cells Expressing Insulin to a Subject with Type 1 Diabetes According to the methods disclosed herein, a physician of skill in the art can treat a patient, such as a human patient, with Type 1 diabetes to increase insulin levels. To this end, a physician of skill in the art can administer to the human patient cloaked cells (e.g., cloaked stem cells, cloaked pancreatic beta cells, or cloaked stem cells that have been differentiated into pancreatic beta cells) that express one or more (e.g., one, two, three, four, five, six, seven, or all eight) of PD-L1, HLA-G (H2-M3), Cd47, Cd200, FASLG (FasL), Ccl21 (Ccl21b), Mfge8, and Serpin B9 (Spi6) under the control of a constitutive promoter (e.g., CMV or CAG) and insulin under the control of a constitutive promoter (e.g., CMV or CAG). The cloaked cells can also be modified to allow for control of their proliferation by linking the expression of a CDL with that of a DNA sequence encoding an inducible activator system. For example, a dox-bridge can be inserted into two CDLs (e.g., Cdk1 and Top2A) to generate homozygous modifications in both CDLs in a cloaked cell, such that in the presence of an inducer (e.g., doxycycline) the dox-bridge permits CDL expression, thereby allowing cell division and proliferation. The cloaked cells may be administered to the patient, for example, by subcutaneous injection (e.g., to create a cloaked subcutaneous tissue), to treat Type 1 diabetes. One million to three billion cloaked cells expressing insulin (e.g., $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, or $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, or $3\times10^9$ cloaked cells) can be administered subcutaneously.

Following administration of the cloaked cells to a patient, a practitioner of skill in the art can monitor the expression of the patient's improvement in response to the therapy by a variety of methods. For example, a physician can monitor insulin levels or symptoms of Type 1 diabetes (e.g., unintended weight loss, fatigue, or blurred vision) using standard approaches. A finding that the patient's insulin levels are increased or the symptoms of Type 1 diabetes are reduced compared to measurements taken prior to administration of the cloaked cells indicates that the patient is responding favorably to the treatment. Subsequent doses can be determined and administered as needed. If the practitioner determines that the subject needs a higher level of insulin, the practitioner can allow the cloaked cells to proliferate by treating the subject with doxycycline. Once the desired level of insulin is reached, treatment with doxycycline can be stopped and the cloaked cells will cease to proliferate.

TABLE 5

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Actr8 | 56249 | ACTR8 | 93973 | −1.88 | chromatin remodeling | Cell cycle | CS score, function | |
| Alg11 | 207958 | ALG11 | 440138 | −1.27 | dolichol-linked oligosaccharide biosynthetic process | Cell cycle | CS score, function | |
| Anapc11 | 66156 | ANAPC11 | 51529 | −2.68 | protein ubiquitination involved in ubiquitin-dependent protein catabolic process | Cell cycle | CS score, function | |
| Anapc2 | 99152 | ANAPC2 | 29882 | −2.88 | mitotic cell cycle | Cell cycle | CS score, mouse K.O., function | Wirth KG, et al. Genes Dev. 2004 Jan. 1; 18(1): 88-98 |
| Anapc4 | 52206 | ANAPC4 | 29945 | −1.79 | regulation of mitotic metaphase/anaphase transition | Cell cycle | CS score, function | |
| Anapc5 | 59008 | ANAPC5 | 51433 | −1.66 | mitotic cell cycle | Cell cycle | CS score, function | |
| Aurka | 20878 | AURKA | 6790 | −2.26 | meiotic spindle organization | Cell cycle | CS score, mouse K.O., function | Sasai K, et al. Oncogene. 2008 Jul. 3; 27(29):4122-7 |
| Banf1 | 23825 | BANF1 | 8815 | −2.14 | mitotic cell cycle | Cell cycle | CS score, function | |
| Birc5 | 11799 | BIRC5 | 332 | −2.24 | regulation of signal transduction | Cell cycle | CS score, mouse K.O., function | Uren AG, et al. Curr Biol. 2000 Nov. 2; 10(21):1319-28 |
| Bub3 | 12237 | BUB3 | 9184 | −3.15 | mitotic sister chromatid segregation | Cell cycle | CS score, mouse K.O., function | Kalitsis P, et al. Genes Dev. 2000 Sep. 15; 14(18): 2277-82 |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Casc5 | 76464 | CASC5 | 57082 | −1.16 | mitotic cell cycle | Cell cycle | CS score, mouse K.O., function | Overbeek PA, et al. MGI Direct Data Submission. 2011 |
| Ccna2 | 12428 | CCNA2 | 890 | −1.59 | regulation of cyclin-dependent protein serine/threonine kinase activity | Cell cycle | CS score, mouse K.O., function | Kalaszczynska I, et al. Cell. 2009 Jul. 23; 138(2): 352-65 |
| Ccnh | 66671 | CCNH | 902 | −2.01 | regulation of cyclin-dependent protein serine/threonine kinase activity | Cell cycle | CS score, function | |
| Cdc123 | 98828 | CDC123 | 8872 | −2.45 | cell cycle | Cell cycle | CS score, function | |
| Cdc16 | 69957 | CDC16 | 8881 | −3.58 | cell division | Cell cycle | CS score, function | |
| Cdc20 | 107995 | CDC20 | 991 | −2.97 | mitotic cell cycle | Cell cycle | CS score, mouse K.O., function | Li M, et al. Mol Cell Biol. 2007 May; 27(9): 3481-8 |
| Cdc23 | 52563 | CDC23 | 8697 | −2.28 | mitotic cell cycle | Cell cycle | CS score, function | |
| Cdk1 | 12534 | CDK1 | 983 | −2.44 | cell cycle | Cell cycle | CS score, mouse K.O., function | Diril MK, et al. Proc Natl Acad Sci U S A. 2012 Mar. 6; 109(10): 3826-31 |
| Cenpa | 12615 | CENPA | 1058 | −1.87 | cell cycle | Cell cycle | CS score, mouse K.O., function | Howman EV, et al. Proc Natl Acad Sci USA. 2000 Feb. 1; 97(3):1148-53 |
| Cenpm | 66570 | CENPM | 79019 | −2.53 | mitotic cell cycle | Cell cycle | CS score, function | |
| Chek1 | 12649 | CHEK1 | 1111 | −1.67 | protein phosphorylation | Cell cycle | CS score, mouse K.O., function | Takai H, et al. Genes Dev. 2000 Jun. 15; 14(12): 1439-47 |
| Chmp2a | 68953 | CHMP2A | 27243 | −2.40 | vacuolar transport | Cell cycle | CS score, function | |
| Ckap5 | 75786 | CKAP5 | 9793 | −2.94 | G2/M transition of mitotic cell cycle | Cell cycle | CS score, mouse K.O., function | Barbarese E, et al. PLOS One. 2013; 8(8): e69989 |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Cltc | 67300 | CLTC | 1213 | −1.75 | intracellular protein transport | Cell cycle | CS score, function | |
| Cops5 | 26754 | COPS5 | 10987 | −1.75 | protein deneddylation | Cell cycle | CS score, mouse K.O., function | Tian L, et al. Oncogene. 2010 Nov. 18; 29(46): 6125-37 |
| Dctn2 | 69654 | DCTN2 | 10540 | −1.48 | G2/M transition of mitotic cell cycle | Cell cycle | CS score, function | |
| Dctn3 | 53598 | DCTN3 | 11258 | −1.77 | G2/M transition of mitotic cell cycle | Cell cycle | CS score, function | |
| Dhfr | 13361 | DHFR | 1719 | −2.84 | G1/S transition of mitotic cell cycle | Cell cycle | CS score, function | |
| Dtl | 76843 | DTL | 51514 | −2.69 | protein poly-ubiquitination | Cell cycle | CS score, mouse K.O., function | Liu CL, et al. J Biol Chem. 2007 Jan. 12; 282(2): 1109-18 |
| Dync1h1 | 13424 | DYNC1H1 | 1778 | −3.44 | G2/M transition of mitotic cell cycle | Cell cycle | CS score, mouse K.O., function | Harada A, et al. J Cell Biol. 1998 Apr. 6; 141(1):51-9 |
| Ecd | 70601 | ECD | 11319 | −3.18 | regulation of glycolytic process | Cell cycle | CS score, function | |
| Ect2 | 13605 | ECT2 | 1894 | −1.80 | cell morphogenesis | Cell cycle | CS score, mouse K.O., function | Hansen J, et al. Proc Natl Acad Sci U S A. 2003 Aug. 19; 100(17): 9918-22 |
| Ep300 | 328572 | EP300 | 2033 | −2.04 | G2/M transition of mitotic cell cycle | Cell cycle | CS score, mouse K.O., function | Yao TP, et al. Cell. 1998 May 1; 93(3):361-72 |
| Ercc3 | 13872 | ERCC3 | 2071 | −2.10 | nucleotide-excision repair | Cell cycle | CS score, mouse K.O., function | Andressoo JO, et al. Mol Cell Biol. 2009 March; 29(5): 1276-90 |
| Espl1 | 105988 | ESPL1 | 9700 | −3.24 | proteolysis | Cell cycle | CS score, mouse K.O., function | Wirth KG, et al. J Cell Biol. 2006 Mar. 13; 172(6): 847-60 |
| Fntb | 110606 | FNTB | 2342 | −2.42 | phototransduction, visible light | Cell cycle | CS score, mouse K.O., function | Mijimolle N, et al. Cancer Cell. 2005 April; 7(4):313-24 |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Gadd45gip1 | 102060 | GADD45GIP1 | 90480 | −1.81 | organelle organization | Cell cycle | CS score, mouse K.O., function | Kwon MC, et al. EMBO J. 2008 Feb. 20; 27(4):642-53 |
| Gins1 | 69270 | GINS1 | 9837 | −1.84 | mitotic cell cycle | Cell cycle | CS score, mouse K.O., function | Ueno M, et al. Mol Cell Biol. 2005 December; 25(23):10528-32 |
| Gnb2l1 | 14694 | GNB2L1 | 10399 | −2.84 | osteoblast differentiation | Cell cycle | CS score, function | |
| Gspt1 | 14852 | GSPT1 | 2935 | −1.77 | G1/S transition of mitotic cell cycle | Cell cycle | CS score, function | |
| Haus1 | 225745 | HAUS1 | 115106 | −1.92 | spindle assembly | Cell cycle | CS score, function | |
| Haus3 | 231123 | HAUS3 | 79441 | −1.38 | mitotic nuclear division | Cell cycle | CS score, function | |
| Haus5 | 71909 | HAUS5 | 23354 | −2.55 | spindle assembly | Cell cycle | CS score, function | |
| Haus8 | 76478 | HAUS8 | 93323 | −1.73 | mitotic nuclear division | Cell cycle | CS score, function | |
| Hdac3 | 15183 | HDAC3 | 8841 | −2.12 | histone deacetylation | Cell cycle | CS score, mouse K.O., function | Bhaskara S, et al. Mol Cell. 2008 Apr. 11; 30(1):61-72 |
| Kif11 | 16551 | KIF11 | 3832 | −3.23 | microtubule-based movement | Cell cycle | CS score, mouse K.O., function | Castillo A, et al. Biochem Biophys Res Commun. 2007 Jun. 8; 357(3):694-9 |
| Kif23 | 71819 | KIF23 | 9493 | −1.59 | microtubule-based movement | Cell cycle | CS score, function | |
| Kpnb1 | 16211 | KPNB1 | 3837 | −3.19 | nucleocytoplasmic transport | Cell cycle | CS score, mouse K.O., function | Miura K, et al. Biochem Biophys Res Commun. 2006 Mar. 3; 341(1):132-8 |
| Mastl | 67121 | MASTL | 84930 | −2.36 | protein phosphorylation | Cell cycle | CS score, mouse K.O., function | Alvarez-Fernandez M, et al. Proc Natl Acad Sci USA. 2013 Oct. 22; 110(43):17374-9 |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Mau2 | 74549 | MAU2 | 23383 | −2.71 | mitotic cell cycle | Cell cycle | CS score, mouse K.O., function | Smith TG, et al. Genesis. 2014 July; 52(7):687-94 |
| Mcm3 | 17215 | MCM3 | 4172 | −2.52 | G1/S transition of mitotic cell cycle | Cell cycle | CS score, function | |
| Mcm4 | 17217 | MCM4 | 4173 | −1.87 | G1/S transition of mitotic cell cycle | Cell cycle | CS score, mouse K.O., function | Shima N, et al. Nat Genet. 2007 January; 39(1):93-8 |
| Mcm7 | 17220 | MCM7 | 4176 | −2.39 | G1/S transition of mitotic cell cycle | Cell cycle | CS score, function | |
| Mnat1 | 17420 | MNAT1 | 4331 | −1.22 | regulation of cyclin-dependent protein serine/threonine kinase activity | Cell cycle | CS score, mouse K.O., function | Rossi DJ, et al. EMBO J. 2001 Jun. 1; 20(11):2844-56 |
| Mybbp1a | 18432 | MYBBP1A | 10514 | −2.17 | osteoblast differentiation | Cell cycle | CS score, mouse K.O., function | Mori S, et al. PLOS One. 2012; 7(10): e39723 |
| Ncapd2 | 68298 | NCAPD2 | 9918 | −2.03 | mitotic chromosome condensation | Cell cycle | CS score, function | |
| Ncaph | 215387 | NCAPH | 23397 | −2.33 | mitotic chromosome condensation | Cell cycle | CS score, mouse K.O., function | Nishide K, et al. PLOS Genet. 2014 December; 10(12):e1004847 |
| Ndc80 | 67052 | NDC80 | 10403 | −2.98 | attachment of mitotic spindle microtubules to kinetochore | Cell cycle | CS score, function | |
| Nle1 | 217011 | NLE1 | 54475 | −1.88 | somitogenesis | Cell cycle | CS score, mouse K.O., function | Hentges KE, et al. Gene Expr Patterns. 2006 August; 6(6):653-65 |
| Nsl1 | 381318 | NSL1 | 25936 | −1.90 | mitotic cell cycle | Cell cycle | CS score, function | |
| Nudc | 18221 | NUDC | 10726 | −1.93 | mitotic cell cycle | Cell cycle | CS score, function | |
| Nuf2 | 66977 | NUF2 | 83540 | −1.78 | mitotic nuclear division | Cell cycle | CS score, function | |
| Nup133 | 234865 | NUP133 | 55746 | −2.26 | mitotic cell cycle | Cell cycle | CS score, mouse K.O., | Garcia-Garcia MJ, et al. Proc Natl |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| | | | | | | | function | Acad Sci USA. 2005 Apr. 26; 102(17):5913-9 |
| Nup160 | 59015 | NUP160 | 23279 | −2.64 | mitotic cell cycle | Cell cycle | CS score, function | |
| Nup188 | 227699 | NUP188 | 23511 | −1.16 | mitotic cell cycle | Cell cycle | CS score, function | |
| Nup214 | 227720 | NUP214 | 8021 | −2.70 | mitotic cell cycle | Cell cycle | CS score, mouse K.O., function | van Deursen J, et al. EMBO J. 1996 Oct. 15; 15(20): 5574-83 |
| n/a | n/a | NUP62 | 23636 | −2.35 | mitotic cell cycle | Cell cycle | CS score, function | |
| Nup85 | 445007 | NUP85 | 79902 | −2.47 | mitotic cell cycle | Cell cycle | CS score, function | |
| Orc3 | 50793 | ORC3 | 23595 | −1.67 | G1/S transition of mitotic cell cycle | Cell cycle | CS score, function | |
| Pafah1b1 | 18472 | PAFAH1B1 | 5048 | −2.34 | G2/M transition of mitotic cell cycle | Cell cycle | CS score, mouse K.O., function | Cahana A, et al. Proc Natl Acad Sci U S A. 2001 May 22; 98(11): 6429-34 |
| Pcid2 | 234069 | PCID2 | 55795 | −1.98 | negative regulation of apoptotic process | Cell cycle | CS score, function | |
| Pfas | 237823 | PFAS | 5198 | −2.58 | purine nucleotide biosynthetic process | Cell cycle | CS score, function | |
| Phb2 | 12034 | PHB2 | 11331 | −2.98 | protein import into nucleus, translocation | Cell cycle | CS score, mouse K.O., function | Park SE, et al. Mol Cell Biol. 2005 March; 25(5): 1989-99 |
| Pkmyt1 | 268930 | PKMYT1 | 9088 | −1.93 | regulation of cyclin-dependent protein serine/threonine kinase activity | Cell cycle | CS score, function | |
| Plk1 | 18817 | PLK1 | 5347 | −2.83 | protein phosphorylation | Cell cycle | CS score, mouse K.O., function | Lu LY, et al. Mol Cell Biol. 2008 November; 28(22):6870-6 |
| Pmf1 | 67037 | PMF1 | 11243 | −2.15 | mitotic cell cycle | Cell cycle | CS score, function | |
| Pole2 | 18974 | POLE2 | 5427 | −3.08 | G1/S transition of mitotic cell cycle | Cell cycle | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Ppat | 231327 | PPAT | 5471 | −2.15 | G1/S transition of mitotic cell cycle | Cell cycle | CS score, function | |
| Psma6 | 26443 | PSMA6 | 5687 | −3.51 | G1/S transition of mitotic cell cycle | Cell cycle | CS score, function | |
| Psma7 | 26444 | PSMA7 | 5688 | −2.91 | G1/S transition of mitotic cell cycle | Cell cycle | CS score, function | |
| Psmb1 | 19170 | PSMB1 | 5689 | −1.63 | G1/S transition of mitotic cell cycle | Cell cycle | CS score, function | |
| Psmb4 | 19172 | PSMB4 | 5692 | −2.91 | G1/S transition of mitotic cell cycle | Cell cycle | CS score, function | |
| Psmd12 | 66997 | PSMD12 | 5718 | −1.69 | G1/S transition of mitotic cell cycle | Cell cycle | CS score, function | |
| Psmd13 | 23997 | PSMD13 | 5719 | −1.57 | G1/S transition of mitotic cell cycle | Cell cycle | CS score, function | |
| Psmd14 | 59029 | PSMD14 | 10213 | −3.01 | G1/S transition of mitotic cell cycle | Cell cycle | CS score, function | |
| Psmd7 | 17463 | PSMD7 | 5713 | −2.18 | G1/S transition of mitotic cell cycle | Cell cycle | CS score, mouse K.O., function | Soriano P, et al. Genes Dev. 1987 June; 1(4):366-75 |
| Racgap1 | 26934 | RACGAP1 | 29127 | −1.94 | mitotic spindle assembly | Cell cycle | CS score, mouse K.O., function | Van de Putte T, et al. Mech al. Dev. 2001 April; 102(1-2):33-44 |
| Rad21 | 19357 | RAD21 | 5885 | −2.12 | mitotic cell cycle | Cell cycle | CS score, function | |
| Rae1 | 66679 | RAE1 | 8480 | −2.15 | mitotic cell cycle | Cell cycle | CS score, mouse K.O., function | Babu JR, et al. J Cell Biol. 2003 Feb. 3; 160(3): 341-53 |
| Rcc1 | 100088 | RCC1 | 1104 | −2.91 | G1/S transition of mitotic cell cycle | Cell cycle | CS score, function | |
| Rfc3 | 69263 | RFC3 | 5983 | −2.74 | mitotic cell cycle | Cell cycle | CS score, function | |
| Rps27a | 78294 | RPS27A | 6233 | −2.74 | G1/S transition of mitotic cell cycle | Cell cycle | CS score, function | |
| Rrm2 | 20135 | RRM2 | 6241 | −3.09 | G1/S transition of mitotic cell cycle | Cell cycle | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Sae1 | 56459 | SAE1 | 10055 | −2.08 | cellular protein modification process | Cell cycle | CS score, function | |
| Sec13 | 110379 | SEC13 | 6396 | −2.96 | mitotic cell cycle | Cell cycle | CS score, function | |
| Smarcb1 | 20587 | SMARCB1 | 6598 | −1.98 | chromatin remodeling | Cell cycle | CS score, mouse K.O., function | Guidi CJ, et al. Mol Cell Biol. 2001 May 15; 21(10): 3598-603 |
| Smc2 | 14211 | SMC2 | 10592 | −2.13 | mitotic chromosome condensation | Cell cycle | CS score, mouse K.O., function | Nishide K, et al. PLoS Genet. 2014 December; 10 (12):e1004847 |
| Smc4 | 70099 | SMC4 | 10051 | −1.47 | chromosome organization | Cell cycle | CS score, function | |
| Son | 20658 | SON | 6651 | −1.99 | microtubule cytoskeleton organization | Cell cycle | CS score, function | |
| Spc24 | 67629 | SPC24 | 147841 | −2.83 | mitotic cell cycle | Cell cycle | CS score, function | |
| Spc25 | 66442 | SPC25 | 57405 | −1.63 | mitotic cell cycle | Cell cycle | CS score, function | |
| Terf2 | 21750 | TERF2 | 7014 | −2.17 | telomere maintenance | Cell cycle | CS score, mouse K.O., function | Celli GB, et al. Nat Cell Biol. 2005 July; 7(7):712-8 |
| Tpx2 | 72119 | TPX2 | 22974 | −2.08 | apoptotic process | Cell cycle | CS score, mouse K.O., function | Aguirre-Portoles C, et al. Cancer Res. 2012 Mar. 15; 72(6):1518-28 |
| Tubg1 | 103733 | TUBG1 | 7283 | −2.08 | microtubule nucleation | Cell cycle | CS score, mouse K.O., function | Yuba-Kubo A, et al. Dev Biol. 2005 Jun. 15; 282(2): 361-73 |
| Tubgcp2 | 74237 | TUBGCP2 | 10844 | −2.78 | microtubule cytoskeleton organization | Cell cycle | CS score, function | |
| Tubgcp5 | 233276 | TUBGCP5 | 114791 | −1.76 | microtubule cytoskeleton organization | Cell cycle | CS score, function | |
| Tubgcp6 | 328580 | TUBGCP6 | 85378 | −1.52 | microtubule cytoskeleton organization | Cell cycle | CS score, function | |
| Txnl4a | 27366 | TXNL4A | 10907 | −3.89 | mitotic nuclear division | Cell cycle | CS score, function | |
| Usp39 | 28035 | USP39 | 10713 | −2.85 | spliceosomal complex assembly | Cell cycle | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Wdr43 | 72515 | WDR43 | 23160 | −3.02 | reproduction | Cell cycle | CS score, function | |
| Zfp830 | 66983 | ZNF830 | 91603 | −1.52 | blastocyst growth | Cell cycle | CS score, mouse K.O., function | Houlard M, et al. Cell Cycle. 2011 Jan. 1; 10(1):108-17 |
| Aatf | 56321 | AATF | 26574 | −1.46 | cellular response to DNA damage stimulus | DNA replication, DNA repair | CS score, mouse K.O., function | Thomas T, et al. Dev Biol. 2000 Nov. 15; 227(2): 324-42 |
| Alyref | 21681 | ALYREF | 10189 | −1.92 | regulation of DNA recombination | DNA replication, DNA repair | CS score, function | |
| Brf2 | 66653 | BRF2 | 55290 | −2.30 | DNA-templated transcription, initiation | DNA replication, DNA repair | CS score, function | |
| Cdc45 | 12544 | CDC45 | 8318 | −3.69 | DNA replication checkpoint | DNA replication, DNA repair | CS score, mouse K.O., function | Yoshida K, et al. Mol Cell Biol. 2001 July; 21(14): 4598-603 |
| Cdc6 | 23834 | CDC6 | 990 | −1.87 | DNA replication initiation | DNA replication, DNA repair | CS score, function | |
| Cdt1 | 67177 | CDT1 | 81620 | −2.74 | DNA replication checkpoint | DNA replication, DNA repair | CS score, function | |
| Cinp | 67236 | CINP | 51550 | −1.64 | DNA replication | DNA replication, DNA repair | CS score, function | |
| Cirh1a | 21771 | CIRH1A | 84916 | −2.62 | transcription, DNA-templated | DNA replication, DNA repair | CS score, function | |
| Ddb1 | 13194 | DDB1 | 1642 | −2.14 | nucleotide-excision repair, DNA damage removal | DNA replication, DNA repair | CS score, mouse K.O., function | Cang Y, et al. Cell. 2006 Dec. 1; 127(5):929-40 de Boer J, et al. |
| Ercc2 | 13871 | ERCC2 | 2068 | −2.80 | DNA duplex unwinding | DNA replication, DNA repair | CS score, mouse K.O., function | Cancer Res. 1998 Jan. 1; 58(1):89-94 |
| Gabpb1 | 14391 | GABPB1 | 2553 | −1.74 | transcription, DNA-templated | DNA replication, DNA repair | CS score, mouse K.O., function | Xue HH, et al. Mol Cell Biol. 2008 July; 28(13): 4300-9 |
| Gtf2b | 229906 | GTF2B | 2959 | −2.76 | regulation of transcription, DNA-templated | DNA replication, DNA repair | CS score, function | |
| Gtf2h4 | 14885 | GTF2H4 | 2968 | −1.93 | nucleotide-excision repair, DNA damage removal | DNA replication, DNA repair | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Gtf3a | 66596 | GTF3A | 2971 | −2.25 | regulation of transcription, DNA-templated | DNA replication, DNA repair | CS score, function | |
| Gtf3c1 | 233863 | GTF3C1 | 2975 | −2.45 | transcription, DNA-templated | DNA replication, DNA repair | CS score, function | |
| Gtf3c2 | 71752 | GTF3C2 | 2976 | −2.09 | transcription, DNA-templated | DNA replication, DNA repair | CS score, function | |
| Hinfp | 102423 | HINFP | 25988 | −2.35 | DNA damage checkpoint | DNA replication, DNA repair | CS score, mouse K.O., function | Xie R, et al. Proc Natl Acad Sci U S A. 2009 Jul. 9 |
| n/a | n/a | HIST2H2AA3 | 8337 | −1.71 | DNA repair | DNA replication, DNA repair | CS score, function | |
| Ints3 | 229543 | INTS3 | 65123 | −3.14 | DNA repair | DNA replication, DNA repair | CS score, function | |
| Kin | 16588 | KIN | 22944 | −1.99 | DNA replication | DNA replication, DNA repair | CS score, function | |
| Mcm2 | 17216 | MCM2 | 4171 | −2.86 | DNA replication initiation | DNA replication, DNA repair | CS score, function | |
| Mcm6 | 17219 | MCM6 | 4175 | −1.55 | DNA replication | DNA replication, DNA repair | CS score, function | |
| Mcrs1 | 51812 | MCRS1 | 10445 | −1.23 | DNA repair | DNA replication, DNA repair | CS score, function | |
| Med11 | 66172 | MED11 | 400569 | −2.39 | transcription, DNA-templated | DNA replication, DNA repair | CS score, function | |
| Mtpap | 67440 | MTPAP | 55149 | −1.86 | transcription, DNA-templated | DNA replication, DNA repair | CS score, function | |
| Myc | 17869 | MYC | 4609 | −2.49 | regulation of transcription, DNA-templated | DNA replication, DNA repair | CS score, mouse K.O., function | Trumpp A, et al. Nature. 2001 Dec. 13; 414(6865):768-73 |
| Ndnl2 | 66647 | NDNL2 | 56160 | −2.03 | DNA repair | DNA replication, DNA repair | CS score, function | |
| Nol11 | 68979 | NOL11 | 25926 | −1.59 | transcription, DNA-templated | DNA replication, DNA repair | CS score, function | |
| Nol8 | 70930 | NOL8 | 55035 | −1.35 | DNA replication | DNA replication, DNA repair | CS score, function | |
| Pcna | 18538 | PCNA | 5111 | −3.60 | DNA replication | DNA replication, DNA repair | CS score, mouse K.O., function | Roa S, et al. Proc Natl Acad Sci U S A. 2008 Oct. 21; 105(42): 16248-53 |
| Pola1 | 18968 | POLA1 | 5422 | −2.28 | DNA-dependent DNA replication | DNA replication, DNA repair | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Pold2 | 18972 | POLD2 | 5425 | −2.51 | DNA replication | DNA replication, DNA repair | CS score, function | |
| Pole | 18973 | POLE | 5426 | −2.90 | DNA replication | DNA replication, DNA repair | CS score, function | |
| Polr1a | 20019 | POLR1A | 25885 | −2.62 | transcription, DNA-templated | DNA replication, DNA repair | CS score, function | |
| n/a | n/a | POLR2J2 | 246721 | −3.08 | transcription, DNA-templated | DNA replication, DNA repair | CS score, function | |
| Polr3a | 218832 | POLR3A | 11128 | −2.43 | transcription, DNA-templated | DNA replication, DNA repair | CS score, function | |
| Polr3c | 74414 | POLR3C | 10623 | −2.02 | transcription, DNA-templated | DNA replication, DNA repair | CS score, function | |
| Polr3h | 78929 | POLR3H | 171568 | −2.66 | transcription, DNA-templated | DNA replication, DNA repair | CS score, function | |
| Prmt1 | 15469 | PRMT1 | 3276 | −2.40 | regulation of transcription, DNA-templated | DNA replication, DNA repair | CS score, mouse K.O., function | Pawlak MR, et al. Mol Cell Biol. 2000 July; 20(13): 4859-69 |
| Prmt5 | 27374 | PRMT5 | 10419 | −2.69 | regulation of transcription, DNA-templated | DNA replication, DNA repair | CS score, mouse K.O., function | Tee WW, et al. Genes Dev. 2010 Dec. 15; 24(24): 2772-7 |
| Puf60 | 67959 | PUF60 | 22827 | −2.69 | transcription, DNA-templated | DNA replication, DNA repair | CS score, function | |
| Rad51 | 19361 | RAD51 | 5888 | −2.29 | DNA repair | DNA replication, DNA repair | CS score, mouse K.O., function | Tsuzuki T, et al. Proc Natl Acad Sci U S A. 1996 Jun. 25; 93(13): 6236-40 |
| Rad51c | 114714 | RAD51C | 5889 | −1.62 | DNA repair | DNA replication, DNA repair | CS score, mouse K.O., function | Smeenk G, et al. Mutat Res. 2010 Jul. 7; 689(1-2):50-58 |
| Rbx1 | 56438 | RBX1 | 9978 | −2.19 | DNA repair | DNA replication, DNA repair | CS score, mouse K.O., function | Tan M, et al. Proc Natl Acad Sci U S A. 2009 Apr. 14; 106(15): 6203-8 |
| Rfc2 | 19718 | RFC2 | 5982 | −2.88 | DNA-dependent DNA replication | DNA replication, DNA repair | CS score, function | |
| Rfc4 | 106344 | RFC4 | 5984 | −1.92 | DNA-dependent DNA replication | DNA replication, DNA repair | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Rfc5 | 72151 | RFC5 | 5985 | −2.78 | DNA-dependent DNA replication | DNA replication, DNA repair | CS score, function | |
| Rpa1 | 68275 | RPA1 | 6117 | −2.61 | DNA replication | DNA replication, DNA repair | CS score, mouse K.O., function | Wang Y, et al. Nat Genet. 2005 July; 37(7): 750-5 |
| Rps3 | 27050 | RPS3 | 6188 | −2.75 | DNA repair | DNA replication, DNA repair | CS score, function | |
| Rrm1 | 20133 | RRM1 | 6240 | −4.16 | DNA replication | DNA replication, DNA repair | CS score, function | |
| Ruvbl1 | 56505 | RUVBL1 | 8607 | −3.26 | DNA duplex unwinding | DNA replication, DNA repair | CS score, function | |
| Ruvbl2 | 20174 | RUVBL2 | 10856 | −3.91 | DNA repair | DNA replication, DNA repair | CS score, function | |
| Sap30bp | 57230 | SAP30BP | 29115 | −2.18 | regulation of transcription, DNA-templated | DNA replication, DNA repair | CS score, function | |
| Smc1a | 24061 | SMC1A | 8243 | −2.76 | DNA repair | DNA replication, DNA repair | CS score, function | |
| Smc3 | 13006 | SMC3 | 9126 | −3.22 | DNA repair | DNA replication, DNA repair | CS score, mouse K.O., function | White JK, et al. Cell. 2013 Jul. 18; 154(2): 452-64 |
| Snapc4 | 227644 | SNAPC4 | 6621 | −2.78 | regulation of transcription, DNA-templated | DNA replication, DNA repair | CS score, function | |
| Snapc5 | 330959 | SNAPC5 | 10302 | −2.24 | regulation of transcription, DNA-templated | DNA replication, DNA repair | CS score, function | |
| Snip1 | 76793 | SNIP1 | 79753 | −1.78 | regulation of transcription, DNA-templated | DNA replication, DNA repair | CS score, function | |
| Srrt | 83701 | SRRT | 51593 | −2.18 | transcription, DNA-templated | DNA replication, DNA repair | CS score, mouse K.O., function | Wilson MD, et al. Mol Cell Biol. 2008 March; 28(5): 1503-14 |
| Ssrp1 | 20833 | SSRP1 | 6749 | −1.45 | DNA replication | DNA replication, DNA repair | CS score, mouse K.O., function | Cao S, et al. 5 mouse embryos. Mol Cell Biol. 2003 August; 23 (15):5301-7 |
| Taf10 | 24075 | TAF10 | 6881 | −1.38 | DNA-templated transcription, initiation | DNA replication DNA repair | CS score, mouse K.O., function | Mohan WS Jr, et al. Mol Cell Biol. 2003 June; 23(12): 4307-18 |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Taf1c | 21341 | TAF1C | 9013 | −1.80 | chromatin silencing at rDNA | DNA replication, DNA repair | CS score, function | |
| Taf6 | 21343 | TAF6 | 6878 | −1.84 | DNA-templated transcription, initiation | DNA replication, DNA repair | CS score, function | |
| Taf6l | 67706 | TAF6L | 10629 | −1.53 | DNA-templated transcription, initiation | DNA replication, DNA repair | CS score, function | |
| Ticrr | 77011 | TICRR | 90381 | −2.03 | DNA replication | DNA replication, DNA repair | CS score, function | |
| Top1 | 21969 | TOP1 | 7150 | −2.02 | DNA topological change | DNA replication, DNA repair | CS score, mouse K.O., function | Morham SG, et al. Mol Cell Biol. 1996 December; 16(12):6804-9 |
| Top2a | 21973 | TOP2A | 7153 | −1.50 | DNA replication | DNA replication, DNA repair | CS score, function | |
| Trrap | 100683 | TRRAP | 8295 | −2.36 | DNA repair | DNA replication, DNA repair | CS score, mouse K.O., function | Herceg Z, et al. Nat Genet. 2001 October; 29(2): 206-11 |
| Zbtb11 | 271377 | ZBTB11 | 27107 | −2.34 | transcription, DNA-templated | DNA replication, DNA repair | CS score, function | |
| Actl6a | 56456 | ACTL6A | 86 | −2.33 | neural retina development | DNA replication, DNA repair | CS score, mouse K.O., function | Krasteva V, et al. Blood. 2012 Dec. 6; 120(24): 4720-32 |
| Atr | 245000 | ATR | 545 | −2.01 | double-strand break repair via homologous recombination | DNA replication, DNA repair | CS score, mouse K.O., function | de Klein A, et al. Curr Biol. 2000 Apr. 20; 10(8): 479-82 |
| Chd4 | 107932 | CHD4 | 1108 | −1.71 | chromatin organization | DNA replication, DNA repair | CS score, function | |
| Ciao1 | 26371 | CIAO1 | 9391 | −1.94 | chromosome segregation | DNA replication, DNA repair | CS score, function | |
| Ddx21 | 56200 | DDX21 | 9188 | −2.84 | osteoblast differentiation | DNA replication, DNA repair | CS score, function | |
| Dnaja3 | 83945 | DNAJA3 | 9093 | −2.19 | mitochondrion organization | DNA replication, DNA repair | CS score, mouse K.O., function | Lo JF, et al. Mol Cell Biol. 2004 March; 24(6): 2226-36 |
| Dnmt1 | 13433 | DNMT1 | 1786 | −1.97 | methylation | DNA replication, DNA repair | CS score, mouse K.O., function | Lei H, et al. Development. 1996 October; 122(10):3195-205 |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Gins2 | 272551 | GINS2 | 51659 | −3.32 | double-strand break repair via break-induced replication | DNA replication, DNA repair | CS score, function | |
| Gtf2h3 | 209357 | GTF2H3 | 2967 | −1.84 | nucleotide-excision repair | DNA replication, DNA repair | CS score, function | |
| n/a | n/a | HIST2H2BF | 440689 | −1.70 | chromatin organization | DNA replication, DNA repair | CS score, function | |
| Mms22l | 212377 | MMS22L | 253714 | −1.38 | double-strand break repair via homologous recombination | DNA replication, DNA repair | CS score, function | |
| Mtor | 56717 | MTOR | 2475 | −1.98 | double-strand break repair via homologous recombination | DNA replication, DNA repair | CS score, mouse K.O., function | Murakami M, et al. Mol Cell Biol. 2004 August; 24(15):6710-8 |
| Narfl | 67563 | NARFL | 64428 | −2.13 | response to hypoxia | DNA replication, DNA repair | CS score, mouse K.O., function | Song D, et al. J Biol Chem. 2011 Mar. 2 |
| Ndufa13 | 67184 | NDUFA13 | 51079 | −1.31 | positive regulation of peptidase activity | DNA replication, DNA repair | CS score, mouse K.O., function | Huang G, et al. Mol Cell Biol. 2004 October; 24(19):8447-56 |
| Nol12 | 97961 | NOL12 | 79159 | −1.61 | poly(A) RNA binding | DNA replication, DNA repair | CS score, function | |
| Nup107 | 103468 | NUP107 | 57122 | −1.30 | transport | DNA replication, DNA repair | CS score, function | |
| Oraov1 | 72284 | ORAOV1 | 220064 | −2.26 | biological_process | DNA replication, DNA repair | CS score, function | |
| Pam16 | 66449 | PAM16 | 51025 | −2.13 | protein import into mitochondrial matrix | DNA replication, DNA repair | CS score, function | |
| Pola2 | 18969 | POLA2 | 23649 | −2.84 | protein import into nucleus, translocation | DNA replication, DNA repair | CS score, function | |
| Ppie | 56031 | PPIE | 10450 | −1.63 | protein peptidyl-prolyl isomerization | DNA replication, DNA repair | CS score, function | |
| Prpf19 | 28000 | PRPF19 | 27339 | −3.96 | generation of catalytic spliceosome for first trans-esterification step | DNA replication, DNA repair | CS score, mouse K.O., function | Fortschegger K, et al. Mol Cell Biol. 2007 April; 27(8): 3123-30 |
| Psmc5 | 19184 | PSMC5 | 5705 | −2.57 | ER-associated ubiquitin-dependent protein catabolic process | DNA replication, DNA repair | CS score, function | |
| Rbbp5 | 213464 | RBBP5 | 5929 | −1.70 | chromatin organization | DNA replication, DNA repair | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Rbbp6 | 19647 | RBBP6 | 5930 | −1.78 | in utero embryonic development | DNA replication, DNA repair | CS score, mouse K.O., function | Li L, et al. Proc Natl Acad Sci USA. 2007 May 8; 104(19): 7951-6 |
| Rptor | 74370 | RPTOR | 57521 | −2.43 | TOR signaling | DNA replication, DNA repair | CS score, mouse K.O., function | Guertin DA, et al. Dev Cell. 2006 December; 11(6):859-71 |
| Rrn3 | 106298 | RRN3 | 54700 | −1.85 | in utero embryonic development | DNA replication, DNA repair | CS score, mouse K.O., function | Yuan X, et al. Mol Cell. 2005 Jul. 1; 19(1):77-87 |
| Smg1 | 233789 | SMG1 | 23049 | −1.94 | double-strand break repair via homologous recombination | DNA replication, DNA repair | CS score, mouse K.O., function | Roberts TL, et al. Proc Natl Acad Sci USA. 2013 Jan. 22; 110(4): E285-94 |
| Supt6 | 20926 | SUPT6H | 6830 | −1.78 | chromatin remodeling | DNA replication, DNA repair | CS score, mouse K.O., function | Dietrich JE, et al. EMBO Rep. 2015 August; 16(8): 1005-21 |
| Tada2b | 231151 | TADA2B | 93624 | −1.23 | chromatin organization | DNA replication, DNA repair | CS score, function | |
| Tfip11 | 54723 | TFIP11 | 24144 | −2.19 | spliceosomal complex disassembly | DNA replication, DNA repair | CS score, function | |
| Tonsl | 66914 | TONSL | 4796 | −3.03 | double-strand break repair via homologous recombination | DNA replication, DNA repair | CS score, function | |
| Tpt1 | 22070 | TPT1 | 7178 | −2.05 | calcium ion transport | DNA replication, DNA repair | CS score, mouse K.O., function | Susini L, et al. Cell Death Differ. 2008 August; 15(8): 1211-20 |
| Uba1 | 22201 | UBA1 | 7317 | −2.90 | protein ubiquitination | DNA replication, DNA repair | CS score, function | |
| Vps25 | 28084 | VPS25 | 84313 | −2.31 | protein targeting to vacuole involved in ubiquitin-dependent protein catabolic process via the multivesicular body sorting pathway | DNA replication, DNA repair | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Wbscr22 | 66138 | WBSCR22 | 114049 | −2.70 | methylation | DNA replication, DNA repair | CS score, function | |
| Wdr5 | 140858 | WDR5 | 11091 | −1.99 | skeletal system development | DNA replication, DNA repair | CS score, function | |
| Xab2 | 67439 | XAB2 | 56949 | −2.86 | generation of catalytic spliceosome for first transesterification step | DNA replication, DNA repair | CS score, mouse K.O., function | Yonemasu R, et al. DNA Repair (Amst). 2005 Apr. 4; 4(4):479-91 |
| Zmat2 | 66492 | ZMAT2 | 153527 | −2.17 | histidine-tRNA ligase activity | DNA replication, DNA repair | CS score, function | |
| Zfp335 | 329559 | ZNF335 | 63925 | −1.58 | in utero embryonic development | DNA replication, DNA repair | CS score, mouse K.O., function | Yang YJ, et al. Cell. 2012 Nov. 21; 151(5): 1097-112 |
| Acly | 104112 | ACLY | 47 | −1.54 | acetyl-CoA metabolic process | Metabolism | CS score, mouse K.O., function | Beigneux AP, et al. J Biol Chem. 2004 Mar. 5; 279(10): 9557-64 |
| Adsl | 11564 | ADSL | 158 | −2.39 | metabolic process | Metabolism | CS score, function | |
| Ahcy | 269378 | AHCY | 191 | −2.07 | sulfur amino acid metabolic process | Metabolism | CS score, function | |
| Arl2 | 56327 | ARL2 | 402 | −2.29 | energy reserve metabolic process | Metabolism | CS score, function | |
| Chka | 12660 | CHKA | 1119 | −1.64 | lipid metabolic process | Metabolism | CS score, mouse K.O., function | Wu G, et al. J Biol Chem. 2008 Jan. 18; 283(3): 1456-62 |
| Coasy | 71743 | COASY | 80347 | −1.82 | vitamin metabolic process | Metabolism | CS score, function | |
| Cox4i1 | 12857 | COX4I1 | 1327 | −2.00 | generation of precursor metabolites and energy | Metabolism | CS score, function | |
| n/a | n/a | COX7C | 1350 | −1.59 | generation of precursor metabolites and energy | Metabolism | CS score, function | |
| n/a | n/a | CTPS1 | 1503 | −2.52 | nucleobase-containing compound metabolic process | Metabolism | CS score, function | |
| Ddx10 | 77591 | DDX10 | 1662 | −2.02 | metabolic process | Metabolism | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Ddx20 | 53975 | DDX20 | 11218 | −2.49 | metabolic process | Metabolism | CS score, mouse K.O., function | Mouillet JF, et al. Endocrinology. 2008 May; 149(5): 2168-75 |
| Dhdds | 67422 | DHDDS | 79947 | −2.86 | metabolic process | Metabolism | CS score, function | |
| Dhx30 | 72831 | DHX30 | 22907 | −1.93 | metabolic process | Metabolism | CS score, function | |
| Dhx8 | 217207 | DHX8 | 1659 | −2.61 | metabolic process | Metabolism | CS score, function | |
| Dhx9 | 13211 | DHX9 | 1660 | −1.73 | metabolic process | Metabolism | CS score, mouse K.O., function | Lee CG, et al. Proc Natl Acad Sci U S A. 1998 Nov. 10; 95(23): 13709-13 |
| Dlst | 78920 | DLST | 1743 | −1.93 | metabolic process | Metabolism | CS score, function | |
| Dpagt1 | 13478 | DPAGT1 | 1798 | −2.80 | UDP-N-acetylglucosamine metabolic process | Metabolism | CS score, mouse K.O., function | Marek KW, et al. Glycobiology. 1999 November; 9(11):1263-71 |
| Gfpt1 | 14583 | GFPT1 | 2673 | −1.81 | fructose 6-phosphate metabolic process | Metabolism | CS score, function | |
| Gmps | 229363 | GMPS | 8833 | −1.80 | purine nucleobase metabolic process | Metabolism | CS score, function | |
| Gpn1 | 74254 | GPN1 | 11321 | −1.79 | metabolic process | Metabolism | CS score, function | |
| Gpn3 | 68080 | GPN3 | 51184 | −3.12 | metabolic process | Metabolism | CS score, function | |
| Guk1 | 14923 | GUK1 | 2987 | −2.67 | purine nucleotide metabolic process | Metabolism | CS score, function | |
| Hsd17b10 | 15108 | HSD17B10 | 3028 | −1.84 | lipid metabolic process | Metabolism | CS score, function | |
| Lrr1 | 69706 | LRR1 | 122769 | −3.44 | metabolic process | Metabolism | CS score, function | |
| Mtg2 | 52856 | MTG2 | 26164 | −2.04 | metabolic process | Metabolism | CS score, function | |
| Myh9 | 17886 | MYH9 | 4627 | −1.70 | metabolic process | Metabolism | CS score, mouse K.O., function | Matsushita T, et al. Biochem Biophys Res Commun. 2004 Dec. 24; 325(4): 1163-71 |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Nampt | 59027 | NAMPT | 10135 | −2.40 | vitamin metabolic process | Metabolism | CS score, mouse K.O., function | Revollo JR, et al. Cell Metab. 2007 November; 6(5):363-75 |
| Ncbp1 | 433702 | NCBP1 | 4686 | −1.62 | RNA metabolic process | Metabolism | CS score, function | |
| Nfs1 | 18041 | NFS1 | 9054 | −2.40 | metabolic process | Metabolism | CS score, function | |
| Ppcdc | 66812 | PPCDC | 60490 | −1.98 | metabolic process | Metabolism | CS score, function | |
| Qrsl1 | 76563 | QRSL1 | 55278 | −1.67 | metabolic process | Metabolism | CS score, function | |
| Rpp14 | 67053 | RPP14 | 11102 | −1.72 | fatty acid metabolic process | Metabolism | CS score, function | |
| Smarca4 | 20586 | SMARCA4 | 6597 | −1.89 | metabolic process | Metabolism | CS score, mouse K.O., function | Bultman S, et al. Mol Cell. 2000 December; 6(6): 1287-95 |
| Snrnp200 | 320632 | SNRNP200 | 230200 | −2.50 | metabolic process | Metabolism | CS score, function | |
| Srbd1 | 78586 | SRBD1 | 55133 | −2.35 | nucleobase-containing compound metabolic process | Metabolism | CS score, function | |
| Srcap | 100043597 | SRCAP | 10847 | −1.43 | metabolic process | Metabolism | CS score, function | |
| Ube2i | 22196 | UBE2I | 7329 | −2.55 | metabolic process | Metabolism | CS score, mouse K.O., function | Nacerddine K, et al. Dev Cell. 2005 December; 9(6):769-79 |
| Ube2m | 22192 | UBE2M | 9040 | −2.39 | metabolic process | Metabolism | CS score, function | |
| Vcp | 269523 | VCP | 7415 | −2.85 | metabolic process | Metabolism | CS score, mouse K.O., function | Muller JM, et al. Biochem Biophys Res Commun. 2007 Mar. 9; 354(2):459-465 |
| Aamp | 227290 | AAMP | 14 | −2.37 | angiogenesis | Metabolism | CS score, function | |
| Acin1 | 56215 | ACIN1 | 22985 | −1.53 | positive regulation of defense response to virus by host | Metabolism | CS score, function | |
| Aco2 | 11429 | ACO2 | 50 | −2.08 | tricarboxylic acid cycle | Metabolism | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Adss | 11566 | ADSS | 159 | −2.46 | purine nucleotide biosynthetic process | Metabolism | CS score, function | |
| Alg2 | 56737 | ALG2 | 85365 | −2.29 | biosynthetic process | Metabolism | CS score, function | |
| Ap2s1 | 232910 | AP2S1 | 1175 | −2.00 | intracellular protein transport | Metabolism | CS score, function | |
| Arcn1 | 213827 | ARCN1 | 372 | −1.91 | intracellular protein transport | Metabolism | CS score, function | |
| Armc7 | 276905 | ARMC7 | 79637 | −2.02 | molecular_function | Metabolism | CS score, function | |
| Atp2a2 | 11938 | ATP2A2 | 488 | −3.01 | calcium ion transmembrane transport | Metabolism | CS score, mouse K.O., function | Andersson KB, et al. Cell Calcium. 2009 September; 46(3): 219-25 |
| Atp5a1 | 11946 | ATP5A1 | 498 | −1.99 | negative regulation of endothelial cell proliferation | Metabolism | CS score, function | |
| Atp5d | 66043 | ATP5D | 513 | −2.21 | oxidative phosphorylation | Metabolism | CS score, function | |
| Atp5o | 28080 | ATP5O | 539 | −1.17 | ATP biosynthetic process | Metabolism | CS score, function | |
| Atp6v0b | 114143 | ATP6V0B | 533 | −3.01 | cellular iron ion homeostasis | Metabolism | CS score, function | |
| Atp6v0c | 11984 | ATP6V0C | 527 | −3.84 | cellular iron ion homeostasis | Metabolism | CS score, mouse K.O., function | Sun-Wada GH, et al. Dev Biol. 2000 Dec. 15; 228(2): 315-25 |
| Atp6v1a | 11964 | ATP6V1A | 523 | −3.58 | proton transport | Metabolism | CS score, function | |
| Atp6v1b2 | 11966 | ATP6V1B2 | 526 | −2.94 | cellular iron ion homeostasis | Metabolism | CS score, function | |
| Atp6v1d | 73834 | ATP6V1D | 51382 | −2.58 | transmembrane transport | Metabolism | CS score, function | |
| Aurkaip1 | 66077 | AURKAIP1 | 54998 | −1.56 | organelle organization | Metabolism | CS score, function | |
| n/a | n/a | C1orf109 | 54955 | −2.43 | molecular_function | Metabolism | CS score, function | |
| n/a | n/a | C21orf59 | 56683 | −2.77 | cell projection morphogenesis | Metabolism | CS score, function | |
| Ccdc84 | 382073 | CCDC84 | 338657 | −1.86 | molecular_function | Metabolism | CS score, function | |
| Cct2 | 12461 | CCT2 | 10576 | −3.23 | protein folding | Metabolism | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Cct3 | 12462 | CCT3 | 7203 | −3.31 | protein folding | Metabolism | CS score, function | |
| Cct4 | 12464 | CCT4 | 10575 | −2.62 | protein folding | Metabolism | CS score, function | |
| Cct5 | 12465 | CCT5 | 22948 | −2.84 | protein folding | Metabolism | CS score, function | |
| Cct7 | 12468 | CCT7 | 10574 | −2.47 | protein folding | Metabolism | CS score, function | |
| Cct8 | 12469 | CCT8 | 10694 | −2.03 | protein folding | Metabolism | CS score, function | |
| Cdipt | 52858 | CDIPT | 10423 | −2.53 | phospholipid biosynthetic process | Metabolism | CS score, function | |
| Cenpi | 102920 | CENPI | 2491 | −1.81 | centromere complex assembly | Metabolism | CS score, function | |
| Chordc1 | 66917 | CHORDC1 | 26973 | −1.52 | regulation of centrosome duplication | Metabolism | CS score, mouse K.O., function | Ferretti R, et al. Dev Cell. 2010 Mar. 16; 18(3):486-95 |
| Coa5 | 76178 | COA5 | 493753 | −2.33 | mitochondrion | Metabolism | CS score, function | |
| Cog4 | 102339 | COG4 | 25839 | −1.39 | Golgi vesicle transport | Metabolism | CS score, function | |
| Copa | 12847 | COPA | 1314 | −1.63 | intracellular protein transport | Metabolism | CS score, function | |
| Copb1 | 70349 | COPB1 | 1315 | −2.30 | intracellular protein transport | Metabolism | CS score, function | |
| Copb2 | 50797 | COPB2 | 9276 | −2.65 | intracellular protein transport | Metabolism | CS score, function | |
| Cope | 59042 | COPE | 11316 | −2.93 | ER to Golgi vesicle-mediated transport | Metabolism | CS score, function | |
| Copz1 | 56447 | COPZ1 | 22818 | −1.87 | transport | Metabolism | CS score, function | |
| Coq4 | 227683 | COQ4 | 51117 | −1.29 | ubiquinone biosynthetic process | Metabolism | CS score, function | |
| Cox15 | 226139 | COX15 | 1355 | −2.14 | mitochondrial electron transport, cytochrome c to oxygen | Metabolism | CS score, mouse K.O., function | Viscomi C, et al. Cell Metab. 2011 Jul. 6; 14(1):80-90 |
| Cox17 | 12856 | COX17 | 10063 | −1.97 | copper ion transport | Metabolism | CS score, mouse K.O., function | Takahashi Y, et al. Mol Cell Biol. 2002 November; 22(21):7614-21 |
| Cse1l | 110750 | CSE1L | 1434 | −2.31 | protein export from nucleus | Metabolism | CS score, mouse K.O., function | Bera TK, et al. Mol Cell Biol. 2001 October; 21(20):7020-4 |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Csnk2b | 13001 | CSNK2B | 1460 | −1.94 | regulation of protein kinase activity | Metabolism | CS score, mouse K.O., function | Buchou T, et al. Mol Cell Biol. 2003 February; 23(3): 908-15 |
| Cycs | 13063 | CYCS | 54205 | −2.36 | response to reactive oxygen species | Metabolism | CS score, mouse K.O., function | Li K, et al. Cell. 2000 May 12; 101(4): 389-99 |
| Dad1 | 13135 | DAD1 | 1603 | −2.21 | protein glycosylation | Metabolism | CS score, mouse K.O., function | Brewster JL, et al. Genesis. 2000 April; 26(4): 271-8 |
| Dap3 | 65111 | DAP3 | 7818 | −1.70 | apoptotic process | Metabolism | CS score, mouse K.O., function | Kim HR, et al. FASEB J. 2007 January; 21(1): 188-96 |
| Dctn5 | 59288 | DCTN5 | 84516 | −2.39 | antigen processing and presentation of exogenous peptide antigen via MHC class II | Metabolism | CS score, function | |
| Ddost | 13200 | DDOST | 1650 | −2.38 | protein N-linked glycosylation via asparagine | Metabolism | CS score, function | |
| Dgcr8 | 94223 | DGCR8 | 54487 | −2.10 | gene expression | Metabolism | CS score, mouse K.O., function | Ouchi Y, et al. J Neurosci. 2013 May 29; 33(22): 9408-19 |
| Dhodh | 56749 | DHODH | 1723 | −2.57 | de novo' pyrimidine nucleobase biosynthetic process | Metabolism | CS score, function | |
| Dnlz | 52838 | DNLZ | 728489 | −1.92 | protein folding | Metabolism | CS score, function | |
| Dnm1l | 74006 | DNM1L | 10059 | −3.25 | mitochondrial fission | Metabolism | CS score, mouse K.O., function | Wakabayashi J, et al. J Cell Biol. 2009 Sep. 21; 186(6): 805-16 |
| Dnm2 | 13430 | DNM2 | 1785 | −3.98 | endocytosis | Metabolism | CS score, mouse K.O., function | Ferguson SM, et al. Dev Cell. 2009 December; 17(6): 811-22 |
| Dohh | 102115 | DOHH | 83475 | −1.76 | peptidyl-lysine modification to peptidyl-hypusine | Metabolism | CS score, function | |
| Dolk | 227697 | DOLK | 22845 | −2.38 | dolichol-linked | Metabolism | CS score, | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| | | | | | oligosaccharide biosynthetic process | | function | |
| Donson | 60364 | DONSON | 29980 | −2.30 | multicellular organismal development | Metabolism | CS score, function | |
| Dph3 | 105638 | DPH3 | 285381 | −1.62 | peptidyl-diphthamide biosynthetic process from peptidyl-histidine | Metabolism | CS score, mouse K.O., function | Liu S, et al. Mol Cell Biol. 2006 May; 26(10): 3835-41 |
| Dtymk | 21915 | DTYMK | 1841 | −3.54 | phosphorylation | Metabolism | CS score, function | |
| Eif2b2 | 217715 | EIF2B2 | 8892 | −2.24 | ovarian follicle development | Metabolism | CS score, function | |
| Eif2s2 | 67204 | EIF2S2 | 8894 | −2.33 | in utero embryonic development | Metabolism | CS score, mouse K.O., function | Heaney JD, et al. Hum Mol Genet. 2009 Apr. 15; 18(8):1395-404 |
| Emc1 | 230866 | EMC1 | 23065 | −1.34 | protein folding in endoplasmic reticulum | Metabolism | CS score, function | |
| Emc7 | 73024 | EMC7 | 56851 | −2.27 | biological_process | Metabolism | CS score, function | |
| Eno1 | 13806 | ENO1 | 2023 | −2.03 | glycolytic process | Metabolism | CS score, mouse K.O., function | Couldrey C, et al. Dev Dyn. 1998 June; 212(2): 284-92 |
| Fam50a | 108160 | FAM50A | 9130 | −3.16 | spermatogenesis | Metabolism | CS score, function | |
| Fam96b | 68523 | FAM96B | 51647 | −1.90 | iron-sulfur cluster assembly | Metabolism | CS score, function | |
| Fdps | 110196 | FDPS | 2224 | −2.41 | isoprenoid biosynthetic process | Metabolism | CS score, function | |
| Gapdh | 14433 | GAPDH | 2597 | −2.40 | oxidation-reduction process | Metabolism | CS score, function | |
| Gart | 14450 | GART | 2618 | −1.87 | purine nucleobase biosynthetic process | Metabolism | CS score, function | |
| Gemin4 | 276919 | GEMIN4 | 50628 | −1.56 | spliceosomal snRNP assembly | Metabolism | CS score, function | |
| Gemin5 | 216766 | GEMIN5 | 25929 | −2.51 | spliceosomal snRNP assembly | Metabolism | CS score, function | |
| Ggps1 | 14593 | GGPS1 | 9453 | −1.62 | cholesterol biosynthetic process | Metabolism | CS score, function | |
| Gmppb | 331026 | GMPPB | 29925 | −3.22 | biosynthetic process | Metabolism | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Gnb1l | 13972 | GNB1L | 54584 | −1.93 | G-protein coupled receptor signaling pathway | Metabolism | CS score, function | |
| n/a | n/a | GOLGA6L1 | 283767 | −3.15 | | Metabolism | CS score, function | |
| Gosr2 | 56494 | GOSR2 | 9570 | −1.13 | protein targeting to vacuole | Metabolism | CS score, function | |
| Gpkow | 209416 | GPKOW | 27238 | −1.36 | biological_process | Metabolism | CS score, function | |
| Gpn2 | 100210 | GPN2 | 54707 | −3.71 | biological_process | Metabolism | CS score, function | |
| Gps1 | 209318 | GPS1 | 2873 | −2.11 | inactivation of MAPK activity | Metabolism | CS score, function | |
| Grpel1 | 17713 | GRPEL1 | 80273 | −2.61 | protein folding | Metabolism | CS score, function | |
| Grwd1 | 101612 | GRWD1 | 83743 | −1.90 | poly(A) RNA binding | Metabolism | CS score, function | |
| Hmgcr | 15357 | HMGCR | 3156 | −2.94 | cholesterol biosynthetic process | Metabolism | CS score, mouse K.O., function | Ohashi K, et al. J Biol Chem. 2003 Oct. 31; 278(44): 42936-41 |
| Hmgcs1 | 208715 | HMGCS1 | 3157 | −2.41 | liver development | Metabolism | CS score, function | |
| Hspa5 | 14828 | HSPA5 | 3309 | −3.86 | platelet degranulation | Metabolism | CS score, mouse K.O., function | Luo S, et al. Mol Cell Biol. 2006 August; 26(15): 5688-97 |
| Hspa9 | 15526 | HSPA9 | 3313 | −3.55 | protein folding | Metabolism | CS score, function | |
| Hspd1 | 15510 | HSPD1 | 3329 | −1.95 | response to hypoxia | Metabolism | CS score, mouse K.O., function | Christensen JH, et al. Cell Stress Chaperones. 2010 November; 15(6): 851-63 |
| Hspe1 | 15528 | HSPE1 | 3336 | −3.75 | osteoblast differentiation | Metabolism | CS score, function | |
| Hyou1 | 12282 | HYOU1 | 10525 | −2.06 | response to ischemia | Metabolism | CS score, function | |
| Ipo13 | 230673 | IPO13 | 9670 | −2.84 | intracellular protein transport | Metabolism | CS score, function | |
| Iscu | 66383 | ISCU | 23479 | −2.40 | cellular iron ion homeostasis | Metabolism | CS score, function | |
| Itpk1 | 217837 | ITPK1 | 3705 | −1.55 | phosphorylation | Metabolism | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Kansl2 | 69612 | KANSL2 | 54934 | −1.19 | chromatin organization | Metabolism | CS score, function | |
| Kansl3 | 226976 | KANSL3 | 55683 | −1.53 | chromatin organization | Metabolism | CS score, function | |
| Kri1 | 215194 | KRI1 | 65095 | −2.49 | poly(A) RNA binding | Metabolism | CS score, function | |
| Lamtor2 | 83409 | LAMTOR2 | 28956 | −1.62 | activation of MAPKK activity | Metabolism | CS score, mouse K.O., function | Teis D, et al. J Cell Biol. 2006 Dec. 18; 175(6): 861-8 |
| Leng8 | 232798 | LENG8 | 114823 | −1.75 | biological_process | Metabolism | CS score, function | |
| Ltv1 | 353258 | LTV1 | 84946 | −1.81 | nucleoplasm | Metabolism | CS score, function | |
| Mak16 | 67920 | MAK16 | 84549 | −2.30 | poly(A) RNA binding | Metabolism | CS score, function | |
| Mat2a | 232087 | MAT2A | 4144 | −2.34 | S-adenosylmethionine biosynthetic process | Metabolism | CS score, function | |
| Mcm3ap | 54387 | MCM3AP | 8888 | −1.58 | immune system process | Metabolism | CS score, mouse K.O., function | Yoshida M, et al. Genes Cells. 2007 October; 12(10): 1205-13 |
| Mdn1 | 100019 | MDN1 | 23195 | −1.68 | protein complex assembly | Metabolism | CS score, function | |
| n/a | n/a | MFAP1 | 4236 | −1.94 | biological_process | Metabolism | CS score, function | |
| Mmgt1 | 236792 | MMGT1 | 93380 | −1.55 | magnesium ion transport | Metabolism | CS score, function | |
| Mrpl16 | 94063 | MRPL16 | 54948 | −1.80 | organelle organization | Metabolism | CS score, function | |
| Mrpl17 | 27397 | MRPL17 | 63875 | −1.80 | mitochondrial genome maintenance | Metabolism | CS score, function | |
| Mrpl33 | 66845 | MRPL33 | 9553 | −1.62 | organelle organization | Metabolism | CS score, function | |
| Mrpl38 | 60441 | MRPL38 | 64978 | −1.95 | organelle organization | Metabolism | CS score, function | |
| Mrpl39 | 27393 | MRPL39 | 54148 | −1.71 | organelle organization | Metabolism | CS score, function | |
| Mrpl45 | 67036 | MRPL45 | 84311 | −1.75 | organelle organization | Metabolism | CS score, function | |
| Mrpl46 | 67308 | MRPL46 | 26589 | −1.83 | organelle organization | Metabolism | CS score, function | |
| Mrpl53 | 68499 | MRPL53 | 116540 | −1.84 | organelle organization | Metabolism | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Mrps22 | 64655 | MRPS22 | 56945 | −1.32 | organelle organization | Metabolism | CS score, function | |
| Mrps25 | 64658 | MRPS25 | 64432 | −1.63 | organelle organization | Metabolism | CS score, function | |
| Mrps35 | 232536 | MRPS35 | 60488 | −1.60 | organelle organization | Metabolism | CS score, function | |
| Mrps5 | 77721 | MRPS5 | 64969 | −1.65 | organelle organization | Metabolism | CS score, function | |
| Mvd | 192156 | MVD | 4597 | −3.24 | isoprenoid biosynthetic process | Metabolism | CS score, function | |
| Mvk | 17855 | MVK | 4598 | −1.73 | isoprenoid biosynthetic process | Metabolism | CS score, function | |
| Naa25 | 231713 | NAA25 | 80018 | −2.40 | peptide alpha-N-acetyltransferase activity | Metabolism | CS score, function | |
| Napa | 108124 | NAPA | 8775 | −2.31 | intracellular protein transport | Metabolism | CS score, function | |
| Nat10 | 98956 | NAT10 | 55226 | −2.16 | biological_process | Metabolism | CS score, function | |
| Ndor1 | 78797 | NDOR1 | 27158 | −2.10 | cell death | Metabolism | CS score, function | |
| Ndufab1 | 70316 | NDUFAB1 | 4706 | −1.83 | fatty acid biosynthetic process | Metabolism | CS score, function | |
| Nol10 | 217431 | NOL10 | 79954 | −1.79 | poly(A) RNA binding | Metabolism | CS score, function | |
| Nop9 | 67842 | NOP9 | 161424 | −1.44 | biological_process | Metabolism | CS score, function | |
| Nrde2 | 217827 | NRDE2 | 55051 | −2.69 | biological_process | Metabolism | CS score, function | |
| Nsf | 18195 | NSF | 4905 | −2.76 | intra-Golgi vesicle-mediated transport | Metabolism | CS score, function | |
| Nubp1 | 26425 | NUBP1 | 4682 | −2.05 | cellular iron ion homeostasis | Metabolism | CS score, function | |
| Nudcd3 | 209586 | NUDCD3 | 23386 | −1.71 | molecular_function | Metabolism | CS score, function | |
| Nup155 | 170762 | NUP155 | 9631 | −1.59 | nucleocytoplasmic transport | Metabolism | CS score, mouse K.O., function | Zhang X, et al. Cell. 2008 Dec. 12; 135(6): 1017-27 |
| Nup93 | 71805 | NUP93 | 9688 | −2.11 | protein import into nucleus | Metabolism | CS score, function | |
| Nus1 | 52014 | NUS1 | 116150 | −1.94 | angiogenesis | Metabolism | CS score, mouse K.O., function | Park EJ, et al. Cell Metab. 2014 Sep. 2; 20(3):448-57 |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Nvl | 67459 | NVL | 4931 | −2.61 | positive regulation of telomerase activity | Metabolism | CS score, function | |
| Ogdh | 18293 | OGDH | 4967 | −2.98 | tricarboxylic acid cycle | Metabolism | CS score, function | |
| Osbp | 76303 | OSBP | 5007 | −2.06 | lipid transport | Metabolism | CS score, function | |
| Pak1ip1 | 68083 | PAK1IP1 | 55003 | −2.28 | cell proliferation | Metabolism | CS score, function | |
| Pfdn2 | 18637 | PFDN2 | 5202 | −1.32 | protein folding | Metabolism | CS score, function | |
| Pgam1 | 18648 | PGAM1 | 5223 | −2.37 | glycolytic process | Metabolism | CS score, function | |
| Pkm | 18746 | PKM | 5315 | −1.68 | glycolytic process | Metabolism | CS score, mouse K.O., function | Lewis SE, et al. 1983:267-78. Plenum Publ. Corp. |
| Pmpcb | 73078 | PMPCB | 9512 | −1.77 | proteolysis | Metabolism | CS score, function | |
| Ppil2 | 66053 | PPIL2 | 23759 | −3.01 | protein polyubiquitination | Metabolism | CS score, function | |
| Ppp4c | 56420 | PPP4C | 5531 | −2.89 | protein dephosphorylation | Metabolism | CS score, mouse K.O., function | Toyo-oka K, et al. J Cell Biol. 2008 Mar. 24; 180(6): 1133-47 |
| Prelid1 | 66494 | PRELID1 | 27166 | −2.27 | apoptotic process | Metabolism | CS score, function | |
| Prpf31 | 68988 | PRPF31 | 26121 | −3.20 | spliceosomal tri-snRNP complex assembly | Metabolism | CS score, mouse K.O., function | Bujakowska K, et al. Invest Ophthalmol Vis Sci. 2009 December; 50(12): 5927-33 |
| Prpf6 | 68879 | PRPF6 | 24148 | −2.96 | spliceosomal tri-snRNP complex assembly | Metabolism | CS score, function | |
| Psma1 | 26440 | PSMA1 | 5682 | −2.39 | proteasomal ubiquitin-independent protein catabolic process | Metabolism | CS score, function | |
| Psma2 | 19166 | PSMA2 | 5683 | −2.23 | proteasomal ubiquitin-independent protein catabolic process | Metabolism | CS score, function | |
| Psma3 | 19167 | PSMA3 | 5684 | −2.30 | proteasomal ubiquitin-independent protein | Metabolism | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Psmb2 | 26445 | PSMB2 | 5690 | −2.12 | catabolic process proteasomal ubiquitin-independent protein catabolic process | Metabolism | CS score, function | |
| Psmb3 | 26446 | PSMB3 | 5691 | −2.78 | proteolysis involved in cellular protein catabolic process | Metabolism | CS score, function | |
| Psmb5 | 19173 | PSMB5 | 5693 | −1.67 | proteasomal ubiquitin-independent protein catabolic process | Metabolism | CS score, function | |
| Psmb6 | 19175 | PSMB6 | 5694 | −2.42 | proteasomal ubiquitin-independent protein catabolic process | Metabolism | CS score, function | |
| Psmb7 | 19177 | PSMB7 | 5695 | −2.69 | proteasomal ubiquitin-independent protein catabolic process | Metabolism | CS score, function | |
| Psmc2 | 19181 | PSMC2 | 5701 | −2.35 | protein catabolic process | Metabolism | CS score, function | |
| Psmc3 | 19182 | PSMC3 | 5702 | −2.76 | ER-associated ubiquitin-dependent protein catabolic process | Metabolism | CS score, mouse K.O., function | Sakao Y, et al. Genomics. 2000 Jul. 1; 67(1):1-7 |
| Psmc4 | 23996 | PSMC4 | 5704 | −2.36 | blastocyst development | Metabolism | CS score, mouse K.O., function | Sakao Y, et al. Genomics. 2000 Jul. 1; 67(1):1-7 |
| Psmd1 | 70247 | PSMD1 | 5707 | −1.88 | regulation of protein catabolic process | Metabolism | CS score, function | |
| Psmd2 | 21762 | PSMD2 | 5708 | −2.16 | regulation of protein catabolic process | Metabolism | CS score, function | |
| Psmd3 | 22123 | PSMD3 | 5709 | −2.10 | regulation of protein catabolic process | Metabolism | CS score, function | |
| Psmd4 | 19185 | PSMD4 | 5710 | −1.77 | ubiquitin-dependent protein catabolic process | Metabolism | CS score, mouse K.O., function | Soriano P, et al. Genes Dev. 1987 June; 1(4):366-75 |
| Psmd6 | 66413 | PSMD6 | 9861 | −2.27 | proteasome-mediated ubiquitin- | Metabolism | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Psmg3 | 66506 | PSMG3 | 84262 | −2.57 | dependent protein catabolic process molecular_function | Metabolism | CS score, function | |
| Ptpmt1 | 66461 | PTPMT1 | 114971 | −2.89 | protein dephosphorylation | Metabolism | CS score, mouse K.O., function | Shen J, et al. Mol Cell Biol. 2011 December; 31(24): 4902-16 |
| Ptpn23 | 104831 | PTPN23 | 25930 | −1.59 | negative regulation of epithelial cell migration | Metabolism | CS score, mouse K.O., function | Gingras MC, et al. Int J Dev Biol. 2009; 53(7): 1069-74 |
| Rabggta | 56187 | RABGGTA | 5875 | −3.18 | protein prenylation | Metabolism | CS score, function | |
| Rabggtb | 19352 | RABGGTB | 5876 | −2.44 | protein geranyl-geranylation | Metabolism | CS score, function | |
| Rbm19 | 74111 | RBM19 | 9904 | −2.03 | multicellular organismal development | Metabolism | CS score, mouse K.O., function | Zhang J, et al. BMC Dev Biol. 2008; 8:11 5 |
| Rfk | 54391 | RFK | 55312 | −1.56 | riboflavin biosynthetic process | Metabolism | CS score, mouse K.O., function | Yazdanpanah B, et al. Nature. 2009 Aug. 27; 460(7259):1159-63 |
| Rheb | 19744 | RHEB | 6009 | −1.38 | signal transduction | Metabolism | CS score, mouse K.O., function | Zou J, et al. Dev Cell. 2011 Jan. 18; 20(1):97-108 |
| Riok1 | 71340 | RIOK1 | 83732 | −1.27 | protein phosphorylation | Metabolism | CS score, function | |
| Rpn1 | 103963 | RPN1 | 6184 | −2.13 | protein glycosylation | Metabolism | CS score, function | |
| Rtfdc1 | 66404 | RTFDC1 | 51507 | −2.09 | biological_process | Metabolism | CS score, function | |
| Sacm1l | 83493 | SACM1L | 22908 | −1.80 | protein dephosphorylation | Metabolism | CS score, function | |
| Samm50 | 68653 | SAMM50 | 25813 | −1.62 | protein targeting to mitochondrion | Metabolism | CS score, function | |
| Sco2 | 100126824 | SCO2 | 9997 | −1.60 | eye development | Metabolism | CS score, mouse K.O., function | Yang H, et al. Hum Mol Genet. 2010 Jan. 1; 19(1):170-80 |
| Sdha | 66945 | SDHA | 6389 | −2.20 | tricarboxylic acid cycle | Metabolism | CS score, function | |

TABLE 5-continued

Predicted CDLs (ID refers to EntrezGene identification number; CS score refers
to the CRISPR score average provided in Wang et al., 2015; function refers to the known or
predicted function of the locus, predictions being based on GO terms, as set forth in the Gene
Ontology Consortium website http://geneontology.org/; functional category refers to 4 categories
of cell functions based on the GO term-predicted function; CDL (basis) refers to information that
the inventors used to predict that a gene is a CDL, predictions being based on CS score, available
gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Sdhb | 67680 | SDHB | 6390 | −2.33 | tricarboxylic acid cycle | Metabolism | CS score, function | |
| Sec61a1 | 53421 | SEC61A1 | 29927 | −2.42 | protein transport | Metabolism | CS score, function | |
| Slc20a1 | 20515 | SLC20A1 | 6574 | −2.38 | sodium ion transport | Metabolism | CS score, mouse K.O., function | Festing MH, et al. Genesis. 2009 December; 47(12):858-63 |
| Slc7a6os | 66432 | SLC7A6OS | 84138 | −2.30 | hematopoietic progenitor cell differentiation | Metabolism | CS score, function | |
| Smn1 | 20595 | SMN1 | 6606 | −1.58 | spliceosomal complex assembly | Metabolism | CS score, mouse K.O., function | Hsieh-Li HM, et al. Nat Genet. 2000 January; 24(1): 66-70 |
| Smu1 | 74255 | SMU1 | 55234 | −3.65 | molecular_function | Metabolism | CS score, function | |
| Snrpd1 | 20641 | SNRPD1 | 6632 | −2.79 | spliceosomal complex assembly | Metabolism | CS score, function | |
| Snrpd3 | 67332 | SNRPD3 | 6634 | −3.62 | spliceosomal complex assembly | Metabolism | CS score, function | |
| Snrpe | 20643 | SNRPE | 6635 | −2.74 | spliceosomal complex assembly | Metabolism | CS score, function | |
| Spata5 | 57815 | SPATA5 | 166378 | −1.50 | multicellular organismal development | Metabolism | CS score, function | |
| Spata5l1 | 214616 | SPATA5L1 | 79029 | −2.70 | molecular_function | Metabolism | CS score, function | |
| Tango6 | 272538 | TANGO6 | 79613 | −2.29 | integral component of membrane | Metabolism | CS score, function | |
| n/a | n/a | TBC1D3B | 414059 | −1.67 | positive regulation of GTPase activity | Metabolism | CS score, function | |
| n/a | n/a | TBC1D3C | 414060 | −2.01 | positive regulation of GTPase activity | Metabolism | CS score, function | |
| Tbcb | 66411 | TBCB | 1155 | −1.97 | nervous system development | Metabolism | CS score, function | |
| Tbcc | 72726 | TBCC | 6903 | −3.02 | cell morphogenesis | Metabolism | CS score, function | |
| Tbcd | 108903 | TBCD | 6904 | −1.82 | microtubule cytoskeleton organization | Metabolism | CS score, function | |
| Tcp1 | 21454 | TCP1 | 6950 | −2.34 | protein folding | Metabolism | CS score, function | |
| Telo2 | 71718 | TELO2 | 9894 | −2.34 | regulation of TOR signaling | Metabolism | CS score, mouse K.O., function | Takai H, et al. Cell. 2007 Dec. 28; 131(7): 1248-59 |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Tex10 | 269536 | TEX10 | 54881 | −1.26 | integral component of membrane | Metabolism | CS score, function | |
| Tfrc | 22042 | TFRC | 7037 | −3.40 | cellular iron ion homeostasis | Metabolism | CS score, mouse K.O., function | Levy JE, et al. Nat Genet. 1999 April; 21(4): 396-9 |
| Timm10 | 30059 | TIMM10 | 26519 | −1.99 | protein targeting to mitochondrion | Metabolism | CS score, function | |
| Timm13 | 30055 | TIMM13 | 26517 | −1.62 | protein targeting to mitochondrion | Metabolism | CS score, function | |
| Timm23 | 53600 | TIMM23 | 100287932 | −2.00 | protein targeting to mitochondrion | Metabolism | CS score, mouse K.O., function | Ahting U, et al. Biochim Biophys Acta. 2009 May; 1787(5):371-6 |
| Timm44 | 21856 | TIMM44 | 10469 | −1.73 | protein import into mitochondrial matrix | Metabolism | CS score, function | |
| Tmx2 | 66958 | TMX2 | 51075 | −2.29 | biological_process | Metabolism | CS score, function | |
| Tnpo3 | 320938 | TNPO3 | 23534 | −1.82 | splicing factor protein import into nucleus | Metabolism | CS score, function | |
| Trmt112 | 67674 | TRMT112 | 51504 | −3.70 | peptidyl-glutamine methylation | Metabolism | CS score, function | |
| Trnau1ap | 71787 | TRNAU1AP | 54952 | −1.40 | selenocysteine incorporation | Metabolism | CS score, function | |
| Ttc1 | 66827 | TTC1 | 7265 | −1.74 | protein folding | Metabolism | CS score, function | |
| Ttc27 | 74196 | TTC27 | 55622 | −2.54 | biological_process | Metabolism | CS score, function | |
| Tti1 | 75425 | TTI1 | 9675 | −2.91 | regulation of TOR signaling | Metabolism | CS score, function | |
| Tti2 | 234138 | TTI2 | 80185 | −1.94 | molecular_function | Metabolism | CS score, function | |
| n/a | n/a | TUBB | 203068 | −3.40 | microtubule-based process | Metabolism | CS score, function | |
| Txn2 | 56551 | TXN2 | 25828 | −1.41 | sulfate assimilation | Metabolism | CS score, mouse K.O., function | Nonn L, et al. Mol Cell Biol. 2003 February; 23(3): 916-22 |
| Uqcrc1 | 22273 | UQCRC1 | 7384 | −1.29 | oxidative phosphorylation | Metabolism | CS score, function | |
| Uqcrh | 66576 | UQCRH | 7388 | −1.28 | oxidative phosphorylation | Metabolism | CS score, function | |
| Urb2 | 382038 | URB2 | 9816 | −2.25 | molecular_function | Metabolism | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Vmp1 | 75909 | VMP1 | 81671 | −1.75 | exocytosis | Metabolism | CS score, function | |
| n/a | n/a | VPS28 | 51160 | −3.06 | protein targeting to vacuole involved in ubiquitin-dependent protein catabolic process via the multivesicular body sorting pathway | Metabolism | CS score, function | |
| Vps29 | 56433 | VPS29 | 51699 | −2.05 | intracellular protein transport | Metabolism | CS score, function | |
| Vps52 | 224705 | VPS52 | 6293 | −1.85 | ectodermal cell differentiation | Metabolism | CS score, mouse K.O., function | Sugimoto M, et al. Cell Rep. 2012 Nov. 29; 2(5):1363-74 |
| Wars2 | 70560 | WARS2 | 10352 | −1.16 | vasculogenesis | Metabolism | CS score, function | |
| Wdr7 | 104082 | WDR7 | 23335 | −1.47 | hematopoietic progenitor cell differentiation | Metabolism | CS score, function | |
| Wdr70 | 545085 | WDR70 | 55100 | −1.69 | enzyme binding | Metabolism | CS score, function | |
| Wdr74 | 107071 | WDR74 | 54663 | −2.84 | blastocyst formation | Metabolism | CS score, function | |
| Wdr77 | 70465 | WDR77 | 79084 | −2.19 | spliceosomal snRNP assembly | Metabolism | CS score, mouse K.O., function | Zhou L, et al. J Mol Endocrinol. 2006 October; 37(2): 283-300 |
| Yae1d1 | 67008 | YAE1D1 | 57002 | −1.71 | molecular_function | Metabolism | CS score, function | |
| Yrdc | 230734 | YRDC | 79693 | −2.33 | negative regulation of transport | Metabolism | CS score, function | |
| Znhit2 | 29805 | ZNHIT2 | 741 | −2.70 | metal ion binding | Metabolism | CS score, function | |
| Aars | 234734 | AARS | 16 | −2.48 | alanyl-tRNA aminoacylation | RNA transcription, protein translation | CS score, function | |
| Bms1 | 213895 | BMS1 | 9790 | −1.36 | ribosome assembly | RNA transcription, protein translation | CS score, function | |
| Bud31 | 231889 | BUD31 | 8896 | −2.46 | mRNA splicing, via spliceosome | RNA transcription, protein translation | CS score, function | |
| Bysl | 53414 | BYSL | 705 | −2.24 | maturation of SSU-rRNA from tricistronic rRNA | RNA transcription, protein translation | CS score, mouse K.O., function | Aoki R, et al. FEBS Lett. 2006 Nov. 13; 580(26): |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| | | | | | transcript (SSU-rRNA, 5.8S rRNA, LSU-rRNA) | | | 6062-8 |
| Cars | 27267 | CARS | 833 | −2.45 | tRNA aminoacylation for protein translation | RNA transcription, protein translation | CS score, function | |
| Cdc5l | 71702 | CDC5L | 988 | −2.09 | mRNA splicing, via spliceosome | RNA transcription, protein translation | CS score, function | |
| Cdc73 | 214498 | CDC73 | 79577 | −2.58 | negative regulation of transcription from RNA polymerase II promoter | RNA transcription, protein translation | CS score, mouse K.O., function | Wang P, et al. Mol Cell Biol. 2008 May; 28(9): 2930-40 |
| Cebpz | 12607 | CEBPZ | 10153 | −2.11 | transcription from RNA polymerase II promoter | RNA transcription, protein translation | CS score, function | |
| Clasrp | 53609 | CLASRP | 11129 | −1.30 | mRNA processing | RNA transcription, protein translation | CS score, function | |
| Clp1 | 98985 | CLP1 | 10978 | −3.47 | mRNA splicing, via spliceosome | RNA transcription, protein translation | CS score, mouse K.O., function | Hanada T, et al. Nature. 2013 Mar. 28; 495(7442):474-80 |
| Cox5b | 12859 | COX5B | 1329 | −1.50 | transcription initiation from RNA polymerase II promoter | RNA transcription, protein translation | CS score, function | |
| Cpsf1 | 94230 | CPSF1 | 29894 | −2.58 | mRNA splicing, via spliceosome | RNA transcription, protein translation | CS score, function | |
| Cpsf2 | 51786 | CPSF2 | 53981 | −2.55 | mRNA polyadenylation | RNA transcription, protein translation | CS score, function | |
| Cpsf3l | 71957 | CPSF3L | 54973 | −2.09 | snRNA processing | RNA transcription, protein translation | CS score, function | |
| Dars | 226414 | DARS | 1615 | −2.90 | translation | RNA transcription, protein translation | CS score, function | |
| Dbr1 | 83703 | DBR1 | 51163 | −3.75 | RNA splicing, via transesterification reactions | RNA transcription, protein translation | CS score, function | |
| Ddx18 | 66942 | DDX18 | 8886 | −2.33 | RNA secondary structure unwinding | RNA transcription, protein translation | CS score, function | |
| Ddx23 | 74351 | DDX23 | 9416 | −3.01 | RNA secondary structure unwinding | RNA transcription, protein translation | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Ddx24 | 27225 | DDX24 | 57062 | −1.40 | RNA secondary structure unwinding | RNA transcription, protein translation | CS score, function | |
| Ddx41 | 72935 | DDX41 | 51428 | −1.74 | RNA secondary structure unwinding | RNA transcription, protein translation | CS score, function | |
| Ddx46 | 212880 | DDX46 | 9879 | −2.79 | mRNA splicing, via spliceosome | RNA transcription, protein translation | CS score, function | |
| Ddx47 | 67755 | DDX47 | 51202 | −2.20 | RNA secondary structure unwinding | RNA transcription, protein translation | CS score, function | |
| Ddx49 | 234374 | DDX49 | 54555 | −3.20 | RNA secondary structure unwinding | RNA transcription, protein translation | CS score, function | |
| Ddx54 | 71990 | DDX54 | 79039 | −2.94 | RNA secondary structure unwinding | RNA transcription, protein translation | CS score, function | |
| Ddx56 | 52513 | DDX56 | 54606 | −2.85 | rRNA processing | RNA transcription, protein translation | CS score, function | |
| Dgcr14 | 27886 | DGCR14 | 8220 | −1.76 | mRNA splicing, via spliceosome | RNA transcription, protein translation | CS score, function | |
| Dhx15 | 13204 | DHX15 | 1665 | −2.58 | mRNA processing | RNA transcription, protein translation | CS score, function | |
| Dhx16 | 69192 | DHX16 | 8449 | −1.35 | mRNA processing | RNA transcription, protein translation | CS score, function | |
| Dhx38 | 64340 | DHX38 | 9785 | −1.76 | mRNA splicing, via spliceosome | RNA transcription, protein translation | CS score, function | |
| Diexf | 215193 | DIEXF | 27042 | −2.03 | maturation of SSU-rRNA from tricistronic rRNA transcript (SSU-rRNA, 5.8S rRNA, LSU-rRNA) | RNA transcription, protein translation | CS score, function | |
| Dimt1 | 66254 | DIMT1 | 27292 | −1.87 | rRNA methylation | RNA transcription, protein translation | CS score, function | |
| Dis3 | 72662 | DIS3 | 22894 | −1.77 | mRNA catabolic process | RNA transcription, protein translation | CS score, function | |
| Dkc1 | 245474 | DKC1 | 1736 | −2.37 | box H/ACA snoRNA 3'-end processing | RNA transcription, protein translation | CS score, mouse K.O., function | He J, et al. Oncogene. 2002 Oct. 31; 21(50): 7740-4 |
| Dnajc17 | 69408 | DNAJC17 | 55192 | −2.25 | negative regulation of transcription | RNA transcription, protein | CS score, | Amendola E, et al. Endocrinology. |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| | | | | | from RNA polymerase II promoter | translation | mouse K.O., function | 2010 April; 151(4): 1948-58 |
| Ears2 | 67417 | EARS2 | 124454 | −1.91 | tRNA aminoacylation for protein translation | RNA transcription, protein translation | CS score, function | |
| Ebna1bp2 | 69072 | EBNA1BP2 | 10969 | −1.52 | ribosome biogenesis | RNA transcription, protein translation | CS score, function | |
| Eef1a1 | 13627 | EEF1A1 | 1915 | −3.11 | translational elongation | RNA transcription, protein translation | CS score, function | |
| Eef1g | 67160 | EEF1G | 1937 | −1.42 | translation | RNA transcription, protein translation | CS score, function | |
| Eef2 | 13629 | EEF2 | 1938 | −3.53 | translation | RNA transcription, protein translation | CS score, function | |
| Eftud2 | 20624 | EFTUD2 | 9343 | −3.79 | mRNA splicing, via spliceosome | RNA transcription, protein translation | CS score, function | |
| Eif1ad | 69860 | EIF1AD | 84285 | −2.26 | translational initiation | RNA transcription, protein translation | CS score, function | |
| Eif2b1 | 209354 | EIF2B1 | 1967 | −2.23 | regulation of translational initiation | RNA transcription, protein translation | CS score, function | |
| Eif2b3 | 108067 | EIF2B3 | 8891 | −3.00 | translational initiation | RNA transcription, protein translation | CS score, function | |
| Eif2s1 | 13665 | EIF2S1 | 1965 | −3.93 | translation | RNA transcription, protein translation | CS score, function | |
| Eif3c | 56347 | EIF3C | 8663 | −2.59 | formation of translation preinitiation complex | RNA transcription, protein translation | CS score, function | |
| n/a | n/a | EIF3CL | 728689 | −2.71 | formation of translation preinitiation complex | RNA transcription, protein translation | CS score, function | |
| Eif3d | 55944 | EIF3D | 8664 | −3.23 | formation of translation preinitiation complex | RNA transcription, protein translation | CS score, function | |
| Eif3f | 66085 | EIF3F | 8665 | −1.44 | formation of translation preinitiation complex | RNA transcription, protein translation | CS score, function | |
| Eif3g | 53356 | EIF3G | 8666 | −3.10 | translational initiation | RNA transcription, protein translation | CS score, function | |
| Eif3i | 54709 | EIF3I | 8668 | −2.24 | formation of translation preinitiation complex | RNA transcription, protein translation | CS score, function | |
| Eif3l | 223691 | EIF3L | 51386 | −1.28 | translational initiation | RNA transcription, | CS score, | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Eif4a1 | 13681 | EIF4A1 | 1973 | −1.97 | translational initiation | protein translation RNA transcription, protein translation | function CS score, function | |
| Eif4a3 | 192170 | EIF4A3 | 9775 | −4.32 | RNA splicing | RNA transcription, protein translation | CS score, function | |
| Eif4g1 | 208643 | EIF4G1 | 1981 | −1.79 | nuclear-transcribed mRNA catabolic process, nonsense-mediated decay | RNA transcription, protein translation | CS score, function | |
| Eif5b | 226982 | EIF5B | 9669 | −2.93 | translational initiation | RNA transcription, protein translation | CS score, function | |
| Eif6 | 16418 | EIF6 | 3692 | −2.75 | mature ribosome assembly | RNA transcription, protein translation | CS score, mouse K.O., function | Gandin V, et al. Nature. 2008 Oct. 2; 455(7213): 684-8 |
| Elac2 | 68626 | ELAC2 | 60528 | −2.06 | tRNA 3'-trailer cleavage, endonucleolytic | RNA transcription, protein translation | CS score, function | |
| Ell | 13716 | ELL | 8178 | −2.23 | transcription elongation from RNA polymerase II promoter | RNA transcription, protein translation | CS score, mouse K.O., function | Mitani K, et al. Biochem Biophys Res Commun. 2000 Dec. 20; 279(2): 563-7 |
| Etf1 | 225363 | ETF1 | 2107 | −2.44 | translational termination | RNA transcription, protein translation | CS score, function | |
| Exosc2 | 227715 | EXOSC2 | 23404 | −1.66 | exonucleolytic trimming to generate mature 3'-end of 5.8S rRNA from tricistronic rRNA transcript (SSU-rRNA, 5.8S rRNA, LSU-rRNA) | RNA transcription, protein translation | CS score, function | |
| Exosc4 | 109075 | EXOSC4 | 54512 | −3.21 | nuclear-transcribed mRNA catabolic process, deadenylation-dependent decay | RNA transcription, protein translation | CS score, function | |
| Exosc5 | 27998 | EXOSC5 | 56915 | −2.09 | rRNA catabolic process | RNA transcription, protein translation | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| n/a | n/a | EXOSC6 | 118460 | −3.20 | nuclear-transcribed mRNA catabolic process, deadenylation-dependent decay | RNA transcription, protein translation | CS score, function | |
| Exosc7 | 66446 | EXOSC7 | 23016 | −2.17 | nuclear-transcribed mRNA catabolic process, deadenylation-dependent decay | RNA transcription, protein translation | CS score, function | |
| Exosc8 | 69639 | EXOSC8 | 11340 | −2.08 | nuclear-transcribed mRNA catabolic process, deadenylation-dependent decay | RNA transcription, protein translation | CS score, function | |
| Fars2 | 69955 | FARS2 | 10667 | −1.90 | tRNA aminoacylation for protein translation | RNA transcription, protein translation | CS score, function | |
| Farsa | 66590 | FARSA | 2193 | −3.30 | phenylalanyl-tRNA aminoacylation | RNA transcription, protein translation | CS score, function | |
| Farsb | 23874 | FARSB | 10056 | −2.49 | phenylalanyl-tRNA aminoacylation | RNA transcription, protein translation | CS score, function | |
| Fau | 14109 | FAU | 2197 | −2.64 | translation | RNA transcription, protein translation | CS score, function | |
| Fip1l1 | 66899 | FIP1L1 | 81608 | −1.93 | mRNA processing | RNA transcription, protein translation | CS score, function | |
| Ftsj3 | 56095 | FTSJ3 | 117246 | −1.50 | rRNA methylation | RNA transcription, protein translation | CS score, function | |
| Gle1 | 74412 | GLE1 | 2733 | −1.89 | mRNA export from nucleus | RNA transcription, protein translation | CS score, function | |
| Gnl3l | 237107 | GNL3L | 54552 | −1.35 | ribosome biogenesis | RNA transcription, protein translation | CS score, function | |
| Gtf2e1 | 74197 | GTF2E1 | 2960 | −1.22 | transcriptional open complex formation at RNA polymerase II promoter | RNA transcription, protein translation | CS score, function | |
| Gtpbp4 | 69237 | GTPBP4 | 23560 | −2.25 | ribosome biogenesis | RNA transcription, protein translation | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Hars | 15115 | HARS | 3035 | −3.49 | histidyl-tRNA aminoacylation | RNA transcription, protein translation | CS score, function | |
| Hars2 | 70791 | HARS2 | 23438 | −1.92 | histidyl-tRNA aminoacylation | RNA transcription, protein translation | CS score, function | |
| Heatr1 | 217995 | HEATR1 | 55127 | −2.58 | maturation of SSU-rRNA from tricistronic rRNA transcript (SSU-rRNA, 5.8S rRNA, LSU-rRNA) | RNA transcription, protein translation | CS score, function | |
| Hnrnpc | 15381 | HNRNPC | 3183 | −1.95 | mRNA splicing, via spliceosome | RNA transcription, protein translation | CS score, mouse K.O., function | Williamson DJ, et al. Mol Cell Biol. 2000 June; 20(11): 4094-105 |
| Hnrnpk | 15387 | HNRNPK | 3190 | −2.39 | mRNA splicing, via spliceosome | RNA transcription, protein translation | CS score, function | |
| Hnrnpl | 15388 | HNRNPL | 3191 | −1.88 | mRNA processing | RNA transcription, protein translation | CS score, mouse K.O., function | Gaudreau MC, et al. J Immunol. 2012 Jun. 1; 188(11): 5377-88 |
| Hnrnpu | 51810 | HNRNPU | 3192 | −2.44 | mRNA splicing, via spliceosome | RNA transcription, protein translation | CS score, mouse K.O., function | Roshon MJ, et al. Transgenic Res. 2005 April; 14(2): 179-92 |
| Iars | 105148 | IARS | 3376 | −3.87 | isoleucyl-tRNA aminoacylation | RNA transcription, protein translation | CS score, function | |
| Iars2 | 381314 | IARS2 | 55699 | −2.83 | tRNA aminoacylation for protein translation | RNA transcription, protein translation | CS score, function | |
| Imp3 | 102462 | IMP3 | 55272 | −3.46 | rRNA processing | RNA transcription, protein translation | CS score, function | |
| Imp4 | 27993 | IMP4 | 92856 | −2.01 | rRNA processing | RNA transcription, protein translation | CS score, function | |
| Ints1 | 68510 | INTS1 | 26173 | −1.93 | snRNA processing | RNA transcription, protein translation | CS score, mouse K.O., function | Nakayama M, et al. FASEB J. 2006 August; 20(10): 1718-20 |
| Ints4 | 101861 | INTS4 | 92105 | −1.75 | snRNA processing | RNA transcription, protein translation | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Ints5 | 109077 | INTS5 | 80789 | −2.10 | snRNA processing | RNA transcription, protein translation | CS score, function | |
| Ints8 | 72656 | INTS8 | 55656 | −1.35 | snRNA processing | RNA transcription, protein translation | CS score, function | |
| Ints9 | 210925 | INTS9 | 55756 | −2.26 | snRNA processing | RNA transcription, protein translation | CS score, function | |
| Isg20l2 | 229504 | ISG20L2 | 81875 | −2.27 | ribosome biogenesis | RNA transcription, protein translation | CS score, function | |
| Kars | 85305 | KARS | 3735 | −2.76 | tRNA aminoacylation for protein translation | RNA transcription, protein translation | CS score, function | |
| n/a | n/a | KIAA0391 | 9692 | −1.56 | tRNA processing | RNA transcription, protein translation | CS score, function | |
| Lars | 107045 | LARS | 51520 | −1.83 | tRNA aminoacylation for protein translation | RNA transcription, protein translation | CS score, function | |
| Lars2 | 102436 | LARS2 | 23395 | −1.60 | tRNA aminoacylation for protein translation | RNA transcription, protein translation | CS score, function | |
| Las1l | 76130 | LAS1L | 81887 | −2.12 | rRNA processing | RNA transcription, protein translation | CS score, function | |
| Lrpprc | 72416 | LRPPRC | 10128 | −1.39 | negative regulation of mitochondrial RNA catabolic process | RNA transcription, protein translation | CS score, mouse K.O., function | Ruzzenente B, et al. EMBO J. 2012 Jan. 18; 31(2):443-56 |
| Lsm2 | 27756 | LSM2 | 57819 | −2.96 | nuclear-transcribed mRNA catabolic process, deadenylation-dependent decay | RNA transcription, protein translation | CS score, function | |
| Lsm3 | 67678 | LSM3 | 27258 | −1.66 | nuclear-transcribed mRNA catabolic process, deadenylation-dependent decay | RNA transcription, protein translation | CS score function | |
| Lsm7 | 66094 | LSM7 | 51690 | −1.96 | nuclear-transcribed mRNA catabolic process, deadenylation-dependent decay | RNA transcription, protein translation | CS score, function | |
| Magoh | 17149 | MAGOH | 4116 | −1.78 | nuclear-transcribed mRNA | RNA transcription, protein | CS score, mouse | Silver DL, et al. Nat Neurosci. |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| | | | | | catabolic process, nonsense-mediated decay | translation | K.O., function | 2010 May; 13(5): 551-8 |
| Mars | 216443 | MARS | 4141 | −3.24 | methionyl-tRNA aminoacylation | RNA transcription, protein translation | CS score, function | |
| Mars2 | 212679 | MARS2 | 92935 | −2.31 | tRNA aminoacylation for protein translation | RNA transcription, protein translation | CS score, function | |
| Med17 | 234959 | MED17 | 9440 | −1.78 | regulation of transcription from RNA polymerase II promoter | RNA transcription, protein translation | CS score, function | |
| Med20 | 56771 | MED20 | 9477 | −2.00 | regulation of transcription from RNA polymerase II promoter | RNA transcription, protein translation | CS score, function | |
| Med22 | 20933 | MED22 | 6837 | −1.86 | regulation of transcription from RNA polymerase II promoter | RNA transcription, protein translation | CS score, function | |
| Med27 | 68975 | MED27 | 9442 | −1.48 | regulation of transcription from RNA polymerase II promoter | RNA transcription, protein translation | CS score, function | |
| Med30 | 69790 | MED30 | 90390 | −2.21 | regulation of transcription from RNA polymerase II promoter | RNA transcription, protein translation | CS score, function | |
| Med8 | 80509 | MED8 | 112950 | −1.64 | regulation of transcription from RNA polymerase II promoter | RNA transcription, protein translation | CS score, function | |
| Mepce | 231803 | MEPCE | 56257 | −2.08 | negative regulation of transcription from RNA polymerase II promoter | RNA transcription, protein translation | CS score, function | |
| Mettl16 | 67493 | METTL16 | 79066 | −2.10 | rRNA base methylation | RNA transcription, protein translation | CS score, function | |
| Mphosph10 | 67973 | MPHOSPH10 | 10199 | −1.85 | RNA splicing, via transesterification reactions | RNA transcription, protein translation | CS score, function | |
| Mrpl10 | 107732 | MRPL10 | 124995 | −1.38 | translation | RNA transcription, protein translation | CS score, function | |
| Mrpl12 | 56282 | MRPL12 | 6182 | −1.56 | translation | RNA transcription, protein translation | CS score, function | |
| Mrpl21 | 353242 | MRPL21 | 219927 | −1.91 | translation | RNA transcription, protein translation | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Mrpl28 | 68611 | MRPL28 | 10573 | −1.50 | translation | RNA transcription, protein translation | CS score, function | |
| Mrpl3 | 94062 | MRPL3 | 11222 | −1.58 | translation | RNA transcription, protein translation | CS score, function | |
| Mrpl34 | 94065 | MRPL34 | 64981 | −1.66 | translation | RNA transcription, protein translation | CS score, function | |
| Mrpl4 | 66163 | MRPL4 | 51073 | −2.41 | translation | RNA transcription, protein translation | CS score, function | |
| Mrpl41 | 107733 | MRPL41 | 64975 | −2.15 | translation | RNA transcription, protein translation | CS score, function | |
| Mrpl51 | 66493 | MRPL51 | 51258 | −1.40 | translation | RNA transcription, protein translation | CS score, function | |
| Mrps14 | 64659 | MRPS14 | 63931 | −1.82 | translation | RNA transcription, protein translation | CS score, function | |
| Mrps15 | 66407 | MRPS15 | 64960 | −1.28 | translation | RNA transcription, protein translation | CS score, function | |
| Mrps16 | 66242 | MRPS16 | 51021 | −2.29 | translation | RNA transcription, protein translation | CS score, function | |
| Mrps18a | 68565 | MRPS18A | 55168 | −1.55 | translation | RNA transcription, protein translation | CS score, function | |
| Mrps2 | 118451 | MRPS2 | 51116 | −1.59 | translation | RNA transcription, protein translation | CS score, function | |
| Mrps21 | 66292 | MRPS21 | 54460 | −1.51 | translation | RNA transcription, protein translation | CS score, function | |
| Mrps24 | 64660 | MRPS24 | 64951 | −1.71 | translation | RNA transcription, protein translation | CS score, function | |
| Mrps6 | 121022 | MRPS6 | 64968 | −1.65 | translation | RNA transcription, protein translation | CS score, function | |
| Nars | 70223 | NARS | 4677 | −3.31 | tRNA aminoacylation for protein translation | RNA transcription, protein translation | CS score, function | |
| Nars2 | 244141 | NARS2 | 79731 | −1.32 | tRNA aminoacylation for protein translation | RNA transcription, protein translation | CS score, function | |
| Ncbp2 | 68092 | NCBP2 | 22916 | −3.00 | mRNA cis splicing, via spliceosome | RNA transcription, protein translation | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Nedd8 | 18002 | NEDD8 | 4738 | −2.45 | regulation of transcription from RNA polymerase II promoter | RNA transcription, protein translation | CS score, function | |
| Ngdn | 68966 | NGDN | 25983 | −2.35 | maturation of SSU-rRNA from tricistronic rRNA transcript (SSU-rRNA, 5.8S rRNA, LSU-rRNA) | RNA transcription, protein translation | CS score, function | |
| Nhp2 | 52530 | NHP2 | 55651 | −1.74 | rRNA pseudouridine synthesis | RNA transcription, protein translation | CS score, function | |
| Nip7 | 66164 | NIP7 | 51388 | −2.03 | ribosome assembly | RNA transcription, protein translation | CS score, function | |
| Noc2l | 57741 | NOC2L | 26155 | −2.34 | negative regulation of transcription from RNA polymerase I promoter | RNA transcription, protein translation | CS score, function | |
| Noc4l | 100608 | NOC4L | 79050 | −2.11 | ribosome biogenesis | RNA transcription, protein translation | CS score, function | |
| Nol6 | 230082 | NOL6 | 65083 | −2.28 | rRNA processing | RNA transcription, protein translation | CS score, function | |
| Nol9 | 74035 | NOL9 | 79707 | −2.20 | cleavage in ITS2 between 5.8S rRNA and LSU-rRNA of tricistronic rRNA transcript (SSU-rRNA, 5.8S rRNA, LSU-rRNA) | RNA transcription, protein translation | CS score, function | |
| Nop16 | 28126 | NOP16 | 51491 | −2.10 | ribosomal large subunit biogenesis | RNA transcription, protein translation | CS score, function | |
| Nop2 | 110109 | NOP2 | 4839 | −2.14 | rRNA processing | RNA transcription, protein translation | CS score, function | |
| Nop58 | 55989 | NOP58 | 51602 | −2.54 | rRNA modification | RNA transcription, protein translation | CS score, function | |
| Nsa2 | 59050 | NSA2 | 10412 | −1.78 | rRNA processing | RNA transcription, protein translation | CS score, function | |
| Nudt21 | 68219 | NUDT21 | 11051 | −2.36 | mRNA polyadenylation | RNA transcription, protein translation | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Osgep | 66246 | OSGEP | 55644 | −1.98 | tRNA processing | RNA transcription, protein translation | CS score, function | |
| Pabpn1 | 54196 | PABPN1 | 8106 | −1.92 | mRNA splicing, via spliceosome | RNA transcription, protein translation | CS score, function | |
| Pdcd11 | 18572 | PDCD11 | 22984 | −1.47 | rRNA processing | RNA transcription, protein translation | CS score, function | |
| Pes1 | 64934 | PES1 | 23481 | −2.92 | maturation of LSU-rRNA from tricistronic rRNA transcript (SSU-rRNA, 5.8S rRNA, LSU-rRNA) | RNA transcription, protein translation | CS score, mouse K.O., function | Lerch-Gaggl A, et al. J Biol Chem. 2002 Nov. 22; 277(47): 45347-55 |
| Phb | 18673 | PHB | 5245 | −2.26 | regulation of transcription from RNA polymerase II promoter | RNA transcription, protein translation | CS score, mouse K.O., function | He B, et al. Endocrinology. 2011 March; 152(3): 1047-56 |
| Phf5a | 68479 | PHF5A | 84844 | −3.52 | mRNA splicing, via spliceosome | RNA transcription, protein translation | CS score, function | |
| Pnn | 18949 | PNN | 5411 | −1.34 | mRNA splicing, via spliceosome | RNA transcription, protein translation | CS score, mouse K.O., function | Joo JH, et al. Dev Dyn. 2007 August; 236(8): 2147-58 |
| Polr1b | 20017 | POLR1B | 84172 | −3.23 | transcription from RNA polymerase I promoter | RNA transcription, protein translation | CS score, mouse K.O., function | Chen H, et al. Biochem Biophys Res Commun. 2008 Jan. 25; 365(4): 636-42 |
| Polr1c | 20016 | POLR1C | 9533 | −2.79 | transcription from RNA polymerase I promoter | RNA transcription, protein translation | CS score, function | |
| Polr2a | 20020 | POLR2A | 5430 | −3.15 | transcription from RNA polymerase II promoter | RNA transcription, protein translation | CS score, function | |
| Polr2b | 231329 | POLR2B | 5431 | −3.09 | transcription from RNA polymerase II promoter | RNA transcription, protein translation | CS score, function | |
| Polr2c | 20021 | POLR2C | 5432 | −3.15 | mRNA splicing, via spliceosome | RNA transcription, protein translation | CS score, function | |
| Polr2d | 69241 | POLR2D | 5433 | −2.23 | nuclear-transcribed mRNA catabolic process, deadenylation-dependent decay | RNA transcription, protein translation | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Polr2f | 69833 | POLR2F | 5435 | −2.31 | transcription from RNA polymerase I promoter | RNA transcription, protein translation | CS score, function | |
| Polr2g | 67710 | POLR2G | 5436 | −2.78 | nuclear-transcribed mRNA catabolic process, exonucleolytic | RNA transcription, protein translation | CS score, function | |
| Polr2h | 245841 | POLR2H | 5437 | −1.83 | transcription from RNA polymerase I promoter | RNA transcription, protein translation | CS score, function | |
| Polr2i | 69920 | POLR2I | 5438 | −2.92 | maintenance of transcriptional fidelity during DNA-templated transcription elongation from RNA polymerase II promoter | RNA transcription, protein translation | CS score, function | |
| Polr2j | 20022 | POLR2J | 5439 | −3.31 | mRNA splicing, via spliceosome | RNA transcription, protein translation | CS score, function | |
| Polr2l | 66491 | POLR2L | 5441 | −3.55 | mRNA splicing, via spliceosome | RNA transcription, protein translation | CS score, function | |
| Polr3e | 26939 | POLR3E | 55718 | −2.33 | transcription from RNA polymerase III promoter | RNA transcription, protein translation | CS score, function | |
| Pop1 | 67724 | POP1 | 10940 | −1.79 | tRNA 5′-leader removal | RNA transcription, protein translation | CS score, function | |
| Pop4 | 66161 | POP4 | 10775 | −1.87 | RNA phosphodiester bond hydrolysis | RNA transcription, protein translation | CS score, function | |
| Ppa1 | 67895 | PPA1 | 5464 | −1.63 | tRNA aminoacylation for protein translation | RNA transcription, protein translation | CS score, function | |
| Ppan | 235036 | PPAN | 56342 | −1.62 | ribosomal large subunit assembly | RNA transcription, protein translation | CS score, function | |
| Ppp2ca | 19052 | PPP2CA | 5515 | −3.01 | nuclear-transcribed mRNA catabolic process, nonsense-mediated decay | RNA transcription, protein translation | CS score, mouse K.O., function | Gu P, et al. Genesis. 2012 May; 50(5): 429-36 |
| Prim1 | 19075 | PRIM1 | 5557 | −2.07 | DNA replication, synthesis of RNA primer | RNA transcription, protein translation | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Prpf38b | 66921 | PRPF38B | 55119 | −2.68 | mRNA processing | RNA transcription, protein translation | CS score, function | |
| Prpf4 | 70052 | PRPF4 | 9128 | −2.24 | RNA splicing | RNA transcription, protein translation | CS score, function | |
| Prpf8 | 192159 | PRPF8 | 10594 | −3.43 | mRNA splicing, via spliceosome | RNA transcription, protein translation | CS score, function | |
| Ptcd1 | 71799 | PTCD1 | 26024 | −1.77 | tRNA 3'-end processing | RNA transcription, protein translation | CS score, function | |
| Pwp2 | 110816 | PWP2 | 5822 | −2.52 | ribosomal small subunit assembly | RNA transcription, protein translation | CS score, function | |
| Qars | 97541 | QARS | 5859 | −3.35 | tRNA aminoacylation for protein translation | RNA transcription, protein translation | CS score, function | |
| Ran | 19384 | RAN | 5901 | −3.09 | ribosomal large subunit export from nucleus | RNA transcription, protein translation | CS score, function | |
| Rars | 104458 | RARS | 5917 | −2.30 | tRNA aminoacylation for protein translation | RNA transcription, protein translation | CS score, function | |
| Rars2 | 109093 | RARS2 | 57038 | −1.93 | arginyl-tRNA aminoacylation | RNA transcription, protein translation | CS score, function | |
| Rbm25 | 67039 | RBM25 | 58517 | −2.15 | regulation of alternative mRNA splicing, via spliceosome | RNA transcription, protein translation | CS score, function | |
| Rbm8a | 60365 | RBM8A | 9939 | −2.97 | nuclear-transcribed mRNA catabolic process, nonsense-mediated decay | RNA transcription, protein translation | CS score, function | |
| Rbmx | 19655 | RBMX | 27316 | −1.95 | regulation of alternative mRNA splicing, via spliceosome | RNA transcription, protein translation | CS score, function | |
| Rcl1 | 59028 | RCL1 | 10171 | −2.08 | endonucleolytic cleavage of tricistronic rRNA transcript (SSU-rRNA, 5.8S rRNA, LSU-rRNA) | RNA transcription, protein translation | CS score, function | |
| Rngtt | 24018 | RNGTT | 8732 | −2.90 | transcription from RNA polymerase II promoter | RNA transcription, protein translation | CS score, function | |
| Rnmt | 67897 | RNMT | 8731 | −1.45 | 7-methylguanosine | RNA transcription, | CS score, | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Rnpc3 | 67225 | RNPC3 | 55599 | −1.95 | mRNA capping mRNA splicing, via spliceosome | protein translation RNA transcription, protein translation | function CS score, function | |
| Rpap1 | 68925 | RPAP1 | 26015 | −2.58 | transcription from RNA polymerase II promoter | RNA transcription, protein translation | CS score, function | |
| Rpl10 | 110954 | RPL10 | 6134 | −3.76 | translation | RNA transcription, protein translation | CS score, function | |
| Rpl10a | 19896 | RPL10A | 4736 | −2.15 | nuclear-transcribed mRNA catabolic process, nonsense-mediated decay | RNA transcription, protein translation | CS score, function | |
| Rpl11 | 67025 | RPL11 | 6135 | −2.99 | translation | RNA transcription, protein translation | CS score, function | |
| Rpl12 | 269261 | RPL12 | 6136 | −2.64 | ribosomal large subunit assembly | RNA transcription, protein translation | CS score, function | |
| Rpl13 | 270106 | RPL13 | 6137 | −3.28 | translation | RNA transcription, protein translation | CS score, function | |
| Rpl14 | 67115 | RPL14 | 9045 | −2.92 | nuclear-transcribed mRNA catabolic process, nonsense-mediated decay | RNA transcription, protein translation | CS score, function | |
| Rpl15 | 66480 | RPL15 | 6138 | −3.50 | translation | RNA transcription, protein translation | CS score, function | |
| Rpl18 | 19899 | RPL18 | 6141 | −3.72 | translation | RNA transcription, protein translation | CS score, function | |
| Rpl18a | 76808 | RPL18A | 6142 | −3.37 | translation | RNA transcription, protein translation | CS score, function | |
| Rpl23 | 65019 | RPL23 | 9349 | −3.02 | translation | RNA transcription, protein translation | CS score, function | |
| n/a | n/a | RPL23A | 6147 | −4.25 | translation | RNA transcription, protein translation | CS score, function | |
| Rpl24 | 68193 | RPL24 | 6152 | −2.55 | ribosomal large subunit assembly | RNA transcription, protein translation | CS score, mouse K.O., function | Oliver ER, et al. Development. 2004 August; 131(16):3907-20 |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Rpl26 | 19941 | RPL26 | 6154 | −2.88 | translation | RNA transcription, protein translation | CS score, function | |
| Rpl27 | 19942 | RPL27 | 6155 | −2.25 | translation | RNA transcription, protein translation | CS score, function | |
| Rpl27a | 26451 | RPL27A | 6157 | −2.87 | translation | RNA transcription, protein translation | CS score, mouse K.O., function | Terzian T, et al. J Pathol. 2011 August; 224(4):540-52 |
| Rpl3 | 27367 | RPL3 | 6122 | −3.27 | ribosomal large subunit assembly | RNA transcription, protein translation | CS score, function | |
| Rpl30 | 19946 | RPL30 | 6156 | −2.53 | nuclear-transcribed mRNA catabolic process, nonsense-mediated decay | RNA transcription, protein translation | CS score, function | |
| Rpl31 | 114641 | RPL31 | 6160 | −1.92 | translation | RNA transcription, protein translation | CS score, function | |
| Rpl32 | 19951 | RPL32 | 6161 | −3.70 | nuclear-transcribed mRNA catabolic process, nonsense-mediated decay | RNA transcription, protein translation | CS score, function | |
| n/a | n/a | RPL34 | 6164 | −2.37 | nuclear-transcribed mRNA catabolic process, nonsense-mediated decay | RNA transcription, protein translation | CS score, function | |
| Rpl35 | 66489 | RPL35 | 11224 | −2.25 | nuclear-transcribed mRNA catabolic process, nonsense-mediated decay | RNA transcription, protein translation | CS score, function | |
| Rpl35a | 57808 | RPL35A | 6165 | −3.20 | translation | RNA transcription, protein translation | CS score, function | |
| Rpl36 | 54217 | RPL36 | 25873 | −3.44 | nuclear-transcribed mRNA catabolic process, nonsense-mediated decay | RNA transcription, protein translation | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Rpl37 | 67281 | RPL37 | 6167 | −3.02 | translation | RNA transcription, protein translation | CS score, function | |
| Rpl37a | 19981 | RPL37A | 6168 | −2.62 | nuclear-transcribed mRNA catabolic process, nonsense-mediated decay | RNA transcription, protein translation | CS score, function | |
| Rpl38 | 67671 | RPL38 | 6169 | −2.57 | translation | RNA transcription, protein translation | CS score, mouse K.O., function | MORGAN WC, et al. J Hered. 1950 August; 41(8): 208-15 |
| Rpl4 | 67891 | RPL4 | 6124 | −2.67 | nuclear-transcribed mRNA catabolic process, nonsense-mediated decay | RNA transcription, protein translation | CS score, function | |
| Rpl5 | 100503670 | RPL5 | 6125 | −3.20 | translation | RNA transcription, protein translation | CS score, function | |
| Rpl6 | 19988 | RPL6 | 6128 | −3.07 | translation | RNA transcription, protein translation | CS score, function | |
| Rpl7 | 19989 | RPL7 | 6129 | −2.15 | nuclear-transcribed mRNA catabolic process, nonsense-mediated decay | RNA transcription, protein translation | CS score, function | |
| Rpl7a | 27176 | RPL7A | 6130 | −3.45 | ribosome | RNA biogenesisn, protein translation | CS score, function | |
| Rpl7l1 | 66229 | RPL7L1 | 285855 | −1.86 | maturation of LSU-rRNA from tricistronic rRNA transcript (SSU-rRNA, 5.8S rRNA, LSU-rRNA) | RNA transcription, protein translation | CS score, function | |
| Rpl8 | 26961 | RPL8 | 6132 | −4.00 | translation | RNA transcription, protein translation | CS score, function | |
| Rpl9 | 20005 | RPL9 | 6133 | −3.57 | translation | RNA transcription, protein translation | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Rplp0 | 11837 | RPLP0 | 6175 | −2.61 | nuclear-transcribed mRNA catabolic process, nonsense-mediated decay | RNA transcription, protein translation | CS score, function | |
| Rpp21 | 67676 | RPP21 | 79897 | −2.96 | tRNA processing | RNA transcription, protein translation | CS score, function | |
| Rpp30 | 54364 | RPP30 | 10556 | −1.79 | tRNA processing | RNA transcription, protein translation | CS score, function | |
| Rps10 | 67097 | RPS10 | 6204 | −2.88 | ribosomal small subunit assembly | RNA transcription, protein translation | CS score, function | |
| Rps11 | 27207 | RPS11 | 6205 | −2.93 | translation | RNA transcription, protein translation | CS score, function | |
| Rps12 | 20042 | RPS12 | 6206 | −3.33 | nuclear-transcribed mRNA catabolic process, nonsense-mediated decay | RNA transcription, protein translation | CS score, function | |
| Rps13 | 68052 | RPS13 | 6207 | −3.13 | translation | RNA transcription, protein translation | CS score, function | |
| n/a | n/a | RPS14 | 6208 | −3.18 | translation | RNA transcription, protein translation | CS score, function | |
| Rps15 | 20054 | RPS15 | 6209 | −3.20 | ribosomal small subunit assembly | RNA transcription, protein translation | CS score, function | |
| Rps15a | 267019 | RPS15A | 6210 | −3.18 | translation | RNA transcription, protein translation | CS score, function | |
| Rps16 | 20055 | RPS16 | 6217 | −2.35 | translation | RNA transcription, protein translation | CS score, function | |
| Rps17 | 20068 | RPS17 | 6218 | −2.69 | ribosomal small subunit assembly | RNA transcription, protein translation | CS score, function | |
| Rps19 | 20085 | RPS19 | 6223 | −3.49 | translation | RNA transcription, protein translation | CS score, mouse K.O., function | Matsson H, et al. Mol Cell Biol. 2004 May; 24(9): 4032-7 |
| Rps2 | 16898 | RPS2 | 6187 | −2.50 | translation | RNA transcription, protein translation | CS score, function | |
| Rps21 | 66481 | RPS21 | 6227 | −1.84 | nuclear-transcribed mRNA | RNA transcription, protein | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| | | | | | catabolic process, nonsense-mediated decay | translation | | |
| Rps23 | 66475 | RPS23 | 6228 | −2.86 | translation | RNA transcription, protein translation | CS score, function | |
| Rps25 | 75617 | RPS25 | 6230 | −2.38 | nuclear-transcribed mRNA catabolic process, nonsense-mediated decay | RNA transcription, protein translation | CS score, function | |
| n/a | n/a | RPS3A | 6189 | −3.72 | translation | RNA transcription, protein translation | CS score, function | |
| Rps4x | 20102 | RPS4X | 6191 | −3.04 | translation | RNA transcription, protein translation | CS score, function | |
| Rps5 | 20103 | RPS5 | 6193 | −2.61 | translation | RNA transcription, protein translation | CS score, function | |
| Rps6 | 20104 | RPS6 | 6194 | −3.31 | translation | RNA transcription, protein translation | CS score, function | |
| Rps7 | 20115 | RPS7 | 6201 | −2.97 | nuclear-transcribed mRNA catabolic process, nonsense-mediated decay | RNA transcription, protein translation | CS score, function | |
| Rps8 | 20116 | RPS8 | 6202 | −3.44 | nuclear-transcribed mRNA catabolic process, nonsense-mediated decay | RNA transcription, protein translation | CS score, function | |
| Rps9 | 76846 | RPS9 | 6203 | −3.16 | translation | RNA transcription, protein translation | CS score, function | |
| Rpsa | 16785 | RPSA | 3921 | −3.06 | ribosomal small subunit assembly | RNA transcription, protein translation | CS score, mouse K.O., function | Han J, et al. MGI Direct Data Submission. 2008 |
| Rsl24d1 | 225215 | RSL24D1 | 51187 | −2.76 | translation | RNA transcription, protein translation | CS score, function | |
| Sars | 20226 | SARS | 6301 | −2.67 | tRNA aminoacylation for protein translation | RNA transcription, protein translation | CS score, function | |
| Sars2 | 71984 | SARS2 | 54938 | −2.25 | seryl-tRNA aminoacylation | RNA transcription, | CS score, | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Sart1 | 20227 | SART1 | 9092 | −2.13 | maturation of 5S rRNA | protein translation RNA transcription, protein translation | function CS score, function | |
| Sart3 | 53890 | SART3 | 9733 | −1.88 | RNA processing | RNA transcription, protein translation | CS score, function | |
| Sdad1 | 231452 | SDAD1 | 55153 | −1.96 | ribosomal large subunit export from nucleus | RNA transcription, protein translation | CS score, function | |
| Sf1 | 22668 | SF1 | 7536 | −3.04 | mRNA splicing, via spliceosome | RNA transcription, protein translation | CS score, mouse K.O., function | Shitashige M, et al. Cancer Sci. 2007 December; 98(12):1862-7 |
| Sf3a1 | 67465 | SF3A1 | 10291 | −3.18 | mRNA 3'-splice site recognition | RNA transcription, protein translation | CS score, function | |
| Sf3a2 | 20222 | SF3A2 | 8175 | −2.66 | mRNA 3'-splice site recognition | RNA transcription, protein translation | CS score, function | |
| Sf3a3 | 75062 | SF3A3 | 10946 | −2.26 | RNA splicing, via transesterification reactions | RNA transcription, protein translation | CS score, function | |
| Sf3b2 | 319322 | SF3B2 | 10992 | −2.51 | mRNA splicing, via spliceosome | RNA transcription, protein translation | CS score, function | |
| Sf3b3 | 101943 | SF3B3 | 23450 | −4.13 | RNA splicing, via transesterification reactions | RNA transcription, protein translation | CS score, function | |
| Sf3b4 | 107701 | SF3B4 | 10262 | −2.60 | RNA splicing, via transesterification reactions | RNA transcription, protein translation | CS score, function | |
| Sfpq | 71514 | SFPQ | 6421 | −2.27 | negative regulation of transcription from RNA polymerase II promoter | RNA transcription, protein translation | CS score, function | |
| Sin3a | 20466 | SIN3A | 25942 | −1.74 | negative regulation of transcription from RNA polymerase II promoter | RNA transcription, protein translation | CS score, mouse K.O., function | Dannenberg JH, et al. Genes Dev. 2005 Jul. 1; 19(13):1581-95 |
| Smg5 | 229512 | SMG5 | 23381 | −2.35 | nuclear-transcribed mRNA catabolic process, nonsense-mediated decay | RNA transcription, protein translation | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Smg6 | 103677 | SMG6 | 23293 | −1.18 | nuclear-transcribed mRNA catabolic process, nonsense-mediated decay | RNA transcription, protein translation | CS score, function | |
| Snrnp25 | 78372 | SNRNP25 | 79622 | −2.43 | mRNA processing | RNA transcription, protein translation | CS score, function | |
| Snrnp27 | 66618 | SNRNP27 | 11017 | −1.36 | mRNA processing | RNA transcription, protein translation | CS score, function | |
| Snrpd2 | 107686 | SNRPD2 | 6633 | −2.47 | RNA splicing | RNA transcription, protein translation | CS score, function | |
| Snrpf | 69878 | SNRPF | 6636 | −3.58 | mRNA splicing, via spliceosome | RNA transcription, protein translation | CS score, function | |
| Srrm1 | 51796 | SRRM1 | 10250 | −1.81 | mRNA processing | RNA transcription, protein translation | CS score, function | |
| Srsf1 | 110809 | SRSF1 | 6426 | −2.75 | mRNA 5'-splice site recognition | RNA transcription, protein translation | CS score, mouse K.O., function | Xu X, et al. Cell. 2005 Jan. 14; 120(1): 59-72 |
| Srsf2 | 20382 | SRSF2 | 6427 | −3.66 | regulation of alternative mRNA splicing, via spliceosome | RNA transcription, protein translation | CS score, mouse K.O., function | Ding JH, et al. EMBO J. 2004 Feb. 25; 23(4):885-96 |
| Srsf3 | 20383 | SRSF3 | 6428 | −2.28 | mRNA splicing, via spliceosome | RNA transcription, protein translation | CS score, mouse K.O., function | Jumaa H, et al. Curr Biol. 1999 Aug. 26; 9(16):899-902 |
| Srsf7 | 225027 | SRSF7 | 6432 | −2.06 | mRNA splicing, via spliceosome | RNA transcription, protein translation | CS score, function | |
| Ssu72 | 68991 | SSU72 | 29101 | −2.57 | mRNA polyadenylation | RNA transcription, protein translation | CS score, function | |
| Sugp1 | 70616 | SUGP1 | 57794 | −1.36 | RNA processing | RNA transcription, protein translation | CS score, function | |
| Tars | 110960 | TARS | 6897 | −2.53 | tRNA aminoacylation for protein translation | RNA transcription, protein translation | CS score, function | |
| Tars2 | 71807 | TARS2 | 80222 | −1.91 | threonyl-tRNA aminoacylation | RNA transcription, protein translation | CS score, function | |
| Tbl3 | 213773 | TBL3 | 10607 | −2.4 | maturation of SSU-rRNA from tricistronic | RNA transcription, protein translation | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Thoc2 | 331401 | THOC2 | 57187 | −2.52 | rRNA transcript (SSU-rRNA, 5.8S rRNA, LSU-rRNA) mRNA processing | RNA transcription, protein translation | CS score, function | |
| Thoc5 | 107829 | THOC5 | 8563 | −1.57 | mRNA processing | RNA transcription, protein translation | CS score, mouse K.O., function | Mancini A, et al. BMC Biol. 2010; 8:1 |
| Thoc7 | 66231 | THOC7 | 80145 | −2.23 | mRNA processing | RNA transcription, protein translation | CS score, function | |
| Timeless | 21853 | TIMELESS | 8914 | −2.27 | negative regulation of transcription from RNA polymerase II promoter | RNA transcription, protein translation | CS score, mouse K.O., function | Gotter AL, et al. Nat Neurosci. 2000 August; 3(8):755-6 |
| Tsen2 | 381802 | TSEN2 | 80746 | −1.41 | tRNA-type intron splice site recognition and cleavage | RNA transcription, protein translation | CS score, function | |
| Tsr1 | 104662 | TSR1 | 55720 | −1.76 | ribosome biogenesis | RNA transcription, protein translation | CS score, function | |
| Tsr2 | 69499 | TSR2 | 90121 | −2.82 | maturation of SSU-rRNA from tricistronic rRNA transcript (SSU-rRNA, 5.8S rRNA, LSU-rRNA) | RNA transcription, protein translation | CS score, function | |
| Tufm | 233870 | TUFM | 7284 | −1.92 | translational elongation | RNA transcription, protein translation | CS score, function | |
| Tut1 | 70044 | TUT1 | 64852 | −2.65 | mRNA polyadenylation | RNA transcription, protein translation | CS score, function | |
| Twistnb | 28071 | TWISTNB | 221830 | −2.17 | transcription from RNA polymerase I promoter | RNA transcription, protein translation | CS score, function | |
| U2af1 | 108121 | U2AF1 | 7307 | −2.41 | mRNA splicing, via spliceosome | RNA transcription, protein translation | CS score, function | |
| U2af2 | 22185 | U2AF2 | 11338 | −2.80 | mRNA processing | RNA transcription, protein translation | CS score, function | |
| Uba52 | 22186 | UBA52 | 7311 | −2.54 | translation | RNA transcription, protein translation | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Ubl5 | 66177 | UBL5 | 59286 | −2.56 | mRNA splicing, via spliceosome | RNA transcription, protein translation | CS score, function | |
| Upf1 | 19704 | UPF1 | 5976 | −2.63 | nuclear-transcribed mRNA catabolic process, nonsense-mediated decay | RNA transcription, protein translation | CS score, mouse K.O., function | Medghalchi SM, et al. Hum Mol Genet. 2001 Jan. 15; 10(2):99-105 |
| Upf2 | 326622 | UPF2 | 26019 | −2.16 | nuclear-transcribed nRNA catabolic process, nonsense-mediated decay | RNA transcription, protein translation | CS score, mouse K.O., function | Weischenfeldt J, et al. Genes Dev. 2008 May 15; 22(10): 1381-96 |
| Utp15 | 105372 | UTP15 | 84135 | −1.65 | maturation of SSU-rRNA from tricistronic rRNA transcript (SSU-rRNA, 5.8S rRNA, LSU-rRNA) | RNA transcription, protein translation | CS score, function | |
| Utp20 | 70683 | UTP20 | 27340 | −2.28 | endonucleolytic cleavage in ITS1 to separate SSU-rRNA from 5.8S rRNA and LSU-rRNA from tricistronic rRNA transcript (SSU-rRNA, 5.8S rRNA, LSU-rRNA) | RNA transcription, protein translation | CS score, function | |
| Utp23 | 78581 | UTP23 | 84294 | −2.54 | rRNA processing | RNA transcription, protein translation | CS score, function | |
| Utp3 | 65961 | UTP3 | 57050 | −1.58 | maturation of SSU-rRNA from tricistronic rRNA transcript (SSU-rRNA, 5.8S rRNA, LSU-rRNA) | RNA transcription, protein translation | CS score, function | |
| Utp6 | 216987 | UTP6 | 55813 | −1.99 | maturation of SSU-rRNA from tricistronic rRNA transcript (SSU-rRNA, 5.8S rRNA, LSU-rRNA) | RNA transcription, protein translation | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Vars | 22321 | VARS | 7407 | −3.35 | tRNA aminoacylation for protein translation | RNA transcription, protein translation | CS score, function | |
| Wars | 22375 | WARS | 7453 | −2.22 | tryptophanyl-tRNA aminoacylation | RNA transcription, protein translation | CS score, function | |
| Wdr12 | 57750 | WDR12 | 55759 | −2.16 | maturation of LSU-rRNA from tricistronic rRNA transcript (SSU-rRNA, 5.8S rRNA, LSU-rRNA) | RNA transcription, protein translation | CS score, function | |
| Wdr3 | 269470 | WDR3 | 10885 | −2.65 | maturation of SSU-rRNA from tricistronic rRNA transcript (SSU-rRNA, 5.8S rRNA, LSU-rRNA) | RNA transcription, protein translation | CS score, function | |
| Wdr33 | 74320 | WDR33 | 55339 | −2.63 | mRNA polyadenylation | RNA transcription, protein translation | CS score, function | |
| Wdr36 | 225348 | WDR36 | 134430 | −2.04 | rRNA processing | RNA transcription, protein translation | CS score, mouse K.O., function | Gallenberger M, et al. Hum Mol Genet. 2011 Feb. 1; 20(3):422-35 |
| Wdr46 | 57315 | WDR46 | 9277 | −2.41 | maturation of SSU-rRNA from tricistronic rRNA transcript (SSU-rRNA, 5.8S rRNA, LSU-rRNA) | RNA transcription, protein translation | CS score, function | |
| Wdr61 | 66317 | WDR61 | 80349 | −2.63 | nuclear-transcribed mRNA catabolic process, exonucleolytic, 3'-5' | RNA transcription, protein translation | CS score, function | |
| Wdr75 | 73674 | WDR75 | 84128 | −2.12 | regulation of transcription from RNA polymerase II promoter | RNA transcription, protein translation | CS score, function | |
| Xpo1 | 103573 | XPO1 | 7514 | −3.50 | ribosomal large subunit export from nucleus | RNA transcription, protein translation | CS score, function | |
| Yars | 107271 | YARS | 8565 | −2.78 | tRNA aminoacylation for protein translation | RNA transcription, protein translation | CS score, function | |

TABLE 5-continued

Predicted CDLs (ID refers to EntrezGene identification number; CS score refers to the CRISPR score average provided in Wang et al., 2015; function refers to the known or predicted function of the locus, predictions being based on GO terms, as set forth in the Gene Ontology Consortium website http://geneontology.org/; functional category refers to 4 categories of cell functions based on the GO term-predicted function; CDL (basis) refers to information that the inventors used to predict that a gene is a CDL, predictions being based on CS score, available gene knockout (KO) data, gene function, and experimental data provided in WO 2016 141480).

| Name (mouse) | ID (mouse) | Name (human) | ID (human) | CS score | Function (GO term) | Functional category | CDL (basis) | Citation |
|---|---|---|---|---|---|---|---|---|
| Yars2 | 70120 | YARS2 | 51067 | −2.40 | translation | RNA transcription, protein translation | CS score, function | |
| Ythdc1 | 231386 | YTHDC1 | 91746 | −2.35 | mRNA splice site selection | RNA transcription, protein translation | CS score, function | |
| Zbtb8os | 67106 | ZBTB8OS | 339487 | −2.54 | tRNA splicing, via endonucleolytic cleavage and ligation | RNA transcription, protein translation | CS score, function | |
| Zc3h3 | 223642 | ZC3H3 | 23144 | −1.22 | mRNA polyadenylation | RNA transcription, protein translation | CS score, function | |

Although the disclosure has been described with reference to certain specific embodiments, various modifications thereof will be apparent to those skilled in the art. Any examples provided herein are included solely for the purpose of illustrating the disclosure and are not intended to limit the disclosure in any way. Any drawings provided herein are solely for the purpose of illustrating various aspects of the disclosure and are not intended to be drawn to scale or to limit the disclosure in any way. The scope of the claims appended hereto should not be limited by the preferred embodiments set forth in the above description, but should be given the broadest interpretation consistent with the present specification as a whole. The disclosures of all prior art recited herein are incorporated herein by reference in their entirety.

The invention claimed is:

1. A cell genetically modified to comprise transgenes comprising:

human Fas ligand (FASLG), CD200, C-C motif chemokine ligand 21 (CCL21), serpin family B member 9 (SERPINB9), milk fat globule-EFG factor 8 (MFGE8), Programmed cell death-ligand 1 (PD-L1), major histocompatibility complex, class I, G (HLA-G), and CD47; or murine Fas ligand (FasL), Cd200, C-C motif chemokine ligand 21B (Ccl21b), Serine Protease Inhibitor 6 (Spi6), Mfge8, Pd-l1, histocompatibility 2, M region locus 3 (H2-M3), and Cd47; and wherein the human FASLG transgene encodes a protein having at least 95% sequence identity to the sequence as set forth in SEQ ID NO: 10, the human CD200 transgene encodes a protein having at least 95% sequence identity to the sequence as set forth in SEQ ID NO: 6, the human CCL21 transgene encodes a protein having at least 95% sequence identity to the sequence as set forth in SEQ ID NO: 2, the human SERPINB9 transgene encodes a protein having at least 95% sequence identity to sequence as set forth in SEQ ID NO: 8, the human MFGE8 transgene encodes a protein having at least 95% identity to sequence as set forth in SEQ ID NO: 14, the human PD-L1 transgene encodes a protein having at least 95% sequence identity to sequence as set forth in SEQ ID NO: 12, the human HLA-G transgene encodes a protein having at least 95% sequence identity to sequence as set forth in SEQ ID NO: 16, and the human CD47 transgene encodes a protein having at least 95% sequence identity to sequence as set forth in SEQ ID NO: 4; or the murine FasI transgene encodes a protein having at least 95% sequence identity to sequence as set forth in SEQ ID NO: 9, the murine Cd200 transgene encodes a protein having at least 95% sequence identity to sequence as set forth in SEQ ID NO: 5, the murine Ccl21b transgene encodes a protein having at least 95% sequence identity to sequence as set forth in SEQ ID NO: 1, the murine Spi6 transgene encodes a protein having at least 95% sequence identity to sequence as set forth in SEQ ID NO: 7, the murine Mfge8 transgene encodes a protein having at least 95% sequence identity to sequence as set forth in SEQ ID NO: 13, the murine Pd-l1 transgene encodes a protein having at least 95% sequence identity to sequence as set forth in SEQ ID NO: 11, the murine H2-M3 transgene encodes a protein having at least 95% sequence identity to sequence as set forth in SEQ ID NO: 15, and the murine Cd47 transgene encodes a protein having at least 95% sequence identity to sequence as set forth in SEQ ID NO: 3.

2. The cell of claim 1, wherein the cell is an allogeneic cell in reference to a subject.

3. The cell of claim 1, wherein the cell is a human cell or a murine cell.

4. The cell of claim 1, wherein the cell is a stem cell.

5. The cell of claim 1, where the cell further comprises a heterologous sequence encoding a therapeutic agent.

6. The cell of claim 5, wherein the therapeutic agent comprises a wild-type version of a gene that is mutated within a subject.

7. The cell of claim 5, wherein the therapeutic agent comprises an enzyme, an antibody, a growth factor, or a cytokine.

8. The cell of claim 1, wherein expression of the transgenes is under the control of one or more constitutive promoters.

9. The cell of claim 8, wherein the one or more constitutive promoters comprise a cytomegalovirus (CMV) immediate-early enhancer/chicken β-actin (CAG) promoter, a cytomegalovirus (CMV) promoter, a human elongation factor-1 alpha (EF1a) promoter, a 3-phosphoglycerate kinase (PGK) promoter, an adenovirus late promoter, a vaccinia virus 7.5K promoter, a Simian Virus 40 (SV40) promoter, a thymidine kinase (tk) promoter of herpes simplex virus (HSV), mouse mammary tumor virus (MMTV) promoter, a long terminal repeat (LTR) promoter of human immunodeficiency virus (HIV), a promoter of Moloney virus, an Epstein barr virus (EBV) promoter, or a Rous sarcoma virus (RSV) promoter.

10. The cell of claim 1, wherein the cell further comprises one or more of the following transgenes: transforming growth factor beta (TGF-β), 5'-nucleotidase ecto (Cd73), ectonucleoside triphosphate diphosphohydrolase 1 (Cd39), lymphocyte activating 3 (Lag3), interleukin 1 receptor type 2 (Il1r2), atypical chemokine receptor 2 (Ackr2), tumor necrosis factor receptor superfamily, member 22 (Tnfrsf22), tumor necrosis factor receptor superfamily, member 23 (Tnfrsf23), tumor necrosis factor receptor superfamily, member 10 (Tnfrsf10), defender against cell death 1 (Dad1), or a dominant negative form of the IFNγ receptor (IFNγR1 d39).

11. The cell of claim 1, wherein the cell further comprises a genetic modification of one or more cell division locus/loci (CDL).

12. The cell of claim 11, wherein the genetic modification of the one or more cell division locus/loci (CDL) comprises insertion of an ablation link (ALINK) system or an exogenous activator of regulation of cell division locus/loci (EARC) system.

13. The cell of claim 11, wherein the CDL comprises cyclin dependent kinase 1 (CDK1), DNA topoisomerase II alpha (TOP2A), centromere protein A (CENPA), baculoviral IAP repeat containing 5 (BIRC5), or eukaryotic translation elongation factor 2 (EEF2).

14. A composition comprising the cell of claim 1 and a pharmaceutically acceptable excipient.

* * * * *

```
                          SEQUENCE LISTING

Sequence total quantity: 17
SEQ ID NO: 1            moltype = AA  length = 133
FEATURE                 Location/Qualifiers
source                  1..133
                        mol_type = protein
                        organism = Mus musculus
SEQUENCE: 1
MAQMMTLSLL SLVLALCIPW TQGSDGGGQD CCLKYSQKKI PYSIVRGYRK QEPSLGCPIP    60
AILFLPRKHS KPELCANPEE GWVQNLMRRL DQPPAPGKQS PGCRKNRGTS KSGKKGKGSK   120
GCKRTEQTQP SRG                                                     133

SEQ ID NO: 2            moltype = AA  length = 134
FEATURE                 Location/Qualifiers
source                  1..134
                        mol_type = protein
                        organism = Homo sapiens
SEQUENCE: 2
MAQSLALSLL ILVLAFGIPR TQGSDGGAQD CCLKYSQRKI PAKVVRSYRK QEPSLGCSIP    60
AILFLPRKRS QAELCADPKE LWVQQLMQHL DKTPSPQKPA QGCRKDRGAS KTGKKGKGSK   120
GCKRTERSQT PKGP                                                    134

SEQ ID NO: 3            moltype = AA  length = 303
FEATURE                 Location/Qualifiers
source                  1..303
                        mol_type = protein
                        organism = Mus musculus
SEQUENCE: 3
MWPLAAALLL GSCCCGSAQL LFSNVNSIEF TSCNETVVIP CIVRNVEAQS TEEMFVKWKL    60
NKSYIFIYDG NKNSTTTDQN FTSAKISVSD LINGIASLKM DKRDAMVGNY TCEVTELSRE   120
GKTVIELKNR TVSWFSPNEK ILIVIFPILA ILLFWGKFGI LTLKYKSSHT NKRIILLLVA   180
GLVLTVIVVV GAILLIPGEK PVKNASGLGL IVISTGILIL LQYNVFMTAF GMTSFTIAIL   240
ITQVLGYVLA LVGLCLCIMA CEPVHGPLLI SGLGIIALAE LLGLVYMKFV ASNQRTIQPP   300
RNR                                                                303
```

```
SEQ ID NO: 4              moltype = AA   length = 323
FEATURE                   Location/Qualifiers
source                    1..323
                          mol_type = protein
                          organism = Homo sapiens
SEQUENCE: 4
MWPLVAALLL GSACCGSAQL LFNKTKSVEF TFCNDTVVIP CFVTNMEAQN TTEVYVKWKF   60
KGRDIYTFDG ALNKSTVPTD FSSAKIEVSQ LLKGDASLKM DKSDAVSHTG NYTCEVTELT  120
REGETIIELK YRVVSWFSPN ENILIVIFPI FAILLFWGDL GIKTLKYRSG GMDEKTIALL  180
VAGLVITVIV IVGAILFVPG EYSLKNATGL GLIVTSTGIL ILLHYYVFST AIGLTSFVIA  240
ILVIQVIAYI LAVVGLSLCI AACIPMHGPL LISGLSILAL AQLLGLVYMK FVASNQKTIQ  300
PPRKAVEEPL NAFKESKGMM NDE                                         323

SEQ ID NO: 5              moltype = AA   length = 278
FEATURE                   Location/Qualifiers
source                    1..278
                          mol_type = protein
                          organism = Mus musculus
SEQUENCE: 5
MGSLVFRRPF CHLSTYSLIW GMAAVALSTA QVEVVTQDER KALHTTASLR CSLKTSQEPL   60
IVTWQKKKAV SPENMVTYSK THGVVIQPAY KDRINVTELG LWNSSITFWN TTLEDEGCYM  120
CLFNTFGSQK VSGTACLTLY VQPIVHLHYN YFEDHLNITC SATARPAPAI SWKGTGTGIE  180
NSTESHFHSN GTTSVTSILR VKDPKTQVGK EVICQVLYLG NVIDYKQSLD KGFWFSVPLL  240
LSIVSLVILL VLISILLYWK RHRNQERGES SQGMQRMK                         278

SEQ ID NO: 6              moltype = AA   length = 278
FEATURE                   Location/Qualifiers
source                    1..278
                          mol_type = protein
                          organism = Homo sapiens
SEQUENCE: 6
MERLVIRMPF SHLSTYSLVW VMAAVVLCTA QVQVVTQDER EQLYTPASLK CSLQNAQEAL   60
IVTWQKKKAV SPENMVTFSE NHGVVIQPAY KDKINITQLG LQNSTITFWN ITLEDEGCYM  120
CLFNTFGFGK ISGTACLTVY VQPIVSLHYK FSEDHLNITC SATARPAPMV PWKVPRSGIE  180
NSTVTLSHPN GTTSVTSILH IKDPKNQVGK EVICQVLHLG TVTDFKQTVN KGYWFSVPLL  240
LSIVSLVILL VLISILLYWK RHRNQDRGEL SQGVQKMT                         278

SEQ ID NO: 7              moltype = AA   length = 374
FEATURE                   Location/Qualifiers
source                    1..374
                          mol_type = protein
                          organism = Mus musculus
SEQUENCE: 7
MNTLSEGNGT FAIHLLKMLC QSNPSKNVCY SPASISSALA MVLLGAKGQT AVQISQALGL   60
NKEEGIHQGF QLLLRKLNKP DRKYSLRVAN RLFADKTCEV LQTFKESSLH FYDSEMEQLS  120
FAEEEAEVSRQ HINTWVSKQT EGKIPELLSG GSVDSETRLV LINALYFKGK WHQPFNKEYT  180
MDMPFKINKD EKRPVQMMCR EDTYNLAYVK EVQAQVLVMP YEGMELSLVV LLPDEGVDLS  240
KVENNLTFEK LTAWMEADFM KSTDVEVFLP KFKLQEDYDM ESLFQRLGVV DVFQEDKADL  300
SGMSPERNLC VSKFVHQSVV EINEEGTEAA AASAIIEFCC ASSVPTFCAD HPFLFFIRHN  360
KANSILFCGR FSSP                                                   374

SEQ ID NO: 8              moltype = AA   length = 376
FEATURE                   Location/Qualifiers
source                    1..376
                          mol_type = protein
                          organism = Homo sapiens
SEQUENCE: 8
METLSNASGT FAIRLLKILC QDNPSHNVFC SPVSISSALA MVLLGAKGNT ATQMAQALSL   60
NTEEDIHRAF QSLLTEVNKA GTQYLLRTAN RLFGEKTQF LSTFKESCLQ FYHAELKELS  120
FIRAAEESRK HINTWVSKKT EGKIEELLPG SSIDAETRLV LVNAIYFKGK WNEPFDETYT  180
REMPFKINQE EQRPVQMMYQ EATFKLAHVG EVRAQLLELP YARKELSLLV LLPDDGVELS  240
TVEKSLTFEK LTAWTKPDCM KSTEVEVLLP KFKLQEDYDM ESVLRHLGIV DAFQQGKADL  300
SAMSAERDLC LSKFVHKSFV EVNEEGTEAA AASSCFVVAE CCMESGPRFC ADHPFLFFIR  360
HNRANSILFC GRFSSP                                                 376

SEQ ID NO: 9              moltype = AA   length = 279
FEATURE                   Location/Qualifiers
source                    1..279
                          mol_type = protein
                          organism = Mus musculus
SEQUENCE: 9
MQQPMNYPCP QIFWDSSAT SSWTPPGSVF PCPSSGPRGP DQRRPPPPPP PVSPLPPPSQ    60
PLPLPPLTPL KKKDHNTNLW LPVVFFMVLV ALVGMGLGMY QLFHLQKELA ELREFTNQSL  120
KVSSFEKQIA NPSTPSEKKE LRSVAHLTGN PHSRSIPLEW EDTYGTALIS GVKYKKGSLV  180
INEAGLYFVY SKVYFRGQSC NNQPLNHKVY MRNSKYPGDL VLMEEKRLNY CTTGQIWAHS  240
SYLGAVFNLT SADHLYVNIS QLSLINFEES KTFFGLYKL                        279

SEQ ID NO: 10             moltype = AA   length = 281
FEATURE                   Location/Qualifiers
```

```
source                       1..281
                             mol_type = protein
                             organism = Homo sapiens
SEQUENCE: 10
MQQPFNYPYP QIYWVDSSAS SPWAPPGTVL PCPTSVPRRP GQRRPPPPPP PPPLPPPPPP      60
PPLPPLPLPP LKKRGNHSTG LCLLVMFFMV LVALVGLGLG MFQLFHLQKE LAELRESTSQ     120
MHTASSLEKQ IGHPSPPPEK KELRKVAHLT GKSNSRSMPL EWEDTYGIVL LSGVKYKKGG     180
LVINETGLYF VYSKVYFRGQ SCNNLPLSHK VYMRNSKYPQ DLVMMEGKMM SYCTTGQMWA     240
RSSYLGAVFN LTSADHLYVN VSELSLVNFE ESQTFFGLYK L                        281

SEQ ID NO: 11                moltype = AA    length = 290
FEATURE                      Location/Qualifiers
source                       1..290
                             mol_type = protein
                             organism = Mus musculus
SEQUENCE: 11
MRIFAGIIFT ACCHLLRAFT ITAPKDLYVV EYGSNVTMEC RFPVERELDL LALVVYWEKE      60
DEQVIQFVAG EEDLKPQHSN FRGRASLPKD QLLKGNAALQ ITDVKLQDAG VYCCIISYGG     120
ADYKRITLKV NAPYRKINQR ISVDPATSEH ELICQAEGYP EAEVIWTNSD HQPVSGKRSV     180
TTSRTEGMLL NVTSSLRVNA TANDVFYCTF WRSQPGQNHT AELIIPELPA THPPQNRTHW     240
VLLGSILLFL IVVSTVLLFL RKQVRMLDVE KCGVEDTSSK NRNDTQFEET               290

SEQ ID NO: 12                moltype = AA    length = 290
FEATURE                      Location/Qualifiers
source                       1..290
                             mol_type = protein
                             organism = Homo sapiens
SEQUENCE: 12
MRIFAVFIFM TYWHLLNAFT VTVPKDLYVV EYGSNMTIEC KFPVEKQLDL AALIVYWEME      60
DKNIIQFVHG EEDLKVQHSS YRQRARLLKD QLSLGNAALQ ITDVKLQDAG VYRCMISYGG     120
ADYKRITVKV NAPYNKINQR ILVVDPVTSE HELTCQAEGY PKAEVIWTSS DHQVLSGKTT     180
TTNSKREEKL FNVTSTLRIN TTTNEIFYCT FRRLDPEENH TAELVIPELP LAHPPNERTH     240
LVILGAILLC LGVALTFIFR LRKGRMMDVK KCGIQDTNSK KQSDTHLEET               290

SEQ ID NO: 13                moltype = AA    length = 463
FEATURE                      Location/Qualifiers
source                       1..463
                             mol_type = protein
                             organism = Mus musculus
SEQUENCE: 13
MQVSRVLAAL CGMLLCASGL FAASGDFCDS SLCLNGGTCL TGQDNDIYCL CPEGFTGLVC      60
NETERGPCSP NPCYNDAKCL VTLDTQRGDI FTEYICQCPV GYSGIHCETE TNYYNLDGEY     120
MFTTAVPNTA VPTPAPTPDL SNNLASRCST QLGMEGGAIA DSQISASSVY MGFMGLQRWG     180
PELARLYRTG IVNAWTASNY DSKPWIQVNL LRKRVSGVM TQGASRAGRA EYLKTFKVAY     240
SLDGRKFEFI QDESGGDKEF LGNLDNNSLK VNMFNPTLEA QYIKLYPVSC HRGCTLRFEL     300
LGCELHGCSE PLGLKNNTIP DSQMSASSSY KTWNLRAFGW YPHLGRLDNQ GKINAWTAQS     360
NSAKEWLQVD LGTQRQVTGI ITQGARDFGH IQYVASYKVA HSDDGVQWTV YEEQGSSKVF     420
QGNLDNNSHK KNIFEKPFMA RYVRVLPVSW HNRITLRLEL LGC                      463

SEQ ID NO: 14                moltype = AA    length = 387
FEATURE                      Location/Qualifiers
source                       1..387
                             mol_type = protein
                             organism = Homo sapiens
SEQUENCE: 14
MPRPRLLAAL CGALLCAPSL LVALDICSKN PCHNGGLCEE ISQEVRGDVF PSYTCTCLKG      60
YAGNHCETKC VEPLGMENGN IANSQIAASS VRVTFLGLQH WVPELARLNR AGMVNAWTPS     120
SNDDNPWIQV NLLRRMWVTG VVTQGASRLA SHEYLKAFKV AYSLNGHEFD FIHDVNKKHK     180
EFVGNWNKNA VHVNLFETPV EAQYVRLYPT SCHTACTLRF ELLGCELNGC ANPLGLKNNS     240
IPDKQITASS SYKTWGLHLF SWNPSYARLD KQGNFNAWVA GSYGNDQWLQ VDLGSSKEVT     300
GIITQGARNF GSVQFVASYK VAYSNDSANW TEYQDPRTGS SKIFPGNWDN HSHKKNLFET     360
PILARYVRIL PVAWHNRIAL RLELLGC                                        387

SEQ ID NO: 15                moltype = AA    length = 249
FEATURE                      Location/Qualifiers
source                       1..249
                             mol_type = protein
                             organism = Mus musculus
SEQUENCE: 15
SIEEIPRMEP RAPWMEKERP EYWKELKLKV KNIAQSARAN LRTLLRYYNQ SEGGSHILQW      60
MVSCEVGPDM RLLGAHYQAA YDGSDYITLN EDLSSWTAVD MVSQITKSRL ESAGTAEYFR     120
AYVEGECLEL LHRFLRNGKE ILQRADPPKA HVAHHPRPKG DVTLRCWALG FYPADITLTW     180
QKDEEDLTQD MELVETRPSG DGTFQKWAAV VVPSGEEQRY TCYVHHEGLT EPLALKWGRS     240
SQSSVVIMV                                                            249

SEQ ID NO: 16                moltype = AA    length = 338
FEATURE                      Location/Qualifiers
source                       1..338
                             mol_type = protein
```

```
                        organism = Homo sapiens
SEQUENCE: 16
MVVMAPRTLF LLLSGALTLT ETWAGSHSMR YFSAAVSRPG RGEPRFIAMG YVDDTQFVRF    60
DSDSACPRME PRAPWVEQEG PEYWEEETRN TKAHAQTDRM NLQTLRGYYN QSEASSHTLQ   120
WMIGCDLGSD GRLLRGYEQY AYDGKDYLAL NEDLRSWTAA DTAAQISKRK CEAANVAEQR   180
RAYLEGTCVE WLHRYLENGK EMLQRADPPK THVTHHPVFD YEATLRCWAL GFYPAEIILT   240
WQRDGEDQTQ DVELVETRPA GDGTFQKWAA VVVPSGEEQR YTCHVQHEGL PEPLMLRWKQ   300
SSLPTIPIMG IVAGLVVLAA VVTGAAVAAV LWRKKSSD                          338

SEQ ID NO: 17           moltype = AA  length = 439
FEATURE                 Location/Qualifiers
source                  1..439
                        mol_type = protein
                        organism = synthetic construct
SEQUENCE: 17
MGPQAAAGRM ILLVVLMLSA KVGSGALTST EDPEPPSVPV PTNVLIKSYN LNPVVCWEYQ    60
NMSQTPIFTV QVKVYSGSWT DSCTNISDHC CNIYGQIMYP DVSAWARVKA KVGQKESDYA   120
RSKEFLMCLK GKVGPPGLEI RRKKEEQLSV LVFHPEVVVN GESQGTMFGD GSTCYTFDYT   180
VYVEHNRSGE ILHTKHTVEK EECNETLCEL NISVSTLDSR YCISVDGISS FWQVRTEKSK   240
DVCIPPFHDD RKDSIWILVV APLTVFTVVI LVFAYWYTKK NSFKRKSIML PKSLLSVVKS   300
ATLETKPESK YSLVTPHQPA VLESETVICE EPLSTVTAPD SPEAAEQEEL SKETKALEAG   360
GSTSAMTPDS PPTPTQRRSF SLLSSNQSGP CSLTAYHSRN GSDSGLVGSG SSISDLESLP   420
NNNSETKMAE HDPPPVRKA                                               439
```